United States Patent
Klahn et al.

(10) Patent No.: US 11,236,059 B2
(45) Date of Patent: Feb. 1, 2022

(54) TARGETED CYTOTOXIC RATJADONE DERIVATIVES AND CONJUGATES THEREOF

(71) Applicant: HELMHOLTZ-ZENTRUM FUER INFEKTIONSFORSCHUNG GMBH, Braunschweig (DE)

(72) Inventors: Philipp Klahn, Braunschweig (DE); Mark Broenstrup, Braunschweig (DE); Verena Fetz, Berlin (DE); Wera Collisi, Peine (DE); Katrin I Mohr, Braunschweig (DE); Stephan Huettel, Braunschweig (DE); Werner Tegge, Braunschweig (DE)

(73) Assignee: HELMHOLTZ-ZENTRUM FUER INFEKTIONSFORSCHUNG GMBH, Braunschweig (DE)

( * ) Notice: Subject to any disclaimer, the term of this patent is extended or adjusted under 35 U.S.C. 154(b) by 127 days.

(21) Appl. No.: 16/637,257

(22) PCT Filed: Aug. 8, 2018

(86) PCT No.: PCT/EP2018/071507
§ 371 (c)(1),
(2) Date: Feb. 6, 2020

(87) PCT Pub. No.: WO2019/030284
PCT Pub. Date: Feb. 14, 2019

(65) Prior Publication Data
US 2020/0239426 A1    Jul. 30, 2020

(30) Foreign Application Priority Data

Aug. 9, 2017    (EP) .................................... 17185598

(51) Int. Cl.
| | |
|---|---|
| C07D 309/32 | (2006.01) |
| C07D 487/04 | (2006.01) |
| C07D 495/04 | (2006.01) |
| A61P 35/00 | (2006.01) |

(52) U.S. Cl.
CPC ............ C07D 309/32 (2013.01); A61P 35/00 (2018.01); C07D 487/04 (2013.01); C07D 495/04 (2013.01)

(58) Field of Classification Search
CPC .. C07D 309/32; C07D 487/04; C07D 495/04; A61P 35/00
See application file for complete search history.

(56) References Cited

U.S. PATENT DOCUMENTS

2004/0092581 A1* 5/2004 Burzlaff ................. A61P 35/00
514/460

FOREIGN PATENT DOCUMENTS

EP         1 864 682 A1    12/2007

* cited by examiner

*Primary Examiner* — Erich A Leeser
(74) *Attorney, Agent, or Firm* — Prismatic Law Group, PLLC

(57) ABSTRACT

The present invention is directed to novel natural product-derived ratjadone-based compounds useful as payloads (or toxins) in drug-conjugates constructs with cell target binding moieties (CTBM) and payload-linker compounds useful in connection with drug conjugates. The present invention further relates to new ratjadone compositions including the aforementioned payloads, payload-linkers and drug conjugates, and methods for using these payloads, payload-linkers and drug conjugates, to treat pathological conditions including cancer, inflammatory and infectious diseases.

16 Claims, 16 Drawing Sheets

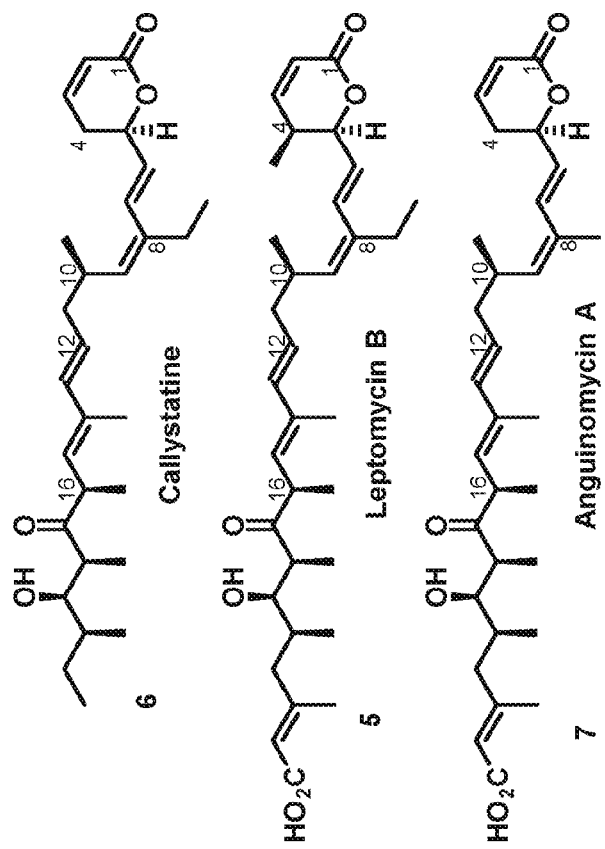
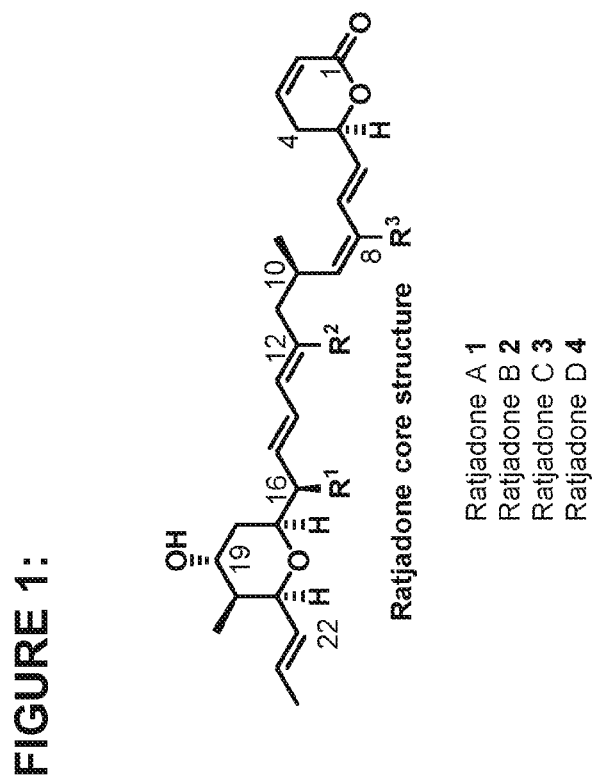
FIGURE 1:

FIGURE 3:
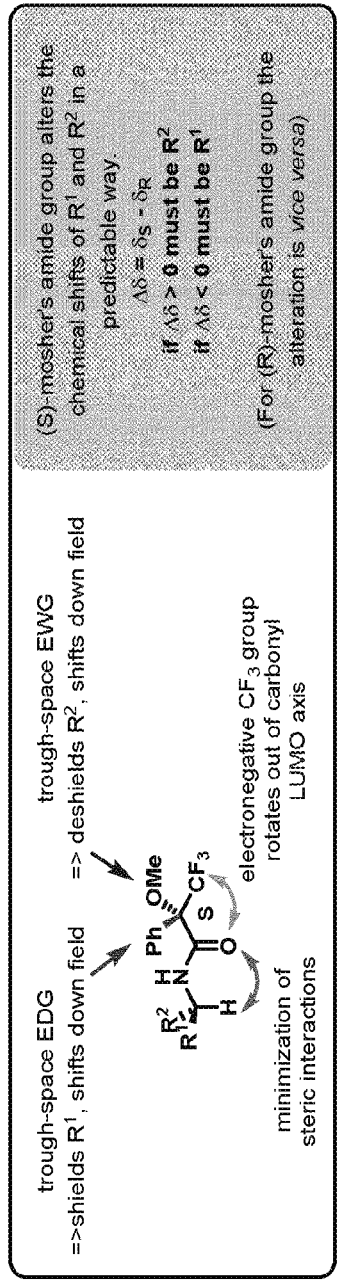

FIGURE 6 (contd.):
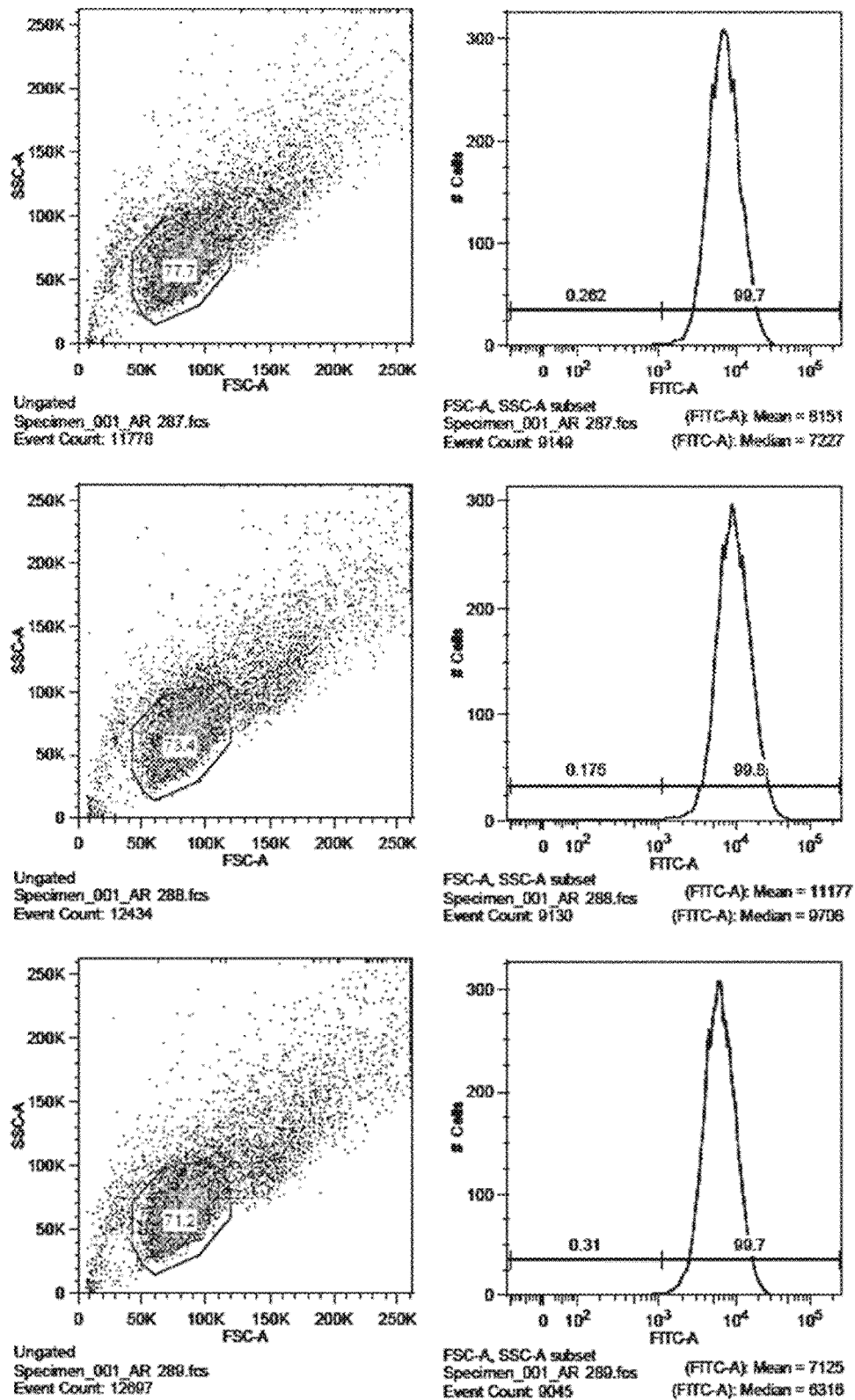

TARGETED CYTOTOXIC RATJADONE DERIVATIVES AND CONJUGATES THEREOF

CROSS-REFERENCE TO RELATED APPLICATIONS

This application is a 371 national phase of International Patent Application No. PCT/EP2018/071507 filed Aug. 8, 2018, which claims priority to European Patent Application No. EP 17185598.4 filed Aug. 9, 2017, the content of each of which applications is incorporated herein by reference.

FIELD OF THE INVENTION

The present invention is directed to novel natural product-derived ratjadone-based compounds useful as payloads (or toxins) in drug-conjugates constructs with cell target binding moieties (CTBM) and payload-linker compounds useful in connection with drug conjugates. The present invention further relates to new ratjadone compositions including the aforementioned payloads, payload-linkers and drug conjugates, and methods for using these payloads, payload-linkers and drug conjugates, to treat pathological conditions including cancer, inflammatory and infectious diseases.

BACKGROUND OF THE INVENTION

For many types of cancer classic chemotherapy is still the only effective form of treatment. Chemotherapy functions on the basis of a cytotoxic effect: a toxin kills cancer cells, thus halting tumor growth. Chemotherapeutic agents primarily damage and destroy cells with a high level of cell-division activity. However, these therapeutics have long struggled with the need to target and destroy malignant cells while minimizing undesired collateral toxicity to normal tissue. Since such drugs also damage healthy cells, patients suffer severe side effects. Numerous highly cytotoxic drugs are of limited clinical utility because they are equally aggressive against both normal and malignant tumoral cells. Healthy tissue can be heavily affected by cytotoxins. Since these drugs do not explicitly discriminate between tumor cells and normal cells, leading to side effects, drugs are often dosed at minimum levels, which may be not effective. This is the reason why it is important to find a way to specifically target tumor cells.

Improving the delivery of drugs and other agents to target cells, tissues and tumors to achieve maximal efficacy and minimal toxicity has been the focus, of considerable research for many years. Modern cancer therapies now target the cancer more precisely using large molecules such as antibodies. Antibodies are an important, naturally occurring part of the immune system, large molecules that can specifically bind to the cell surface of an 'intruder' (e.g. a virus) and in this way eliminate it. However, since antibodies are often not curative, they need to be combined with chemotherapeutic agents.

Though many attempts have been made to develop effective methods for importing biologically active molecules into cells, both in vivo and in vitro, none has proved to be entirely satisfactory. Optimizing the association of the drug with its intracellular target, while minimizing intercellular redistribution of the drug, e.g., to neighboring cells, is often difficult or inefficient.

Extracellular targeted carrier-drug conjugates (EDCs) seek to overcome these limitations of both nonspecific cytotoxic drugs and specific CTBM. EDCs are composed of three key elements: an CTBM (antibody, small molecule, antibody fragment, antibody mimic, etc. (see below), designed to selectively target the tumor of interest), a toxic payload (a cytotoxic compound that will kill the tumor) and a linker (used to conjugate the toxic payload to the antibody) and are an extensively investigated research field for the development of novel selective cancer therapies.[1-10] Within such extracellular targeted therapies a highly cytotoxic drug is attached via an intracellularly cleavable linker to a carrier molecule with a high affinity for a specific biomarker[11-13] that is overexpressed on the surface of cancer cells. Thus the drug can selectively be delivered to those cells. After uptake via endocytosis, the linker is enzymatically cleaved and the cytotoxic payload is released and kills the cancer cell. Since the exposition of healthy cells to the cytotoxin is significantly reduced, very potent cytotoxins, by far too potent for any systemic, conventional application, can be utilized in such approaches, the minimal-effective dose (MED) is significantly reduced and the maximal-tolerated dose (MTD) is increased, leading to a broadened therapeutic window. Carrier molecules, designed to selectively target the tumor of interest, which can be utilized for such EDCs, can be antibodies,[1,3,9] probodies, antibody fragments, peptides with high affinity for receptors on cancer cell surfaces such as octreotide,[14-17]gonadotropins [18-22] or anticalins[23-25] and vitamins such as folic acid,[26-29] vitamin B9, essential for growth of cancer cell and taken up by specific high-affinity receptor. For instance, ADCs (Antibody Drug Conjugates) are composed of 3 key elements: an antibody (designed to selectively target the tumor of interest), a toxic payload (a cytotoxic compound that will kill the tumor) and the linker (used to conjugate the toxic payload to the antibody). The benefits of such constructs are the significant improvement of the therapeutic window: increased half-life and specificity of the toxic payload, reducing off-target effects and toxicity. The use of ADCs has been extensively investigated for the last three decades (Moolten et al. (1972), J Natl. Cancer Inst. 49(4): 1057-62, Chari et al., (2014) Angew. Chem. Int. Ed., 53:3796-3827; Jackson, (2016) Org. Process Res. Dev. 2016, 20:852-866). Two ADCs are already approved and commercialized: Kadcyla® (from Roche) and Adcetris® (from Seattle Genetics) are approved for the treatment of breast cancer and systemic anaplastic large-cell lymphoma, respectively. Several further ADCs are in clinical trials for the treatment of different cancer types.[9] Furthermore, several peptide conjugates are under preclinical and clinical evaluation for their use with in extracellular targeted therapies. Remarkably, the cytotoxic payloads utilized in the far majority of these approaches are all derived from natural products; which can be classified according to their mode of action in two groups: 1) antimitotic, microtubule binding agents, 2) agents causing DNA damage by alkylation or intercalation.

Thus, payloads (or toxins) used in ADCs include bacterial toxins such as diphtheria toxin (Levy et al. (1975) Cancer Res. 35(5):1182-6), plant toxins such as ricin, small molecule toxins such as maytansinoids (EP 1391213; Liu et al., (1996) Proc. Natl. Acad. Sci. USA 93:8618-8623), calicheamicin (Lode et al. (1998) Cancer Res. 58:2925-2928; Upeslacis et al., (1993) Cancer Res. 53, 3336-3342), auristatins (Sanderson et al. (2005) Clin. Cancer Res. 11:843-52), SN-38 or irinotecan analogs (Govidan et al. (2013) Mol. Cancer. Ther. 12:968-78, US 2014/0227180A1, Goldenberg et al. (2007), Clin. Cancer Res. 13, 5556s-5563s), pyrrolobenzodiazepins (US 2011/0256157A1, Kung Sutherland et al. Blood (2013) 122:1455-1463, Chari et al., (2009) Mol.

Cancer Ther. 8, B126.) or cryptophycines (WO 2011/001052A1, Verma et al. (2015) Bioorg. Med. Chem. Lett. 25:864-8, US 2012/0225089). Currently, more than 60% of all ADCs currently in clinical evaluation carry toxins related to monomethyl Auristatin E and F (MMAE, MMAF tubulin inhibitor). MMAE could be considered by the skilled person as the standard payload to compare with.

Conjugation of drugs to CTBM, either directly or via linkers, involves a consideration of a variety of factors, including the identity and location of the chemical group for conjugation of the drug, the mechanism of drug release, the structural elements providing drug release, and the structural modification to the released free drug. In addition, if the drug has to be released after antibody internalization, the mechanism of drug release must be consonant with the intracellular trafficking of the conjugate. Therefore, while a number of different drug classes have been tried as payloads, only a few drug classes have proved efficacious as antibody drug conjugates, because of limited effectiveness, selectivity and/or stability (Tolcher et al. (2000) J Clin. Oncol. 18:4000, Laguzza et al (1989) J. Med. Chem. 32:548-555, Uadia P, (1984). Cancer Res. 44:4263-4266). It turns out that compounds, in order to successfully be eligible as conjugates, should present a level of cytotoxicity below the nanomolar $IC_{50}$ level. (Casi and Neri, (2012) J. Control Release. 20; 161(2):422-8.; Wu and Senter (2005) Nat. Biotechnol. 23(9):1137-46). Ideal payloads should escape from the multi-drug resistance mechanism (MDR). In the case of MMAE, which is subject to MDR, some tumors can develop a mechanism of resistance (Chen et al., 2015). Thus, the few payloads accessible are not effective against the large spectrum of cancer indications.

Thus, even though, the development of the first EDCs was a milestone in cancer therapy, cancer is an extremely complex disease with a multitude of different origins as well as forms of occurrence in various human tissues—genetically, no two tumors are the same. This high heterogeneity of tumors often causes cancer relapse after putatively successful chemotherapeutic treatment.[13,30-32] Furthermore, tumors not responding to established chemotherapeutics and multi-drug resistant tumors are still a big problem in cancer therapy.[33,34] As the far majority of current EDCs rely only on tubulin binding as cytotoxic mode of action, there is a need to investigate cytotoxic payloads with new mode of actions for the development of EDCs to address specific cancer phenotypes which cannot be sufficiently treated yet.

Ratjadone A is the most abundant member of the small class of polyketidic natural products, the ratjadones (see FIG. 1), which have been isolated from cultures of the myxobacterium *Sorangium cellulosum*.[35-37] The ratjadones have been found to be highly potent anti-proliferating agents showing sub-nanomolar $IC_{50}$ values for the growth inhibition of several cancer cell lines.[37]

The anti-proliferating activity of the ratjadones is based on the covalent inhibition of Crm1,[37-39] an evolutionary highly conserved protein, which is responsible for the nuclear export of several proteins as well as mRNA into the cytoplasm.

Considering that it has been demonstrated that the relation between nuclear import and export is significantly shifted towards higher export in cancer cell due to their high metabolism,[40] and since the inactivation of Crm1 leads to major inhibition of central cellular functions,[41] sensitization of the cancer cell to other drugs[42,43] and finally to cell death, rendering the ratjadones highly interesting for the development of targeted anti-cancer drugs with a so far under-investigated mode of action.

Several derivatives of ratjadone A have been synthesized by Kalesse and co-workers through a de novo total synthesis [44,45] and have been claimed to be potent cell growth inhibitors. However, all derivatives of Kalesse and co-workers miss appropriate functionalities for selective conjugation to carrier molecules and can therefore not be utilized for the development and construction of EDCs, which may explain why all patent applications filed by this group[46-48] have apparently been abandoned or withdrawn in the meantime.

In addition, several derivatives of leptomycin B, a structurally related natural product (see FIG. 1), inhibiting Crm1 by the same mechanism,[39] have been synthesized and patented by researchers of Sanofi-Aventis.[49-53] These derivatives have been used as cytotoxic payload in antibody-leptomycin conjugates.[51-53] Additionally, several derivatives of leptomycin B were synthesized and patented by researchers of Kosan Biosciences.[54] these derivatives have been used as cytotoxic payloads in antibody-leptomycin conjugates.[55] However, the corresponding ADCs showed several systemic late toxicities. Since Leptomycin B is structurally closely related to ratjadone A, one of ordinary skill in the art might expect such systemic toxicity for ratjadone derivatives as well.

As a conclusion, there is still a clinical demand for new payloads with differentiated mode of actions, improved selectivity and toxicity profile, and appropriate functionalities for selective conjugation to carrier molecules. These and other matters are addressed by the present invention.

SUMMARY OF THE INVENTION

As a result of intensive studies for solving the problem described above, the present inventors have found derivatives of ratjadone A with improved efficacy against cancer and a structure allowing proper efficient conjugation. This approach has so far neither been taught nor suggested by the prior art.

Thus, in first aspect, the present invention relates to a compound according to Formula I

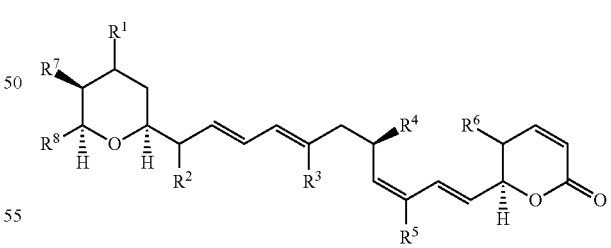

wherein:

one of $R^1$ and $R^2$ is $NHR^9$ and one is selected from H and OH;

$R^3$, $R^4$ and $R^5$ are independently of one another selected from the group that consists of H, $CH_3$ and $C_2H_5$;

$R^6$ is $CH_3$ or $C_2H_5$;

$R^7$ and $R^8$ are independently of one another selected from the group that consists of H, $CH_3$, $C_2H_5$, n-$C_3H_7$,

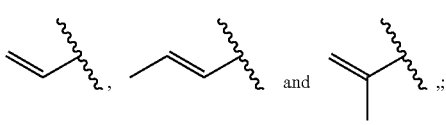

and

R⁹ is H.

In a second aspect, the present invention relates to a compound according to Formula I; wherein:

$R^1$ to $R^8$ are as defined above; and $R^9$ is L-RM*, wherein L is a linker, particularly a self-immolative linker, RM* is selected from RM and RM', wherein RM is a reactive moiety being able to form a covalent bond with a targeting moiety, particularly a target-binding antibody or functional fragment thereof, and wherein RM' is a moiety RM carrying a protecting group.

In a third aspect, the present invention relates to a compound according to Formula I, wherein $R^1$ to $R^8$ are as defined above; and $R^9$ is L-TM, wherein L is a linker, particularly a self-immolative linker, and TM is a targeting moiety.

In a fourth aspect, the present invention relates to a method of synthesizing a toxic compound-linker-reactive moiety compound of the present invention, comprising the step of reacting a free toxic compound of the present invention via the amino group $R^1$ or $R^2$ with a compound X-L'-RM*, wherein X is a group that is (i) able to react with an amine, or (ii) can be replaced by an amine; and L' is a linker;

wherein the reaction of said amino group with the moiety X-L' results in the formation of the moiety —NH-L-RM*.

In a fifth aspect, the present invention relates to a method of synthesizing a toxic compound-linker-targeting moiety compound of the present invention, comprising the step of reacting a toxic compound-linker-reactive moiety compound of the present invention with a targeting moiety.

In a sixth aspect, the present invention relates to a pharmaceutical composition comprising the toxic compound-linker-targeting moiety compound of the present invention or a toxic compound-linker-targeting moiety compound synthesized according to the present invention.

In a seventh aspect, the present invention relates to a pharmaceutical composition of the present invention for use in the treatment of cancer.

In an eighth aspect, the present invention relates to a method for the treatment of cancer comprising the step of administering a toxic compound-linker-targeting moiety compound of the present invention or the pharmaceutical composition of the present invention to a patient in need of such treatment.

BRIEF DESCRIPTION OF THE DRAWINGS

FIG. 1 shows the structure of ratjadones (Ratjadone A: $R^1$=OH, $R^2$=CH₃, $R^3$=CH₃; Ratjadone B: $R^1$=OH, $R^2$=H, $R^3$=CH₃; Ratjadone C: $R^1$=OH, $R^2$=H, $R^3$=CH₂—CH₃; Ratjadone D: $R^1$=H, $R^2$=H, $R^3$=CH₂—CH₃) and other CRM1 inhibitors of same structure type (Callystatine, Leptomycin B, Anguinomycin A).

FIG. 3 shows the determination of the absolute stereo configuration at C16 for the 16-amino-ratjadones via the Mosher amide 18.

DETAILED DESCRIPTION OF THE INVENTION

Figure 2:
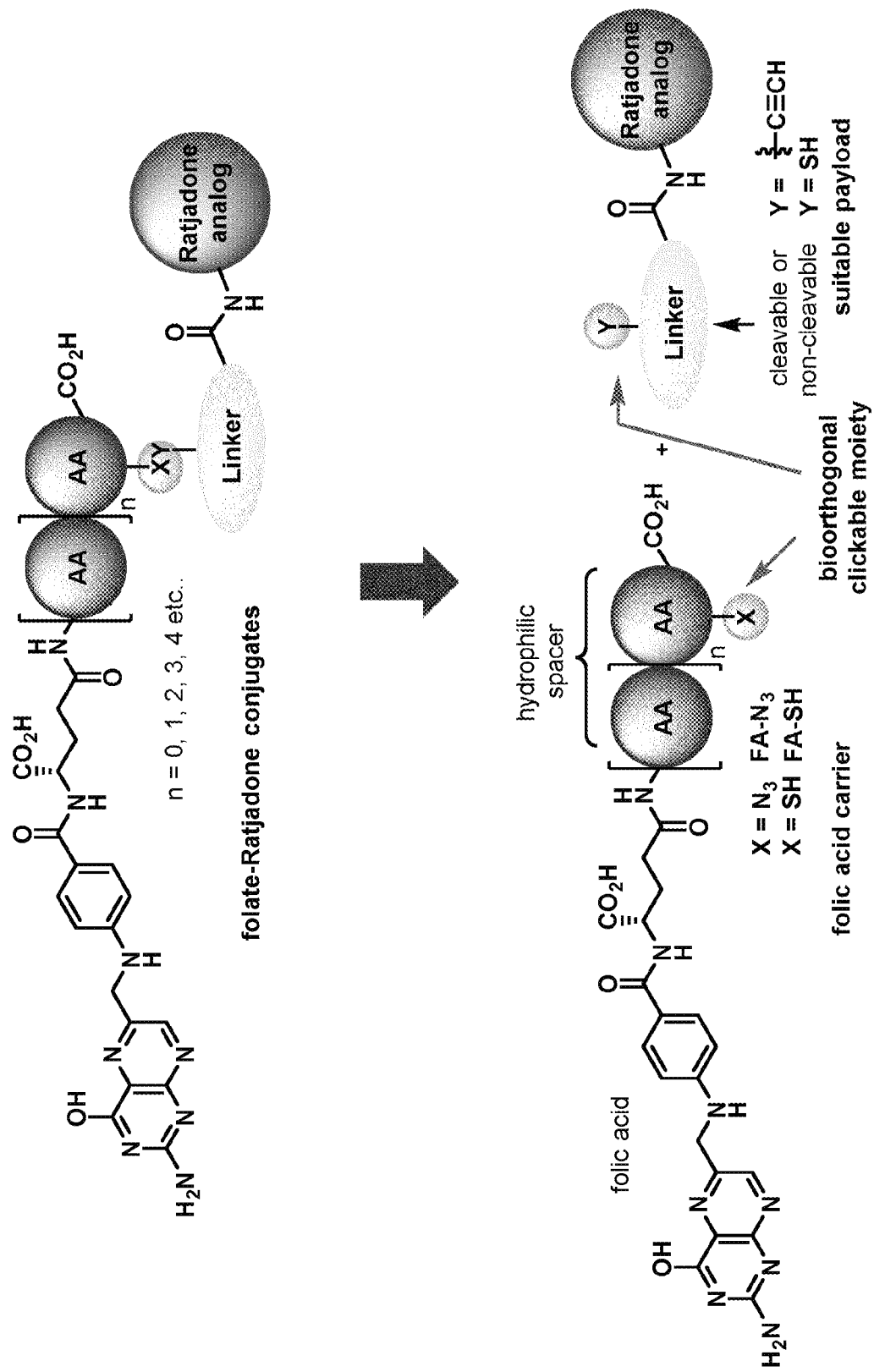
FIG. 2 shows the design of folate-ratjadone conjugates.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Particularly, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law.

The present invention will now be further described. In the following passages different aspects of the invention are defined in more detail. Each aspect so defined may be combined with any other aspect or aspects unless clearly indicated to the contrary. In particular, any feature indicated as being of particular relevance or advantageous may be combined with any other feature or features indicated as being of particular relevance or advantageous.

The present invention is based on a combination of different advantageous elements and features and in particular on the unexpected observation that amino-substituted derivatives of ratjadone are particularly stable, while simultaneously being highly toxic in target cells.

Thus, in first aspect, the present invention relates to a compound according to Formula I

I 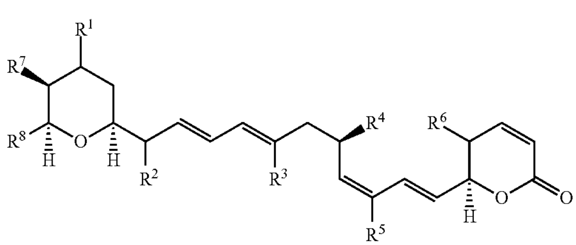 wherein:

one of $R^1$ and $R^2$ is $NHR^9$ and one is selected from H and OH;

$R^3$, $R^4$ and $R^5$ are independently of one another selected from the group that consists of H, $CH_3$ and $C_2H_5$;

$R^6$ is $CH_3$ or $C_2H_5$;

$R^7$ and $R^8$ are independently of one another selected from the group that consists of H, $CH_3$, $C_2H_5$, n-$C_3H_7$, 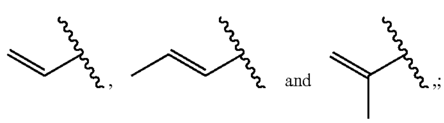 and $R^9$ is H.

We developed a procedure for the semi-synthesis of novel amino-substituted ratjadone derivatives, particularly ratjadone A derivatives, for example starting from ratjadone A produced by a fermentation procedure or by chemical synthesis[45; 72], ratjadone B or C [37; 72], or from derivatives thereof synthesized according to published procedures [44 to 48], and demonstrated their use as cytotoxic payload within extracellular-targeted drug conjugates.

In a second aspect, the present invention relates to a compound according to Formula I; wherein:

$R^1$ to $R^8$ are as defined above; and $R^9$ is L-RM*, wherein L is a linker, particularly a self-immolative linker, RM* is selected from RM and RM', wherein RM is a reactive moiety being able to form a covalent bond with a targeting moiety, particularly a target-binding antibody or functional fragment thereof, and wherein RM' is a moiety RM carrying a protecting group.

The synthesized derivatives of ratjadone present different RM functionalities such as ketones, amino groups, terminal alkynes, cyclooctyne moieties or reactive disulfides, which allow bio-orthogonal or orthogonal coupling to biologically active carrier molecules. Therefore, these compounds enable the development and construction of extracellular-targeted drug conjugates using ratjadone derivatives as cytotoxic payloads with new mode of action for the targeted therapy of cancer.

In the context of the present invention, the term "protecting group" refers to a group that is attached to a functional group present in RM in order to block said functional group from reacting with other reactants used to synthesize and/or to further functionalize compounds according to Formula I. One of ordinary skill in the art is well familiar with the different protecting groups that are available in the art and that can be attached to the corresponding functional group when needed to protect that functional group, and that can be cleaved off subsequently, when such protection is no longer needed. In particular embodiments, where the functional group present in RM is an amino group, that amino group may be N-protected by using an N-acylating reagent. Thus, in such embodiments, RM' is an amino group-containing moiety RM carrying an N-acyl group as protecting group. In particular other embodiments, the N-protection uses an N-alkylating reagent. Thus, in such embodiments, RM' is an amino group-containing moiety RM carrying an N-alkyl group as protecting group.

In a third aspect, the present invention relates to a compound according to Formula I, wherein $R^1$ to $R^8$ are as defined above; and $R^9$ is L-TM, wherein L is a linker, particularly a self-immolative linker, and TM is a targeting moiety.

We demonstrated this ability to develop and construct extracellular-targeted drug conjugates by the synthesis of folate-ratjadone conjugates and conjugates of ratjadone with novel derivatives of the carrier peptide-hormones gonadoliberin and goserellin (see FIG. 2). In similar manner, these derivatives can be used with in antibody-, probody- or nanobody-ratjadone conjugates.

In particular embodiments of these first three aspects, one of $R^1$ and $R^2$ is $NHR^9$ and one is OH.

In particular embodiments, $R^1$ is OH and $R^2$ is $NHR^9$.

In particular such embodiments, $R^2$ is 16R—$NHR^9$.

In other such embodiments, $R^2$ is 16S—$NHR^9$.

In particular other embodiments, $R^1$ is $NHR^9$ and $R^2$ is OH.

The terms "targeting moiety" or "target-binding moiety", as used herein, refer to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40 000 Da (40 kDa) or more.

As used herein, a first compound (e.g. an antibody) is considered to "specifically bind" to a second compound (e.g. an antigen, such as a target protein), if it has a dissociation constant KD to said second compound of 100 μM or less, particularly 50 μM or less, particularly 30 μM or less, particularly 20 μM or less, particularly 10 μM or less, particularly 5 μM or less, more particularly 1 μM or less, more particularly 900 nM or less, more particularly 800 nM or less, more particularly 700 nM or less, more particularly 600 nM or less, more particularly 500 nM or less, more particularly 400 nM or less, more particularly 300 nM or less, more particularly 200 nM or less, even more particularly 100 nM or less, even more particularly 90 nM or less, even more particularly 80 nM or less, even more particularly 70 nM or less, even more particularly 60 nM or less, even more particularly 50 nM or less, even more particularly 40 nM or less, even more particularly 30 nM or less, even more particularly 20 nM or less, and even more particularly 10 nM or less.

In the context of the present application the terms "target molecule" and "target epitope", respectively, refers to an antigen and an epitope of an antigen, respectively, that is specifically bound by a target-binding moiety. Particularly the target molecule is a tumor-associated antigen, in particular an antigen or an epitope which is present on the surface of one or more tumor cell types in an increased concentration and/or in a different steric configuration as compared to the surface of non-tumor cells. Particularly, said antigen or epitope is present on the surface of one or more tumor cell types, but not on the surface of non-tumor cells.

The term "antibody or antigen binding fragment thereof", as used herein, refers to immunoglobulin molecules and immunologically active portions of immunoglobulin molecules, i.e. molecules that contain an antigen-binding site that immunospecifically binds an antigen. Thus, the term "antigen-binding fragments thereof" refers to a fragment of an antibody comprising at least a functional antigen-binding domain. Also comprised are immunoglobulin-like proteins that are selected through techniques including, for example, phage display to specifically bind to a target molecule. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')2 fragments, fragments produced by a Fab expression library, diabodies or tetrabodies (Holliger P. et al., Proc Natl Acad Sci USA. 90 (1993) 6444-8), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and F(ab')2, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Particularly, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Particularly, the scaffold protein is a small globular protein. Antibody-like proteins include without limitation affibodies, anticalins, and designed ankyrin repeat proteins (for review see: Binz et al. (2005) Nat Biotechnol, 1257-68). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, (2000) J Biotechnol. 74:5-13). The nucleic acid aptamer may be a DNA or RNA molecule. The aptamers may contain modifications, e.g. modified nucleotides such as 2'-fluorine-substituted pyrimidines.

A "linker" in the context of the present invention refers to a structure that is connecting two components, each being attached to one end of the linker. In the case of the linker being a bond, a direct linkage of the toxic compound to the antibody may decrease the ability of the toxic compound to interact with its molecular target inside the cell. In particular embodiments, the linker increases the distance between two components and alleviates steric interference between these components, such as in the present case between the antibody and the toxic compound. In particular embodiments, the linker has a continuous chain of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the toxic compound moiety and the antibody, wherein one side of the linker backbone has been reacted with the toxic compound and, the other side is available for reaction, or has been reacted, with an antibody. In the context of the present invention, a linker particularly is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the toxic compound and the antibody. To that end the linker to be will carry two groups, particularly at a proximal and distal end, which can (i) form a covalent bond to a group present in one of the components to be linked, particularly an activated group on an toxic compound or the target binding-peptide or (ii) which is or can be activated to form a covalent bond with a group on an toxic compound. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($-CH_2-$), ethylene ($-CH_2-CH_2-$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($-CH=CH-$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" rr electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" rr electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein.

When a substituent is a keto (or oxo, i.e. $=O$) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio) ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl (thio)ureido, cycloalkyl(thio)ureido, aryloxy, aralkoxy, or $-O(CH_2)_n-OH$, $-O(CH_2)_n-NH_2$, $-O(CH_2)_nCOOH$, $-(CH_2)_nCOOH$, $-C(O)O(CH_2)_nR$, $-(CH_2)_nN(H)C(O)$ OR, or $-N(R)S(O)_2R$ wherein n is an integer selected from 1 to 4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the C atoms in the linear chain are independently part of optionally substituted methylene groups (—CH$_2$—). In particular such embodiments, the optional substituents are independently selected from halogen and C$_{1-6}$-alkyl, particularly methyl.

In particular embodiments, the linker L is a stable linker.

In the context of the present invention, the term "stable linker" refers to a linker that is stable (i) in the presence of enzymes, and (ii) in an intracellular reducing environment.

In particular embodiments, the stable linker does not contain (i) an enzyme-cleavable substructure, and/or (ii) a disulfide group. In particular such embodiments, the linker has a length of up to 12 atoms, particularly from 2 to 10, more particularly from 4 to 9, and most particularly from 6 to 8 atoms.

In certain embodiments the linker is a cleavable linker.

In the context of the present invention, the term "cleavable linker" refers to a linker that is (i) cleavable by chemical cleavage, or (ii) a reducible linker.

In certain such embodiments, the linker is cleavable by reduction. In the context of the present invention, the term "cleavable by reduction" refers to a linker that can be cleaved in the intracellular reducing environment, particularly a linker that contains a disulfide groups, resulting in the intracellular release of the toxin cargo conjugated to the target-binding moiety after internalization by the intracellular reducing environment (see Shen et al., (1985) J. Biol. Chem. 260:10905-10908).

In certain such embodiments, the linker comprises a disulfide bond, particularly a —CMe$_2$-S—S—CMe$_2$— moiety. In certain other embodiments, the linker is attached to the thiol group of the targeting moiety via a disulfide bond.

In certain other such embodiments, the linker is cleavable by chemical cleavage, particularly by hydrolysis or proteolysis, particularly wherein such chemical cleavage is catalyzed by an enzyme.

In the context of the present invention, the term "chemical cleavage is catalyzed by an enzyme" refers to a linker that can be cleaved by an enzyme, particularly by a lysosomal peptidase, such as Cathepsin B, resulting in the intracellular release of the toxin cargo conjugated to the targeting antibody after internalization (see Dubowchik et al., (2002) Bioconjug Chem. 13:855-69). In particular embodiments, the cleavable linker comprises a dipeptide selected from: Phe-Lys, Val-Lys, Phe-Ala, Val-Ala, Phe-Cit and Val-Cit, in particular Val-Cit.

In certain such embodiments, the linker comprises a hydrazone group. In particular such embodiments, cleavage occurs by hydrolysis in the lysosome.

In certain embodiments, the linker is a self-immolative linker.

In the context of the present invention, the term "self-immolative linker" refers to a linker that comprises a cleavable bond, wherein after cleavage a fragmentation takes place that removes that part of the linker that is still attached to the toxin after said cleavage. In certain embodiments, the linker comprises a group -(cleavable bond)-X-phenyl-CH$_2$—O—C(=O)—, wherein the carbonyl group is attached to the amino group attached to the ratjadone moiety in the compounds of the present invention, wherein after cleavage of the cleavable bond, the compound of the present invention with a free amino group —NR$^6$H=—NH$_2$ is released. In particular such embodiments, the self-immolative linker comprises a p-aminobenzyl (PAB) spacer between a cleavable dipeptide and the toxic payload.

In particular such embodiments, the cleavable linker comprises a structure L$^1$-L*-L$^2$, wherein L* is p-aminobenzyl dipeptide moiety, L$^1$ is a part of the linker that connects L* to the toxic payload, in particular, wherein L$^1$ is connected to L* via a —NH— group, and wherein L$^2$ is a part of the linker that connects L* to the target-binding moiety, in particular wherein L$^2$ is connected to L* via a —(CH$_2$)$_m$— moiety, with m being an integer selected from 1 to 8, in particular from 1 to 5, or via a —(CH$_2$ CH$_2$O)$_n$— moiety, with n being an integer selected from 1 to 3, in particular from 1 to 2. For example, in the case of the cleavable linker comprising the dipeptide Val-Ala, the structure of L$^1$-L*-L$^2$ is as follows:

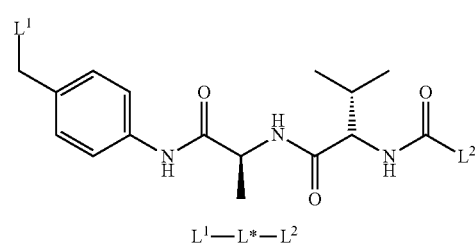

L$^1$—L*—L$^2$

In particular other such embodiments, L* comprises the dipeptide Val-Lys and has the following structure:

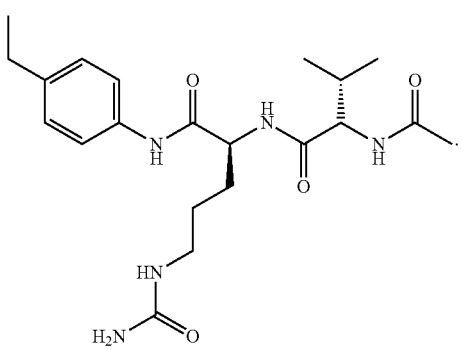

In particular embodiments, the linker $L^1$ is a linear chain of between 1 and 4 atoms independently selected from C, O, N and S, particularly between 1 and 3 atoms, more particularly between 1 and 2 atoms, and even more just 1 atom. In particular embodiments, at least 50% of the atoms in the linear chain are C atoms. In particular embodiments, the atoms in the linear chain are linked by single bonds.

In a particular embodiment, $L^1$ is the —NH— group that is part of substituent $R^1$ or $R^2$ of the toxic payload according to the present invention.

In a fourth aspect, the present invention relates to a method of synthesizing a toxic compound-linker-reactive moiety compound of the present invention, comprising the step of reacting a compound according to the present invention via the amino group $R^1$ or $R^2$ with a compound X-L'-RM*, wherein X is a group that is (i) able to react with an amine, or (ii) can be replaced by an amine; and L' is a linker;

wherein the reaction of said amino group with the moiety X-L' results in the formation of the moiety —NH-L-RM*.

In a particular embodiment, wherein RM* is RM', the method further comprises the step of deprotecting the moiety RM' to result in RM.

In a fifth aspect, the present invention relates to a method of synthesizing a toxic compound-linker-targeting moiety compound of the present invention, comprising the step of reacting a toxic compound-linker-reactive moiety compound of the present invention with a targeting moiety.

In a particular embodiment, wherein RM* in Formula I is RM', the method further comprises the step of first deprotecting the moiety RM' to result in RM.

Conjugation to the targeting moiety may be achieved via coupling of the toxin-L-RM construct to free amino groups present in the targeting moiety. In such case, the group RM may be selected from an activated carboxylic acid derivative, such as an N-hydroxy succinimide ester; or an activated carbonic acid derivative, such as an isothiocyanate.

Conjugation to the targeting moiety may further be achieved via coupling of the toxin-L-RM construct to free thiol groups present in the targeting moiety. In such case, the group RM may be selected from a haloacetyl group; an RM group comprising an acceptor-substituted alkene (Michael system), particularly a maleimide group or propenoyl group (see Badescu et al., (2014) Bioconjugate Chem. 25:460-469); a maleimide group substituted in 3-position or disubstituted in 3,4-positions with a leaving group X, particularly wherein X is selected from Cl, Br, and aryl-S—, particularly Ph-S—.

In certain such embodiments, the thiol group is part of a single, uncoupled cysteine residue present in the wildtype targeting moiety. In certain other such embodiments, the thiol group is part of a single, uncoupled cysteine residue that has been generated from a wildtype targeting moiety, particularly by recombinant genetic engineering, for example by insertion into the wildtype sequence, by removing a second cysteine that is forming a disulfide bridge with the first cysteine residue in the wildtype targeting moiety, or by replacing a non-cysteine residue. In certain other such embodiments, the thiol group is generated by reduction of a disulfide linkage between two cysteines present in the wildtype targeting moiety.

Conjugation to the targeting moiety may further be achieved via coupling of the toxin-L-RM construct to two free thiol groups present in the targeting moiety. In such case, the group RM may be a maleimide group disubstituted in 3,4-positions with leaving groups X, particularly wherein X is selected from Cl, Br, and aryl-S—, particularly Ph-S—.

In certain such embodiments, the two thiol groups are each part of a single, uncoupled cysteine residue present in the wildtype targeting moiety. In certain other such embodiments, the thiol groups are part of two single, uncoupled cysteine residues that have been generated from a wildtype targeting moiety, particularly by recombinant genetic engineering, for example by insertion into the wildtype sequence, by removing a second cysteine that is forming a disulfide bridge with the first cysteine residue in the wildtype targeting moiety, or by replacing a non-cysteine residue. In particular embodiments, the two thiol groups are generated by reduction of a disulfide linkage between two cysteines present in the wildtype targeting moiety.

By reaction of such two thiol groups with a disubstituted maleimide, the thiol groups are bridged, thus mimicking the originally present disulfide bridge.

In certain other embodiments, a free thiol group may be generated by thiolation of free amino groups present in the targeting moiety, particularly by reaction of such free amino groups with a thiolation reagent selected from 2-iminothiolane (see Still et al., (1984) Can. J. Org. Chem. 62:586) and an activated acylthioacetic acid derivative (X—C(═O)—$CH_2$—SAcyl), such as an N-hydroxy succinimide ester of acetylthioacetic acid.

Conjugation to the targeting moiety may further be achieved by coupling to unnatural amino acids introduced by genetic engineering, for example by introducing p-acetyl phenylalanine and subsequent oxime ligation (see Kazane et al., (2012) Proc. Natl. Acad. Sci. U.S.A, 109:3731-3736).

Conjugation to the targeting moiety may further be achieved by coupling of cyclic diazodicarboxamides to the phenyl ring of tyrosine residues in the targeting moiety (see Ban et al., (2010) J Am. Chem. Soc. 13:1523-5).

Conjugation to the targeting moiety may be achieved via 1,3-dipolar cycloaddition (click chemistry).

In certain such embodiment the targeting moiety comprises a double or triple bond and the toxin-L-RM construct comprises a 1,3-dipole, particularly an azide group. In certain such embodiments, the targeting moiety is first reacted with dibenzocyclooctyne-N-hydroxysuccinimide ester or azadibenzocyclooctyne-N-hydroxysuccinimide ester (see, for example, Zhou et al., (2013) J Am Chem Soc. 135:12994-7).

In certain other such embodiment the targeting moiety comprises a 1,3-dipole, particularly an azide group and the toxin-L-RM construct comprises a double or triple bond. In certain such embodiments, the targeting moiety is a glycosylated antibody that is first coupled to an azide-containing molecule by an enzyme-catalyzed reaction (tradename SiteClick; see Zeglis et al., (2013) Bioconjug Chem. 24:1057-67). In certain other embodiments an azido group is incorporated via the unnatural amino acid p-azido-phenylalanine (see Kazane et al., (2012) Proc. Natl. Acad. Sci. U.S.A, 109:3731-3736).

In a sixth aspect, the present invention relates to a pharmaceutical composition comprising the toxic compound-linker-targeting moiety compound of the present invention or a toxic compound-linker-targeting moiety compound synthesized according to the present invention.

In a seventh aspect, the present invention relates to a pharmaceutical composition of the present invention for use in the treatment of cancer.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

And further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxic compound conjugates of the invention to proteins or polymers or they can also be added with the aim to reduce the adsorption of the target-binding moiety toxic compound conjugates of the invention to materials like injection instruments or packaging-materials, for example, plastic or glass.

The toxic compounds (payloads) of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the conjugates of the present invention are introduced in finely dispersed, dispersed and suspended form, respectively, or as a suspension of crystals in the medicament or based on the "single unit principle" if the conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are particularly aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatin, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatin can be used.

In an eighth aspect, the present invention relates to a method for the treatment of cancer comprising the step of administering a toxic compound-linker-targeting moiety compound of the present invention or the pharmaceutical composition of the present invention to a patient in need of such treatment.

EXAMPLES

In order to illustrate the invention, the following examples are included. However, it is to be understood that these examples do not limit the invention and are only meant to suggest a method of practicing the invention.

Example 1: Generation and Synthesis of the Toxin Unit ICQO-1

Experimental Details
General Material and Equipment

Unless otherwise noted, all reagents were purchased from commercial suppliers and used without further purification. All solvents used for workup and purification were of HPLC grade. Moisture sensitive reactions were performed under argon atmosphere in dried glass ware. Reactions were monitored by TLC, LCMS or NMR.

Flash chromatography was done either manually using appropriate glass columns filled with silicagel (Merck, Silicagel 60, 1.15111.1000, 15-40 µm) or using the Reveleris® X2 flash chromatography system and prepacked cartridges (Reveleris® Flash Cartridges Silica 40 µm) from the company Buchi.

Preparative reversed phase high pressure liquid chromatography (prep. HPLC RP) was performed on a Phenomenex Gemini C18 RP-column OOG-4436-NO, 10 µm, 110 A, 250×10.00 mm (5 mL/min) or a Phenomenex Gemini C18 RP-column 00G-4435-PO-AX, 5 µm, 110 A, 250×21.20 mm (9 mL/min) or a Thermo Fisher Scientific BDS Hypersil C18 RP-column 28105-259370, 5 µm, 250×30 mm, (25 mL/min) or a Macherey-Nagel Nucleosil 100-7 VP C18 RP column715691-1116949, 250×40 mm (45 mL/min) using a Thermo Fisher Scientific Dionex Ultimate 3000 HPLC system. Eluents, gradients and additives are given in parentheses. Product containing fractions were combined diluted with dest. $H_2O$ (min. 1:1/solvent:$H_2O$), frozen and lyophilized.

Thin-layer chromatography (TLC) was performed on pre-coated glass plates (Merck TLC Silicagel 60 $F_{254}$, 1.15341.0001, 2.5×7.5 cm) and components were visualized by observation under UV light ($\lambda$=254 nm [$UV^{254}$] or $\lambda$=366 nm [$UV^{366}$]), treatment of developed plates in an iodine chamber or by treating the plates with TLC staining solutions (for preparation see list below) followed by heating. Eluent or eluent-mixtures used are reported in parentheses.

$KMnO_4$ staining solution [$KMnO_4$]: 1.5 g $KMnO_4$, 10 g $K_2CO_3$, and 1.25 mL 10% NaOH in 200 mL $H_2O$.

PMA staining solution [PMA]: 10 g phosphomolybdic acid in 100 mL abs. EtOH.

CAM staining solution [CAM]: 1 g Ce(IV)($SO_4$)$_2$, 2.5 g $(NH_4)_6Mo_7O_{24}$ in 100 mL 10% $H_2SO_4$ Anisaldehyde staining solution [AA]: 135 mL abs. EtOH, 5 mL conc. $H_2SO_4$, 1.5 mL HOAc and 3.7 mL p-anisaldehyde.

Ninhydrin staining solution [Ninhydrin]: 1.5 g ninhydrin in 100 mL abs. EtOH and 3.0 mL HOAc.

Vanillin staining solution [Van]: 15 g vanillin in 250 mL abs. EtOH and 2.5 mL conc. $H_2SO_4$.

Preparative thin-layer chromatography was performed on pre-coated glass plates (Merck TLC Silicagel 60 $F_{254}$, 1.05715.0001, 20×20 cm, max. 10-15 mg/plate and Analtech Uniplate Silica gel GF Z51305-9, 20×20 cm×2 mm, max 100-150 mg/plate). Eluent or eluent-mixtures used and number of developments are reported in parentheses. Compounds were visualized by observation under UV light ($\lambda$=254 or 366 nm). Compound containing silica gel fractions were scratched from the plate with a scalpel, crushed to small pieces and compounds were eluted by appropriate solvent mixtures.

NMR spectra were recorded on a Bruker Avance III or a Bruker Avance III HD with cryoprobe system. $^1$H NMR spectra were recorded at 500 MHz and 700 MHz. $^{13}$C NMR spectra were recorded at 126 MHz and 176 MHz. Chemical shifts are reported in ppm relative to solvent signal. Multiplicity is indicated as follows: s (singlet); bs (broad singlet); d (doublet); t (triplet); q (quartet); m (multiplet); dd (doublet of doublets), etc.

Optical rotation values were determined on a Perkin-Elmer 241 MC and calculated along Lambert-Beer's equation.

IR spectra were recorded on a Bruker ALPHA FT IR spectrometer with ATR-technique. Only the wave numbers of observed absorption peaks are given.

Low resolution mass spectrometry (LRMS) data were recorded using an Agilent 1100 HPLC system equipped with DAD detector and an API 150 EX quadrupole mass detector with electron spray ionization (ESI) (ACN—$H_2O$+0.05% TFA) or a Dionex Ultimate 3000 HPLC system equipped with a DAD detector and a Bruker amazon ion trap mass detector with electron spray ionization (ESI).

High resolution mass spectrometry (HRMS) data were recorded using a Dionex Ultimate 3000 HPLC system equipped with a DAD detector and a Bruker maXis HD QTOF mass detector with electron spray ionization (ESI).

Fermentation and Isolation of Ratjadone A

Isolation of Ratjadone A (1)—(R)-6-((1E,3Z,5R,7E,9E,11R)-11-hydroxy-11-((2S,4R,5S,6S)-4-hydroxy-5-methyl-6-((E)-prop-1-en-1-yl)tetrahydro-2H-pyran-2-yl)-3,5,7-trimethylundeca-1,3,7,9-tetraen-1-yl)-5,6-dihydro-2H-pyran-2-one

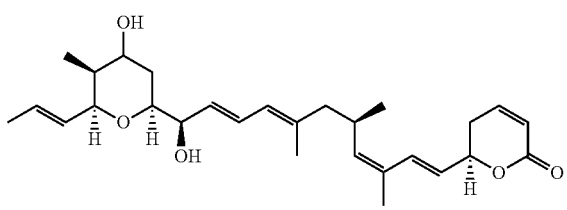

Chemical Formula: $C_{28}H_{40}O_5$
Molecular Weight: 456.62
Ratjadone A

Fermentation and isolation of Ratjadone A can be done according to the published procedures[35,36,56].

Ratjadone A (1): TCL ($CH_2Cl_2$:MeOH/95:5) $R_f$: 0.35 [$UV^{254}$, CAM], IR (ATR) [$cm^{-1}$]: 3417, 2962, 2921, 2871, 1715, 1653, 1625, 1451, 1438, 1380, 1344, 1295, 1245, 1149, 1121, 1056, 1011, 963, 916, 881, 814, 732, 660. $^1$H-NMR (500 MHz, CDCl$_3$) δ [ppm]: 6.88 (ddd, J=9.7, 4.6, 3.9 Hz, 1H), 6.70 (d, J=15.6 Hz, 1H), 6.45 (ddd, J=15.2, 10.9, 1.3 Hz, 1H), 6.09-5.99 (m, 1H), 5.76 (d, J=11.0 Hz, 1H), 5.72-5.69 (m, 1H), 5.68-5.66 (m, 1H), 5.54-5.47 (m, 1H), 5.46-5.37 (m, 1H), 5.21 (d, J=9.5 Hz, 1H), 5.03-4.93 (m, 1H), 4.44 (d, J=6.2 Hz, 1H), 4.32 (dd, J=6.0, 2.8 Hz, 1H), 3.98 (q, J=2.8 Hz, 1H), 3.85 (dt, J=12.2, 2.8 Hz, 1H), 2.79 (dq, J=9.6, 6.9 Hz, 1H), 2.50-2.39 (m, 2H), 1.98 (d, J=7.2 Hz, 2H), 1.86 (ddd, J=14.9, 12.3, 2.9 Hz, 1H), 1.77 (d, J=1.2 Hz, 3H), 1.70 (s, 6H), 1.70-1.68 (m, 2H), 1.65-1.58 (m, 2H), 1.43-1.34 (m, 1H), 0.90 (d, J=6.6 Hz, 3H), 0.89 (d, J=7.2 Hz, 3H). $^{13}$C-NMR (126 MHz, CDCl$_3$) δ [ppm]: 164.34, 144.95, 139.55, 137.70, 130.81, 130.37, 129.45, 128.61, 128.51, 127.10, 126.08, 125.52, 121.84, 78.84, 74.97, 74.91, 74.57, 70.42, 47.97, 39.82, 30.74, 30.26, 26.98, 21.20, 20.60, 18.16, 17.29, 11.34. LRMS (ESI-Quad) [m/z]: 479.2 [M+Na]$^+$, 421.3 [M−H$_2$O+H]$^+$, HRMS (ESI-IT) [m/z]: 479.277556, calculated 479.276795 for C$_{28}$H$_{40}$NaO$_5$ [M+Na]$^+$, err [ppm] 1.588.

Synthesis of the Compounds

Derivatization of Ratjadone a 1.1.1.1 Synthesis of 16-Amino-Ratjadones

Scheme 1: Oxidation of Ratjadone and Reductive Amination of 16-Oxo-Ratjadone.

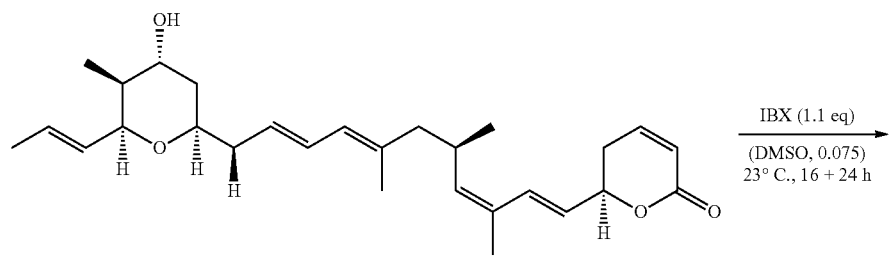

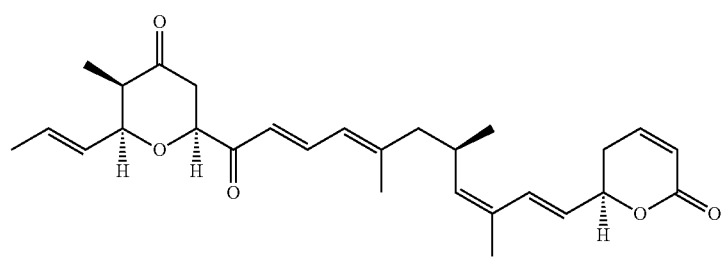

16,19-Dioxo Ratjadone 10
15%, brsm

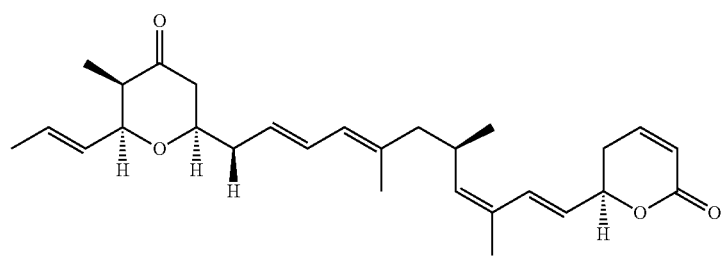

19-Oxo Ratjadone 9
8%, brsm

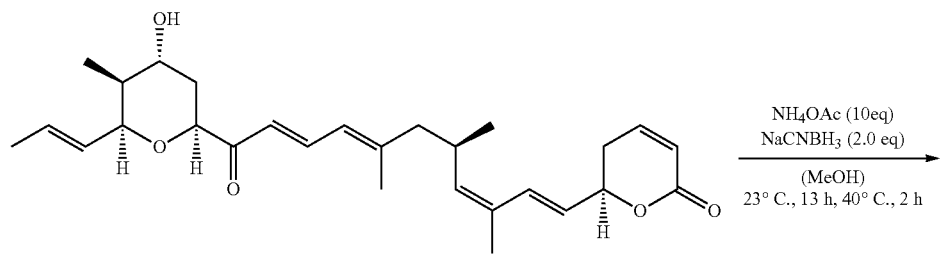

16-Oxo Ratjadone 8
75%, brsm

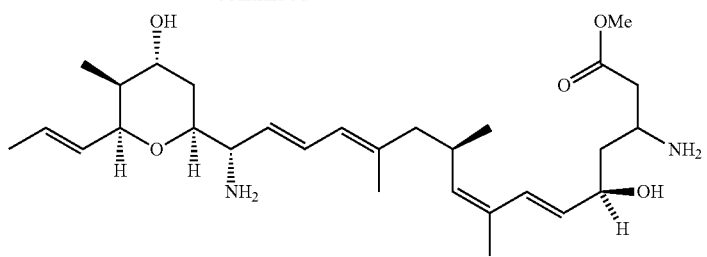
14
2%, brsm
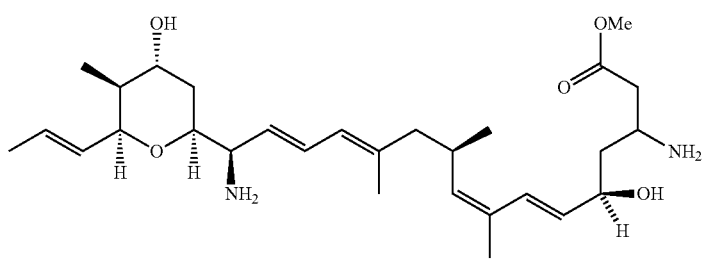
13
8%, brsm
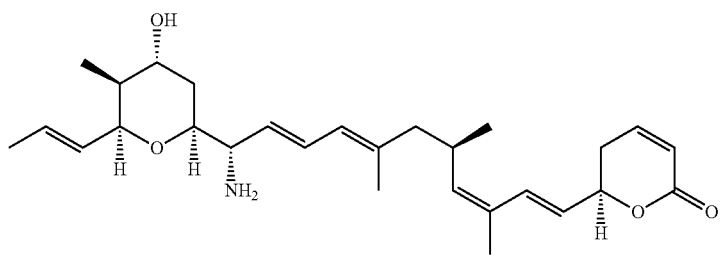
16S-Amino Ratjadone 12
21%, brsm
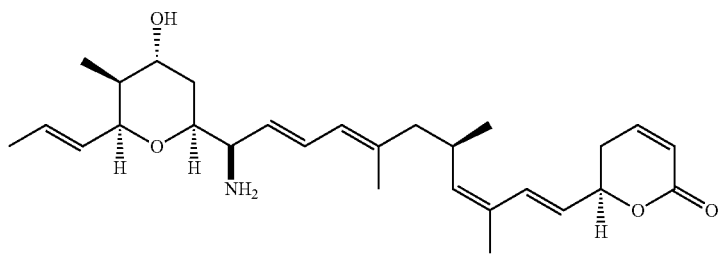
16R-Amino Ratjadone 11
34%, brsm Synthesis of 16-Oxo-Ratjadone (8)—(R)-6-((R,1E, 3Z,7E,9E)-11-((2S,4R,5S,6S)-4-hydroxy-5-methyl-6-((E)-prop-1-en-1-yl)tetrahydro-2H-pyran-2-yl)-3,5,7-trimethyl-11-oxoundeca-1,3,7,9-tetraen-1-yl)-5,6-dihydro-2H-pyran-2-one, 19-Oxo-Ratjadone (9)—(R)-6-((1E,3Z,5R,7E,9E,9E,11R)-11-hydroxy-3,5,7-trimethyl-11-((2S,5R,6S)-5-methyl-4-oxo-6-((E)-prop-1-en-1-yl)tetrahydro-2H-pyran-2-yl)undeca-1,3,7,9-tetraen-1-yl)-5,6-dihydro-2H-pyran-2-one and 16,19-Dioxo-Ratjadone (10)-(R)-6-((R,1E,3Z,7E,9E)-3,5,7-trimethyl-11-((2S,5R,6S)-5-methyl-4-oxo-6-((E)-prop-1-en-1-yl)tetrahydro-2H-pyran-2-yl)-11-oxoundeca-1,3,7,9-tetraen-1-yl)-5,6-dihydro-2H-pyran-2-one

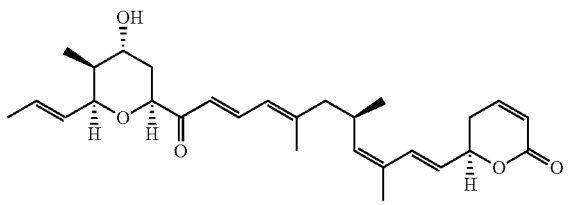

8

Chemical Formula: $C_{28}H_{38}O_5$
Molecular Weight: 454.61
16-Oxo Ratjadone

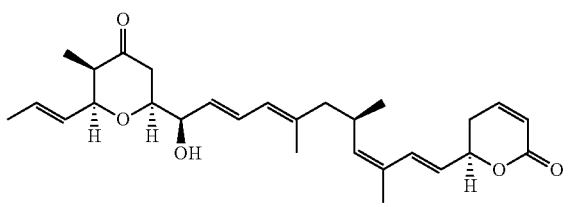

9

Chemical Formula: $C_{28}H_{38}O_5$
Molecular Weight: 454.61
19-Oxo Ratjadone

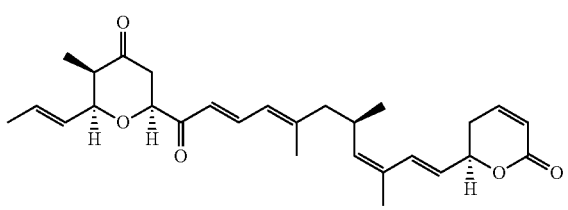

10

Chemical Formula: $C_{28}H_{36}O_5$
Molecular Weight: 452.59
16,19-Oxo Ratjadone A solution of 33.7 mg (0.1205 mmol, 1.1 eq) IBX[1] in 750 μL DMSO was added dropwise over a period of 16 h (Syringe Pump) at 23° C. to a stirred solution of 55 mg (0.1095 mmol, 1.0 eq) of Ratjadone A 1 dissolved in 750 μL DMSO. Afterwards the mixture was stirred for further 24 h at 23° C. The reaction was monitored by HPLC-MS. The mixture was diluted with $CH_2Cl_2$ (15 mL) and stirred for 30 min until IBA precipitates as white solid and could be filtered off using a cellulose filter. The filtrate was washed with $H_2O$ (3×15 mL)[2], dried over anhydrous $Na_2SO_4$ and was concentrated under reduced pressure. The residue was purified by preparative thin-layer chromatography ($CH_2Cl_2$: MeOH/98:2, 2× Development), yielding 34.5 mg (0.076 mmol, 69%, 75% brsm) 16-Oxo Ratjadone 8 as a pale-yellow solid foam, 3.7 mg (8.1 μmol, 7%, 8% brsm) 19-Oxo Ratjadone 9 as a pale-yellow solid foam, 6.9 mg (15.2 μmol, 14%, 15% brsm) 16,19-Dioxo Ratjadone 10 as a pale-yellow solid foam and 4.0 mg (8%) reisolated Ratjadone A 1. The reaction was done in 10-600 mg scale, obtaining similar product distributions and yields.

[1] IBX was freshly prepare from 2-iodobenzoic acid according to the procedure of Santagostino and co-workers.[68]

[2] Important to get rid of DMSO traces, which have a strongly negative influence to the chromatographic separation of the products.

16-Oxo-Ratjadone (8): TCL ($CH_2Cl_2$:MeOH/98:2) $R_f$: 0.26 [$UV^{254}$, CAM], IR (ATR) [$cm^{-1}$]: 3456, 2970, 2922, 2883, 1723, 1682, 1620, 1581, 1451, 1437, 1380, 1362, 1307, 1247, 1218, 1126, 1084, 1056, 1013, 968, 914, 884, 783, 732, 700. $^1$H-NMR (700 MHz, $CDCl_3$) δ [ppm]: 7.61 (dd, J=15.1, 11.7 Hz, 1H), 6.88 (ddd, J=9.8, 5.3, 3.1 Hz, 1H), 6.70 (d, J=15.6 Hz, 1H), 6.50 (d, J=15.2 Hz, 1H), 6.04 (ddd, J=9.8, 2.3, 1.3 Hz, 1H), 5.99 (d, J=11.7 Hz, 1H), 5.77-5.70 (m, 1H), 5.73-5.67 (m, 1H), 5.50 (ddq, J=15.4, 6.1, 1.6 Hz, 1H), 5.19 (d, J=9.6 Hz, 1H), 5.00 (dddd, J=10.2, 6.3, 5.2, 1.1 Hz, 1H), 4.47-4.45 (m, 1H), 4.43 (dd, J=11.1, 3.7 Hz, 1H), 4.01 (q, J=2.7 Hz, 1H), 2.86 (ddq, J=13.8, 9.7, 6.8 Hz, 1H), 2.51-2.39 (m, 2H), 2.10 (dd, J=7.1, 2.2 Hz, 2H), 1.85 (d, J=1.1 Hz, 3H), 1.78-1.73 (m, 2H), 1.77 (d, J=1.2 Hz, 3H), 1.71 (dt, J=6.5, 1.3 Hz, 3H), 1.68 (dtt, J=6.7, 2.7, 1.5 Hz, 1H), 0.93 (d, J=0.8 Hz, 3H), 0.92 (d, J=1.5 Hz, 3H). $^{13}$C-NMR (176 MHz, $CDCl_3$) δ [ppm]: 199.85, 164.29, 150.49, 144.94, 140.32, 138.65, 130.24, 130.13, 129.89, 127.14, 126.05, 125.99, 122.96, 121.84, 78.54, 75.09, 70.23, 48.47, 39.30, 30.87, 30.76, 30.23, 29.92, 21.26, 20.60, 18.17, 18.13, 11.44. LRMS (ESI-Quad) [m/z]: 477.6 [M+Na]$^+$, 455.2 [M–$H_2O$+H]$^+$, HRMS (ESI-IT) [m/z]: 455.279347, calculated 455.279201 for $C_{28}H_{39}O_5$[M+H]$^+$, err [ppm] −0.321.

19-Oxo-Ratjadone (9): TCL ($CH_2Cl_2$:MeOH/98:2) $R_f$: 0.36 [$UV^{254}$, CAM], IR (ATR) [$cm^{-1}$]: 3450, 2970, 2923, 2857, 1713, 1653, 1452, 1419, 1380, 1353, 1302, 1245, 1140, 1093, 1030, 1014, 967, 915, 882, 815, 732, 653. $^1$H-NMR (500 MHz, $CDCl_3$) δ [ppm]: 6.90 (dt, J=9.8, 4.2 Hz, 1H), 6.71 (d, J=15.6 Hz, 1H), 6.50 (ddd, J=15.2, 11.0, 1.3 Hz, 1H), 6.07 (dt, J=9.8, 1.8 Hz, 1H), 5.82-5.74 (m, 2H), 5.71 (dd, J=15.6, 6.9 Hz, 1H), 5.54-5.41 (m, 2H), 5.23 (d, J=9.6 Hz, 1H), 5.04-4.95 (m, 1H), 4.46 (s, 1H), 4.19 (ddt, J=6.1, 2.6, 1.1 Hz, 1H), 3.74 (dt, J=11.8, 3.0 Hz, 1H), 2.85-2.76 (m, 1H), 2.75 (dd, J=14.9, 11.9 Hz, 1H), 2.48 (ddd, J=6.7, 3.8, 1.9 Hz, 2H), 2.39 (qdd, J=7.0, 2.5, 1.1 Hz, 1H), 2.16 (ddd, J=14.9, 2.9, 1.3 Hz, 1H), 2.02 (d, J=7.2 Hz, 2H), 1.80 (d, J=1.2 Hz, 3H), 1.75 (ddd, J=6.5, 1.6, 1.0 Hz, 3H), 1.73 (d, J=1.1 Hz, 3H), 1.13 (d, J=7.2 Hz, 3H), 0.93 (d, J=6.6 Hz, 3H). $^{13}$C-NMR (126 MHz, $CDCl_3$) δ [ppm]: 211.63, 164.07, 144.67, 139.22, 138.44, 130.73, 129.41, 129.36, 128.84, 127.42, 127.00, 125.67, 125.39, 121.70, 79.58, 79.33, 78.72, 73.88, 50.12, 47.86, 37.51, 30.52, 30.09, 21.03, 20.42, 17.94, 17.06, 11.13. LRMS (ESI-Quad) [m/z]: 477.3 [M+Na]$^+$, 455.4 [M+H]$^+$, HRMS (ESI-IT) [m/z]: 477.261253, calculated 477.261145 for $C_{28}H_{38}NaO_5$ [M+Na]$^+$, err [ppm] −0.225.

16,19-Dioxo-Ratjadone (10): TCL ($CH_2Cl_2$:MeOH/98:2) $R_f$: 0.44 [$UV^{254}$, CAM], IR (ATR) [$cm^{-1}$]: 2968, 2923, 2855, 1717, 1684, 1620, 1582, 1451, 1419, 1381, 1333, 1305, 1245, 1186, 1148, 1100, 1059, 1013, 968, 932, 915, 883, 862, 814, 787, 732, 662. $^1$H-NMR (500 MHz, $CDCl_3$) δ [ppm]: 7.68 (dd, J=15.1, 11.7 Hz, 1H), 6.89 (ddd, J=9.7, 5.2, 3.2 Hz, 1H), 6.72 (d, J=15.6 Hz, 1H), 6.55 (d, J=15.1 Hz, 1H), 6.09-6.01 (m, 2H), 5.86-5.77 (m, 1H), 5.72 (dd, J=15.6, 6.3 Hz, 1H), 5.52 (ddd, J=15.4, 6.0, 1.7 Hz, 1H), 5.22 (d, J=9.6 Hz, 1H), 5.06-4.97 (m, 1H), 4.27-4.22 (m, 2H), 2.88 (dtd, J=13.7, 6.9, 3.3 Hz, 1H), 2.66 (dd, J=15.0, 12.0 Hz, 1H), 2.52-2.40 (m, 4H), 2.14 (d, J=7.3 Hz, 2H), 1.91-1.87 (m, 3H), 1.79 (d, J=1.1 Hz, 3H), 1.76 (dt, J=6.4, 1.2 Hz, 3H), 1.15 (d, J=7.2 Hz, 3H), 0.95 (d, J=6.6 Hz, 3H). $^{13}$C-NMR (126 MHz, CDCl$_3$) δ [ppm]: 209.87, 196.26, 164.03, 151.67, 144.70, 141.39, 138.36, 129.95, 129.09, 127.30, 126.07, 125.98, 122.31, 121.82, 84.92, 80.42, 80.20, 78.31, 50.21, 48.60, 39.92, 30.70, 30.19, 21.13, 20.52, 18.07, 18.00, 11.34. LRMS (ESI-Quad) [m/z]: 475.2 [M+Na]*, 453.3 [M+H]$^+$, HRMS (ESI-IT) [m/z]: 453.263800, calculated 47453.263600 for C$_{28}$H$_{37}$O$_5$[M+H]$^+$, err [ppm] −0.7.

Synthesis of 16R-Amino-Ratjadone (11)—(R)-6-((1E,3Z,5R,7E,9E,11R)-11-amino-11-((2S,4R,5S,6S)-4-hydroxy-5-methyl-6-((E)-prop-1-en-1-yl)tetrahydro-2H-pyran-2-yl)-3,5,7-trimethylundeca-1,3,7,9-tetra-en-1-yl)-5,6-dihydro-2H-pyran-2-one, 16S-Amino-Ratjadone (12)—(R)-6-((1E,3Z,5R,7E,9E,11S)-11-amino-11-((2S,4R,5S,6S)-4-hydroxy-5-methyl-6-((E)-prop-1-en-1-yl)tetrahydro-2H-pyran-2-yl)-3,5,7-trimethylun-deca-1,3,7,9-tetraen-1-yl)-5,6-dihydro-2H-pyran-2-one, Compound 13—methyl (5R,6E,8Z,10R,12E,14E,16R)-3,16-diamino-5-hydroxy-16-((2S,4R,5S,6S)-4-hydroxy-5-methyl-6-((E)-prop-1-en-1-yl)tetrahydro-2H-pyran-2-yl)-8,10,12-trimethylhexadeca-6,8,12,14-tetraenoate and Compound 14—methyl (5R,6E,8Z,10R,12E,14E,16S)-3,16-diamino-5-hydroxy-16-((2S,4R,5S,6S)-4-hydroxy-5-methyl-6-((E)-prop-1-en-1-yl)tetrahydro-2H-pyran-2-yl)-8,10,12-trimethylhexadeca-6,8,12,14-tetraenoate

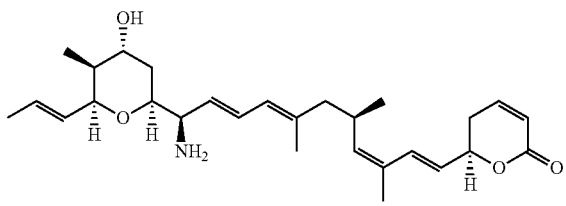

11

Chemical Formula: C$_{28}$H$_{41}$NO$_4$
Molecular Weight: 455.64
16R-Amino Ratjadone

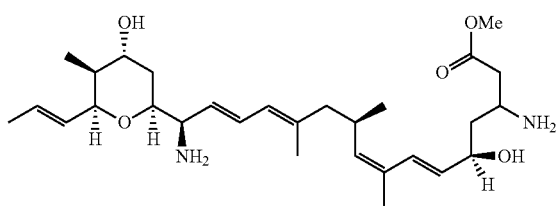

13

Chemical Formula: C$_{29}$H$_{48}$N$_2$O$_5$
Molecular Weight: 504.71

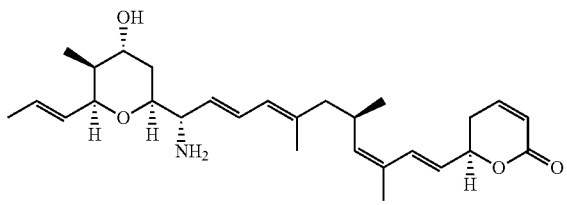

12

Chemical Formula: C$_{28}$H$_{41}$NO$_4$
Molecular Weight: 455.64
16S-Amino Ratjadone

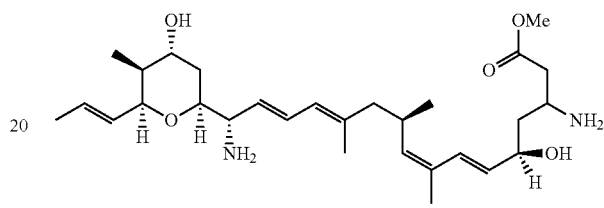

14

Chemical Formula: C$_{29}$H$_{48}$N$_2$O$_5$
Molecular Weight: 504.71

36.6 mg (0.475 mmol, 10 eq) ammonium acetate were added to a solution of 21.6 mg (47.5 µmol, 1.0 eq) 16-Oxo Ratjadone 8 in 950 µL dry MeOH at 23° C. and stirred for 3 min, before 5.9 mg (95.0 µmol, 2.0 eq) sodium cyanoborohydride was added and the mixture was stirred at 23° C. for 14 h. Then the mixture was heated for 2 h to 40° C., before the reaction was quenched by addition of 400 µL of ACN:H$_2$O+TFA/30:70+0.05%. This mixture was directly purified by RP prep HPLC (Phenomenex Gemini C18 RP-column 00G-4435-PO-AX, 5 µm, 110 A, 250×21.20 mm, Flow: 9 mL/min, ACN:H$_2$O+TFA/10:90+0.1%→95:5+0.1% in 90 min) yielding after lyophilization 6.9 mg (15.1 µmol, 32%, 34% brsm) 16R-Amino-Ratjadone 11 as a pale-yellow solid foam, 4.3 mg (9.4 µmol, 20%, 21% brsm) 16S-Amino Ratjadone 12 as a pale-yellow solid foam, 1.5 mg (3.3 µmol, 7%, 8% brsm) of Compound 13 as a yellow solid foam, 0.4 mg (0.9 µmol, 2%, 2.4% brsm) of Compound 14 as a yellow solid foam and 1.6 mg (7%) of reisolated 16-Oxo Ratjadone 8. The compounds 11 and 12 were obtained as pure compounds, whereas compounds 13 and 14 were obtained as their di-TFA salts. The reaction was done in 10-100 mg scale, obtaining similar product distributions and yields.

16R-Amino-Ratjadone (11): IR (ATR) [cm$^{-1}$]: 3403, 2961, 2923, 1674, 1522, 1452, 1436, 1382, 1345, 1253, 1201, 1160, 1134, 1058, 1014, 967, 918, 883, 816, 800, 722, 661. $^1$H-NMR (500 MHz, CDCl$_3$) δ [ppm]: 8.05 (s, 2H), 6.92 (dt, J=9.7, 4.2 Hz, 1H), 6.64 (dd, J=24.0, 15.5 Hz, 1H), 6.51 (dd, J=15.1, 10.9 Hz, 1H), 6.03 (dt, J=9.8, 1.7 Hz, 1H), 5.72 (d, J=10.7 Hz, 1H), 5.70-5.61 (m, 2H), 5.58 (dd, J=15.2, 9.2 Hz, 1H), 5.36 (ddt, J=15.5, 3.9, 1.6 Hz, 1H), 5.20 (d, J=9.5 Hz, 1H), 5.02-4.90 (m, 1H), 4.38 (d, J=5.1 Hz, 1H), 4.17 (d, J=12.2 Hz, 1H), 3.96-3.91 (m, 1H), 3.80 (d, J=9.0 Hz, 1H), 2.78 (dt, J=15.2, 8.3 Hz, 1H), 2.48 (ddd, J=7.2, 3.8, 1.6 Hz, 2H), 2.00 (ddt, J=22.4, 14.1, 6.7 Hz, 2H), 1.81-1.76 (m, 3H), 1.72 (s, 3H), 1.66 (d, J=6.4 Hz, 3H), 1.69-1.53 (m, 2H), 1.40 (d, J=14.0 Hz, 1H), 0.96 (d, J=6.6 Hz, 3H), 0.81 (d, J=7.1 Hz, 3H). $^{13}$C-NMR (126 MHz, CDCl$_3$) δ [ppm]: 164.94, 145.51, 140.31, 139.44, 134.67, 132.19, 129.79, 129.66, 126.71, 125.03, 124.99, 121.45, 120.81, 79.55, 74.77, 71.57, 69.49, 57.54, 47.51, 38.93, 30.57, 30.06, 28.99, 21.55, 20.41, 17.99, 17.48, 11.13. LRMS (ESI-Quad) [m/z]: 456.3 [M+H]$^+$, HRMS (ESI-IT) [m/z]: 456.311233, calculated 456.310835 for $C_{28}H_{42}NO_4$ [M+H]$^+$, err [ppm] −0.872.

16S-Amino-Ratjadone (12): IR (ATR) [cm$^{-1}$]: 3342, 2956, 2925, 1675, 1522, 1436, 1382, 1305, 1254, 1202, 1180, 1136, 1056, 1017, 966, 912, 883, 800, 722, 651. $^1$H-NMR (500 MHz, CDCl$_3$) δ [ppm]: 8.07 (s, 2H), 6.98-6.87 (m, 1H), 6.69 (d, J=15.5 Hz, 1H), 6.56 (dd, J=15.0, 10.9 Hz, 1H), 6.04 (d, J=9.8 Hz, 1H), 5.75 (d, J=10.8 Hz, 1H), 5.68 (dd, J=15.5, 7.7 Hz, 1H), 5.70-5.60 (m, 1H), 5.45-5.34 (m, 2H), 5.20 (d, J=9.9 Hz, 1H), 5.02-4.91 (m, 1H), 4.41 (d, J=5.5 Hz, 1H), 4.04-3.91 (m, 2H), 3.81 (s, 1H), 3.64 (t, J=9.0 Hz, 1H), 2.80 (dh, J=13.0, 6.3 Hz, 1H), 2.56-2.43 (m, 2H), 2.10 (dd, J=13.8, 5.6 Hz, 1H), 1.90 (dd, J=13.8, 8.7 Hz, 1H), 1.78 (s, 3H), 1.69 (s, 3H), 1.68 (d, J=6.5 Hz, 3H), 1.67-1.64 (m, 1H), 1.57 (d, J=14.0 Hz, 1H), 1.49 (t, J=11.8 Hz, 1H), 0.96 (d, J=6.5 Hz, 3H), 0.86 (d, J=7.1 Hz, 3H). $^{13}$C-NMR (126 MHz, CDCl$_3$) δ [ppm]: 165.16, 145.67, 141.69, 139.23, 135.04, 132.47, 129.78, 129.55, 127.42, 124.94, 124.78, 121.42, 120.45, 79.55, 75.20, 71.61, 69.48, 59.36, 47.40, 39.25, 31.49, 30.22, 29.95, 21.44, 20.44, 18.07, 17.99, 11.16. LRMS (ESI-Quad) [m/z]: 456.3 [M+H]$^+$, HRMS (ESI-IT) [m/z]: 456.310562, calculated 456.310835 for $C_{28}H_{42}NO_4$ [M+H]$^+$, err [ppm] 0.598.

Compound 13: $^1$H-NMR (500 MHz, CDCl$_3$) δ [ppm]: 8.35-8.08 (m, 2H), 7.96-7.72 (m, 2H), 6.55 (dd, J=15.0, 11.2 Hz, 1H), 6.21 (d, J=15.3 Hz, 1H), 5.67 (dd, J=15.3, 6.6 Hz, 1H), 5.57 (d, J=11.0 Hz, 1H), 5.46 (ddd, J=23.5, 15.2, 8.4 Hz, 2H), 5.38 (dd, J=15.4, 4.5 Hz, 1H), 5.05 (d, J=9.5 Hz, 1H), 4.38 (d, J=4.6 Hz, 1H), 4.26 (t, J=10.0 Hz, 1H), 4.12 (d, J=11.0 Hz, 1H), 3.95 (s, 1H), 3.77 (s, 2H), 3.71 (s, 3H), 2.87-2.78 (m, 1H), 2.69 (dd, J=17.5, 5.0 Hz, 1H), 2.67-2.57 (m, 2H), 2.04 (d, J=11.6 Hz, 1H), 2.02-1.93 (m, 1H), 1.87-1.79 (m, 1H), 1.78 (s, 3H), 1.74 (s, 3H), 1.69 (d, J=6.1 Hz, 3H), 1.73-1.60 (m, 2H), 1.41 (s, 1H), 1.04 (d, J=6.5 Hz, 3H), 0.83 (d, J=7.1 Hz, 3H). $^{13}$C-NMR (126 MHz, CDCl$_3$) δ [ppm]: 207.14, 171.48, 162.84, 162.47, 162.23, 161.97, 140.63, 137.42, 135.75, 130.88, 129.59, 129.44, 127.16, 125.32, 119.95, 74.90, 73.15, 71.35, 69.62, 62.95, 57.40, 52.49, 47.99, 39.08, 37.08, 31.24, 31.09, 29.85, 29.21, 22.65, 20.57, 17.98, 17.66, 11.16. LRMS (ESI-Quad) [m/z]: 505.4 [M+H]$^+$, HRMS (ESI-IT) [m/z]: 505.363758, calculated 505.363599 for $C_{28}H_{42}NO_4$ [M+H]$^+$, err [ppm] −0.315.

Compound 14: $^1$H-NMR (700 MHz, CDCl$_3$) δ [ppm]: 8.44-8.17 (m, 2H), 8.15-7.85 (m, 2H), 6.56 (dd, J=15.0, 11.0 Hz, 1H), 6.38 (d, J=15.4 Hz, 1H), 5.85 (d, J=10.9 Hz, 1H), 5.66 (ddd, J=15.5, 6.5, 1.2 Hz, 1H), 5.52 (dd, J=15.4, 8.0 Hz, 1H), 5.42-5.38 (m, 1H), 5.37 (dd, J=14.9, 9.3 Hz, 1H), 5.08 (d, J=10.1 Hz, 1H), 4.43 (d, J=6.1 Hz, 1H), 4.26 (s, 1H), 3.99-3.91 (m, 2H), 3.86 (s, 1H), 3.72 (s, 3H), 3.59 (t, J=9.4 Hz, 1H), 2.79-2.71 (m, 2H), 2.65 (dd, J=17.4, 5.0 Hz, 1H), 2.30 (d, J=10.4 Hz, 1H), 2.02-1.94 (m, 1H), 1.73 (d, J=1.1 Hz, 3H), 1.69 (s, 1H), 1.68 (s, 3H), 1.66-1.65 (m, 2H), 1.63 (s, 3H), 1.57 (d, J=14.1 Hz, 1H), 1.48 (ddd, J=14.3, 12.0, 2.7 Hz, 1H), 1.00 (d, J=6.4 Hz, 3H), 0.87 (d, J=7.2 Hz, 3H). $^{13}$C-NMR (176 MHz, CDCl$_3$) δ [ppm]: 207.11, 171.64, 162.76, 162.56, 162.35, 162.15, 143.94, 136.83, 135.91, 130.72, 130.21, 129.58, 129.26, 127.33, 124.62, 119.50, 75.04, 73.72, 71.63, 69.60, 52.54, 46.74, 39.47, 39.38, 36.96, 34.38, 31.09, 30.48, 29.86, 22.06, 20.38, 19.90, 17.97, 11.18. LRMS (ESI-Quad) [m/z]: 505.4 [M+H]$^+$, HRMS (ESI-IT) [m/z]: 505.363803, calculated 505.363599 for $C_{28}H_{42}NO_4$ [M+H]$^+$, err [ppm] −0.404.

1.1.1.2 Determination of the Absolute Stereo Configuration at C16 for the 16-Amino-Ratjadones[57-59]

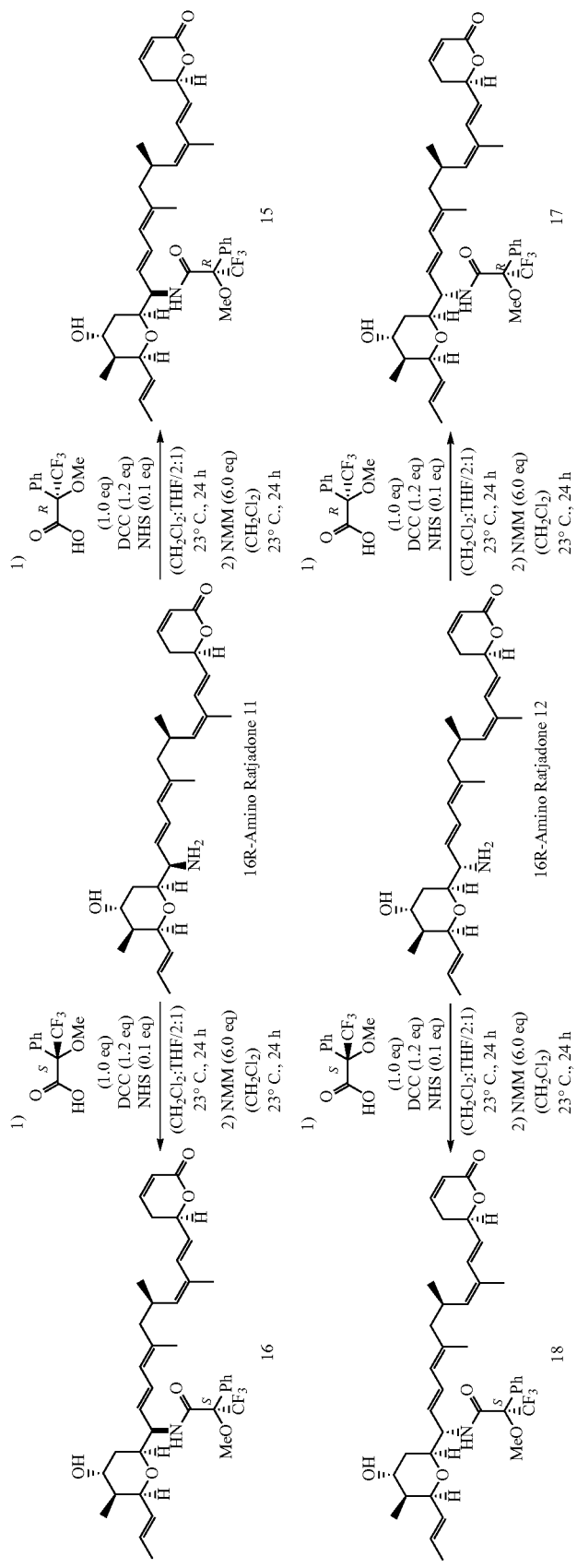
Scheme 2: Synthesis of the 16-Amino-Ratjadone Mosher-Amides

Synthesis of the Mosher amide 15—(R)-3,3,3-trifluoro-N-((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)-2-methoxy-2-phenylpropanamide, Mosher amide 16—(S)-3,3,3-trifluoro-N-((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)-2-methoxy-2-phenylpropanamide, Mosher amide 17—(R)-3,3,3-trifluoro-N-((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)-2-methoxy-2-phenylpropanamide and Mosher amide 18 (S)-3,3,3-trifluoro-N-((1 S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)-2-methoxy-2-phenylpropanamide

15

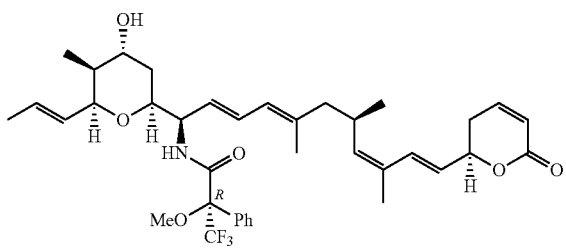

Chemical Formula: $C_{38}H_{48}F_3NO_6$
Molecular Weight: 671.80

17

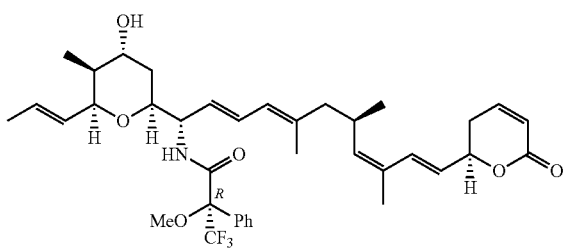

Chemical Formula: $C_{38}H_{48}F_3NO_6$
Molecular Weight: 671.80

To a solution of 1.85 mg (7.896 µmol, 1.2 eq) (R)-3,3,3-trifluoro-2-methoxy-2-phenylpropanoic acid in 10 µL dry $CH_2Cl_2$ were added a solution of 0.91 mg (7.896 µmol, 1.2 eq) N-hydroxysuccinimide in 10 µL dry THF and a solution of 1.63 mg (7.896 µmol, 1.2 eq) DCC in 10 µL dry $CH_2Cl_2$ and the mixture was stirred at 23° C. for 15 h, before 4.4 µL (39.50 µmol, 6.0 eq) NMM and a solution of 3 mg (6.58 µmol, 1.0 eq) 16(R)-amino-ratjadone 11 were added and the mixture was stirred for additional 30 h. The reaction mixture was diluted with 200 µL $CH_2Cl_2$ and directly purified by preparative thin-layer chromatography ($CH_2Cl_2$: MeOH/98:2, 1x Development), yielding 2.3 mg (3.42 µmol, 52%) of Mosher amide 15 as a yellow solid foam.

In similar manner reaction in the presence of 16S-amino-ratjadone 12 led to the formation of Mosher amide 17 isolated in 52% (2.3 mg) as a yellow solid foam.

Both compounds 15 and 17 slightly contained DCU and traces of silicon grease as impurities.

Mosher amide 15: TCL ($CH_2Cl_2$:MeOH/98:2) $R_f$: 0.46 [$UV^{254}$, CAM], IR (ATR) [$cm^{-1}$]: 3421, 2961, 2924, 2854, 1722, 1693, 1625, 1506, 1451, 1380, 1260, 1164, 1080, 1056, 1015, 966, 918, 880, 802, 767, 735, 717, 698, 661. $^{19}$F-NMR (471 MHz, $CDCl_3$) δ [ppm]: −68.80 (s, 3F). $^1$H-NMR (500 MHz, $CDCl_3$) δ [ppm]: 7.55-7.51 (m, 2H), 7.39-7.34 (m, 3H), 7.20 (d, J=9.1 Hz, 1H), 6.94-6.84 (m, 1H), 6.71 (d, J=15.6 Hz, 1H), 6.32 (ddd, J=15.2, 10.9, 1.0 Hz, 1H), 6.06 (dt, J=9.8, 1.8 Hz, 1H), 5.74 (d, J=11.0 Hz, 1H), 5.70 (dd, J=15.6, 6.5 Hz, 1H), 5.64 (ddd, J=15.4, 6.5, 1.4 Hz, 1H), 5.57 (dd, J=15.2, 7.6 Hz, 1H), 5.42 (ddd, J=15.4, 5.7, 1.7 Hz, 1H), 5.22 (d, J=9.1 Hz, 1H), 5.05-4.93 (m, 1H), 4.53 (td, J=8.1, 3.7 Hz, 1H), 4.37 (d, J=5.5 Hz, 1H), 4.02 (s, 1H), 3.98 (d, J=2.5 Hz, 1H), 3.96-3.91 (m, 1H), 3.46 (d, J=1.3 Hz, 3H), 2.80 (dq, J=9.7, 7.0 Hz, 1H), 2.50-2.41 (m, 2H), 2.02-1.96 (m, 2H), 1.97-1.90 (m, 2H), 1.79 (d, J=1.2 Hz, 3H), 1.71 (dt, J=6.5, 1.4 Hz, 3H), 1.63 (d, J=1.1 Hz, 3H), 1.60-1.57 (m, 1H), 0.92 (d, J=6.6 Hz, 3H), 0.86 (d, J=7.1 Hz, 3H). $^{13}$C-NMR (126 MHz, $CDCl_3$) δ [ppm]: 165.29, 164.20, 144.87, 139.34, 137.84, 133.22, 130.39, 130.27, 130.25, 129.52, 129.41, 128.56, 127.78, 126.42, 125.91, 125.80, 125.59, 121.77, 78.55, 74.68, 74.05, 70.31, 55.22, 54.67, 53.58, 49.35, 47.96, 39.59, 34.12, 25.77, 25.10, 21.02, 20.54, 18.10, 17.11, 11.28. LRMS (ESI-Quad) [m/z]: 672.9 [M+H]$^+$, HRMS (ESI-IT) [m/z]: 694.332582, calculated 694.332594 for $C_{38}H_{48}F_3NNaO_6$ [M+Na]$^+$, err [ppm] 0.017.

Mosher amide 17: TCL ($CH_2Cl_2$:MeOH/98:2) $R_f$: 0.41 [$UV^{254}$, CAM], IR (ATR) [$cm^{-1}$]: 3418, 2961, 2925, 2854, 1721, 1696, 1625, 1506, 1451, 1360, 1260, 1164, 1081, 1054, 1017, 965, 918, 877, 802, 767, 734, 718, 698, 668. $^{19}$F-NMR (471 MHz, $CDCl_3$) δ [ppm]: −68.95 (s, 3F). $^1$H-NMR (500 MHz, $CDCl_3$) δ [ppm]: 7.60 (dd, J=6.4, 3.0 Hz, 2H), 7.40-7.35 (m, 3H), 7.04 (d, J=9.0 Hz, 1H), 6.90 (ddd, J=9.8, 4.5, 3.9 Hz, 1H), 6.67 (d, J=15.6 Hz, 1H), 6.43 (ddd, J=15.2, 10.9, 1.2 Hz, 1H), 6.06 (dt, J=9.8, 1.8 Hz, 1H), 5.74 (d, J=10.8 Hz, 1H), 5.71 (dd, J=15.8, 6.6 Hz, 1H), 5.61 (dd, J=6.5, 1.3 Hz, 1H), 5.58 (dd, J=6.5, 1.4 Hz, 1H), 5.36 (ddq, J=15.3, 5.6, 1.4 Hz, 1H), 5.22 (d, J=9.8 Hz, 1H), 5.04-4.95 (m, 1H), 4.42 (t, J=8.0 Hz, 1H), 4.35 (d, J=5.8 Hz, 1H), 4.02 (s, 1H), 3.91 (dt, J=12.1, 2.7 Hz, 1H), 3.86 (d, J=2.7 Hz, 1H), 3.47 (d, J=1.3 Hz, 3H), 2.78 (dq, J=9.7, 6.8 Hz, 1H), 2.47 (ddd, J=7.1, 3.5, 1.6 Hz, 2H), 1.99 (d, J=7.1 Hz, 2H), 1.93 (dt, J=12.1, 3.8 Hz, 2H), 1.79 (d, J=1.2 Hz, 3H), 1.70 (d, J=1.2 Hz, 3H), 1.70-1.68 (m, 3H), 1.60 (dt, J=13.1, 3.9 Hz, 1H), 0.93 (d, J=6.6 Hz, 3H), 0.60 (d, J=7.2 Hz, 3H). $^{13}$C-NMR (126 MHz, $CDCl_3$) δ [ppm]: 165.79, 164.15, 144.74, 139.22, 137.41, 133.05, 130.53, 130.17, 129.35, 129.32, 128.73, 128.40, 128.10, 127.52, 126.20, 125.87, 125.34, 121.61, 78.76, 77.18, 74.39, 73.91, 70.19, 55.09, 54.58, 53.41, 49.19, 47.79, 39.21, 33.96, 25.61, 24.94, 20.98, 20.36, 17.95, 16.97, 10.67. LRMS (ESI-Quad) [m/z]: 672.9 [M+H]$^+$, HRMS (ESI-IT) [m/z]: 694.332578, calculated 694.332594 for $C_{38}H_{48}F_3NNaO_6$ [M+Na]$^+$, err [ppm] 0.022.

LRMS (ESI-Quad) [m/z]: 672.9 [M+H]$^+$, HRMS (ESI-IT) [m/z]: 694.332399, calculated 694.332594 for $C_{38}H_{48}F_3NNaO_6$ [M+Na]$^+$, err [ppm] 0.280.

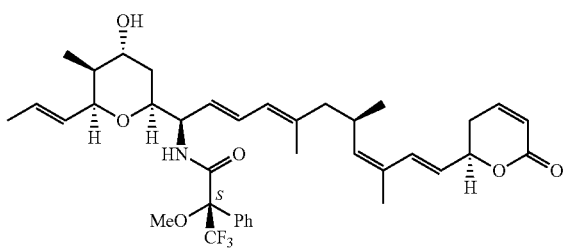

16

Chemical Formula: C38H48F3NO6
Molecular Weight: 671.80

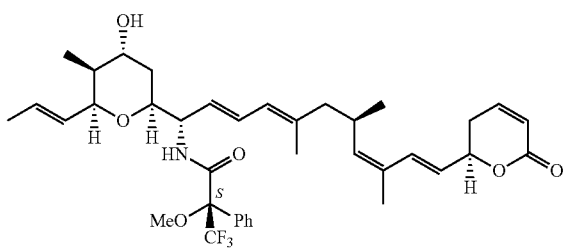

18

Chemical Formula: C38H48F3NO6
Molecular Weight: 671.80

To a solution of 1.85 mg (7.896 μmol, 1.2 eq) (S)-3,3,3-trifluoro-2-methoxy-2-phenylpropanoic acid in 10 μL dry CH$_2$Cl$_2$ were added a solution of 0.91 mg (7.896 μmol, 1.2 eq) N-hydroxysuccinimide in 10 μL dry THF and a solution of 1.63 mg (7.896 μmol, 1.2 eq) DCC in 10 μL dry CH$_2$Cl$_2$ and the mixture was stirred at 23° C. for 15 h, before 4.4 μL (39.50 μmol, 6.0 eq) NMM and a solution of 3 mg (6.58 μmol, 1.0 eq) 16(R)-Amino-Ratjadone 11 were added and the mixture was stirred for additional 30 h. The reaction mixture was diluted with 200 μL CH$_2$Cl$_2$ and directly purified by preparative thin-layer chromatography (CH$_2$Cl$_2$: MeOH/98:2, 1x Development), yielding 2.2 mg (3.27 μmol, 50%) of Mosher amide 16 as a yellow solid foam.

In similar manner reaction in the presence of 16S-Amino-Ratjadone 12 led to the formation of Mosheramide 18 isolated in 52% (2.3 mg) as a yellow solid foam.

Both compounds 16 and 18 slightly contained DCU and traces of silicon grease as impurities.

Mosher amide 16: TCL (CH$_2$Cl$_2$:MeOH/98:2) R$_f$: 0.42 [UV$^{254}$, CAM], IR (ATR) [cm$^{-1}$]: 3417, 2960, 2925, 2854, 1721, 1693, 1552, 1511, 1451, 1380, 1335, 1321, 1260, 1102, 1061, 1056, 1015, 966, 918, 880, 866, 801, 767, 734, 717, 698, 668. $^{19}$F-NMR (471 MHz, CDCl$_3$) δ [ppm]: −69.05 (s, 3F). $^1$H-NMR (500 MHz, CDCl$_3$) δ [ppm]: 7.56 (dd, J=6.1, 3.2 Hz, 1H), 7.39 (tt, J=3.5, 2.3 Hz, 1H), 6.91 (ddd, J=9.8, 5.1, 3.3 Hz, 1H), 6.72 (d, J=15.7 Hz, 1H), 6.44 (ddd, J=15.1, 10.9, 1.1 Hz, 1H), 6.06 (ddd, J=9.8, 2.2, 1.4 Hz, 1H), 5.78 (d, J=10.8 Hz, 1H), 5.71 (dd, J=15.2, 6.5 Hz, 1H), 5.62 (dd, J=6.5, 1.5 Hz, 1H), 5.59 (dd, J=6.5, 1.5 Hz, 1H), 5.39 (ddq, J=15.5, 5.1, 1.6 Hz, 1H), 5.22 (d, J=9.3 Hz, 1H), 5.02 (dt, J=10.8, 5.4 Hz, 1H), 4.52 (td, J=8.1, 4.0 Hz, 1H), 4.31 (d, J=3.0 Hz, 1H), 4.02 (s, 1H), 3.96 (q, J=2.6 Hz, 1H), 3.93-3.87 (m, 1H), 3.37 (d, J=1.2 Hz, 3H), 2.81 (dq, J=9.5, 6.9 Hz, 1H), 2.55-2.41 (m, 2H), 2.00 (d, J=8.4 Hz, 2H), 1.94 (dd, J=12.6, 3.5 Hz, 2H), 1.79 (d, J=1.2 Hz, 3H), 1.71 (d, J=1.1 Hz, 3H), 1.70 (dt, J=6.5, 1.4 Hz, 3H), 1.64-1.60 (m, 1H), 0.93 (d, J=6.6 Hz, 3H), 0.85 (d, J=7.1 Hz, 3H). $^{13}$C-NMR (126 MHz, CDCl$_3$) δ [ppm]: 165.38, 164.24, 144.93, 139.29, 137.94, 132.68, 130.40, 130.30, 130.23, 129.52, 129.48, 128.65, 128.03, 126.22, 125.94, 125.61, 125.52, 121.75, 78.55, 74.46, 73.64, 70.29, 55.03, 54.92, 53.58, 49.35, 47.98, 39.51, 34.12, 25.77, 25.10, 21.11, 20.50, 18.10, 17.16, 11.26. LRMS (ESI-Quad) [m/z]: 672.9 [M+H]$^+$, HRMS (ESI-IT) [m/z]: 694.332531, calculated 694.332594 for C$_{38}$H$_{48}$F$_3$NNaO$_6$ [M+Na]$^+$, err [ppm] 0.090.

Mosher amide 18: TCL (CH$_2$Cl$_2$:MeOH/98:2) R$_f$: 0.42 [UV$^{254}$, CAM], IR (ATR) [cm$^{-1}$]: 3419, 3328, 2926, 2852, 1722, 1654, 1624, 1577, 1534, 1503, 1450, 1380, 1343, 1260, 1245, 1164, 1104, 1088, 1056, 1020, 966, 917, 905, 892, 814, 801, 767, 733, 713, 697, 662. $^{19}$F-NMR (471 MHz, CDCl$_3$) δ [ppm]: −68.80 (s, 3F). $^1$H-NMR (500 MHz, CDCl$_3$) δ [ppm]: 7.56-7.50 (m, 2H), 7.40-7.33 (m, 3H), 7.22 (d, J=8.8 Hz, 1H), 6.89 (dt, J=9.8, 4.2 Hz, 1H), 6.68 (d, J=15.6 Hz, 1H), 6.33 (ddd, J=15.1, 10.9, 1.2 Hz, 1H), 6.05 (dt, J=9.8, 1.8 Hz, 1H), 5.72 (d, J=12.1 Hz, 1H), 5.71 (dd, J=14.7, 6.1 Hz, 1H), 5.65 (ddd, J=15.4, 6.5, 1.3 Hz, 1H), 5.57 (dd, J=15.3, 7.1 Hz, 1H), 5.43 (ddq, J=15.5, 6.1, 1.6 Hz, 1H), 5.22 (d, J=9.5 Hz, 1H), 4.99 (q, J=6.9 Hz, 1H), 4.48-4.41 (m, 1H), 4.41 (d, J=6.1 Hz, 1H), 4.02 (s, 1H), 4.00 (s, 1H), 3.96 (dt, J=12.2, 2.7 Hz, 1H), 3.45 (d, J=1.3 Hz, 3H), 2.78 (dq, J=9.9, 6.8 Hz, 1H), 2.49-2.43 (m, 2H), 1.98 (dd, J=7.1, 4.4 Hz, 2H), 1.96-1.89 (m, 3H), 1.79 (d, J=1.2 Hz, 3H), 1.70 (dt, J=6.5, 1.3 Hz, 3H), 1.63 (d, J=1.1 Hz, 3H), 0.92 (d, J=9.0 Hz, 3H), 0.90 (d, J=9.5 Hz, 3H). $^{13}$C-NMR (126 MHz, CDCl$_3$) δ [ppm]: 165.95, 164.28, 144.90, 139.39, 137.47, 132.91, 130.69, 130.32, 129.56, 129.48, 128.83, 128.62, 128.39, 127.89, 126.55, 126.00, 125.53, 121.77, 78.91, 74.79, 73.95, 70.45, 55.31, 54.86, 53.58, 49.35, 47.93, 39.53, 34.12, 25.77, 25.10, 21.06, 20.54, 18.08, 17.11, 11.07.

FIG. 3 shows the determination of the configuration at position 16 via the Mosher amide 18.

1.1.1.3 Synthesis of 16-Amino-Ratjadones with Bearing Terminal Alkynes Attached Via Short Non-Cleavable Linkers Scheme 3: Synthesis of the 16-Amino-Ratjadone Derivatives 19, 20, 22, 24 and 25

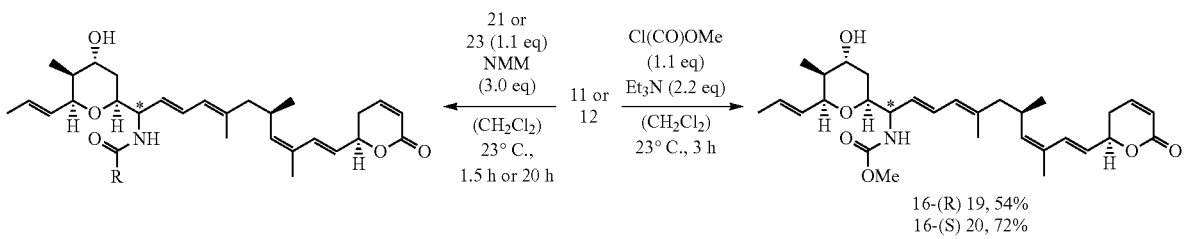

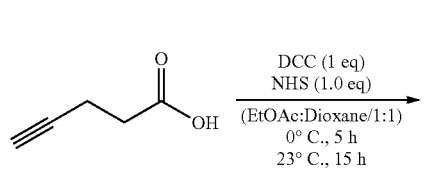 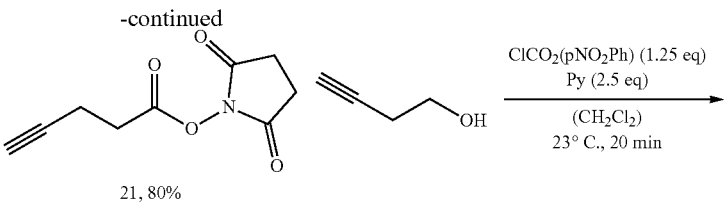

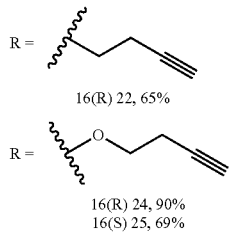

16(R) 22, 65%

R =

16(R) 24, 90%
16(S) 25, 69%

Synthesis of 16R-Amino-Ratjadone methyl carbamate (19)—methyl ((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate and 16S-Amino-Ratjadone methyl carbamate (20)—methyl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

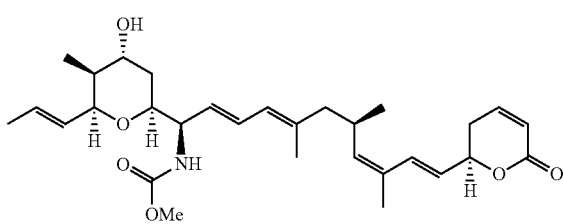

Chemical Formula: $C_{30}H_{43}NO_6$
Molecular Weight: 513.68

19

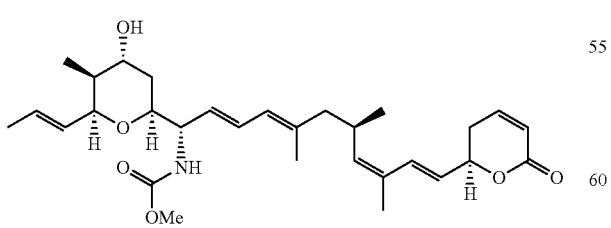

Chemical Formula: $C_{30}H_{43}NO_6$
Molecular Weight: 513.68

20

To a solution of 1.5 mg (3.29 μmol, 1.0 eq) 16R-Amino-Ratjadone 11 in 66 μL dry $CH_2Cl_2$ were added 1.0 μL (7.24 μmol, 2.2 eq) $Et_3N$ and 0.28 μL (3.62 μmol, 1.1 eq) of methyl chloroformate (stock solution in dry $CH_2Cl_2$) and the mixture was stirred at 23° C. for 3 h. The mixture was diluted with 0.1 mL $CH_2Cl_2$ and directly purified by directly purified by preparative thin-layer chromatography ($CH_2Cl_2$:MeOH/98:2, 1× Development), yielding 0.91 mg (1.752 μmol, 54%) of Compound 19 as a pale-yellow solid foam.

In similar manner reaction in the presence of 16S-aminoratjadone 12 led to the formation of Compound 20 isolated in 74% (2.4 mg) as a pale-yellow solid foam.

16R-Amino-Ratjadone methyl carbamate (19): TCL ($CH_2Cl_2$:MeOH/98:2) $R_f$: 0.21 [$UV^{254}$, CAM], LRMS (ESI-Quad) [m/z]: 536.4 [M+H]$^+$, HRMS (ESI-IT) [m/z]: 536.298150, calculated 536.298260 for $C_{38}H_{48}F_3NNaO_6$ [M+Na]$^+$, err [ppm] 0.205.

16S-Amino-Ratjadone methyl carbamate (20): TCL ($CH_2Cl_2$:MeOH/98:2) $R_f$: 0.21 [$UV^{254}$, CAM], LRMS (ESI-Quad) [m/z]: 536.4 [M+Na]$^+$, HRMS (ESI-IT) [m/z]: 536.298223, calculated 536.298260 for $C_{38}H_{48}F_3NNaO_6$ [M+Na]$^+$, err [ppm] 0.069.

Synthesis of N-hydroxysuccinimide ester (21)[3]

[3] Synthesized according to a procedure of Galibert et al.[60]

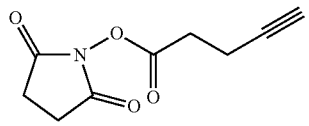

Chemical Formula: $C_9H_9NO_4$
Molecular Weight: 195.17

To a solution of 500 mg (5.096 mmol, 1.0 eq) 3-Butynic acid and 587 mg (5.096 mmol, 1.0 eq) N-hydroxysuccinimide in 64 mL of 1:1-mixture of dry EtOAc and dry dioxane was added 1.051 g (5.096 mmol, 1.0 eq) DCC in one portion at 0° C. The mixture was stirred at 0° C. for 5 h and additional 15 h at 23° C., before it was filtered and the filtrate was concentrated under reduced pressure. The residue was recrystallized from CH$_2$Cl$_2$/Pentane obtaining 800 mg (4.100 mmol, 80%) of 21 as a white amorphous solid.

N-hydroxysuccinimide ester (21): $^1$H-NMR (500 MHz, CDCl$_3$) δ [ppm]: 2.86 (dd, J=8.2, 6.7 Hz, 2H), 2.82 (s, 4H), 2.60 (ddd, J=8.6, 6.7, 2.7 Hz, 2H), 2.03 (t, J=2.7 Hz, 1H). $^{13}$C-NMR (126 MHz, CDCl$_3$) δ [ppm] 169.27, 167.39, 81.23, 70.43, 30.70, 25.97, 14.49.

Synthesis of Compound 22—N-((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)pent-4-ynamide

22

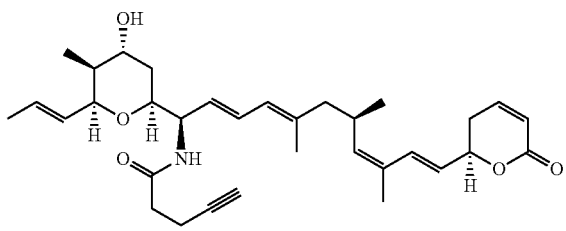

Chemical Formula: C$_{33}$H$_{45}$NO$_5$
Molecular Weight: 535.72500

To a solution of 9.5 mg (16.67 μmol, 1.0 eq) 16R-Amino-Ratjadone 11 in 167 μL dry CH$_2$Cl$_2$ were added 5.5 μL (50.03 μmol, 3.0 eq) NMM and 3.6 mg (18.34 μmol, 1.1 eq) 4-pentynoic acid N-hydroxysuccinimide ester[60] and the mixture was stirred for 1.5 h at 23° C. The mixture was diluted with 0.25 mL CH$_2$Cl$_2$ and directly purified by preparative thin-layer chromatography (CH$_2$Cl$_2$: MeOH/98:2, 1x Development), yielding 5.8 mg (10.82 μmol, 65%) of Compound 22 as a pale-yellow solid foam.

Compound 22: TCL (CH$_2$Cl$_2$:MeOH/98:2) R$_f$: 0.12 [UV$^{254}$, CAM], 1H-NMR (700 MHz, CDCl$_3$) δ [ppm]: 6.91 (ddd, J=9.7, 4.9, 3.6 Hz, 1H), 6.70 (d, J=15.6 Hz, 1H), 6.41 (d, J=11.8 Hz, 1H), 6.39 (dd, J=10.4, 3.8 Hz, 1H), 6.07 (dt, J=9.8, 1.7 Hz, 1H), 5.76 (d, J=10.9 Hz, 1H), 5.70 (dd, J=15.4, 6.7 Hz, 1H), 5.69-5.63 (m, 1H), 5.61 (dd, J=15.2, 8.0 Hz, 1H), 5.43 (ddt, J=13.8, 5.9, 1.7 Hz, 1H), 5.22 (d, J=9.7 Hz, 1H), 5.04-4.94 (m, 1H), 4.43 (td, J=8.3, 3.5 Hz, 1H), 4.37-4.26 (m, 1H), 3.96 (d, J=2.7 Hz, 1H), 3.87 (dt, J=12.4, 2.7 Hz, 1H), 2.80 (dq, J=9.5, 6.9 Hz, 1H), 2.55-2.45 (m, 4H), 2.42 (t, J=7.2 Hz, 2H), 1.99 (dd, J=7.0, 2.0 Hz, 2H), 1.97 (t, J=2.6 Hz, 1H), 1.78 (d, J=1.1 Hz, 3H), 1.72 (dt, J=6.7, 1.3 Hz, 3H), 1.71-1.70 (m, 3H), 1.66-1.60 (m, 2H), 1.38 (d, J=14.2 Hz, 1H), 0.93 (d, J=6.6 Hz, 3H), 0.86 (d, J=7.1 Hz, 3H). $^{13}$C-NMR (176 MHz, CDCl$_3$) δ [ppm] 169.94, 164.26, 144.89, 139.46, 137.22, 130.88, 130.54, 130.02, 129.43, 126.74, 126.30, 126.18, 125.39, 121.77, 83.26, 78.79, 74.56, 74.28, 70.36, 69.43, 54.83, 47.88, 39.63, 35.63, 30.57, 30.54, 30.17, 21.15, 20.52, 18.06, 17.26, 15.07, 11.30. LRMS (ESI-Quad) [m/z]: 536.9 [M+H]$^+$, HRMS (ESI-IT) [m/z]: 558.318041, calculated 558.3189994 for C$_{33}$H$_{45}$NNaO$_5$ [M+Na]$^+$, err [ppm] 1.707.

Synthesis of But-3-yn-1-yl (4-nitrophenyl) carbonate (23)[4]

23

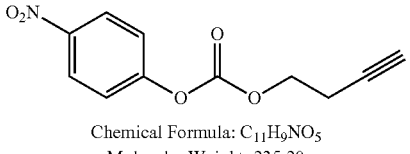

Chemical Formula: C$_{11}$H$_9$NO$_5$
Molecular Weight: 235,20

To a solution of 200 mg (2.853 mmol, 1.0 eq) homoallylic alcohol in 71 mL dry CH$_2$Cl$_2$, 0.58 mL (7.134 mmol, 2.5 eq) pyridine and 719 mg (3.567 mmol, 1.25 eq) para-nitrophenylchloroformate were added and the mixture was stirred for 40 min at 23° C. The mixture was quenched by addition of 90 mL of saturated NH$_4$Cl solution and extracted with CH$_2$Cl$_2$ (3×90 mL). The combined organic layers were dried over Na$_2$SO$_4$ and concentrated under reduced pressure. The residue was purified by flash-chromatography through silicagel (petroleum ether:EtOAc/95:5-9:1) yielding 570 mg (2.423 mmol, 85%) of 22 as a white amorphous solid.

[4] Synthesis was based on a procedure of Dommerholt et al.[69]

But-3-yn-1-yl (4-nitrophenyl) carbonate (23): TCL (petroleum ether:EtOAc/9:1) R$_f$: 0.24 [UV$^{254}$], $^1$H-NMR (500 MHz, CDCl$_3$) δ [ppm]: 8.55-7.98 (m, 2H), 7.48-7.32 (m, 2H), 4.40 (t, J=6.7 Hz, 2H), 2.68 (td, J=6.7, 2.7 Hz, 2H), 2.08 (t, J=2.7 Hz, 1H). $^{13}$C-NMR (126 MHz, CDCl$_3$) δ [ppm] 155.55, 152.39, 145.62, 125.48, 121.89, 79.06, 70.81, 66.81, 19.13.

Synthesis of Compound 24—But-3-yn-1-yl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

24

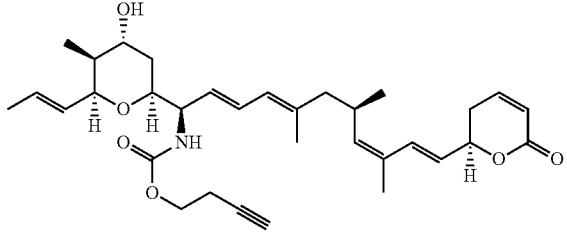

Chemical Formula: C$_{33}$H$_{45}$NO$_6$
Molecular Weight: 551,72400

To a solution of 4.0 mg (8.77 μmol, 1.0 eq) 16R-Amino-Ratjadone 11 in 88 μL dry CH$_2$Cl$_2$ were added 2.9 μL (26.34 μmol, 3.0 eq) NMM and 2.3 mg (9.657 μmol, 1.1 eq) but-3-yn-1-yl (4-nitrophenyl) carbonate 23 and the mixture was stirred for 24 h at 23° C. The mixture was diluted with 0.25 mL CH$_2$Cl$_2$ and directly purified by preparative thin-layer chromatography (CH$_2$Cl$_2$:MeOH/98:2, 1× Development), yielding 4.4 mg (7.90 μmol, 90%) of Compound 24 as a pale-yellow solid foam.

Compound 24: TCL (CH$_2$Cl$_2$:MeOH/98:2) R$_f$: 0.15 [UV$^{254}$, CAM], IR (ATR) [cm$^{-1}$]: 3442, 3309, 3034, 2963, 2923, 1718, 1653, 1605, 1566, 1497, 1437, 1361, 1335, 1291, 1246, 1136, 1081, 1056, 1013, 967, 937, 918, 883, 816, 776, 722, 683, 651. $^1$H-NMR (500 MHz, CDCl$_3$) δ [ppm]: 6.94-6.87 (m, 1H), 6.72 (d, J=15.6 Hz, 1H), 6.39 (dd, J=15.1, 10.8 Hz, 1H), 6.07 (dt, J=9.8, 1.8 Hz, 1H), 5.78 (d, J=10.9 Hz, 1H), 5.76-5.67 (m, 1H), 5.66 (ddd, J=15.4, 6.5, 1.4 Hz, 1H), 5.59 (dd, J=15.1, 8.2 Hz, 1H), 5.49-5.36 (m, 2H), 5.23 (d, J=9.6 Hz, 1H), 5.09-4.97 (m, 1H), 4.35 (d, J=5.5 Hz, 1H), 4.16 (t, J=6.7 Hz, 2H), 4.08 (s, 1H), 3.99-3.95 (m, 1H), 3.91 (dt, J=12.3, 2.7 Hz, 1H), 3.49 (s, 1H), 2.88-2.70 (m, 1H), 2.55-2.45 (m, 4H), 2.10-1.94 (m, 3H), 1.79 (d, J=1.2 Hz, 3H), 1.74-1.69 (m, 6H), 1.65-1.58 (m, 1H), 1.51 (s, 1H), 1.36 (d, J=13.9 Hz, 1H), 0.92 (d, J=6.6 Hz, 3H), 0.85 (d, J=7.1 Hz, 3H). $^{13}$C-NMR (126 MHz, CDCl$_3$) δ [ppm] 164.06, 155.38, 144.70, 139.28, 137.31, 130.35, 130.20, 129.71, 129.20, 126.75, 126.27, 125.93, 125.37, 121.61, 78.50, 74.34, 70.15, 69.70, 62.52, 56.81, 47.78, 39.51, 30.37, 30.22, 30.00, 20.88, 20.36, 19.39, 17.88, 16.99, 11.14. LRMS (ESI-Quad) [m/z]: 552.4 [M+H]$^+$, HRMS (ESI-IT) [m/z]: 552.332090, calculated 552.331965 for $C_{33}H_{46}NO_6$ [M+H]$^+$, err [ppm] −0.228.

Synthesis of Compound 25—But-3-yn-1-yl ((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

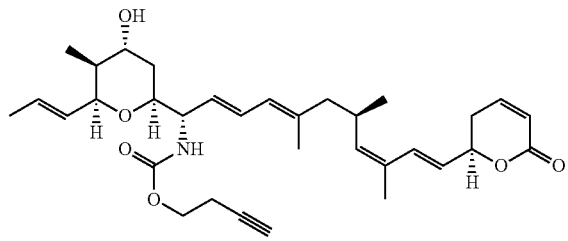

Chemical Formula: C$_{33}$H$_{45}$NO$_6$
Molecular Weight: 551,72

To a solution of 5.0 mg (10.97 μmol, 1.0 eq) 16S-Amino-Ratjadone 11 in 110 μL dry CH$_2$Cl$_2$ were added 7.2 μL (65.82 μmol, 6.0 eq) NMM and 2.84 mg (12.07 μmol, 1.1 eq) but-3-yn-1-yl (4-nitrophenyl) carbonate 23 and the mixture was stirred for 20 h at 23° C. The mixture was diluted with 0.25 mL CH$_2$Cl$_2$ and directly purified by preparative thin-layer chromatography (CH$_2$Cl$_2$:MeOH/98:2, 1x Development), yielding 4.4 mg (7.90 μmol, 90%) of Compound 25 as a pale-yellow solid foam.

Compound 25: TCL (CH$_2$Cl$_2$:MeOH/98:2) R$_f$: 0.16 [UV$^{254}$, CAM], $^1$H-NMR (500 MHz, CDCl$_3$) δ [ppm] 6.90 (dt, J=9.7, 4.2 Hz, 1H), 6.67 (d, J=15.6 Hz, 1H), 6.38 (dd, J=14.7, 11.1 Hz, 1H), 6.10-6.00 (m, 1H), 5.74 (d, J=11.0 Hz, 1H), 5.72-5.68 (m, 1H), 5.65 (dd, J=14.8, 7.2 Hz, 1H), 5.59 (dd, J=15.2, 7.5 Hz, 1H), 5.40 (dd, J=15.4, 4.0 Hz, 1H), 5.25 (s, 1H) 5.22 (d, J=9.6 Hz, 1H), 4.99 (q, J=7.3 Hz, 1H), 4.39 (s, 1H), 4.23-4.12 (m, 2H), 4.05 (s, 1H), 4.02-3.96 (m, 1H), 3.88 (d, J=12.0 Hz, 1H), 2.77 (dt, J=13.7, 6.9 Hz, 1H), 2.52 (td, J=6.7, 2.6 Hz, 2H), 2.49-2.44 (m, 2H), 2.04-1.94 (m, 3H), 1.87-1.80 (m, 1H), 1.79 (s, 3H), 1.73-1.68 (m, 6H), 1.67-1.59 (m, 1H), 1.45 (d, J=14.2 Hz, 1H), 0.92 (d, J=6.6 Hz, 3H), 0.88 (d, J=7.1 Hz, 3H). $^{13}$C-NMR (126 MHz, CDCl$_3$) δ [ppm] 164.31, 156.17, 144.89, 139.45, 137.17, 130.76, 130.34, 129.52, 129.47, 128.28, 126.32, 126.16, 125.47, 121.78, 80.60, 78.96, 74.53, 74.09, 70.47, 69.85, 62.70, 56.99, 47.97, 39.58, 30.63, 30.58, 30.23, 21.12, 20.52, 19.56, 18.07, 17.13, 11.36. LRMS (ESI-Quad) [m/z]: 552.4 [M+H]$^+$, HRMS (ESI-IT) [m/z]: 552.332174, calculated 552.331965 for $C_{33}H_{46}NO_6$ [M+H]$^+$, err [ppm] 0.038.

1.1.1.4 Synthesis of 16-Amino-Ratjadones Bearing Terminal Alkynes and Cyclooctynes Attached Via Intracellular Cleavable Val-Cit Linker Scheme 4: Synthesis of Homopropargyl-O(CO)HN-Val-Cit-PABO(CO)NH-Ratja 34 and BCN-O(CO)HN-Val-Cit-PABO(CO)NH-Ratja 31.

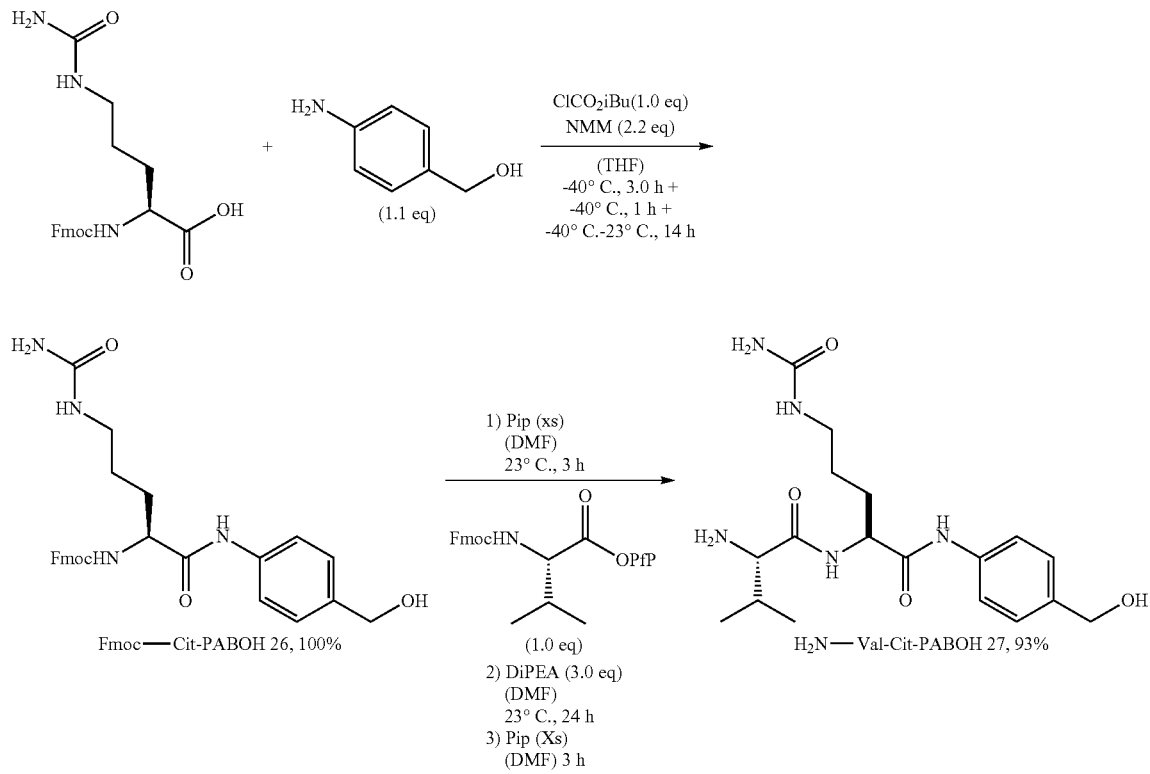

-continued
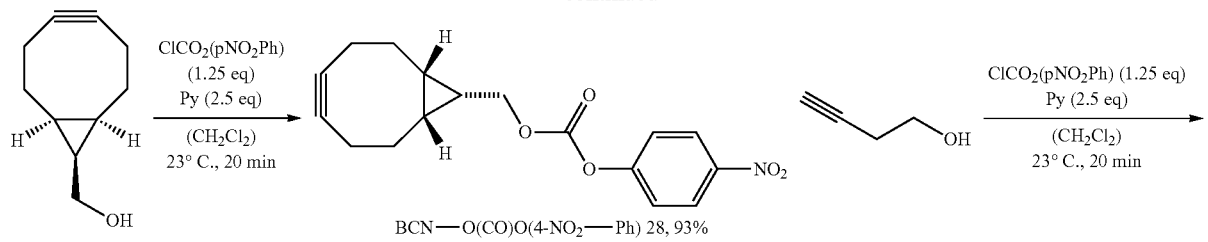
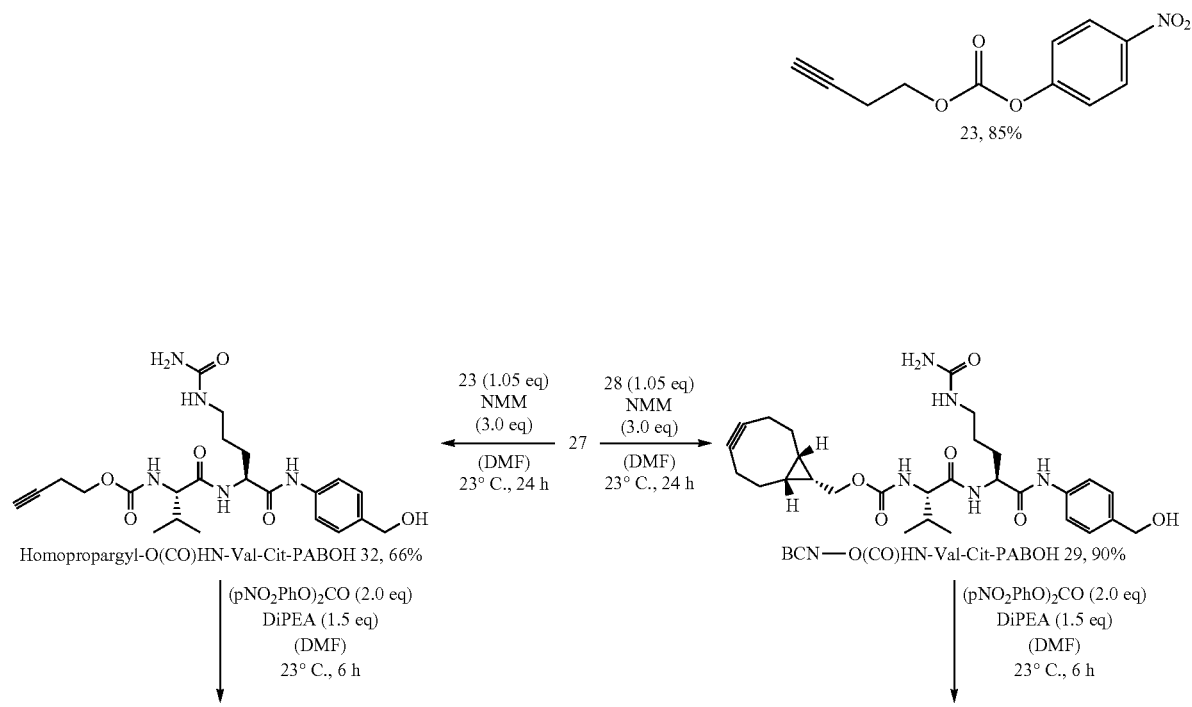
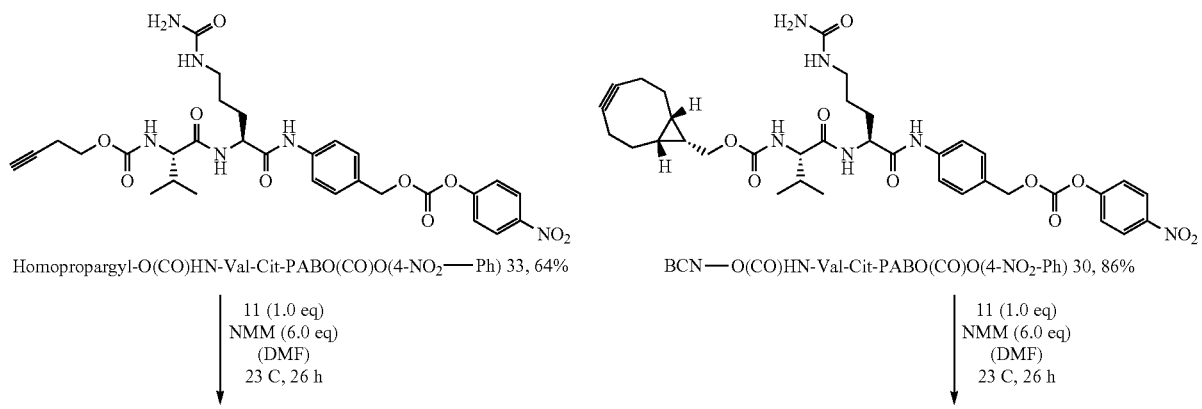

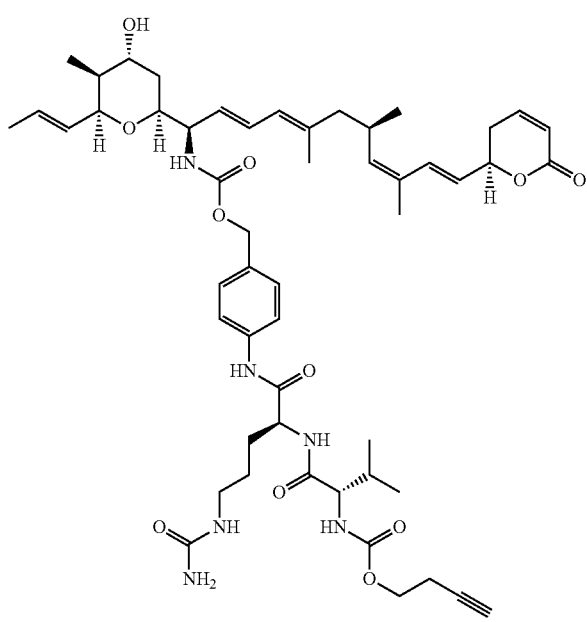

Homopropargyl-O(CO)HN-Val-Cit-PABO(CO)NH-Ratja 34, 66%

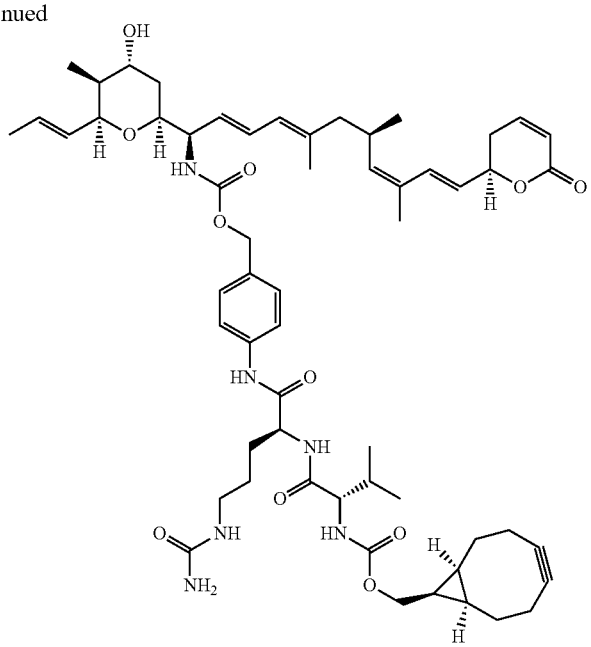

BCN—O(CO)HN-Val-Cit-PABO(CO)NH-Ratja 31, 76%

Synthesis of Fmoc-Cit-PABOH (26)—(9H-fluoren-9-yl)methyl (S)-(1-((4-(hydroxymethyl)phenyl)amino)-1-oxo-5-ureidopentan-2-yl)carbamate[61]

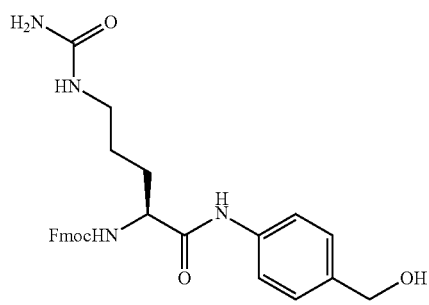

Chemical Formula: $C_{28}H_{30}N_4O_5$
Molecular Weight: 502,57
Fmoc-Cit-PABOH

To a solution of 1.0 g (2.516 mmol, 1.0 eq) Fmoc-Cit-OH in 20 mL dry THF maintained under an argon atm. at −40° C. were added 304 μL (2.768 mmol, 1.1 eq) NMM and 358 μL (2.768 mmol, 1.1 eq) iso-butylchloroformate. The mixture was stirred for 3 h at −40° C. before further 332 μL (3.019 mmol, 1.2 eq) NMM and 372 mg (3.019 mmol, 1.2 eq) para-aminobenzylalcohol were added. The mixture was stirred for an additional 1 h at −40° C. and then allowed to warm to 23° C. over a period of 20 h. The reaction mixture was concentrated under reduced pressure and the solid residue was purified by flash chromatography through silicagel ($CH_2Cl_2$:MeOH/95:5-9:1-8:2) yielding 1.264 g (2.515 mmol, 100%) Fmoc-Cit-PABOH 26 as an amorphous pale-yellow solid.

Fmoc-Cit-PABOH (26):[5] TCL ($CH_2Cl_2$:MeOH/95:5) $R_f$: 0.10 [$UV^{254}$, CAM], IR (ATR) [$cm^{-1}$]: 3280, 3128, 3063, 2923, 2864, 1689, 1653, 1600, 1568, 1532, 1478, 1450, 1414, 1387, 1334, 1281, 12551, 1231, 1164, 1153, 1116, 1103, 1085, 1044, 1033, 1016, 989, 938, 823, 797, 778, 756, 737, 701, 674, 662, 640, 610. $^1$H-NMR (500 MHz, DMSO-$d_6$) δ [ppm]: 9.98 (s, 1H), 7.89 (d, J=7.5 Hz, 2H), 7.75 (t, J=6.5 Hz, 2H), 7.67 (d, J=8.0 Hz, 1H), 7.56 (d, J=8.4 Hz, 2H), 7.42 (t, J=7.4 Hz, 2H), 7.33 (q, J=6.8 Hz, 2H), 7.24 (d, J=8.4 Hz, 2H), 5.99 (t, J=5.5 Hz, 1H), 5.43 (s, 2H), 5.10 (t, J=5.7 Hz, 1H), 4.43 (d, J=5.6 Hz, 2H), 4.30-4.25 (m, 2H), 4.25-4.20 (m, 1H), 4.20-4.13 (m, 1H), 3.11-2.99 (m, 1H), 3.01-2.87 (m, 1H), 1.74-1.63 (m, 2H), 1.65-1.54 (m, 2H), 1.53-1.44 (m, 2H), 1.43-1.34 (m, 2H). $^{13}$C-NMR (126 MHz, DMSO-$d_6$) δ [ppm]: 170.98, 158.90, 156.10, 143.88, 143.79, 140.70, 137.57, 137.39, 127.64, 127.64, 127.08, 127.06, 126.91, 125.36, 120.10, 120.10, 118.85, 66.05, 65.67, 62.60, 55.03, 54.95, 46.66, 46.07, 29.34, 26.93. LRMS (ESI-Quad) [m/z]: 503.3[M+H]$^+$, HRMS (ESI-IT) [m/z]: 503.2294, calculated 503.2289 for $C_{28}H_{31}N_4O_5$ [M+H]$^+$, err [ppm] −1.00.

[5] The obtained analytic data were in completed accordance with prior published ones.[61]

Synthesis of H$_2$N-Val-Cit-PABOH (27)—(S)-2-((S)-2-amino-3-methylbutanamido)-N-(4-(hydroxymethyl)phenyl)-5-ureidopentanamide

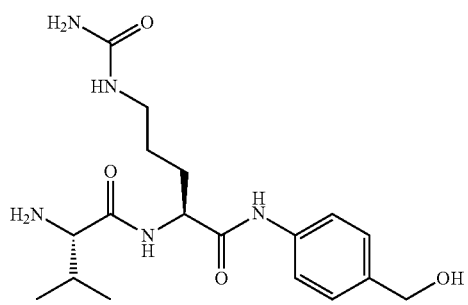

Chemical Formula: $C_{18}H_{29}N_5O_4$
Molecular Weight: 379,46
H$_2$N-Val-Cit-PABOH To a solution of 100 mg (0.199 mmol, 1.0 eq) Fmoc-Cit-PABOH 26 in 3.9 mL dry DMF was added 318 µL (1.6 mL/mmol 26) piperidine and the mixture was stirred for 3 h at 23° C. (TCL (CH$_2$Cl$_2$:MeOH/9:1) R$_f$: 0.05 [Nin]), before the mixture was diluted with 10 mL toluene, concentrated under reduced pressure and co-evaporated three times with 10 mL toluene. The raw solid H$_2$N-Cit-PABOH was re-dissolved in 900 µL dry DMF and added together with 142 µL (0.7956 mmol, 4.0 eq) DiPEA to a solution of 101 mg (0.199 mmol, 1.0 eq) Fmoc-Val-OPfp in 900 µL dry DMF at 23° C. The mixture was stirred for 24 h at 23° C. (TCL (CH$_2$Cl$_2$:MeOH/8:2) R$_f$: 0.15 [UV$^{254}$, CAM]), before 318 µL (1.6 mL/mmol 26) piperidine was added and the mixture was stirred for 1 h at 23° C. The mixture was diluted with 10 mL toluene, concentrated under reduced pressure and co-evaporated three times with 10 mL toluene. The resulting residue was purified by flash chromatography through silicagel (CH$_2$Cl$_2$:MeOH/1:0-95:5-9:1-8:2) yielding 70 mg (0.185 mmol, 93%) H$_2$N-Val-Cit-PABOH 27 as an amorphous, pale-yellow solid.

H$_2$N-Val-Cit-PABOH (27): TCL (CH$_2$Cl$_2$:MeOH/8:2) R$_f$: 0.05 [UV$^{254}$, CAM], $^1$H-NMR (500 MHz, MeOD-d$_4$) δ [ppm]: 7.54 (d, J=8.6 Hz, 2H), 7.30 (d, J=8.7 Hz, 2H), 4.56 (s, 2H), 4.58-4.51 (m, 1H), 3.27 (d, J=5.6 Hz, 1H), 3.21 (dt, J=13.8, 7.0 Hz, 1H), 3.16-3.08 (m, 1H), 2.08-1.96 (m, 1H), 1.94-1.84 (m, 1H), 1.83-1.68 (m, 2H), 1.69-1.50 (m, 2H), 1.00 (d, J=6.9 Hz, 3H), 0.94 (d, J=6.8 Hz, 3H). $^{13}$C-NMR (126 MHz, MeOD-d$_4$) δ [ppm]: 175.88, 172.35, 162.33, 138.74, 138.65, 128.60, 121.20, 64.82, 61.19, 54.83, 33.19, 30.68, 27.86, 19.68, 17.78. LRMS (ESI-Quad) [m/z]: 380.3 [M+H]$^+$, HRMS (ESI-IT) [m/z]: 380.229231, calculated 380.229231 for C$_{18}$H$_{30}$N$_5$O$_4$ [M+H]$^+$, err [ppm] −0.071.

Synthesis of BCN—O(CO)O(4-NO$_2$-Ph) (28)—((1R,8S,9s)-bicyclo[6.1.0]non-4-yn-9-yl)methyl (4-nitrophenyl) carbonate

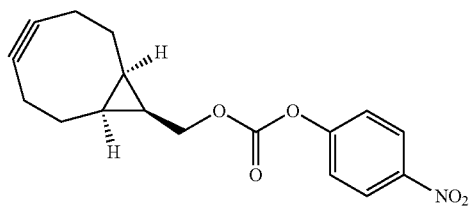

28

Chemical Formula: C$_{17}$H$_{17}$NO$_5$
Molecular Weight: 315,33
BCN—O(CO)O(4-NO$_2$—Ph)

To a solution of 100 mg (0.666 mmol, 1.0 eq) ((1R,8S,9S)-bicyclo[6.1.0]non-4-yn-9-yl)methanol in 16.6 mL dry CH$_2$Cl$_2$ was added 134 µL (1.664 mmol, 2.5 eq) pyridine and 168 mg (0.831 mmol, 1.25 eq) 4-nitrophenyl chloroformate and the mixture was stirred for 20 min at 23° C., before it was quenched by addition of 20 mL saturated ammonium chloride solution. The mixture was extracted with CH$_2$Cl$_2$ (3×20 mL), the combined organic layers were dried over Na$_2$SO$_4$ and concentrated under reduced pressure. The residue was purified by flash chromatography through silicagel (PE:EtOAc/95:5-9:1) yielding 196 mg (0.6215 mmol, 93%) of 28 as a highly viscous liquid, slowly solidifying giving an amorphous white solid.

BCN—O(CO)O(4-NO$_2$-Ph) (28): TCL (PE:EtOAc/9:1) R$_f$: 0.50 [UV$^{254}$, CAM], IR (ATR) [cm$^{-1}$]: 2918, 2852, 1760, 1616, 1595, 1523, 1492, 1470, 1440, 1354, 1340, 1323, 1247, 1203, 1164, 1139, 1108, 1056, 1027, 1013, 989, 944, 921, 859, 817, 776, 733, 703, 670, 628. $^1$H-NMR (700 MHz, CDCl$_3$) δ [ppm]: 8.29-8.24 (m, 2H), 7.44-7.35 (m, 2H), 4.38 (d, J=8.3 Hz, 2H), 2.36-2.26 (m, 4H), 2.25-2.19 (m, 2H), 1.64-1.54 (m, 2H), 1.49 (p, J=8.6 Hz, 1H), 1.09-0.99 (m, 2H). $^{13}$C-NMR (176 MHz, CDCl$_3$) δ [ppm]: 155.73, 152.70, 145.49, 125.45, 121.91, 98.85, 68.16, 29.18, 21.50, 20.65, 17.38.

Synthesis of BCN—O(CO)HN-Val-Cit-PABOH (29)—(S)-2-((S)-2-amino-3-methylbutanamido)-N-(4-(hydroxymethyl)phenyl)-5-ureidopentanamide

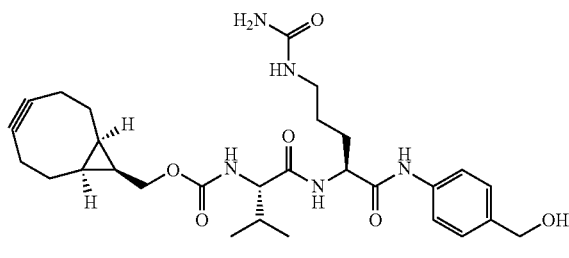

29

Chemical Formula: C$_{29}$H$_{41}$N$_5$O$_6$
Molecular Weight: 555,68

BCN—O(CO)HN-Val-Cit-PABOH

To a solution of 100 mg (0.264 mmol, 1.0 eq) H$_2$N-Val-Cit-PABOH 27 in 2.65 mL dry DMF was added 87 µL (0.791 mmol, 3.0 eq) NMM and a solution of 87 mg (0.277 mmol, 1.05 eq) BCN—O(CO)O(4-NO$_2$-Ph) 28 in 2.65 mL dry DMF and the mixture was stirred for 24 h at 23° C., before the reaction was quenched by addition of 50 mL saturated ammonium chloride solution. The mixture was extracted with EtOAc (3×20 mL). The combined organic layers were dried over Na$_2$SO$_4$, concentrated under reduced pressure and co-evaporated twice with 10 mL toluene. The resulting solid residue was purified by flash chromatography through silicagel (CH$_2$Cl$_2$:MeOH/95:5-9:1-8:2) yielding 132 mg (0.238 mmol, 90%) BCN—O(CO)HN-Val-Cit-PABOH 29 as an amorphous, white solid.

BCN—O(CO)HN-Val-Cit-PABOH (29): TCL (CH$_2$Cl$_2$:MeOH/9:1) R$_f$: 0.21 [UV$^{254}$, CAM], IR (ATR) [cm$^{-1}$]: 3444, 3271, 2925, 2853, 2604, 2468, 1694, 1637, 1516, 1439, 1417, 1381, 1335, 1301, 1238, 1172, 1139, 1120, 1090, 1027, 911, 864, 825, 770, 734, 696, 670, 582, 554. $^1$H-NMR (500 MHz, MeOD-d$_4$) δ [ppm]: 7.56 (d, J=8.4 Hz, 2H), 7.30 (d, J=8.7 Hz, 2H), 4.56 (s, 2H), 4.52 (dd, J=8.9, 5.1 Hz, 1H), 4.17 (dd, J=8.1, 1.5 Hz, 2H), 3.95 (d, J=6.8 Hz, 1H), 3.20 (dt, J=13.8, 7.0 Hz, 1H), 3.11 (dt, J=13.5, 6.7 Hz, 1H), 2.33-2.19 (m, 3H), 2.19-2.10 (m, 2H), 2.10-2.03 (m, 1H), 1.92 (td, J=14.3, 6.1 Hz, 1H), 1.75 (ddp, J=14.1, 9.7, 4.9 Hz, 1H), 1.58 (dtd, J=16.1, 10.9, 9.8, 6.8 Hz, 4H), 1.40 (p, J=8.4 Hz, 1H), 0.99 (d, J=6.8 Hz, 3H), 0.96 (d, J=6.8 Hz, 2H). $^{13}$C-NMR (126 MHz, MeOD-d$_4$) δ [ppm]: 174.50, 172.14, 162.31, 159.17, 138.74, 128.57, 121.20, 120.41, 99.47, 64.83, 64.15, 62.30, 54.87, 40.30, 31.83, 30.50, 30.13, 27.84, 21.92, 21.42, 19.79, 18.92, 18.66. LRMS (ESI-Quad) [m/z]: 556.4 [M+H]$^+$, HRMS (ESI-IT) [m/z]: 556.313070, calculated 556.312961 for C$_{29}$H$_{42}$N$_5$O$_6$ [M+H]$^+$, err [ppm] −0.197.

Synthesis of BCN—O(CO)HN-Val-Cit-PABO(CO)O(4-NO$_2$-Ph) (30)—((1R,8S,9s)-bicyclo[6.1.0]non-4-yn-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate

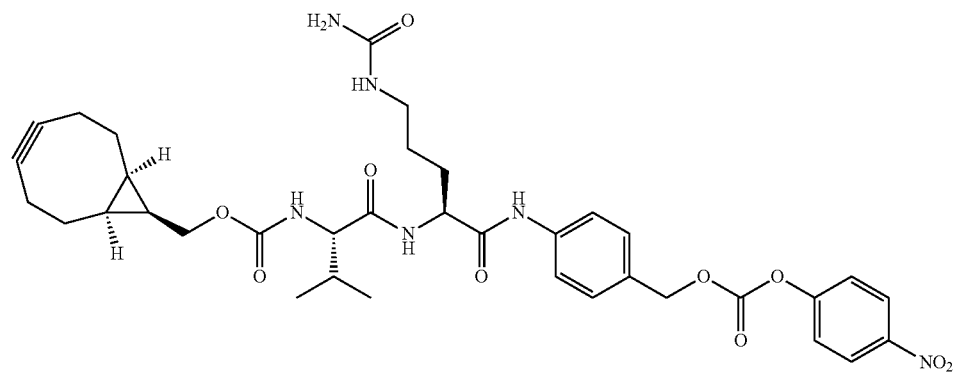

Chemical Formula: C$_{36}$H$_{44}$N$_6$O$_{10}$
Molecular Weight: 720,78
BCN—O(CO)HN-Val-Cit-PABO(CO)O(4-NO$_2$—Ph)

To a solution of 70 mg (0.126 mmol, 1.0 eq) BCN—O(CO)HN-Val-Cit-PABOH 29 in 420 μL dry DMF was added 32 μL (0.189 mmol, 1.5 eq) DiPEA and 77 mg (0.252 mmol, 2.0 eq) bis-4-nitrophenyl carbonate and the mixture was stirred for 16 h at 23° C. The reaction mixture was diluted with 300 μL CH$_2$Cl$_2$ and directly purified by flash chromatography through silicagel (CH$_2$Cl$_2$: MeOH/95:5), yielding 78.1 mg (0.108 mmol, 86%) of BCN—O(CO)HN-Val-Cit-PABO(CO)O(4-NO$_2$-Ph) 30 as an amorphous, white solid.

BCN—O(CO)HN-Val-Cit-PABO(CO)O(4-NO$_2$-Ph) (30): TCL (CH$_2$Cl$_2$:MeOH/9:1) R$_f$: 0.62 [UV$^{254}$], $^1$H-NMR (500 MHz, MeOD-d$_4$) δ [ppm]: 8.33-8.26 (m, 2H), 7.68-7.60 (m, 2H), 7.50-7.43 (m, 2H), 7.43 (s, 2H), 5.26 (s, 2H), 4.54 (dt, J=9.1, 3.9 Hz, 1H), 4.17 (dd, J=8.1, 6.2 Hz, 2H), 3.95 (d, J=6.8 Hz, 1H), 3.20 (dq, J=15.0, 8.1, 7.5 Hz, 1H), 3.11 (dt, J=13.5, 6.6 Hz, 1H), 2.29-2.00 (m, 7H), 1.98-1.86 (m, OH), 1.75 (dqd, J=14.2, 9.3, 4.9 Hz, 1H), 1.67-1.49 (m, 4H), 1.39 (p, J=8.6 Hz, 1H), 0.99 (d, J=6.8 Hz, 3H), 0.96 (d, J=6.8 Hz, 3H), 0.94-0.89 (m, 1H). $^{13}$C-NMR (126 MHz, MeOD-d$_4$) δ [ppm]: 202.71, 200.46, 190.48, 187.35, 185.31, 182.15, 175.05, 168.38, 160.13, 158.69, 154.41, 151.45, 149.34, 127.64, 99.74, 92.31, 90.51, 83.05, 68.43, 59.97, 58.59, 58.31, 58.28, 56.02, 50.08, 49.57, 47.95, 47.07, 46.85. LRMS (ESI-Quad) [m/z]: 721.4 [M+H]$^+$, HRMS (ESI-IT) [m/z]: 721.3198819, calculated 721.319168 for C$_{36}$H$_{45}$N$_6$O$_{10}$ [M+H]$^+$, err [ppm] −0.903.

Synthesis of BCN—O(CO)HN-Val-Cit-PABO(CO)NH-Ratja (31)—((1R,8S,9s)-bicyclo[6.1.0]non-4-yn-9-yl)methyl ((S)-1-(((S)-1-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamate

31

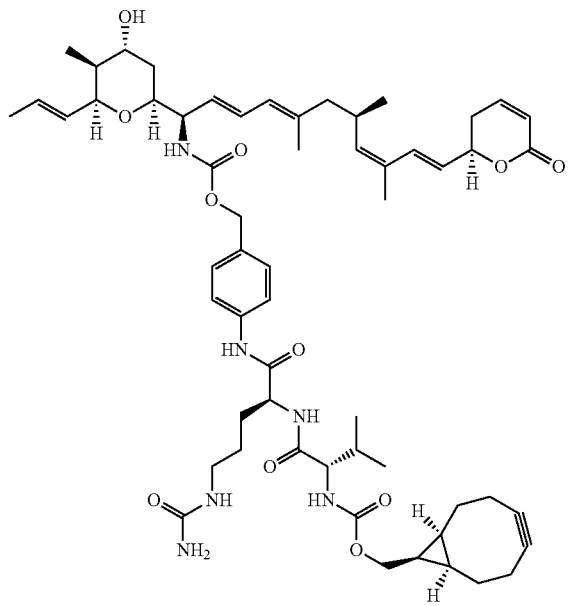

Chemical Formula: $C_{58}H_{80}N_6O_{11}$
Molecular Weight: 1037,31
BCN—O(CO)HN-Val-Cit-PABO(CO)NH-Ratja To a solution of 16.2 mg (35.48 µmol, 1.0 eq) 16R-Amino-Ratjadone 11 in 237 µL dry DMF were added 23.4 µL (0.212 mmol, 6.0 eq) NMM and 28.1 mg (39.03 µmol, 1.1 eq) BCN—O(CO)O(4-$NO_2$-Ph) 28 and the mixture was stirred for 26 h at 23° C. The reaction mixture was diluted with 1.0 mL $CH_2Cl_2$ and directly purified by preparative thin-layer chromatography ($CH_2Cl_2$:MeOH/95:5, 3× Development), yielding 28.0 mg (26.99 µmol, 76%) of BCN—O(CO)HN-Val-Cit-PABO(CO)NH-Ratja 31 as an amorphous, white solid.

BCN—O(CO)HN-Val-Cit-PABO(CO)NH-Ratja (31): TCL ($CH_2Cl_2$:MeOH/95:5) $R_f$: 0.21 [$UV^{254}$, CAM], IR (ATR) [$cm^{-1}$]: 3316, 2963, 2927, 1697, 1657, 1609, 1517, 1451, 1415, 1381, 1311, 1248, 1141, 1057, 1018, 967, 912, 819, 777, 732, 656. $^1$H-NMR (700 MHz, $CDCl_3$) δ [ppm] 9.24 (s, 1H), 7.57-7.47 (m, 2H), 7.24 (d, J=7.2 Hz, 2H), 6.91 (s, 1H), 6.71 (d, J=15.4 Hz, 1H), 6.43-6.30 (m, 1H), 6.06 (d, J=9.5 Hz, 1H), 5.77 (d, J=10.8 Hz, 1H), 5.69 (dd, J=15.7, 6.8 Hz, 1H), 5.67-5.55 (m, 3H), 5.39 (dd, J=15.4, 4.6 Hz, 1H), 5.23 (d, J=9.1 Hz, 1H), 5.01 (dq, J=29.5, 13.4, 11.7 Hz, 3H), 4.69 (s, 1H), 4.33 (s, 1H), 4.20-4.12 (m, 1H), 4.08 (s, 2H), 3.92 (s, 1H), 3.88 (d, J=11.7 Hz, 1H), 3.26 (s, 1H), 3.09 (s, 1H), 2.79 (s, 1H), 2.48 (d, J=5.8 Hz, 2H), 2.30-2.13 (m, 7H), 2.13-2.06 (m, 1H), 2.03-1.94 (m, 2H), 1.92-1.83 (m, 1H), 1.78 (s, 3H), 1.72-1.58 (m, 10H), 1.51 (s, 4H), 1.40-1.27 (m, 3H), 0.95 (d, J=5.9 Hz, 3H), 0.92 (d, J=6.5 Hz, 9H), 0.83 (d, J=7.1 Hz, 3H). $^{13}$C-NMR (176 MHz, $CDCl_3$) δ [ppm]: 172.47, 170.40, 164.57, 161.98, 161.76, 160.52, 157.27, 155.96, 145.30, 139.64, 137.87, 137.40, 132.91, 130.83, 130.44, 129.74, 129.35, 128.91, 127.00, 126.31, 126.11, 125.39, 121.60, 120.20, 120.10, 98.96, 78.96, 74.54, 70.18, 66.37, 63.57, 60.67, 57.03, 53.02, 48.02, 39.48, 31.24, 30.50, 30.38, 30.18, 29.14, 21.55, 21.10, 20.51, 20.31, 19.45, 18.10, 18.05, 17.78, 17.07, 11.31. LRMS (ESI-Quad) [m/z]: 1038.5 [M+H]$^+$, HRMS (ESI-IT) [m/z]: 1037.5958, calculated 1037.5958 for $C_{58}H_{80}N_6O_{11}$ [M+H]$^+$, err [ppm] 0.0.

Synthesis of Homopropargyl-O(CO)HN-Val-Cit-PABOH (32)—But-3-yn-1-yl ((S)-1-(((S)-1-((4-(hydroxymethyl)phenyl)amino)-1-oxo-5-ureidopentan-2-yl)amino)-3-methyl-1-oxobutan-2-yl)carbamate

32

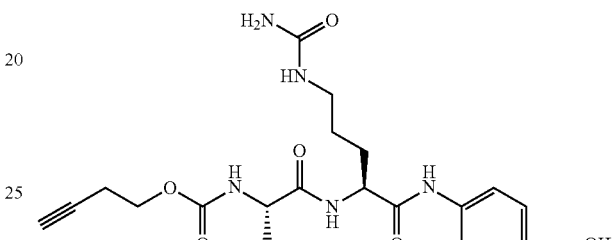

Chemical Formula: $C_{23}H_{33}N_5O_6$
Molecular Weight: 475,55
Homopropargyl-O(CO)HN-Val-Cit-PABOH To a solution of 495 mg (1.304 mmol, 1.0 eq) $H_2$N-Val-Cit-PABOH 27 in 13 mL dry DMF was added 430 µL (3.913 mmol, 3.0 eq) NMM and a solution of 310 mg (1.318 mmol, 1.01 eq) but-3-yn-1-yl (4-nitrophenyl) carbonate 23 in 2.65 mL dry DMF and the mixture was stirred for 16 h at 23° C., before the reaction was quenched by addition of 220 mL saturated ammonium chloride solution. The mixture was extracted with EtOAc (3×220 mL). The combined organic layers were dried over $Na_2SO_4$, concentrated under reduced pressure and co-evaporated twice with 60 mL toluene. The resulting solid residue was purified by flash chromatography through silicagel ($CH_2Cl_2$:MeOH/95:5-8:2-1:1) yielding 409.2 mg (0.861 mmol, 66%) Homopropargyl-O(CO)HN-Val-Cit-PABOH 32 as an amorphous, white solid.

Homopropargyl-O(CO)HN-Val-Cit-PABOH (32): TCL ($CH_2Cl_2$:MeOH/9:1) $R_f$: 0.17 [$UV^{254}$, CAM], IR (ATR) [$cm^{-1}$]: 3267, 2960, 2925, 2871, 1690, 1639, 1602, 1535, 1465, 1445, 1415, 1386, 1339, 1295, 1248, 1184, 1136, 1117, 1094, 1075, 1035, 1015, 924, 823, 803, 774, 697, 661, 651, 606. $^1$H-NMR (500 MHz, DMSO-$d_6$) δ [ppm]: 9.96 (s, 1H), 8.06 (d, J=7.6 Hz, 1H), 7.54 (d, J=8.5 Hz, 2H), 7.23 (d, J=8.6 Hz, 3H), 5.99 (t, J=5.6 Hz, 2H), 5.41 (s, 2H), 5.09 (t, J=5.7 Hz, 1H), 4.42 (d, J=5.6 Hz, 3H), 4.43-4.36 (m, 1H), 4.08-3.96 (m, 3H), 3.89 (dd, J=8.6, 7.0 Hz, 1H), 3.01 (dt, J=13.0, 6.5 Hz, 1H), 2.94 (dq, J=13.0, 6.4 Hz, 1H), 2.86 (t, J=2.6 Hz, 1H), 2.47 (dt, J=6.6, 3.4 Hz, 3H), 1.97 (dq, J=13.5, 6.7 Hz, 1H), 1.77-1.63 (m, 1H), 1.58 (dtd, J=13.5, 9.5, 4.8 Hz, 2H), 1.51-1.27 (m, 4H), 0.87 (d, J=6.8 Hz, 3H), 0.83 (d, J=6.8 Hz, 3H). $^{13}$C-NMR (126 MHz, MeOD-$d_4$) δ [ppm]: 171.13, 170.38, 158.85, 155.94, 137.50, 137.43, 126.92, 118.84, 81.16, 72.48, 62.58, 62.10, 60.07, 53.04, 39.52, 39.35, 39.19, 39.02, 38.57, 30.38, 29.50, 26.77, 19.19, 18.78, 18.18. LRMS (ESI-Quad) [m/z]: 476.3 [M+H]$^+$, HRMS (ESI-IT) [m/z]: 476.250842, calculated 476.250360 for $C_{23}H_{34}N_5O_6$ [M+H]$^+$, err [ppm] −1.012

Synthesis of Homopropargyl-O(CO)HN-Val-Cit-PABO(CO)O(4-NO$_2$-Ph) (33)—But-3-yn-1-yl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate

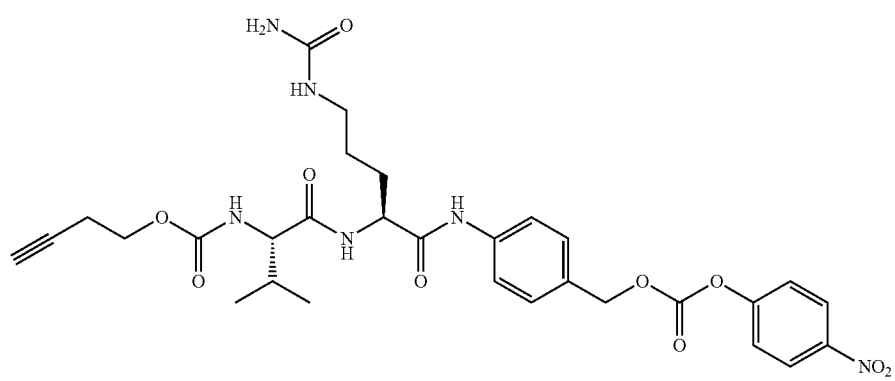

33

Chemical Formula: C$_{30}$H$_{36}$N$_6$O$_{10}$
Molecular Weight: 640,65
Homopropargyl-O(CO)HN-Val-Cit-PABO(CO)O(4-NO$_2$—Ph)

To a solution of 50 mg (0.105 mmol, 1.0 eq) Homopropargyl-O(CO)HN-Val-Cit-PABOH 32 in 350 µL dry DMF was added 27 µL (0.158 mmol, 1.5 eq) DiPEA and 63.5 mg (0.210, 2.0 eq) bis-4-nitrophenyl carbonate and the mixture was stirred for 6 h at 23° C. The reaction mixture was diluted with 300 µL CH$_2$Cl$_2$ and directly purified by flash chromatography through silicagel (CH$_2$Cl$_2$: MeOH/95:5), yielding 43 mg (0.067 mmol, 64%) of Homopropargyl-O(CO)HN-Val-Cit-PABO(CO)O(4-NO$_2$-Ph) 33 as an amorphous, pale-yellow solid.

Homopropargyl-O(CO)HN-Val-Cit-PABO(CO)O(4-NO$_2$-Ph) (33): TCL (CH$_2$Cl$_2$:MeOH/95:5) R$_f$: 0.32 [UV$^{254}$], $^1$H-NMR (700 MHz, DMSO-d$_6$) δ [ppm]: 10.12 (s, 1H), 8.38-8.23 (m, 2H), 8.11 (dd, J=15.3, 8.3 Hz, 1H), 7.64 (d, J=8.5 Hz, 1H), 7.59-7.50 (m, 2H), 7.41 (d, J=8.6 Hz, 1H), 7.24 (d, J=8.8 Hz, 1H), 5.97 (d, J=5.1 Hz, 1H), 5.41 (s, 2H), 5.24 (s, 1H), 4.48-4.35 (m, 1H), 4.02 (tdd, J=10.5, 6.6, 3.9 Hz, 2H), 3.92-3.85 (m, 1H), 3.03 (dq, J=13.0, 6.6 Hz, 1H), 2.95 (dq, J=12.9, 6.3 Hz, 1H), 2.86 (t, J=2.5 Hz, 1H), 2.30-2.09 (m, 1H), 1.97 (dq, J=13.6, 6.8 Hz, 1H), 1.69 (dt, J=15.3, 7.7 Hz, 1H), 1.58 (dd, J=13.5, 4.8 Hz, 1H), 1.44 (ddd, J=17.4, 12.6, 7.6 Hz, 2H), 1.35 (dd, J=8.4, 4.7 Hz, 1H), 0.87 (d, J=6.8 Hz, 3H), 0.83 (d, J=6.7 Hz, 3H). $^{13}$C-NMR (176 MHz, DMSO-d$_6$) δ [ppm]: 171.17, 170.71, 158.84, 155.92, 155.26, 151.93, 145.15, 139.34, 129.47, 129.27, 126.16, 125.38, 122.60, 122.58, 119.00, 115.77, 98.93, 81.14, 72.46, 70.22, 67.60, 62.07, 60.00, 53.55, 53.10, 30.36, 29.36, 28.49, 26.77, 20.77, 19.91, 19.16, 18.76, 18.16, 18.06, 16.92, 16.72, 12.45. LRMS (ESI-Quad) [m/z]: 641.7 [M+H]$^+$.

Synthesis of Homopropargyl-O(CO)HN-Val-Cit-PABO(CO)NH-Ratja (34)—But-3-yn-1-yl ((S)-1-(((S)-1-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)-oxy)methyl)phenyl)amino)-1-oxo-5-ureidopentan-2-yl)amino)-3-methyl-1-oxobutan-2-yl)carbamate

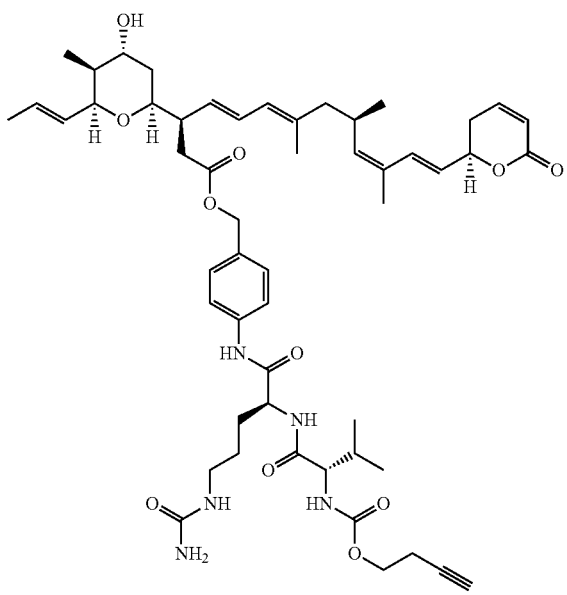

34

Chemical Formula: C$_{52}$H$_{72}$N$_6$O$_{11}$
Molecular Weight: 957,18
Homopropargyl-O(CO)HN-Val-Cit-PABO(CO)NH-Ratja To a solution of 7.0 mg (12.28 µmol, 1.0 eq) 16R-Amino-Ratjadone 11 in 123 µL dry DMF were added 8.1 µL (73.7

μmol, 6.0 eq) NMM and 8.7 mg (13.51 μmol, 1.1 eq) Homopropargyl-O(CO)O(4-NO$_2$-Ph) 33 and the mixture was stirred for 30 h at 23° C. The reaction mixture was diluted with 1.0 mL CH$_2$Cl$_2$ and directly purified by preparative thin-layer chromatography (CH$_2$Cl$_2$:MeOH: EtOAc/9:1:1, 2× Development), yielding 7.8 mg (8.104 μmol, 66%) of Homopropargyl-O(CO)HN-Val-Cit-PABO (CO)NH-Ratja 34 as an amorphous, white solid.

Homopropargyl-O(CO)HN-Val-Cit-PABO(CO)NH-Ratja (34): TCL (CH$_2$Cl$_2$:MeOH/9:1) R$_f$: 0.49 [UV$^{254}$, CAM], $^1$H-NMR (700 MHz, MeOD-d$^4$) δ [ppm]7.57 (dd, J=8.8, 2.2 Hz, 2H), 7.36-7.25 (m, 2H), 7.02 (ddd, J=9.8, 5.6, 2.8 Hz, 1H), 6.78 (d, J=15.7 Hz, 1H), 6.37 (dd, J=15.2, 10.8 Hz, 1H), 6.01 (ddd, J=9.8, 2.5, 1.2 Hz, 1H), 5.77 (d, J=10.9 Hz, 1H), 5.74 (dd, J=15.6, 6.4 Hz, 1H), 5.67 (ddd, J=15.4, 6.5, 1.5 Hz, 1H), 5.59 (dd, J=15.2, 6.9 Hz, 1H), 5.42 (ddd, J=15.4, 5.6, 1.7 Hz, 1H), 5.22 (d, J=9.8 Hz, 1H), 5.10-5.06 (m, 1H), 5.05 (s, 2H), 4.51 (dd, J=9.1, 5.2 Hz, 1H), 4.33 (ddt, J=5.7, 2.8, 1.5 Hz, 1H), 4.18-4.08 (m, 3H), 3.96 (d, J=6.8 Hz, 1H), 3.86 (q, J=3.0 Hz, 1H), 3.78 (dd, J=12.4, 5.5 Hz, 1H), 3.23-3.16 (m, 1H), 3.11 (dt, J=13.4, 6.7 Hz, 1H), 2.89 (dt, J=16.0, 6.9 Hz, 1H), 2.57-2.53 (m, OH), 2.52 (td, J=6.7, 2.5 Hz, 3H), 2.45 (ddt, J=18.5, 10.7, 2.7 Hz, 1H), 2.31 (t, J=2.7 Hz, 1H), 2.11-2.03 (m, 2H), 1.99 (dd, J=13.3, 8.1 Hz, 1H), 1.94-1.87 (m, 2H), 1.79 (d, J=1.3 Hz, 2H), 1.78-1.74 (m, 1H), 1.71 (s, 2H), 1.69 (dt, J=6.5, 1.5 Hz, 3H), 1.65-1.53 (m, 6H), 1.43 (d, J=14.3 Hz, 1H), 0.98 (d, J=6.8 Hz, 3H), 0.95 (d, J=6.9 Hz, 3H), 0.94 (d, J=6.6 Hz, 3H), 0.90 (t, J=7.1 Hz, OH), 0.84 (d, J=7.2 Hz, 3H). $^{13}$C-NMR (176 MHz, MeOD-d$^4$) δ [ppm]: $^{13}$C NMR (176 MHz, MeOD) δ 174.33, 172.24, 166.71, 162.31, 158.58, 158.30, 147.99, 139.98, 139.32, 138.01, 134.36, 131.81, 131.25, 130.90, 129.51, 128.92, 127.27, 127.08, 126.87, 126.24, 123.27, 121.51, 121.09, 81.09, 80.04, 75.72, 71.07, 70.91, 67.06, 64.21, 62.15, 58.17, 54.94, 40.39, 31.92, 31.56, 30.92, 30.74, 30.46, 30.09, 29.53, 27.84, 21.72, 21.42, 20.60, 19.98, 19.77, 18.59, 18.07, 17.05, 11.55. LRMS (ESI-Quad) [m/z]: 958.2 [M+H]$^+$, HRMS (ESI-IT) [m/z]: 957.532547, calculated 957.533184 for C$_{52}$H$_{72}$N$_6$O$_{11}$ [M+H]$^+$, err [ppm] 0.662.

1.1.1.5 Synthesis of 16-Amino-Ratjadones Bearing Terminal Alkynes and Cyclooctynes Attached Via Intracellular Cleavable Disulfide Linker Scheme 5: Synthesis of 2-PySS(CH$_2$)$_2$(CO)NH-Ratja 35 and HCC(CH$_2$)$_2$(CO)-NH-(CH$_2$)$_2$SS(CH$_2$)$_2$(CO)-NH-Ratja 39.

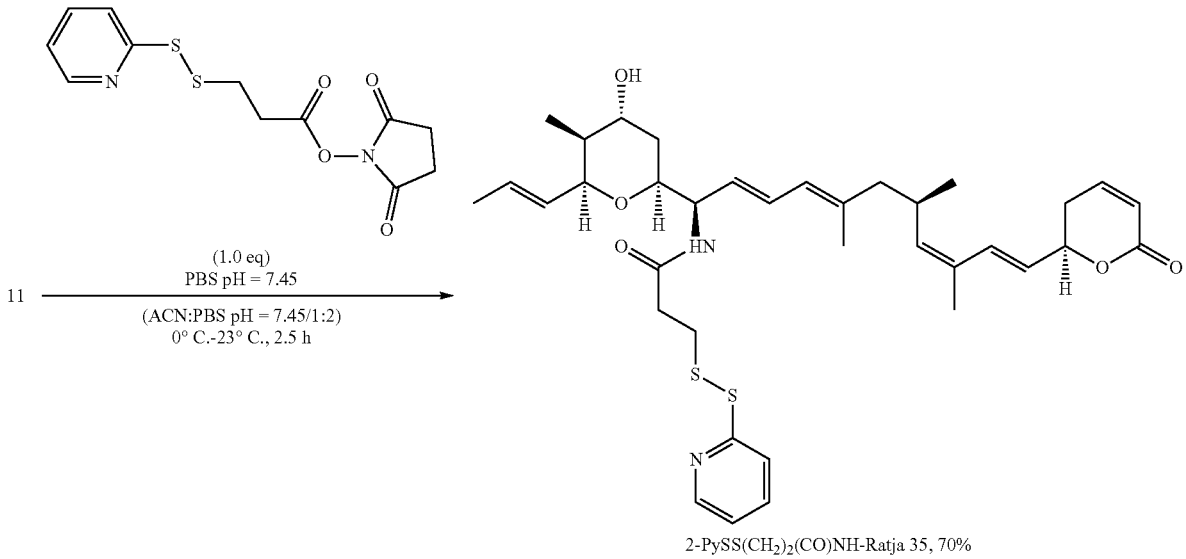

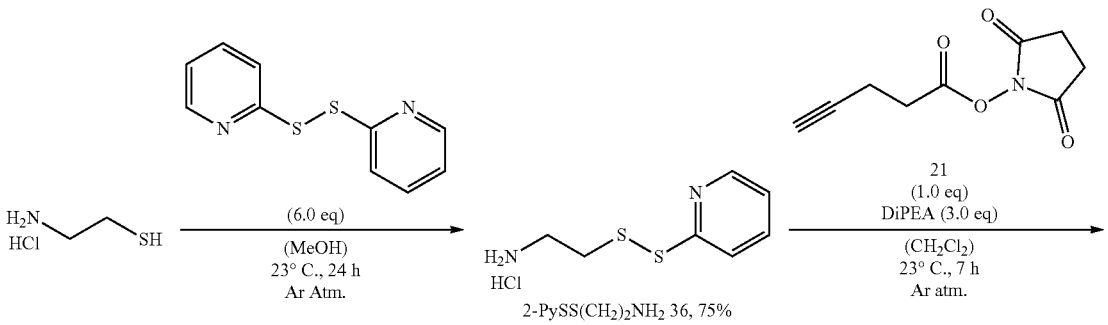

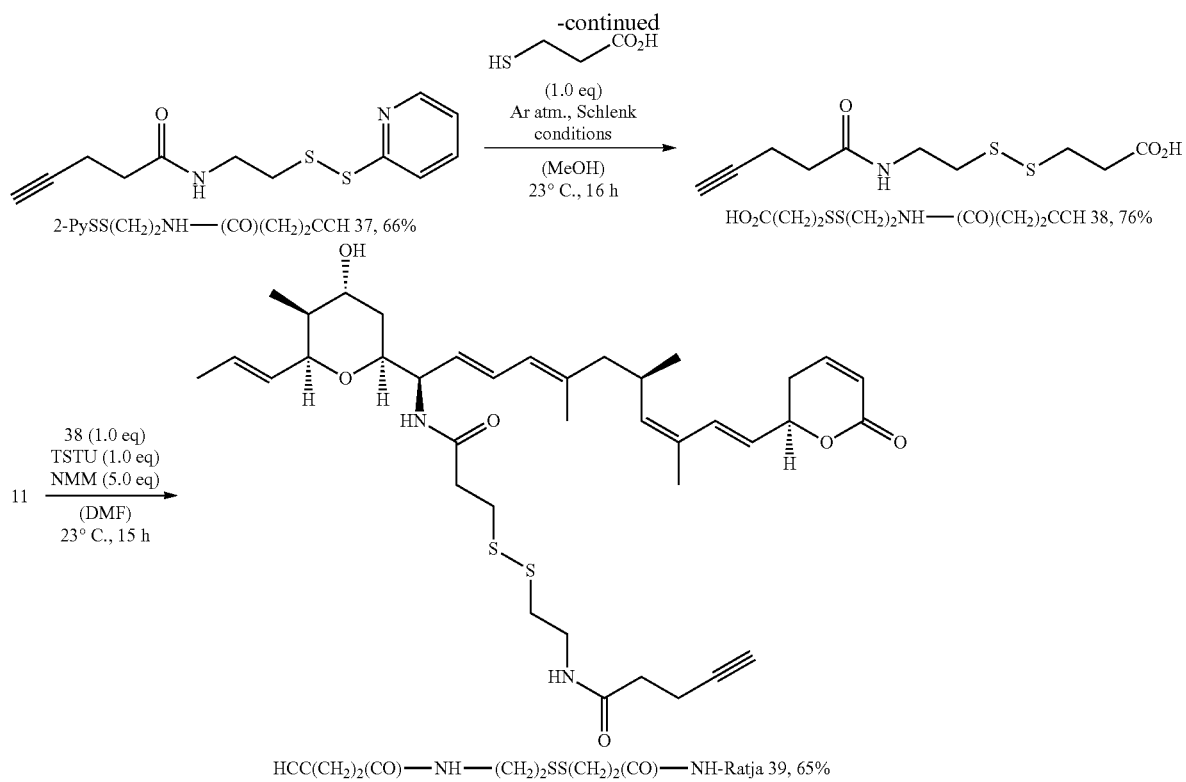

Synthesis of 2-PySS(CH$_2$)$_2$(CO)NH-Ratja (35)—N-((1R,2E,4E,7R,8Z,10E)-1-((2S,4R,5S,6S)-4-Hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)-3-(pyridin-2-yldisulfaneyl)propanamide

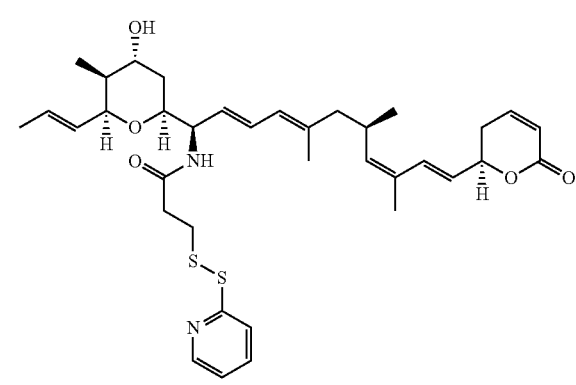

Chemical Formula: C$_{36}$H$_{48}$N$_2$O$_5$S$_2$
Molecular Weight: 652,91
2-PySS(CH$_2$)$_2$(CO)NH-Ratja To a solution of 2.4 mg (4.215 μmol, 1.0 eq) 16R-Amino-Ratjadone 11 in 126 μL of a 1:2 mixture of MeCN and PBS (100 mM, pH=7.45) was added 1.5 mg (4.64 μmol, 1.1 eq) 3-(2-Pyridyldithio)propionic acid N-hydroxysuccinimide ester and the mixture was stirred for 3.5 h at 23° C., before it was diluted with 1 mL H$_2$O and extracted with CH$_2$Cl$_2$ (3×1.5 mL). The combined organic layers were dried over Na$_2$SO$_4$ and concentrated under reduced pressure. The residue was purified by preparative thin-layer chromatography (CH$_2$Cl$_2$:MeOH/95:5), yielding 2.7 mg (4.135 μmol, 98%) of 2-PySS(CH$_2$)$_2$(CO)NH-Ratja 35 as an amorphous, white solid.

2-PySS(CH$_2$)$_2$(CO)NH-Ratja (35): TCL (CH$_2$Cl$_2$:MeOH/95:5) R$_f$: 0.22 [UV$^{254}$, CAM], $^1$H-NMR (500 MHz, benzene-d$_6$) δ [ppm] 8.33 (ddd, J=4.8, 1.8, 0.9 Hz, 1H), 7.42 (d, J=8.1 Hz, 1H), 6.98 (ddd, J=8.1, 7.5, 1.9 Hz, 1H), 6.83 (d, J=9.1 Hz, 1H), 6.72 (ddd, J=15.2, 10.9, 1.0 Hz, 1H), 6.64 (d, J=15.6 Hz, 1H), 6.48 (ddd, J=7.4, 4.8, 1.0 Hz, 1H), 5.99 (dd, J=15.2, 7.3 Hz, 1H), 5.94-5.88 (m, 2H), 5.80 (ddd, J=9.8, 2.5, 1.0 Hz, 1H), 5.73-5.62 (m, 1H), 5.52-5.42 (m, 2H), 5.12 (d, J=9.7 Hz, 1H), 4.90 (td, J=8.0, 4.1 Hz, 1H), 4.56 (d, J=5.8 Hz, 1H), 4.45-4.36 (m, 1H), 4.07 (ddd, J=12.3, 3.9, 2.4 Hz, 1H), 3.57 (d, J=2.7 Hz, 1H), 2.92 (t, J=6.6 Hz, 2H), 2.84-2.71 (m, 2H), 2.27 (td, J=6.6, 3.2 Hz, 2H), 1.98-1.85 (m, 2H), 1.68 (d, J=1.1 Hz, 3H), 1.68-1.67 (m, 3H), 1.57 (dt, J=6.5, 1.2 Hz, 3H), 1.56-1.53 (m, 1H), 1.52-1.48 (m, 2H), 1.26 (d, J=14.1 Hz, 2H), 0.91 (d, J=6.6 Hz, 3H), 0.82 (d, J=7.2 Hz, 3H). $^{13}$C-NMR (126 MHz, benzene-d$_6$) δ [ppm]: 169.79, 163.67, 161.09, 150.27, 144.23, 139.44, 137.10, 136.84, 131.75, 130.88, 130.33, 129.96, 127.34, 126.61, 126.20, 122.12, 120.86, 120.07, 78.44, 75.42, 75.28, 70.47, 55.59, 48.34, 40.07, 36.19, 35.80, 31.38, 31.18, 30.57, 30.19, 21.77, 20.86, 18.35, 17.66, 11.76. LRMS (ESI-Quad) [m/z]: 653.9 [M+H]$^+$, HRMS (ESI-IT) [m/z]: 653.3077, calculated 653.3077 for C$_{36}$H$_{48}$N$_2$O$_5$S$_2$[M+H]$^+$, err [ppm] 0.0.

Synthesis of 2-PySS(CH$_2$)$_2$NH$_2$ (36)—2-(pyridin-2-yldisulfaneyl)ethan-1-amine hydrochloride[6]

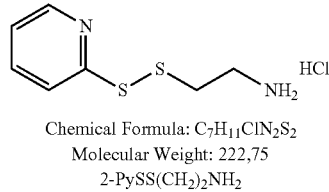

Chemical Formula: C$_7$H$_{11}$ClN$_2$S$_2$
Molecular Weight: 222,75
2-PySS(CH$_2$)$_2$NH$_2$ To a solution of 1.0 g (8.802 mmol, 1.0 eq) 2-aminothioethanol hydrochloride in 5.3 mL of degassed dry MeOH under Argon atm. was added a solution of 5.0 g (22.695 mmol, 2.5 eq) 2,2'-dipyridyl disulfide in 10.6 mL of degassed dry MeOH over a period of 1 h at 23° C. using a syringe pump. The resulting mixture was stirred for 24 h at 23° C. Upon addition of ice-cold Et$_2$O (300 mL) to the mixture a white precipitate was formed, which was collected, washed with ice-cold Et$_2$O and dried in HV yielding 1.478 g (6.634 mmol, 75%) of 36 as a white solid.

[6] Synthesis was based on a procedure of Vu et al.[70]

2-PySS(CH$_2$)$_2$NH$_2$ (36): $^1$H-NMR (700 MHz, MeOD-d$_4$) 8.54 (ddd, J=4.9, 1.8, 0.9 Hz, 1H), 7.95-7.72 (m, 1H), 7.65 (dt, J=8.1, 0.9 Hz, 1H), 7.31 (ddd, J=7.4, 4.9, 1.0 Hz, 1H), 3.30 (t, J=6.2 Hz, 2H), 3.14 (t, J=6.2 Hz, 2H). 6 [ppm] $^{13}$C-NMR (176 MHz, MeOD-d$_4$) δ [ppm]: 159.48, 150.91, 139.14, 123.30, 122.86, 38.72, 36.85. LRMS (ESI-Quad) [m/z]: 187.3 [M+H]$^+$.

Synthesis of 2-PySS(CH$_2$)$_2$NH—(CO)(CH$_2$)$_2$CCH (37)—N-(2-(pyridin-2-yldisulfaneyl)ethyl)pent-4-ynamide

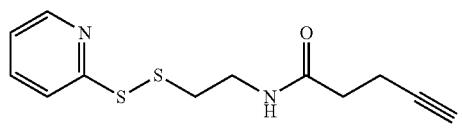

Chemical Formula: C$_{12}$H$_{14}$N$_2$OS$_2$
Molecular Weight: 266,38
2-PySS(CH$_2$)$_2$NH—(CO)(CH$_2$)$_2$CCH To a solution of 300 mg (1.537 µmol, 1.0 eq) 4-pentynoic acid N-hydroxysuccinimide ester[60] in 15.4 mL dry CH$_2$Cl$_2$ were added 803 µL (4.611 mmol, 3.0 eq) DiPEA and 342 mg (1.537 mmol, 1.0 eq) 2-PySS(CH$_2$)$_2$NH$_2$ 36 and the mixture was stirred for 7 h at 23° C., before it was concentrated under reduced pressure and the resulting residue was purified by flash-chromatography through silicagel (EtOAc:MeOH/30:1-15:1-10:1) yielding 271.4 mg (1.019 mmol, 66%) 37 as a pale yellow, amorphous solid.

2-PySS(CH$_2$)$_2$NH—(CO)(CH$_2$)$_2$CCH (37): TCL (EtOAc: MeOH/9:1) R$_f$: 0.77 [UV$^{254}$, CAM], $^1$H-NMR (500 MHz, CDCl$_3$) δ [ppm] 8.54-8.44 (m, 1H), 7.60 (td, J=7.9, 1.8 Hz, 1H), 7.49 (dt, J=8.1, 0.9 Hz, 1H), 7.13 (ddd, J=7.3, 4.9, 0.8 Hz, 1H), 3.56 (q, J=5.9 Hz, 2H), 2.95-2.86 (m, 2H), 2.53 (tdd, J=7.2, 2.6, 0.9 Hz, 2H), 2.45-2.38 (m, 2H), 1.98 (t, J=2.6 Hz, 1H). $^{13}$C-NMR (126 MHz, CDCl$_3$) δ [ppm]: 171.00, 159.25, 149.95, 137.12, 121.51, 121.36, 83.13, 69.42, 39.10, 37.40, 35.68, 15.07. LRMS (ESI-Quad) [m/z]: 267.4 [M+H]$^+$, HRMS (ESI-IT) [m/z]: 267.062375, calculated 267.062032 for C$_{12}$H$_{15}$N$_2$O S$_2$ [M+H]$^+$, err [ppm] −1.287.

Synthesis of HO$_2$C(CH$_2$)$_2$SS(CH$_2$)$_2$NH—(CO)(CH$_2$)$_2$CCH (38)—3-((2-(pent-4-ynamido)ethyl)disulfanyl)propanoic acid

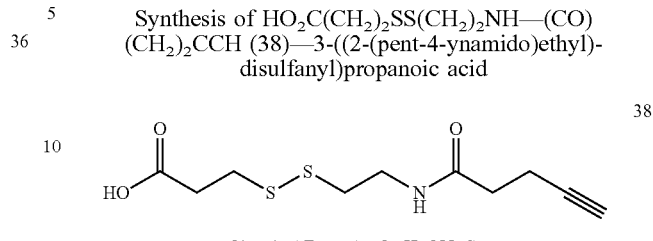

Chemical Formula: C$_{10}$H$_{15}$NO$_3$S$_2$
Molecular Weight: 261,35
HO$_2$C(CH$_2$)$_2$SS(CH$_2$)$_2$NH—(CO)(CH$_2$)$_2$CCH To a solution of 50 mg (0.1877 mmol, 1.0 eq) 2-PySS (CH$_2$)$_2$NH—(CO)(CH$_2$)$_2$CCH 37 in 3.75 mL dry MeOH under Argon atm. was added 16.4 µL (0.1877 mmol, 1.0 eq) 3-mercaptopropionic acid and the mixture was stirred for 19 h at 23° C. The solvent was removed under reduced pressure and the residue was dissolved in 400 µL MeOH and purified by preparative HPLC (Phenomenex Gemini C18 RP-column 00G-4435-PO-AX, 5 µm, 110A, 250×21.20 mm (9 mL/min), ACN:H$_2$O+TFA/5:95+0.1%→95:5+0.1% in 15 min) yielding after lyophilization 37.3 mg (0.1427 mmol, 76%) 38 as a white, amorphous solid.

HO$_2$C(CH$_2$)$_2$SS(CH$_2$)$_2$NH—(CO)(CH$_2$)$_2$CCH (38): TCL (EtOAc:MeOH/98:2+1% HOAc) R$_f$: 0.65 [CAM], $^1$H-NMR (500 MHz, MeOH-d$_4$) 3.49 (t, J=6.7 Hz, 2H), 2.93 (t, J=7.1 Hz, 2H), 2.82 (t, J=6.7 Hz, 2H), 2.69 (t, J=7.1 Hz, 2H), 2.49-2.44 (m, 2H), 2.41-2.36 (m, 2H), 2.26 (t, J=2.6 Hz, 1H). LRMS (ESI-Quad) [m/z]: 262.4 [M+H]$^+$, HRMS (ESI-IT) [m/z]: 262.056032, calculated 262.056612 for C$_{10}$H$_{16}$NO$_3$S$_2$ [M+H]$^+$, err [ppm] 2.213.

Synthesis of HCC(CH$_2$)$_2$(CO)—NH—(CH$_2$)$_2$SS (CH$_2$)$_2$(CO)—NH-Ratja (39)—N-(2-((3-(((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)amino)-3-oxopropyl)disulfaneyl)-ethyl)pent-4-ynamide

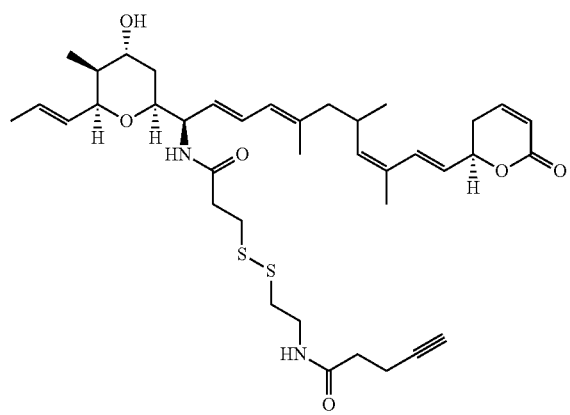

Chemical Formula: C$_{38}$H$_{54}$N$_2$O$_6$S$_2$
Molecular Weight: 698,98
HCC(CH$_2$)$_2$(CO)—NH—(CH$_2$)$_2$SS(CH$_2$)$_2$(CO)—NH-Ratja To a solution of 6.9 mg (26.346 μmol, 1.0 eq) HO$_2$C(CH$_2$)$_2$SS(CH$_2$)$_2$NH—(CO)(CH$_2$)$_2$CCH 38 in 131 μL dry DMF were added 14.5 μL (131.73 μmol, 5.0 eq) NMM and 7.9 mg (26.346 μmol, 1.0 eq) TSTU. The resulting mixture was stirred at 23° C. for 30 min, before a solution of 12.0 mg (26.346 μmol, 1.0 eq) 16R-Amino-Ratjadone 11 in 131 μL dry DMF was added and the mixture was stirred for 16 h at 23° C. The mixture was poured into 20 mL H$_2$O and extracted with CH$_2$Cl$_2$ (3×10 mL). The combined organic layers were dried over Na$_2$SO$_4$ and concentrated under reduced pressure. The residue was purified by preparative thin-layer chromatography (CH$_2$Cl$_2$:MeOH/98:2) yielding 12.0 mg (17.12 μmol, 65%) of 39 as a pale yellow, amorphous solid.

HCC(CH$_2$)$_2$(CO)—NH—(CH$_2$)$_2$SS(CH$_2$)$_2$(CO)—NH-Ratja (39): TCL (CH$_2$Cl$_2$:MeOH/95:5) R$_f$: 0.69 [UV$^{254}$, CAM], $^1$H-NMR (700 MHz, benzene-d$_6$) δ [ppm]6.90 (d, J=9.0 Hz, 1H), 6.72-6.68 (m, 1H), 6.66 (d, J=15.5 Hz, 1H), 6.42 (t, J=5.9 Hz, 1H), 6.04 (dd, J=15.2, 7.2 Hz, 1H), 5.95 (ddd, J=9.8, 5.7, 2.7 Hz, 1H), 5.93-5.90 (m, 1H), 5.80 (ddd, J=9.7, 2.6, 1.1 Hz, 1H), 5.77 (ddd, J=15.4, 6.5, 1.5 Hz, 1H), 5.53-5.51 (m, 1H), 5.50-5.46 (m, 1H), 5.13 (dd, J=9.9, 1.5 Hz, 1H), 4.90 (dddd, J=8.8, 7.2, 4.5, 1.2 Hz, 1H), 4.64 (ddd, J=5.7, 2.8, 1.5 Hz, 1H), 4.43 (dddd, J=11.2, 7.2, 4.2, 1.1 Hz, 1H), 4.14 (ddd, J=12.2, 4.7, 2.4 Hz, 1H), 3.75 (d, J=2.9 Hz, 1H), 3.50 (dq, J=13.9, 6.1 Hz, 1H), 3.46-3.40 (m, 1H), 2.95-02.85 (m, 2H), 2.82 (td, J=9.1, 4.5 Hz, 1H), 2.72-2.63 (m, 2H), 2.53-2.44 (m, 3H), 2.41-2.31 (m, 2H), 2.27-2.22 (m, 2H), 1.98 (dd, J=14.0, 5.5 Hz, 1H), 1.92 (dd, J=14.0, 8.6 Hz, 1H), 1.86 (t, J=2.7 Hz, 1H), 1.81-1.72 (m, 2H), 1.72 (d, J=1.3 Hz, 3H), 1.71 (d, J=1.3 Hz, 3H), 1.61 (dt, J=6.5, 1.5 Hz, 3H), 1.58-1.54 (m, 2H), 1.52-1.48 (m, 1H), 0.93 (d, J=6.6 Hz, 3H), 0.87 (d, J=7.2 Hz, 3H). $^{13}$C-NMR (176 MHz, benzene-d$_6$) δ [ppm]: 171.08, 170.35, 163.75, 144.34, 139.48, 136.41, 131.59, 131.34, 129.93, 129.30, 128.69, 126.89, 126.04, 125.66, 121.63, 83.71, 78.54, 74.99, 74.95, 70.17, 69.60, 55.47, 47.93, 39.75, 38.90, 38.72, 36.61, 35.32, 35.07, 31.17, 30.84, 29.79, 21.59, 20.53, 18.06, 17.41, 15.18, 11.49. LRMS (ESI-Quad) [m/z]: 699.9 [M+H]$^+$, HRMS (ESI-IT) [m/z]: 699.3490, calculated 699.3496 for C$_{38}$H$_{54}$N$_2$O$_6$S$_2$[M+H]$^+$, err [ppm] –0.857.

1.1.1.6 Synthesis of 19-Amino-Ratjadones with Bearing Terminal Alkynes Attached Via Short Non-Cleavable Linkers Scheme 6: Synthesis of 19-Amino-Ratjadones

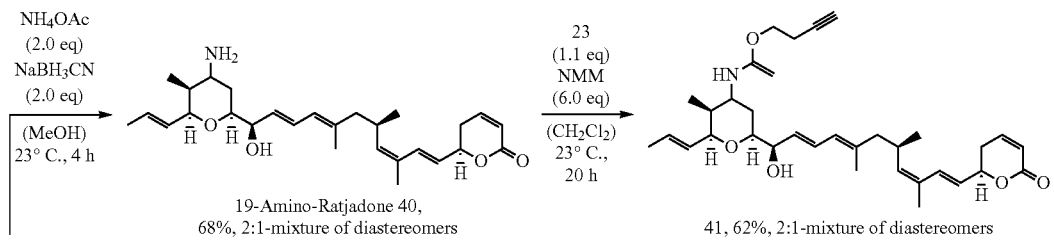

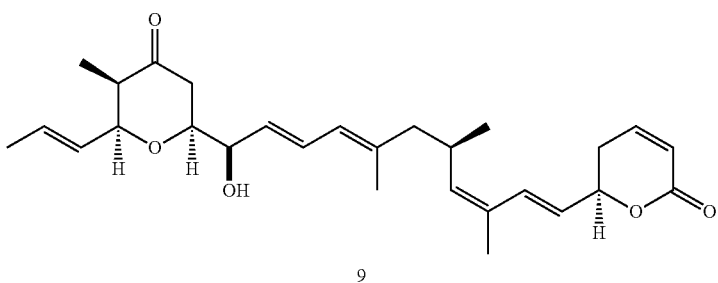

9

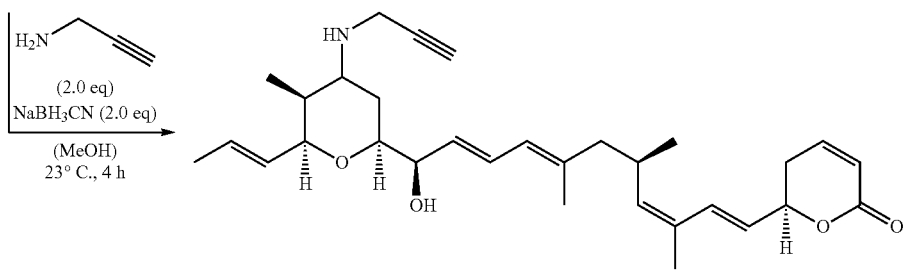

N-Propargyl-19-amino-Ratjadone 42, 99%, 2:1-mixture of diastereomers

Synthesis of 19-Amino-Ratjadone (40)—(6R)-6-((1E,3Z,5R,7E,9E,11R)-11-((2S,5S,6S)-4-amino-5-methyl-6-((E)-prop-1-en-1-yl)tetrahydro-2H-pyran-2-yl)-11-hydroxy-5,7-dimethylundeca-1,3,7,9-tetraen-1-yl)-5,6-dihydro-2H-pyran-2-one

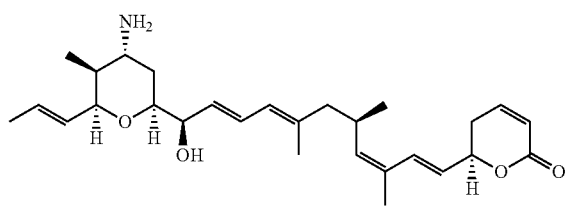

Chemical Formula: $C_{28}H_{41}NO_4$
Molecular Weight: 455,65
19-Amino Ratjadone 2.9 mg (39.595 µmol, 2.0 eq) ammonium acetate were added to a solution of 9.0 mg (19.797 µmol, 1.0 eq) 19-Oxo Ratjadone 9 in 396 µL dry MeOH at 23° C. and stirred for 15 min, before 2.5 mg (39.595 µmol, 2.0 eq) sodium cyanoborohydride was added and the mixture was stirred at 23° C. for 4 h, before the reaction was quenched by addition of 200 µL of ACN:H$_2$O+TFA/30:70+0.05%. This mixture was directly purified by RP prep HPLC (Phenomenex Gemini C18 RP-column 00G-4435-PO-AX, 5 µm, 110 A, 250×21.20 mm, Flow: 9 mL/min, ACN:H$_2$O+TFA/10:90+0.1%→95:5+0.1% in 90 min) yielding after lyophilization 6.9 mg (15.1 µmol, 68%) 19-Amino-Ratjadone 40 as an inseparable 1:2 mixture of 2 diastereoisomers as a pale-yellow solid foam.

19-Amino-Ratjadone (40): LRMS (ESI-Quad) [m/z]: 456.3 [M+H]$^+$, HRMS (ESI-IT) [m/z]: 456.310615, calculated 456.310835 for $C_{28}H_{42}NO_4$ [M+H]$^+$, err [ppm]-0.043.

Synthesis of Compound 41—But-3-yn-1-yl ((2S,3S,6S)-6-((1S,2E,4E,7R,8Z,10E)-1-hydroxy-5,7,9-trimethyl-11-((R)-6-oxo-3,6-dihydro-2H-pyran-2-yl)undeca-2,4,8,10-tetraen-1-yl)-3-methyl-2-((E)-prop-1-en-1-yl)tetrahydro-2H-pyran-4-yl)carbamate

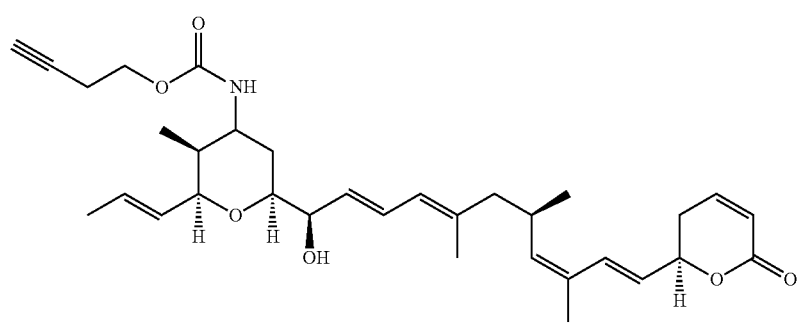

Chemical Formula: $C_{33}H_{45}NO_6$
Molecular Weight: 551,72

To a solution of 4.0 mg (7.02 µmol, 1.0 eq) 19-Amino-Ratjadone 40 in 70 µL dry CH$_2$Cl$_2$ were added 2.31 µL (21.06 µmol, 6.0 eq) NMM and 1.82 mg (7.72 µmol, 1.1 eq) but-3-yn-1-yl (4-nitrophenyl) carbonate 23 and the mixture was stirred for 36 h at 23° C. The mixture was diluted with 0.25 mL CH$_2$Cl$_2$ and directly purified by preparative thin-layer chromatography (CH$_2$Cl$_2$:MeOH/98:2, 1x Development), yielding 2.4 mg (4.35 µmol, 65%) of Compound 41 as a pale-yellow solid foam.

Compound 41: TCL (CH$_2$Cl$_2$:MeOH/98:2) R$_f$: 0.21 [UV$^{254}$, CAM], LRMS (ESI-Quad) [m/z]: 552.9 [M+H]$^+$, HRMS (ESI-IT) [m/z]: 574.312547, calculated 574.313909 for $C_{33}H_{45}NNaO_6$ [M+Na]$^+$, err [ppm] 1.675.

Synthesis of N-Propargyl-19-amino-Ratjadone (42)—(6R)-6-((1E,3Z,5R,7E,9E,11R)-11-hydroxy-3,5,7-trimethyl-11-((2S,5S,6S)-5-methyl-6-((E)-prop-1-en-1-yl)-4-(prop-2-yn-1-ylamino)tetrahydro-2H-pyran-2-yl)undeca-1,3,7,9-tetraen-1-yl)-5,6-dihydro-2H-pyran-2-one

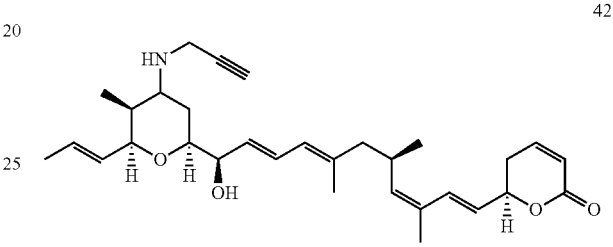

Chemical Formula: $C_{31}H_{43}NO_4$
Molecular Weight: 493,6880
N-Propargyl-19-Amino Ratjadone 2.54 µL (39.595 µmol, 2.0 eq) propargylamine and 2.2 µL (39.595 µmol, 2.0 eq) acetic acid were added to a solution of 9.0 mg (19.797 µmol, 1.0 eq) 19-Oxo Ratjadone 9 in 396 µL dry MeOH at 23° C. and stirred for 15 min, before 2.5 mg (39.595 µmol, 2.0 eq) sodium cyanoborohydride was added and the mixture was stirred at 23° C. for 4 h, before the reaction was quenched by addition of 200 µL of ACN:H$_2$O+TFA/30:70+0.05%. This mixture was directly purified by RP prep HPLC (Phenomenex Gemini C18 RP-column 00G-4435-PO-AX, 5 µm, 110 A, 250×21.20 mm, Flow: 9 mL/min, ACN:H$_2$O+TFA/10:90+0.1%→95:5+0.1% in 90 min) yielding after lyophilization 9.7 mg (19.648 µmol, 99%) N-Propargyl-19-Amino-Ratjadone 42 as an inseparable 1:2 mixture of 2 diastereoisomers as a pale-yellow solid foam.

N-Propargyl-19-Amino-Ratjadone (42): LRMS (ESI-Quad) [m/z]: 494.7 [M+H]$^+$, HRMS (ESI-IT) [m/z]: 494.3268, calculated 494.3265 for $C_{31}H_{44}NO_4$ [M+H]$^+$, err [ppm] −0.6.
Synthesis of Appropriate Carrier Molecules
1.1.1.7 Synthesis of Folate Derivatives in Solution
Scheme 7: Synthesis of FA—N$_3$—1 and FA—N$_3$—2 in solution.
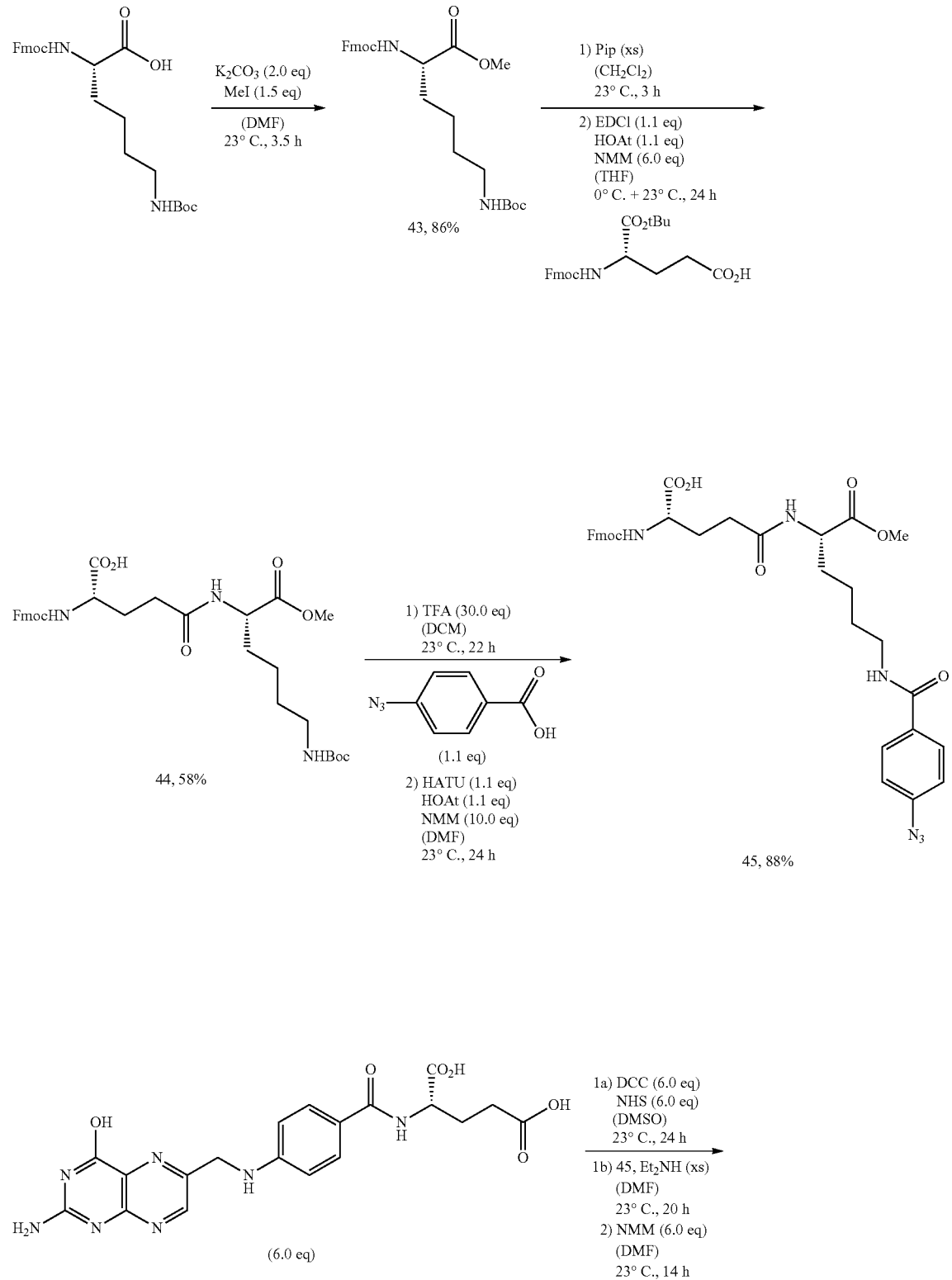

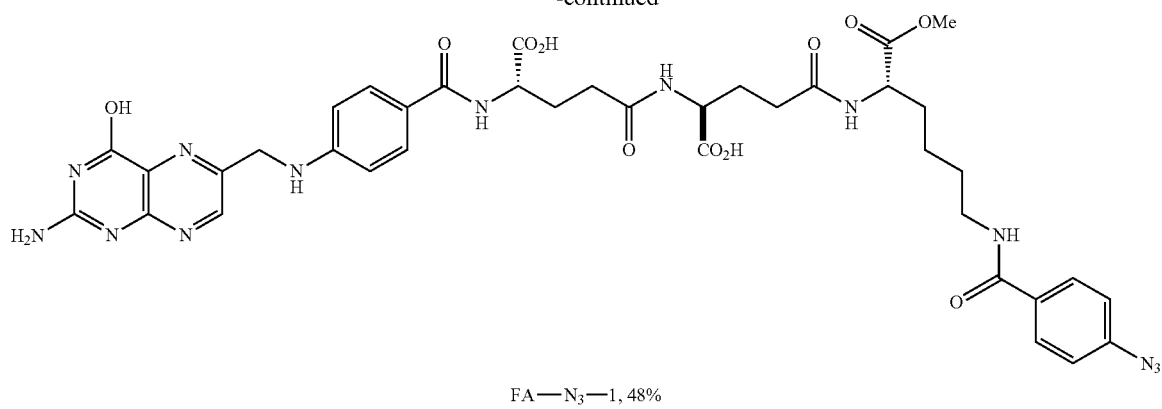
FA—N₃—1, 48%
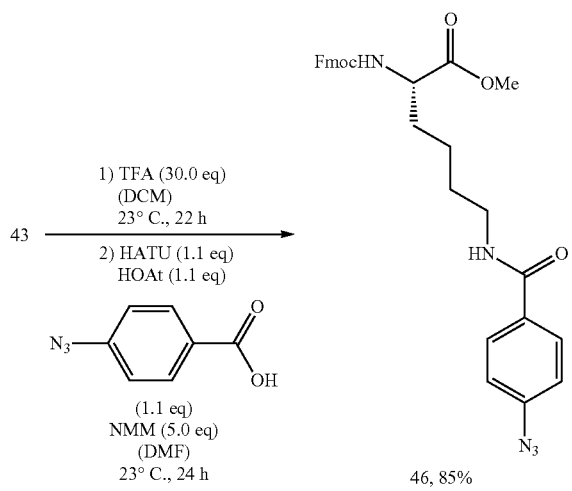
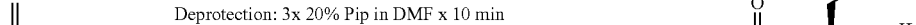
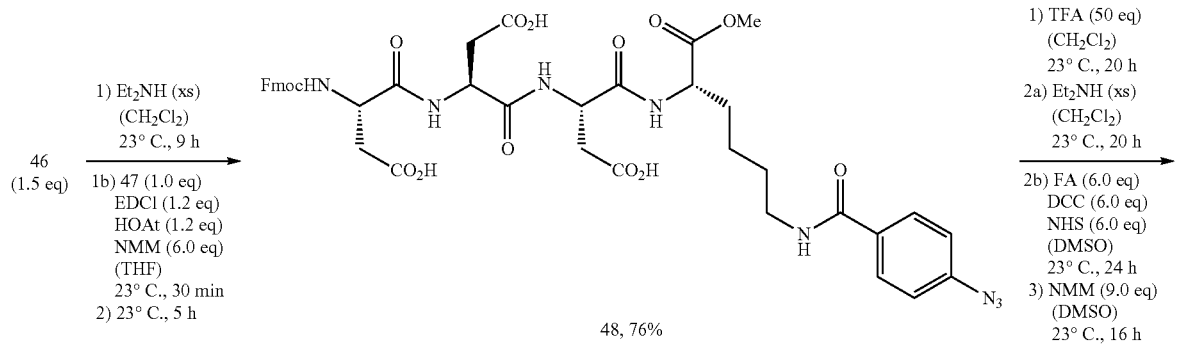

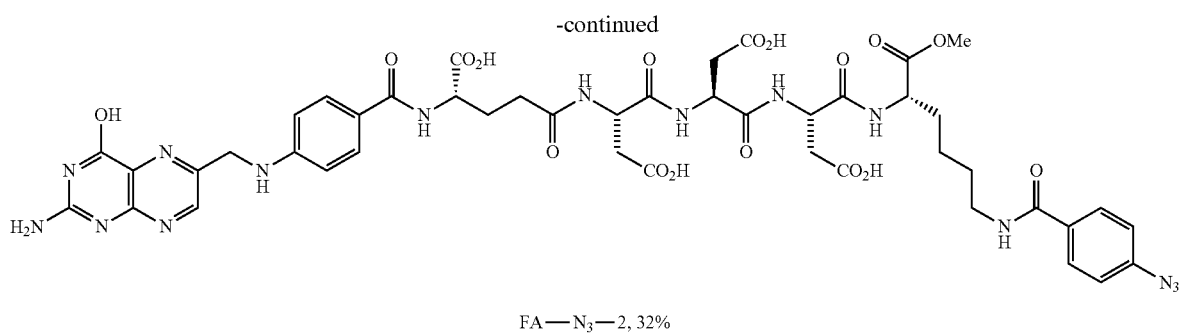

FA—N₃—2, 32%

Synthesis of methyl N²-(((9H-fluoren-9-yl)methoxy)carbonyl)-N⁶-(tert-butoxycarbonyl)-L-lysinate (43)

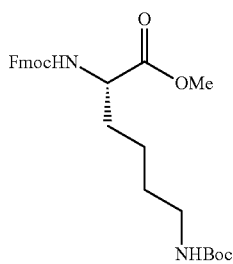

Chemical Formula: C$_{27}$H$_{34}$N$_2$O$_6$
Molecular Weight: 482,58

To a solution of 1.0 g (2.134 mmol, 1.0 eq) N²-(((9H-fluoren-9-yl)methoxy)carbonyl)-N⁶-(tert-butoxycarbonyl)-L-lysine in 10.7 mL dry DMF were added 590 mg (4.268 mmol, 2.0 eq) K$_2$CO$_3$ and 200 μL (3.201 mmol, 1.5 eq) methyl iodide and the mixture was stirred for 3.5 h at 23° C. The reaction was diluted with Et$_2$O (30 mL) and the mixture was washed with saturated aqueous NH$_4$Cl solution (2×150 mL) and H$_2$O (2×50 mL). The organic layer was dried over Na$_2$SO$_4$, concentrated under reduced pressure and dried in HV yielding 885 mg (1.835 mmol, 86%) of 43 as pale-yellow solid.

N²-(((9H-fluoren-9-yl)methoxy)carbonyl)-N⁶-(tert-butoxycarbonyl)-L-lysinate (43): TCL (CH$_2$Cl$_2$:MeOH/95:5) R$_f$: 0.90 [UV$^{254}$], IR (ATR) [cm$^{-1}$]: 3343, 2976, 2951, 2932, 2866, 1653, 1609, 1510, 1478, 1450, 1392, 1366, 1341, 1248, 1211, 1166, 1106, 1081, 1044, 1005, 909, 865, 780, 755, 728, 674, 646, 621. ¹H-NMR (700 MHz, CDCl$_3$) δ [ppm]: 7.74 (d, J=7.4 Hz, 2H), 7.62-7.55 (m, 2H), 7.38 (t, J=7.2 Hz, 2H), 7.29 (t, J=6.9 Hz, 2H), 5.42 (s, 1H), 4.58 (s, 1H), 4.38 (dt, J=17.8, 8.6 Hz, 3H), 4.20 (t, J=6.5 Hz, 1H), 3.73 (s, 3H), 3.09 (s, 2H), 1.83 (s, 1H), 1.68 (s, 1H), 1.41 (s, 9H), 1.52-1.29 (m, 5H). ¹³C-NMR (176 MHz, CDCl$_3$) δ [ppm]: 173.04, 156.18, 156.09, 144.00, 143.85, 141.40, 127.80, 127.17, 125.20, 120.08, 79.26, 67.10, 53.82, 52.52, 47.27, 40.15, 32.22, 29.70, 28.53, 22.47. LRMS (ESI-Quad) [m/z]: 483.2 [M+H]⁺, HRMS (ESI-IT) [m/z]: 483.2493, calculated 483.2490 for C$_{27}$H$_{34}$N$_2$O$_6$ [M+H]⁺, err [ppm] −0.600.

Synthesis of methyl N²—((S)-4-((((9H-fluoren-9-yl)methoxy)carbonyl)amino)-5-(tert-butoxy)-5-oxopentanoyl)-N⁶-(tert-butoxycarbonyl)-L-lysinate (44)

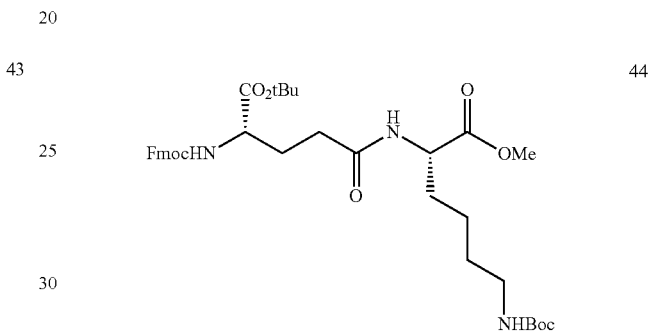

Chemical Formula: C$_{36}$H$_{49}$N$_3$O$_9$
Molecular Weight: 667,80

To a solution of 100 mg (0.207 mmol, 1.2 eq) methyl N²-(((9H-fluoren-9-yl)methoxy)carbonyl)-N⁶-(tert-butoxycarbonyl)-L-lysinate 43 in 4.1 mL CH$_2$Cl$_2$ was added 332 μL (1.6 mL/mmol) piperidine and the mixture was stirred for 3 h at 23° C. until the starting material was consumed. The mixture was diluted with toluene (10 mL), concentrated and co-evaporated with toluene (3×10 mL) under reduced pressure. The residue containing the free amine was dissolved in 1.2 mL dry DMF and 57 mL (0.517 mmol, 3.0 eq) NMM, 74 mg (0.1725 mmol, 1.0 eq) (S)-4-((((9H-fluoren-9-yl)methoxy)carbonyl)amino)-5-(tert-butoxy)-5-oxopentanoic acid and 28.2 mg (0.207 mmol, 1.0 eq) HOAt were added and the mixture was cooled to 0° C. 39.7 mg (0.207 mmol, 1.0 eq) EDCl was added and the mixture was stirred for 12 h at 23° C., before it was poured into 5 mL of H$_2$O and extracted with EtOAc (3×15 mL). The combined organic layers were dried over Na$_2$SO$_4$ and concentrated under reduced pressure. The residue was purified by flash-chromatography through silicagel (PE:EtOAc/8:2-1:1-0:1) yielding 80 mg (0.1197 mmol, 58%) of 44 as a colorless, amorphous solid.

Methyl N²—((S)-4-((((9H-fluoren-9-yl)methoxy)carbonyl)amino)-5-(tert-butoxy)-5-oxopentanoyl)-N⁶-(tert-butoxycarbonyl)-L-lysinate (44): TCL (PE:EtOAc/1:1) R$_f$: 0.16 [UV$^{254}$], IR (ATR) [cm$^{-1}$]: 3329, 2977, 2952, 2931, 2868, 171 1663, 1525, 1479, 1451, 1392, 1367, 1346, 1249, 1158, 1105, 1082, 1052, 912, 848, 760, 738, 647, 621, 591, 575, 526. ¹H-NMR (500 MHz, CDCl$_3$) δ [ppm]: 7.77 (d, J=7.6 Hz, 2H), 7.61 (d, J=7.3 Hz, 2H), 7.40 (td, J=7.4, 2.9 Hz, 2H), 7.35-7.30 (m, 2H), 6.40 (d, J=6.4 Hz, 1H), 5.56 (d, J=8.1 Hz, 1H), 4.64 (s, 1H), 4.58 (q, J=7.6 Hz, 1H), 4.48-4.35 (m, 2H), 4.23 (q, J=7.7, 7.0 Hz, 2H), 3.72 (s, 3H), 3.09 (d, J=5.7 Hz, 2H), 2.29 (t, J=6.8 Hz, 2H), 2.26-2.18 (m, 1H), 1.94-1.80 (m, 2H), 1.70 (q, J=13.4 Hz, 1H), 1.47 (s, 9H), 1.42 (s, 9H), 1.52-1.28 (m, 3H), 0.94-0.75 (m, 2H). $^{13}$C-NMR (126 MHz, CDCl$_3$) δ [ppm]: 172.97, 171.86, 171.23, 156.50, 156.21, 144.06, 143.83, 141.47, 127.87, 127.23, 125.31, 125.25, 120.14, 120.12, 82.73, 79.24, 67.15, 53.97, 52.52, 52.23, 47.36, 40.16, 32.40, 32.04, 29.69, 29.16, 28.57, 28.15, 22.56. LRMS (ESI-Quad) [m/z]: 668.4 [M+H]$^+$, HRMS (ESI-IT) [m/z]: 668.354552, calculated 668354157 for C$_{36}$H$_{50}$N$_3$O$_9$ [M+H]$^+$, err [ppm] −0.592

Synthesis of methyl N$^2$-(((9H-fluoren-9-yl)methoxy)carbonyl)-N$^5$—((S)-6-(4-azidobenzamido)-1-methoxy-1-oxohexan-2-yl)-L-glutamine (45)

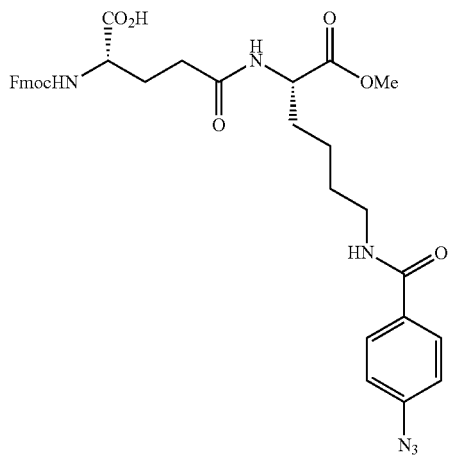

Chemical Formula: C$_{34}$H$_{36}$N$_6$O$_8$
Molecular Weight: 656,70

To a solution of 100 mg (0.149 mmol, 1.0 eq) of methyl N$^2$—((S)-4-((((9H-fluoren-9-yl)methoxy)carbonyl)amino)-5-(tert-butoxy)-5-oxopentanoyl)-N$^6$-(tert-butoxycarbonyl)-L-lysinate 44 in 2.99 mL dry CH$_2$Cl$_2$ was added 344 μL (4.492 mmol, 30 eq) TFA at 23° C. and the mixture was stirred for 22 h at 23° C. until the starting material was completely consumed. The reaction mixture was diluted with toluene (20 mL), concentrated and co-evaporated with toluene (3×10 mL) under reduced pressure and dried in HV. The residue containing the free amine was dissolved together with 83 μL (0.749 mmol, 5.0 eq) NMM in 499 μL dry DMF and added to a preactivated[7] solution of 26.9 mg (0.165 mmol, 1.0 eq) 4-azidobenzoic acid, 83 μL (0.749 mmol, 5.0 eq) NMM, 22.4 mg (0.165 mmol, 1.0 eq) HOAt and 62.6 mg (0.165 mmol, 1.0 eq) HATU in 499 μL dry DMF. The resulting solution was stirred for 3 h at 23° C., before was diluted with toluene (20 mL), concentrated and co-evaporated with toluene (3×20 mL) under reduced pressure. The residue was purified by flash-chromatography through silicagel (CH$_2$Cl$_2$:MeOH:HOAc/95:4.75:0.25) and the product containing fractions were coevaporated with toluene under reduced pressure and dried in HV yielding 86 mg (0.131 mmol, 88%) of 45 as a yellow, amorphous solid.

[7] For preactivation the mixture was stirred for 30 min at 23° C.

Methyl N$^2$-(((9H-fluoren-9-yl)methoxy)carbonyl)-N$^5$—((S)-6-(4-azidobenzamido)-1-methoxy-1-oxohexan-2-yl)-L-glutamine (45): TCL (PE:EtOAc/1:1) R$_f$: 0.16 [UV$^{254}$], IR (ATR) [cm$^{-1}$]: 3415, 2931, 2860, 2123, 1686, 1641, 1604, 1573, 1537, 1500, 1450, 1281, 1205, 1160, 1132, 1064, 1053, 992, 910, 840, 801, 761, 741, 724, 689, 647, 621. $^1$H-NMR (500 MHz, MeOD-d$_4$) δ [ppm]: 7.85-7.79 (m, 1H), 7.78 (d, J=7.5 Hz, 1H), 7.66 (t, J=7.4 Hz, 1H), 7.38 (t, J=7.5 Hz, 1H), 7.30 (td, J=7.5, 1.0 Hz, 1H), 7.14-7.05 (m, 1H), 4.39 (dd, J=9.1, 5.0 Hz, 1H), 4.38-4.26 (m, 1H), 4.20 (t, J=6.9 Hz, 1H), 4.11 (dd, J=8.6, 4.6 Hz, 1H), 3.85-3.76 (m, 2H), 3.68 (s, 2H), 3.36 (t, J=6.9 Hz, 1H), 3.01 (s, 2H), 2.32 (t, J=7.4 Hz, 1H), 2.17 (td, J=13.0, 8.0 Hz, 1H), 1.97-1.81 (m, 2H), 1.72 (dtd, J=14.2, 9.3, 5.7 Hz, 1H), 1.62 (dhept, J=13.6, 6.9 Hz, 2H), 1.51-1.38 (m, 2H). $^{13}$C-NMR (126 MHz, MeOD-d$_4$) δ [ppm]: 177.07, 175.41, 174.25, 169.13, 158.42, 145.39, 145.20, 144.73, 142.55, 132.24, 130.14, 128.76, 128.17, 126.27, 126.24, 120.89, 119.95, 67.91, 65.84, 56.03, 55.09, 53.70, 52.64, 48.42, 44.67, 40.63, 33.15, 32.12, 29.95, 29.55, 24.28. LRMS (ESI-Quad) [m/z]: 657.3 [M+H]$^+$, HRMS (ESI-IT) [m/z]: 657.267199, calculated 657.266739 for C$_{34}$H$_{36}$N$_6$O$_8$ [M+H]$^+$, err [ppm] −0.700.

Synthesis of Fa-N$_3$-1—N$^2$-(4-(((2-amino-4-hydroxypteridin-6-yl)methyl)amino)benzoyl)-N$^5$—((S)-4-(((S)-6-(4-azidobenzamido)-1-methoxy-1-oxohexan-2-yl)amino)-1-carboxy-4-oxobutyl)-L-glutamine

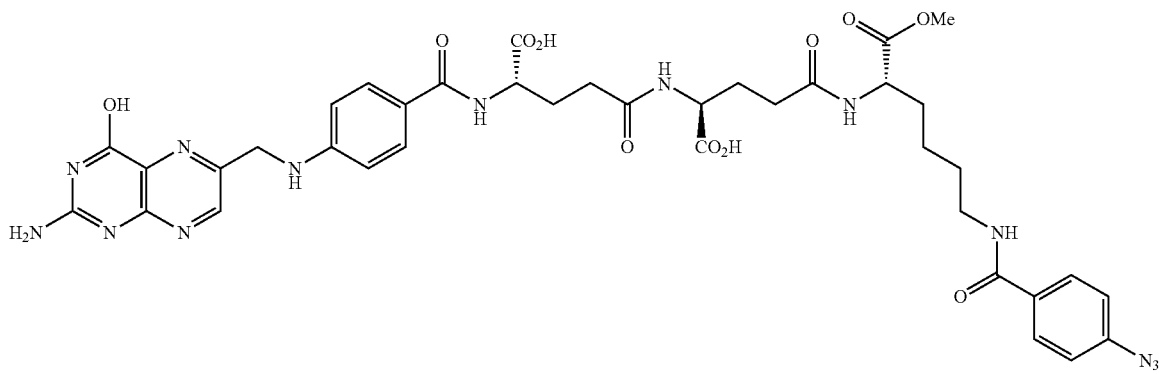

Chemical Formula: C$_{38}$H$_{43}$N$_{13}$O$_{11}$
Molecular Weight: 857,84
FA-N$_3$-1

To a solution of 60 mg (0.091 mmol, 1.0 eq) methyl N²-(((9H-fluoren-9-yl)methoxy)carbonyl)-N⁵—((S)-6-(4-azidobenzamido)-1-methoxy-1-oxohexan-2-yl)-L-glutamine 45 in 456 µL dry DMF was added 146 µL (1.6 mL/mmol) diethylamine and the mixture was stirred for 20 h at 23° C., before it was diluted with toluene (20 mL), concentrated and co-evaporated with toluene (3×10 mL) under reduced pressure and dried in HV obtaining a residue containing the free amine.

In parallel, 63 mg (0.548 mmol, 6.0 eq) N-hydroxysuccinimide and 113 mg (0.548 mmol, 6.0 eq) DCC were added to a solution of 242 mg (0.548 mmol, 6.0 eq) folic acid in 2.7 mL dry DMSO and the mixture was stirred for 24 h at 23° C. under light exclusion to form the corresponding FA-NHS ester in a white suspension. This suspension was then filtered and the filtrate was poured onto the residue containing the free amine (described above). 90 µL (0.823 mmol, 9.0 eq) NMM were added and the mixture was stirred for 14 h at 23° C. The mixture was diluted with 1.2 mL $H_2O$, filtered through a Whatman® filter (45 µm) and directly purified RP prep HPLC (Phenomenex Gemini C18 RP-column 00G-4435-PO-AX, 5 µm, 110 A, 250×21.20 mm, Flow: 9 mL/min, ACN:$H_2O$+TFA/10:90+0.1%→95:5+0.1% in 60 min) yielding after lyophilization 35.3 mg (41.1 µmol, 45%) of Fa-$N_3$-1 as a deep-yellow solid.

Fa-$N_3$-1: LRMS (ESI-Quad) [m/z]: 858.3 $[M+H]^+$, HRMS (ESI-IT) [m/z]: 858.327991, calculated 858.327776 for $C_{38}H_{44}N_{13}O_{11}$ $[M+H]^+$, err [ppm] –0.25

Synthesis of methyl N²-(((9H-fluoren-9-yl)methoxy)carbonyl)-N6-(4-azidobenzoyl)-L-lysinate (46)

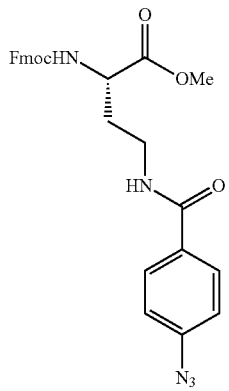

46

Chemical Formula: $C_{29}H_{29}N_5O_5$
Molecular Weight: 527,58

To a solution of 40.5 mg (0.248 mmol, 1.2 eq) 4-azidobenzoic acid and 29.8 mg (0.258 mmol, 1.25 eq) N-hydroxysuccinimide in 1.2 mL dry THF was added 53.4 mg (0.258 mmol, 1.25 eq) DCC and the mixture was stirred for 9 h at 23° C. to form the corresponding 4-azidobenzoic acid NHS ester in a white suspension. In parallel, 237 µL (3.108 mmol, 15 eq) TFA was added to a solution of 100 mg (0.207 mmol, 1.0 eq) methyl N²-(((9H-fluoren-9-yl)methoxy)carbonyl)-N⁶-(tert-butoxycarbonyl)-L-lysinate 43 in 4.2 mL $CH_2Cl_2$ and the mixture was stirred for 3 h at 23° C. until the starting material was consumed. The mixture was diluted with toluene (20 mL), concentrated and coevaporated with toluene (3×10 mL) under reduced pressure. The residue containing the corresponding free amine was dissolved in 0.9 mL dry THF, 136.5 µL (1.242 mmol, 6.0 eq) NMM was added and the filtrate of the suspension containing the 4-azidobenzoic acid NHS ester added. The resulting mixture was stirred for 20 h at 23° C. The solvents were removed under reduced pressure and the residue was purified by flash-chromatography through silicagel ($CH_2Cl_2$:MeOH/1: 0-97.5:2.5) yielding 98 mg (0.186 mmol, 90%) of 46 as an amorphous, yellow solid.

Methyl N²-(((9H-fluoren-9-yl)methoxy)carbonyl)-N⁶-(4-azidobenzoyl)-L-lysinate (46): ¹H-NMR (500 MHz, $CDCl_3$) δ [ppm]: 7.78-7.74 (m, 4H), 7.56 (d, J=7.4 Hz, 2H), 7.40 (td, J=7.4, 3.1 Hz, 2H), 7.32-7.26 (m, 2H), 6.95 (d, J=8.4 Hz, 2H), 6.36 (s, 1H), 5.54 (d, J=8.2 Hz, 1H), 4.43-4.34 (m, 2H), 4.30 (dd, J=10.5, 7.3 Hz, 1H), 4.18 (t, J=7.1 Hz, 1H), 3.75 (s, 3H), 3.44 (q, J=6.4 Hz, 2H), 1.93-1.84 (m, 1H), 1.80-1.59 (m, 4H), 1.46 (dt, J=16.3, 7.9 Hz, 2H), 1.32-1.24 (m, 1H). ¹³C-NMR (126 MHz, $CDCl_3$) δ [ppm]: 173.02, 166.78, 156.30, 143.91, 143.75, 143.28, 141.40, 131.07, 128.82, 127.87, 127.19, 125.15, 120.14, 119.00, 67.22, 53.55, 52.63, 47.24, 39.71, 32.84, 32.54, 28.86, 25.22, 24.51, 22.62. LRMS (ESI-Quad) [m/z]: 528.2 $[M+H]^+$, HRMS (ESI-IT) [m/z]: 528.224467, calculated 528.224146 for $C_{29}H_{30}N_5O_5$ $[M+H]^+$, err [ppm] –0.608.

Synthesis of Fmoc-(Asp(OtBu))₃—OH (47)—(5S,8S,11S)-5,8,11-tris(2-(tert-butoxy)-2-oxoethyl)-1-(9H-fluoren-9-yl)-3,6,9-trioxo-2-oxa-4,7,10-triazadodecan-12-oic acid

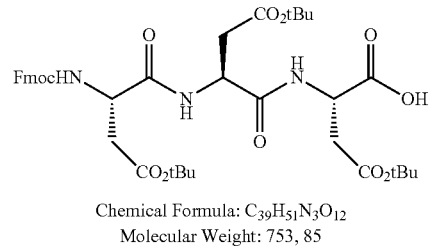

47

Chemical Formula: $C_{39}H_{51}N_3O_{12}$
Molecular Weight: 753, 85

The solid-phase synthesis of the tripeptide Fmoc-(Asp(OtBu))₃—OH 47 was carried out manually on a scale of 100 µmol on Rapp 2-chlorotrityl resin (Rapp Polymere, Tubingen, Germany, 0.91 mmol/g) using fritted glass peptide synthesis vessels. For the loading of the first amino acid to the resin a solution 41.2 mg (100 µmol, 1.0 eq) Fmoc-Asp(OtBu)-OH and 110 µL (1.0 mmol, 10 eq) NMM in 4 mL dry DMF was reacted with the resin shaking it for 24 h at 23° C. The solvent was removed from the resin and the resin was reacted shaking it for 1 h at 23° C. with a solution of 1 mL MeOH and 220 µL (2.0 mmol, 20 eq) NMM in 4 mL dry DMF. The resin was washed with DMF, $CH_2Cl_2$ and DMF (each 3×4 mL, 2 min). Fmoc cleavage achieved by repeated reaction of the resin shaking it with a mixture of piperidine in DMF (Pip:DMF/1:4, 3×4 mL, 10 min) and subsequent washing of the resin with DMF, $CH_2Cl_2$ and DMF (each 3×4 mL, 2 min). The coupling of the amino acids was performed shaking with preactivated solutions of 84.4 mg (200 µmol, 2.0 eq) Fmoc-Asp(OtBu)-OH, 27.2 (200 µmol, 2.0 eq) HOAt, 55 µL (600 µmol, 6.0 eq) NMM and 165 mg (200 µmol, 2.0 eq) HATU in 4 mL of dry DMF with coupling times of 4 h at 23° C. Subsequently the resin was washed with DMF, $CH_2Cl_2$ and DMF (each 3×4 mL, 2 min). The cleavage of the tripeptide from the resin was managed by repeated treatment of the resin with a mixture of $CH_2Cl_2$:HFIP/4:1 (3×4 mL, 10 min). The combined cleavage solutions were concentrated under reduced pressure and the residue was purified by flash-chromatography through silicagel (PE:EtOAc/8:2-1:1) yielding Fmoc-(Asp(OtBu))₃—OH 47 as a white, amorphous solid.

Fmoc-(Asp(OtBu))₃—OH (47): LRMS (ESI-Quad) [m/z]: 776.3 $[M+Na]^+$, HRMS (ESI-IT) [m/z]: 776.3395, calculated 776.3365 for $C_{23}H_{34}N_5NaO_6$ $[M+Na]^+$, err [ppm] 3.86

Synthesis of (7S,10S,13S,16S)-16-((((9H-fluoren-9-yl)methoxy)carbonyl)amino)-1-(4-azidophenyl)-10,13-bis(carboxymethyl)-7-(methoxycarbonyl)-1,9,12,15-tetraoxo-2,8,11,14-tetraazaoctadecan-18-oic acid (48)

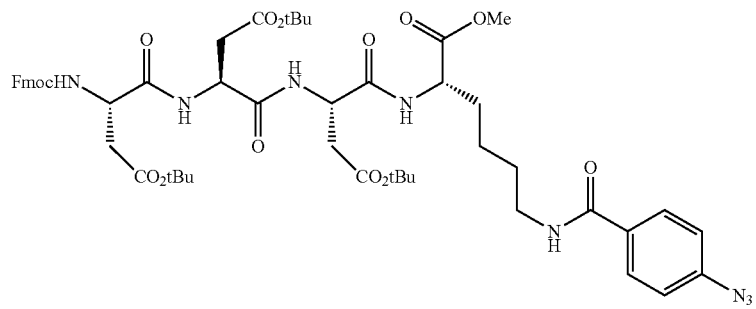

Chemical Formula: $C_{41}H_{44}N_8O_{14}$
Molecular Weight: 872,85

To a solution of 53 mg (99.5 μmol, 1.5 eq) of methyl $N^2$-(((9H-fluoren-9-yl)methoxy)carbonyl)-N6-(4-azidobenzoyl)-L-lysinate 46 in 1.6 mL CH2Cl2 was added 159 μL (1.6 mL/mmol) diethylamine and the mixture was stirred for 9 h at 23° C. The mixture was diluted with toluene (5 mL), concentrated and coevaporated with toluene (3×5 mL) under reduced pressure and dried in HV. The residue was dissolved in 201 μL dry DMF and the resulting solution was added to a preactivated[8] mixture of 50 mg (60.3 μmol, 1.0 eq) Fmoc-(Asp(OtBu))$_3$—OH 47, 9.9 mg (72.5 μmol, 1.2 eq) HOAt, 437 μl (0.397 mmol, 6.0 eq) NMM and 13.9 mg (72.5 μmol, 1.2 eq) HATU and the mixture was stirred for 5.5 h at 23° C. The mixture was poured into 50 mL H$_2$O and extracted with Et$_2$O (3×20 mL). The combined organic extracts were dried over Na$_2$SO$_4$ and concentrated under reduced pressure. The residue was purified by flash-chromatography through silicagel (PE:EtOAc/9:1-7:3-1:1-0:1) yielding 35.6 mg (34.1 μmol, 52%) of 48 as a pale-yellow, amorphous solid.

[8] For preactivation the mixture was stirred for 15 min at 23° C.

(7S,10S,13S,16S)-16-((((9H-fluoren-9-yl)methoxy)carbonyl)amino)-1-(4-azidophenyl)-10,13-bis(carboxymethyl)-7-(methoxycarbonyl)-1,9,12,15-tetraoxo-2,8,11,14-tetraazaoctadecan-18-oic acid (48): TCL (PE:EtOAc/1:1) $R_f$: 0.19 [$UV^{254}$, Ninhydrin], LRMS (ESI-Quad) [m/z]: 895.3 [M+Na]$^+$.

Synthesis of FA-N$_3$-2—$N^2$-(4-(((2-amino-4-hydroxypteridin-6-yl)methyl)amino)benzoyl)-$N^5$—((S)-1-(((S)-1-(((S)-1-(((S)-6-(4-azidobenzamido)-1-methoxy-1-oxohexan-2-yl)amino)-3-carboxy-1-oxopropan-2-yl)amino)-3-carboxy-1-oxopropan-2-yl)amino)-3-carboxy-1-oxopropan-2-yl)-L-glutamine To a solution of 20 mg (0.0233 mmol, 1.0 eq) (7S,10S,13S,16S)-16-((((9H-fluoren-9-yl)methoxy)carbonyl)amino)-1-(4-azidophenyl)-10,13-bis(carboxymethyl)-7-(methoxycarbonyl)-1,9,12,15-tetraoxo-2,8,11,14-

48 tetraazaoctadecan-18-oic acid 48 in 466 μL dry CH$_2$Cl$_2$ was added 89 μL (1.166 mmol, 50.0 eq) TFA and the mixture was stirred for 28 h at 23° C. The reaction was diluted with toluene (5 mL), concentrated and coevaporated with toluene (3×5 mL) under reduced pressure. The resulting residue was dried in HV, re-dissolved in 466 μL CH$_2$Cl$_2$ and 75 μL (3.2 mL/mmol) diethylamine was added and the reactions mixture was stirred for 20 h at 23° C. The mixture was diluted with toluene (5 mL), concentrated and coevaporated with toluene (3×5 mL) under reduced pressure. The resulting residue containing the raw (7S,10S,13S,16S)-16-amino-1-(4-azidophenyl)-10,13-bis(carboxymethyl)-7-(methoxycarbonyl)-1,9,12,15-tetraoxo-2,8,11,14-tetraazaoctadecan-18-oic acid was dried in HV.

In parallel, 16 mg (0.1398 mmol, 6.0 eq) N-hydroxysuccinimide and 29 mg (0.1398 mmol, 6.0 eq) DCC were added to a solution of 62 mg (0.1398 mmol, 6.0 eq) folic acid in 699 μL dry DMSO and the mixture was stirred for 24 h at 23° C. under light exclusion to form the corresponding FA-NHS ester in a white suspension. This suspension was then filtered and the filtrate was poured onto the residue containing the (7S,10S, 13S,16S)-16-amino-1-(4-azidophenyl)-10,13-bis(carboxymethyl)-7-(methoxycarbonyl)-1,9,12,15-tetraoxo-2,8,11,14-tetraazaoctadecan-18-oic acid (described above). 23 μL (0.209 mmol, 9.0 eq) NMM were added and the mixture was stirred for 20 h at 23° C. The mixture was diluted with 600 μL H$_2$O:ACN/70:30+0.05% TFA, filtered through a Whatman® filter (45 μm) and directly purified RP prep HPLC (Phenomenex Gemini C18 RP-column 00G-4435-PO-AX, 5 μm, 110A, 250×21.20

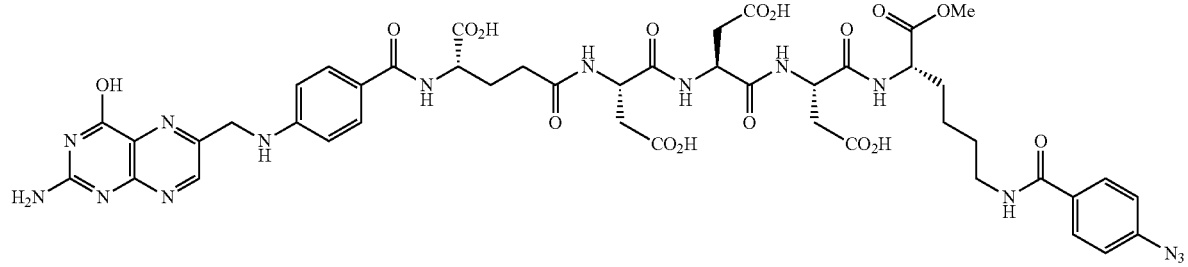

Chemical Formula: $C_{45}H_{51}N_{15}O_{17}$
Molecular Weight: 1073,99
FA-N$_3$-2 mm, Flow: 9 mL/min, ACN:H₂O+TFA/10:90+0.1%→95:5+0.1% in 60 min) yielding after lyophilization 8.0 mg (7.45 µmol, 32%) of FA-N₃-2 as a deep-yellow solid.
Fa-N₃-2: LRMS (ESI-Quad) [m/z]: 1074.4 [M+H]⁺, HRMS (ESI-IT) [m/z]: 1074.36278, calculated 1074.36601 for $C_{45}H_{51}N_{15}O_{17}$ [M+H]⁺, err [ppm] −3.006.
1.1.1.8 Synthesis of Folate Derivatives by Solid-Phase Synthesis
Scheme 8: Synthesis of FA—N₃ or FA-SH on solid support
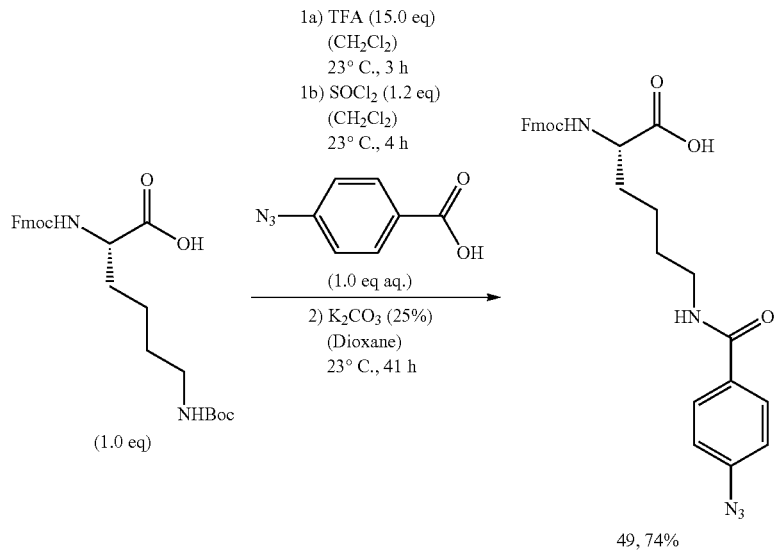
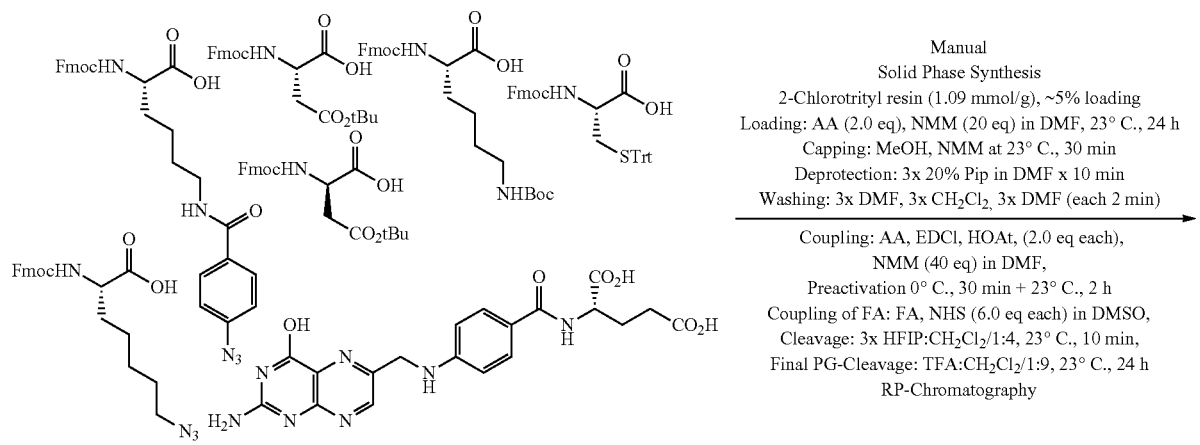

Synthesis of $N^2$-(((9H-fluoren-9-yl)methoxy)carbonyl)-$N^6$-(4-azidobenzoyl)-L-lysine (49)

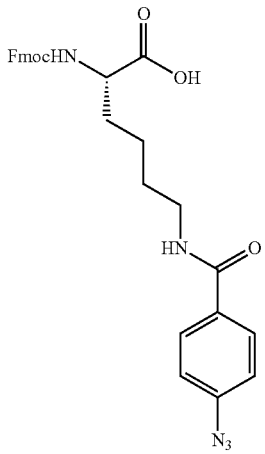

Chemical Formula: $C_{28}H_{27}N_5O_5$
Molecular Weight: 513,55

To a solution of 1.5 g (3.201 mmol, 1.0 eq) $N^2$-(((9H-fluoren-9-yl)methoxy)carbonyl)-$N^6$-(tert-butoxycarbonyl)-L-lysine in 64 mL $CH_2Cl_2$ was added 3.68 mL (48.020 mmol, 15 eq) TFA and the mixture was stirred for 3 h at 23° C. The mixture was diluted with toluene (25 mL), concentrated and co-evaporated with toluene (2×25 mL) under reduced pressure. The residue containing the free amine was dried in HV.

In parallel, 278 µL (3.841 mmol, 1.2 eq) thionyl chloride and 20 µL of dry DMF were added to a solution of 523 mg (3.201 mmol, 1.0 eq) 4-azidobenzoic acid in 10.7 mL $CH_2Cl_2$ at 0° C. and the mixture was stirred at 23° C. for 4 h. The reaction mixture was concentrated under reduced pressure and dried in HV. The residue was redissolved in 2.6 mL dry dioxane and added dropwise to a mixture of the free amine (described above) in 13.3 mL dioxane and 13.3 mL of aqueous 25 w % $K_2CO_3$ solution. The mixture was then stirred for 41 h at 23° C. The mixture was washed with tert-butylmethylether (3×25 mL), the aqueous layer was acidified to pH=2 with concentrated HCl and extracted with $CHCl_3$ (3×25 mL). The combined organic layers were dried over $Na_2SO_4$ and concentrated under reduced pressure. The residue was purified by flash-chromatography through silicagel ($CH_2Cl_2$:MeOH/1:0-95:5-9:1) yielding 1.214 g (2.365 mmol, 74%) of 49 as a white, amorphous solid.

$N^2$-(((9H-fluoren-9-yl)methoxy)carbonyl)-$N^6$-(4-azidobenzoyl)-L-lysine (49): $^1$H-NMR (500 MHz, DMSO-$d_6$) δ [ppm]: 12.56 (s, 1H), 8.47 (t, J=5.6 Hz, 1H), 7.93-7.83 (m, 4H), 7.71 (d, J=7.5 Hz, 2H), 7.63 (d, J=8.0 Hz, 1H), 7.41 (t, J=7.5 Hz, 2H), 7.31 (t, J=7.4 Hz, 2H), 7.22-7.11 (m, 2H), 4.32-4.13 (m, 3H), 3.98-3.86 (m, 1H), 3.24 (q, J=6.5 Hz, 2H), 1.79-1.69 (m, 1H), 1.64 (dtd, J=14.2, 9.6, 5.2 Hz, 1H), 1.51 (dhept, J=13.0, 6.7 Hz, 2H), 1.38 (dt, J=15.8, 8.1 Hz, 2H). $^{13}$C-NMR (126 MHz, DMSO-$d_6$) δ [ppm]: 173.96, 165.07, 156.13, 143.79, 142.03, 140.67, 131.19, 129.00, 127.60, 127.03, 125.24, 120.09, 118.79, 65.58, 53.74, 46.63, 30.45, 28.68, 23.16. LRMS (ESI-Quad) [m/z]: 514.3 $[M+H]^+$, HRMS (ESI-IT) [m/z]: 514.2076, calculated 514.2085 for $C_{28}H_{28}N_5O_5$ $[M+H]^+$, err [ppm] −1.750.

1.1.1.8.1 General Procedure a for the Solid-Supported Synthesis of $FA-N_3$

The solid-phase syntheses of the $FA-N_3$-3-11 were carried out manually on a scale of 218 µmol on Rapp 2-chlorotrityl resin (Rapp Polymere, Tubingen, Germany, 1.09 mmol/g) using fritted glass peptide synthesis vessels and Fmoc-protected amino acids. The side chain protections of the amino acids were as follows: Lys:Boc and Asp:OtBu. Furthermore Fmoc-azidoornithine, (S)-4-((((9H-fluoren-9-yl)methoxy)carbonyl)amino)-5-(tert-butoxy)-5-oxopentanoic acid and $N^2$-(((9H-fluoren-9-yl)methoxy)carbonyl)-$N^6$-(4-azidobenzoyl)-L-lysine 49 were utilized. For the loading of the resin a solution the first Fmoc-protected amino acid (218 µmol, 1.0 eq) Fmoc-Cys(Trt)-OH and 497 µL (4.36 mmol, 20 eq) NMM in 4 mL dry DMF was reacted shaking it with the resin for 24 h at 23° C. The solvent was removed from the resin and the resin was reacted shaking it for 1 h at 23° C. with a solution of 1 mL MeOH and 497 µL (4.36 mmol, 20 eq) NMM in 4 mL dry DMF. The resin was washed with DMF, $CH_2Cl_2$ and DMF (each 3×4 mL, 2 min). Fmoc cleavage was achieved by repeated reaction of the resin shaking it with a mixture of piperidine in DMF (Pip:DMF/1:4, 3×5 mL, 10 min) and subsequent washing of the resin with DMF, $CH_2Cl_2$ and DMF (each 3×4 mL, 2 min). The coupling of the amino acids was performed shaking with preactivated solutions of Fmoc-protected amino acids (436 µmol, 2.0 eq), 59 mg (436 µmol, 2.0 eq) HOAt, 144 µL (1.308 mmol, 6.0 eq) NMM and 166 mg (436 µmol, 2.0 eq) HATU in 4 mL of dry DMF with coupling times of 4 h at 23° C. Subsequently the resin was washed with DMF, $CH_2Cl_2$ and DMF (each 3×4 mL, 2 min). Fmoc cleavage was achieved by repeated reaction of the resin shaking it with a mixture of piperidine in DMF (Pip:DMF/1:4, 3×5 mL, 10 min) and subsequent washing of the resin with DMF, $CH_2Cl_2$ and DMF (each 3×4 mL, 2 min).

For the attachment of the folic acid unit in parallel with the last amino acid coupling 150 mg (1.308 mmol, 6.0 eq) N-hydroxysuccinimide and 270 mg (1.308 mmol, 6.0 eq) DCC, were added to a solution of 577 mg (1.308 mmol, 6.0 eq) folic acid in 4 mL dry DMSO and stirred under light exclusion for 24 h at 23° C. The resulting suspension was filtered through a Whatman® filter (45 µm) onto the peptide-loaded resin presenting free amino groups (described above) and was reacted shaking it for 24 h at 23° C. under light exclusion. The resin was washed with DMF, $CH_2Cl_2$, DMF, $CH_2Cl_2$ (each 3×4 mL, 2 min) and the assembled folic acid derivative was cleaved from the resin by repeated treatment with a 4:1-mixture of $CH_2Cl_2$:HFIP (3×5 mL, 10 min). The cleavage solution was concentrated under reduced pressure and the residue treated with an Argon-flow-degassed mixture of TFA:TIPS:$H_2O$:nPrSH/100:3:3:3 at 23° C. (2×5 mL, 1 h). Upon treatment with ice-cold $Et_2O$ (20 mL) a yellow precipitate formed, which was collected, redissolved in DMSO:$H_2O$/1:3, filtered through a Whatman® filter (45 µm) and purified by RP prep HPLC (Phenomenex Gemini C18 RP-column 00G-4435-PO-AX, 5 µm, 110A, 250×21.20 mm, Flow: 9 mL/min, ACN:$H_2O$+TFA/10:90+0.1%→95:5+0.1% in 60 min) yielding after lyophilization the corresponding $FA-N_3$-3-11 as deep yellow, amorphous solids.

FA-N$_3$-3—N$^2$—((S)-4-(4-(((2-amino-4-hydroxypte-ridin-6-yl)methyl)amino)benzamido)-4-carboxybu-tanoyl)-D-aspartyl-L-aspartyl-L-aspartyl-N$^6$-(4-azi-dobenzoyl)-L-lysine

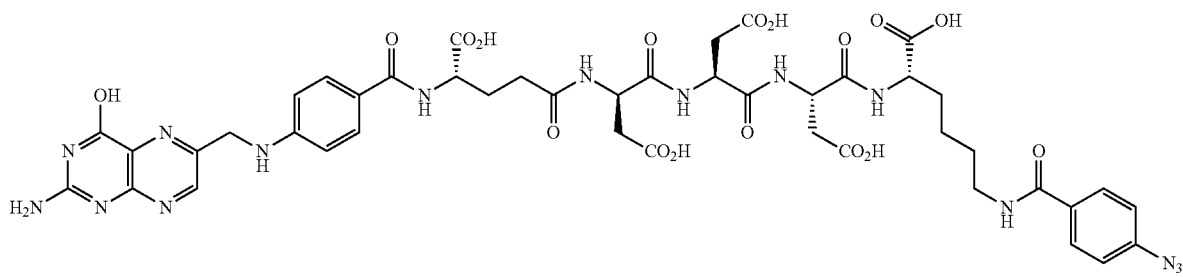

Chemical Formula: C$_{44}$H$_{49}$N$_{15}$O$_{17}$
Molecular Weight: 1059.96
FA-N$_3$-3

Following the general procedure A, 114 mg of FA-N$_3$-3 as a deep yellow, amorphous TFA salt were obtained.

FA-N$_3$-3: LRMS (ESI-Quad) [m/z]: 1060.4 [M+H]$^+$, HRMS (ESI-IT) [m/z]: 530.678558, calculated 530.678819 for C$_{44}$H$_{51}$N$_{15}$O$_{17}$ [M+2H]$^{2+}$, err [ppm] 0.491

FA-N$_3$-4—N$^2$-N$^2$—((S)-4-(4-(((2-amino-4-hy-droxypteridin-6-yl)methyl)amino)benzamido)-4-carboxybutanoyl)-D-aspartyl-D-aspartyl-N$^6$-(4-azi-dobenzoyl)-L-lysyl-L-aspartyl-L-aspartyl-N$^6$-(4-azidobenzoyl)-L-lysine

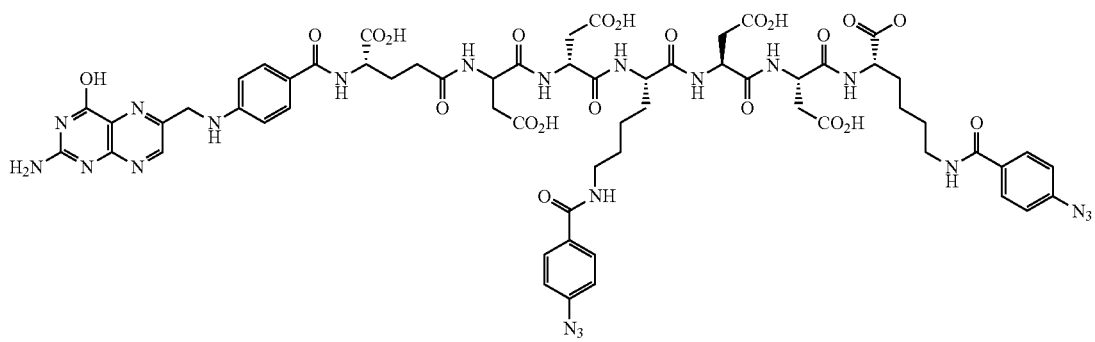

Chemical Formula: C$_{61}$H$_{69}$N$_{21}$O$_{22}$
Molecular Weight: 1448,35
FA—N$_3$—4

Following the general procedure A, 90 mg of FA-N$_3$-4 as a deep yellow, amorphous poly TFA salt were obtained.

FA-N$_3$-4: LRMS (ESI-Quad) [m/z]: 1448.7 [M+H]$^+$, HRMS (ESI-IT) [m/z]: 724.7536, calculated 724.7536 for C$_{61}$H$_{71}$N$_{21}$O$_{22}$ [M+2H]$^{2+}$, err [ppm] 0.00.

FA-N₃-5—$N^2$-(4-(((2-amino-4-hydroxypteridin-6-yl)methyl)amino)benzoyl)-N5-((R)-1-(((R)-1-(((R)-1-(((R)-1-(((R)-1-(((S)-4-azido-1-carboxybutyl)amino)-3-carboxy-1-oxopropan-2-yl)amino)-3-carboxy-1-oxopropan-2-yl)amino)-3-carboxy-1-oxopropan-2-yl)amino)-3-carboxy-1-oxopropan-2-yl)amino)-3-carboxy-1-oxopropan-2-yl)-L-glutamine

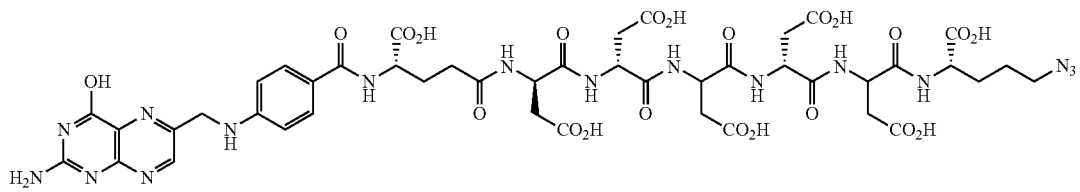

Chemical Formula: $C_{44}H_{52}N_{16}O_{22}$
Molecular Weight: 1156,99

FA—N₃—5

Following the general procedure A, 85 mg of FA-N₃-5 as a deep yellow, amorphous TFA salt were obtained.

FA-N₃-5: LRMS (ESI-Quad) [m/z]: 1157.3 $[M+H]^+$, HRMS (ESI-IT) [m/z]: 579.179534, calculated 579.179380 for $C_{44}H_{54}N_{16}O_{22}$ $[M+2H]^{2+}$, err [ppm] –0.266.

FA-N₃-6—(3S,8S,13S)-1-(4-(((2-amino-4-hydroxypteridin-6-yl)methyl)amino)phenyl)-19-(4-azidophenyl)-1,6,11,19-tetraoxo-2,7,12,18-tetraazanonadecane-3,8,13-tricarboxylic acid

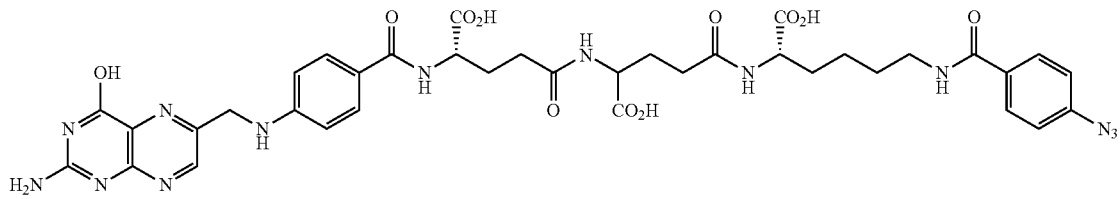

Chemical Formula: $C_{37}H_{41}N_{13}O_{11}$
Molecular Weight: 843,82

FA—N₃—6

Following the general procedure A, 60 mg of FA-N₃-6 as a deep yellow, amorphous TFA salt were obtained.

FA-N₃-6: LRMS (ESI-Quad) [m/z]: 844.3 $[M+H]^+$, HRMS (ESI-IT) [m/z]: 844.311777, calculated 844.312126 for $C_{37}H_{42}N_{13}O_{11}$ $[M+H]^+$, err [ppm] 0.413

FA-N₃-7—$N^2$-(4-(((2-amino-4-hydroxypteridin-6-yl)methyl)amino)benzoyl)-$N^5$—((S)-4-(((S)-4-azido-1-carboxybutyl)amino)-1-carboxy-4-oxobutyl)-L-glutamine

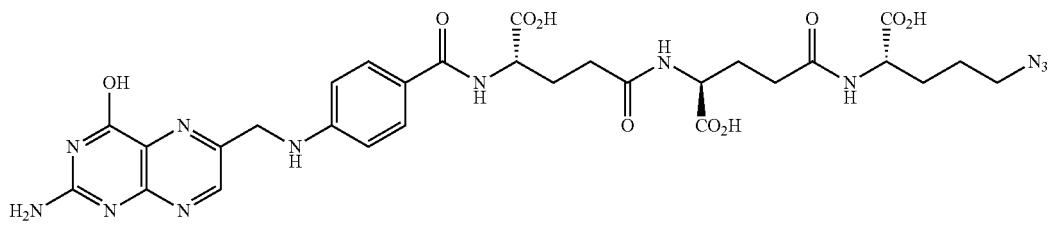

Chemical Formula: $C_{29}H_{34}N_{12}O_{10}$
Molecular Weight: 710,67

FA—N₃—7

Following the general procedure A, 52 mg of FA-N$_3$-7 as a deep yellow, amorphous TFA salt were obtained.

FA-N$_3$-7: LRMS (ESI-Quad) [m/z]: 711.3 [M+H]$^+$, HRMS (ESI-IT) [m/z]: 711.2589, calculated 711.2594 for C$_{29}$H$_{35}$N$_{12}$O$_{10}$ [M+H]$^+$, err [ppm] 0.600.

FA-N$_3$-8—N$^2$—((S)-4-(4-(((2-amino-4-hydroxypteridin-6-yl)methyl)amino)benzamido)-4-carboxybutanoyl)-N$^6$-(4-azidobenzoyl)-L-lysyl-D-lysine

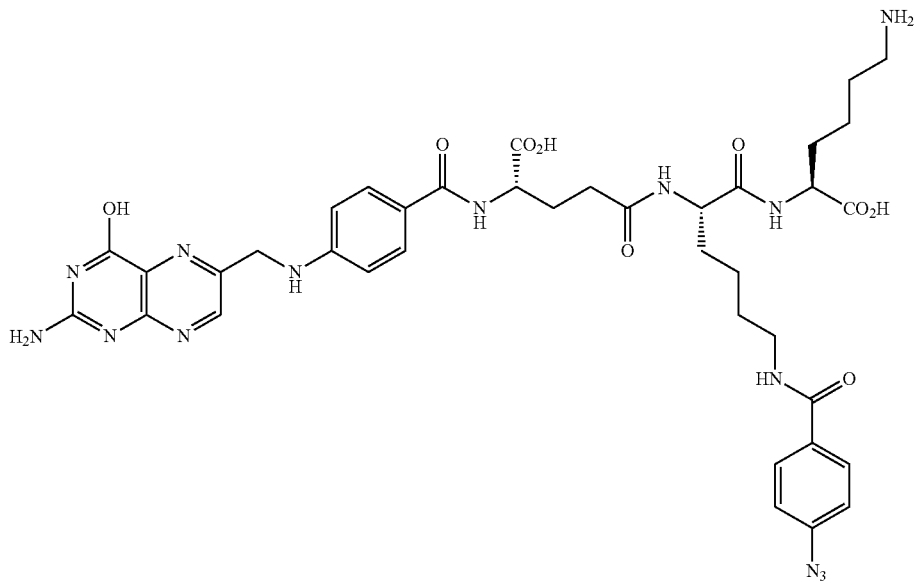

Chemical Formula: C$_{38}$H$_{46}$N$_{14}$O$_9$
Molecular Weight: 842,8750

FA—N$_3$—8

Following the general procedure A, 49 mg of FA-N$_3$-8 as a deep yellow, amorphous TFA salt were obtained.

FA-N$_3$-8: LRMS (ESI-Quad) [m/z]: 843.4 [M+H]$^+$, HRMS (ESI-IT) [m/z]: 843.364120, calculated 843.364496 for C$_{38}$H$_{47}$N$_{14}$O$_9$[M+H]$^+$, err [ppm] 0.445.

FA-N$_3$-9—((S)-2-((S)-4-(4-(((2-amino-4-hydroxypteridin-6-yl)methyl)amino)benzamido)-4-carboxybutanamido)-5-azidopentanoyl)-D-lysine

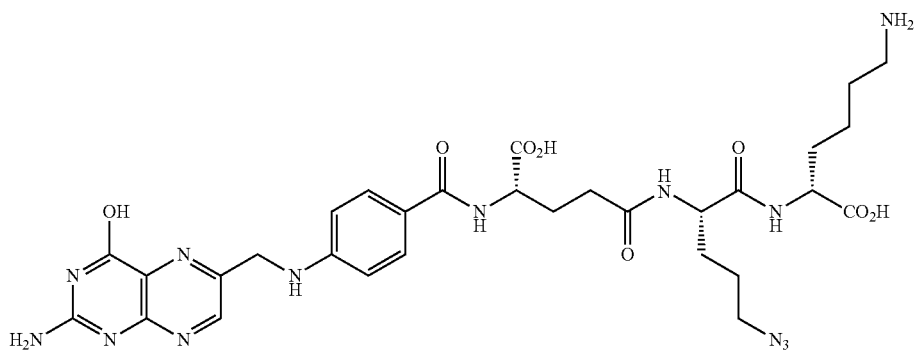

Chemical Formula: C$_{30}$H$_{39}$N$_{13}$O$_8$
Molecular Weight: 709,73

FA—N$_3$—9

Following the general procedure A, 53 mg of FA-N$_3$-9 as a deep yellow, amorphous TFA salt were obtained.

FA-N$_3$-9: LRMS (ESI-Quad) [m/z]: 710.3 [M+H]$^+$, HRMS (ESI-IT) [m/z]: 710.311272, calculated 710.311732 for C$_{30}$H$_{40}$N$_{13}$O$_8$[M+H]$^+$, err [ppm] 0.647.

FA-N$_3$-10—((S)-2-((R)-2-((R)-2-((R)-2-((S)-4-(4-(((2-amino-4-hydroxypteridin-6-yl)methyl)amino)benz-amido)-4-carboxybutanamido)-3-carboxypropanamido)-3-carboxypropanamido)-3-carboxypropanamido)-5-azidopentanoyl)-D-aspartyl-D-aspartyl-D-lysine

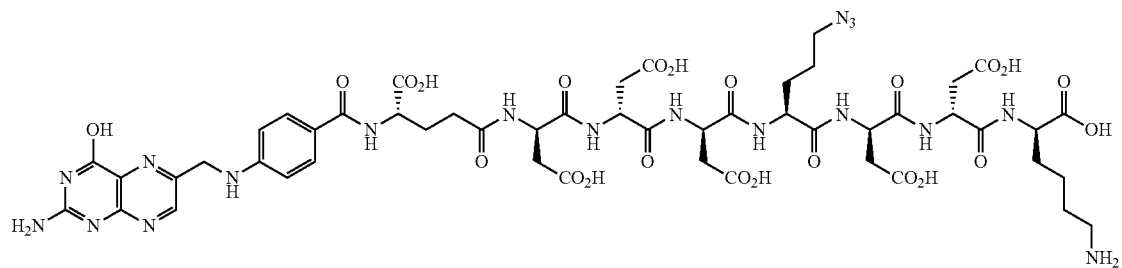

Chemical Formula: C$_{50}$H$_{64}$N$_{18}$O$_{23}$
Molecular Weight: 1285,17

FA—N$_3$—10

Following the general procedure A, 93 mg of FA-N$_3$-10 as a deep yellow, amorphous TFA salt were obtained.

FA-N$_3$-10: LRMS (ESI-Quad) [m/z]: 1285.6 [M+H]$^+$, HRMS (ESI-IT) [m/z]: 643.226691, calculated 643.226862 for C$_{50}$H$_{66}$N$_{18}$O$_{23}$ [M+2H]$^{2+}$, err [ppm] 0.265.

FA-N$_3$-11—N$^2$-(4-(((2-amino-4-hydroxypteridin-6-yl)methyl)amino)benzoyl)-N$^5$-((R)-1-(((R)-1-(((S)-5-azido-1-(((R)-1-(((R)-1-(((S)-5-azido-1-(((R)-1-(((R)-1-(((S)-4-azido-1-carboxybutyl)amino)-3-carboxy-1-oxopropan-2-yl)amino)-3-carboxy-1-oxopropan-2-yl)amino)-1-oxopentan-2-yl)amino)-3-carboxy-1-oxopropan-2-yl)amino)-3-carboxy-1-oxopropan-2-yl)amino)-1-oxopentan-2-yl)amino)-3-carboxy-1-oxopropan-2-yl)amino)-3-carboxy-1-oxopropan-2-yl)-L-glutamine

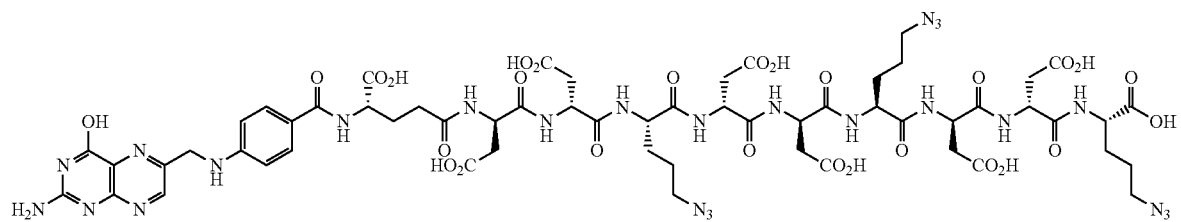

Chemical Formula: C$_{58}$H$_{73}$N$_{25}$O$_{27}$
Molecular Weight: 1552,37

FA—N$_3$—11

Following the general procedure A, 53 mg of FA-N$_3$-11 as a deep yellow, amorphous TFA salt were obtained.

FA-N$_3$-11: LRMS (ESI-Quad) [m/z]: 1552.5 [M+H]$^+$, HRMS (ESI-IT) [m/z]: 776.762091, calculated 776.762663 for C$_{58}$H$_{75}$N$_{25}$O$_{27}$ [M+2H]$^{2+}$, err [ppm] 0.736.

Synthesis of FA-SH-1—N²-(4-(((2-amino-4-hy-droxypteridin-6-yl)methyl)amino)benzoyl)-N⁵-((R)-1-carboxy-2-mercaptoethyl)-L-glutamine

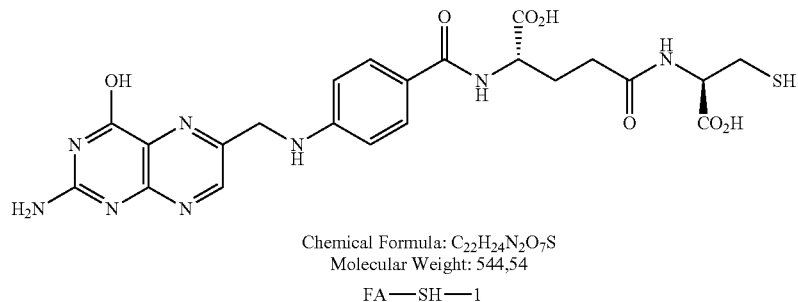

Chemical Formula: C$_{22}$H$_{24}$N$_{2}$O$_{7}$S
Molecular Weight: 544,54

FA—SH—1

The solid-phase synthesis of the FA-SH-1 was carried out manually on a scale of 484 μmol on Rapp 2-chlorotrityl resin (Rapp Polymere, Tubingen, Germany, 1.21 mmol/g) using fritted glass peptide synthesis vessels. For the loading of the resin a solution 567 mg (968 μmol, 2.0 eq) Fmoc-Cys(Trt)-OH and 2.12 mL (19.36 mmol, 20 eq) NMM in 7.5 mL dry DMF was reacted shaking it with the resin for 24 h at 23° C. The solvent was removed from the resin and the resin was reacted shaking it for 1 h at 23° C. with a solution of 1 mL MeOH and 2.12 mL (19.36 mmol, 20 eq) NMM in 7.5 mL dry DMF. The resin was washed with DMF, CH$_2$Cl$_2$ and DMF (each 3×10 mL, 2 min). Fmoc cleavage achieved by repeated reaction of the resin shaking it with a mixture of piperidine in DMF (Pip:DMF/1:4, 3×10 mL, 10 min) and subsequent washing of the resin with DMF, CH$_2$Cl$_2$ and DMF (each 3×10 mL, 2 min).

In parallel, 220 mg (1.94 mmol, 4.0 eq) N-hydroxysuccinimide and 400 mg (1.94 mmol, 4.0 eq) DCC, were added to a solution of 853 mg (1.94 mmol, 4.0 eq) folic acid in 7.5 M dry DMSO and stirred under light exclusion for 24 h at 23° C. The resulting suspension was filtered through a Whatman® filter (45 μm) onto the Cys-loaded resin presenting free amino groups (described above) and was reacted shaking it for 24 h at 23° C. under light exclusion. The resin was washed with DMF, CH$_2$Cl$_2$, DMF, CH$_2$Cl$_2$ (each 3×10 mL, 2 min) and the assembled folic acid derivative was cleaved from the resin by repeated treatment with an Argon-flow-degassed mixture of TFA:TIPS:H$_2$O:nPrSH/ 100:3:3:3 at 23° C. (2×5 mL, 1 h). Upon treatment with ice-cold Et$_2$O (20 mL) a yellow precipitate formed, which was collected, redissolved in DMSO:H$_2$O/1:3, filtered through a Whatman® filter (45 μm) and purified by RP prep HPLC (Thermo Fisher Scientific BDS Hypersil C18 RP-column 28105-259370, 5 μm, 250×30 mm, Flow: 25 mL/min, ACN:H$_2$O+TFA/10:90+0.1%→95:5+0.1% in 60 min) yielding after lyophilization 155.0 mg (285.6 μmol, 59%) of FA-SH as a deep-yellow solid.

FA-SH-1: LRMS (ESI-Quad) [m/z]: 1086.5 [M+H]⁺, HRMS (ESI-IT) [m/z]: 1086.441323, calculated 1086.442337 for C$_{22}$H$_{24}$N$_{8}$O$_{7}$S [M+H]⁺, err [ppm] −0.933.

1.1.1.9 Synthesis of Gonadoliberin Derivatives 1.1.1.9.1 General Procedure B for the Solid-Supported Synthesis of Gonadoliberin-Derivatives Scheme 9: SPS of Gonadoliberin derivatives

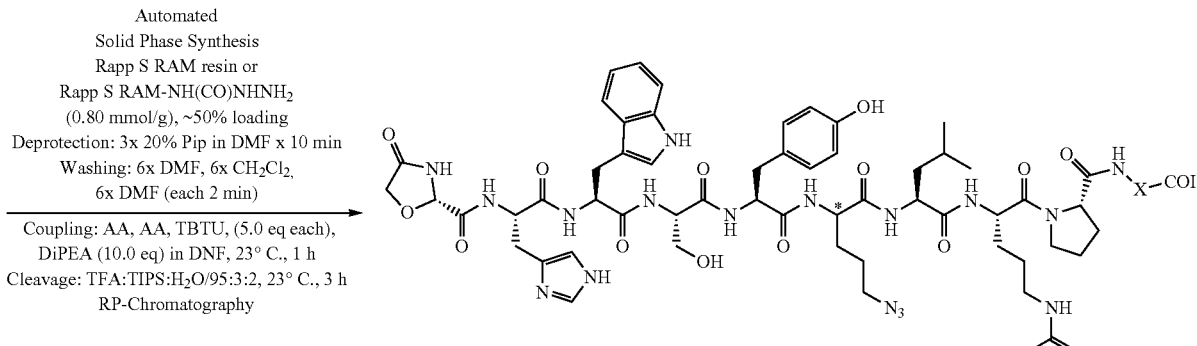

Automated
Solid Phase Synthesis
Rapp S RAM resin or
Rapp S RAM-NH(CO)NHNH$_2$
(0.80 mmol/g), ~50% loading
Deprotection: 3x 20% Pip in DMF x 10 min
Washing: 6x DMF, 6x CH$_2$Cl$_2$,
6x DMF (each 2 min)
Coupling: AA, AA, TBTU, (5.0 eq each),
DiPEA (10.0 eq) in DNF, 23° C., 1 h
Cleavage: TFA:TIPS:H$_2$O/95:3:2, 23° C., 3 h
RP-Chromatography Solid-phase synthesis of the peptide was carried out on a scale of 150 μmol with a Syro Multiple Peptide Synthesizer (MultiSynTech, Witten, Germany) on Rapp S RAM resin (Rapp Polymere, Tubingen, Germany, 0.8 mmol/g). Fmoc-protected amino acids were coupled to the resin using a fivefold excess of Fmoc-protected amino acid:TBTU: DiPEA/1:1:2 and coupling times of 1 h at 23° C. The side chain protections of the amino acids were as follows: Arg: Pbf; His: Trt; Ser and Tyr: t-Bu; Trp: Boc. The peptide was cleaved from the resin and deprotected by a treatment with TFA:TIPS:H$_2$O/95:3:2 (10 ml/g resin) over 3 h at 23° C. After precipitation with t-butylmethyl ether, the resulting crude peptide was purified by reparative HPLC (RP-18) with water/acetonitrile gradients containing 0.1% TFA and characterized by analytical HPLC and MALDI-MS.

Synthesis of LHRH—(S)—N-(2-amino-2-oxoethyl)-1-(((S)-5-oxopyrrolidine-2-carbonyl)-L-histidyl-L-tryptophyl-L-seryl-L-tyrosylglycyl-L-leucyl-L-arginyl)pyrrolidine-2-carboxamide

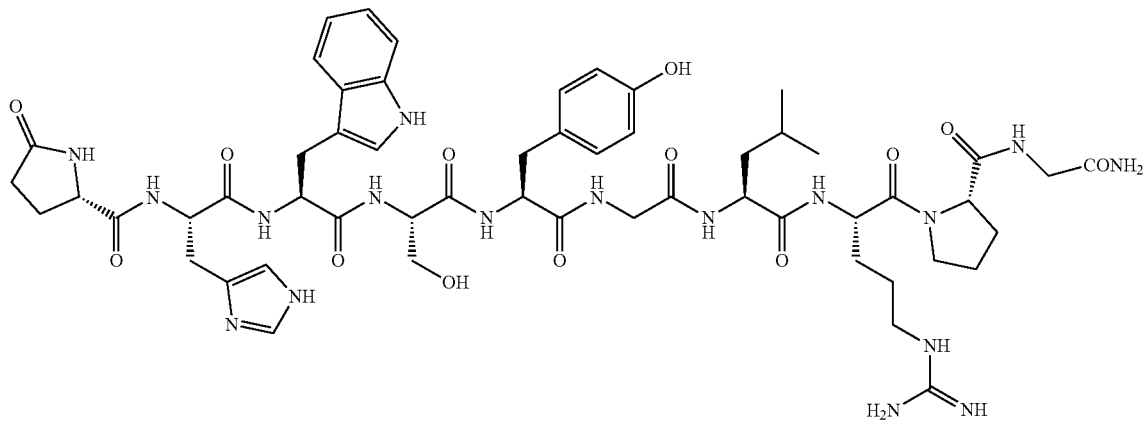

Chemical Formula: $C_{55}H_{75}N_{17}O_{13}$
Molecular Weight: 1182,31

LHRH

Following the general procedure B, 68 mg of LHRH as a white, amorphous TFA salt were obtained.

LHRH: LRMS (MALDI) [m/z]: 1182.5 [M+H]$^+$, HRMS (ESI-IT) [m/z]: 1182.5802, calculated 1182.5803 for $C_{55}H_{76}N_{17}O_{13}$ [M+H]$^+$, err [ppm] 0.1.

Synthesis of L-N$_3$-Orn-LHRH—(S)-1-(((S)-2-((S)-2-((S)-2-((S)-3-(1H-imidazol-4-yl)-2-((S)-5-oxopyrrolidine-2-carboxamido)propanamido)-3-(1H-indol-3-yl)propanamido)-3-hydroxypropanamido)-3-(4-hydroxyphenyl)propanamido)-5-azidopentanoyl)-L-leucyl-L-arginyl)-N-(2-amino-2-oxoethyl)pyrrolidine-2-carboxamide

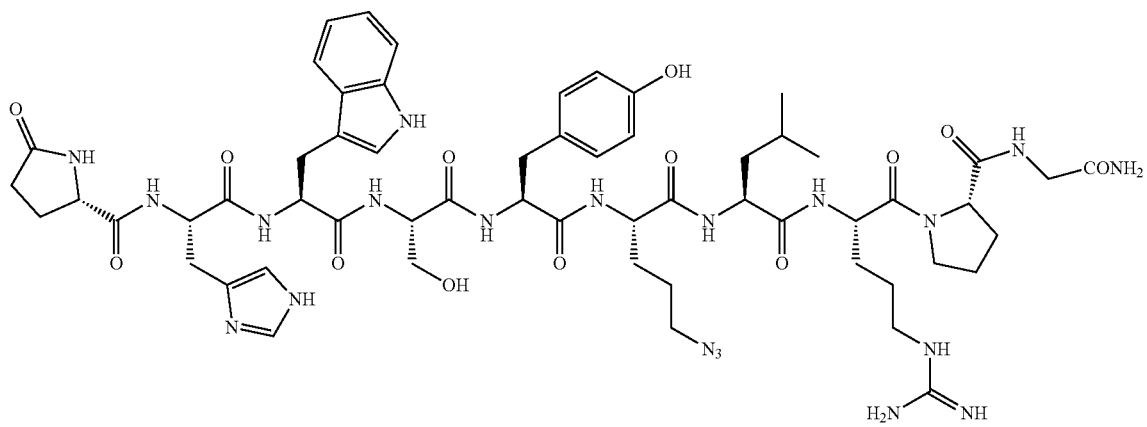

Chemical Formula: $C_{58}H_{80}N_{20}O_{13}$
Molecular Weight: 1265,41

L—N$_3$—Orn—LHRH

Following the general procedure B, 78 mg of L-N$_3$-Orn-LHRH as a white, amorphous TFA salt were obtained.

L-N$_3$-Orn-LHRH: LRMS (MALDI) [m/z]: 1256.6 [M+H]$^+$, HRMS (ESI-IT) [m/z]: 633.3182, calculated 633.3180 for $C_{58}H_{82}N_{20}O_{13}$ [M+2H]$^{2+}$, err [ppm] −0.300.

Synthesis of D-N₃-Orn-LHRH—(S)-1-(((R)-2-((S)-2-((S)-2-((S)-2-((S)-3-(1H-imidazol-4-yl)-2-((S)-5-oxopyrrolidine-2-carboxamido)propanamido)-3-(1H-indol-3-yl)propanamido)-3-hydroxypropanamido)-3-(4-hydroxyphenyl)propanamido)-5-azidopentanoyl)-L-leucyl-L-arginyl)-N-(2-amino-2-oxoethyl)pyrrolidine-2-carboxamide

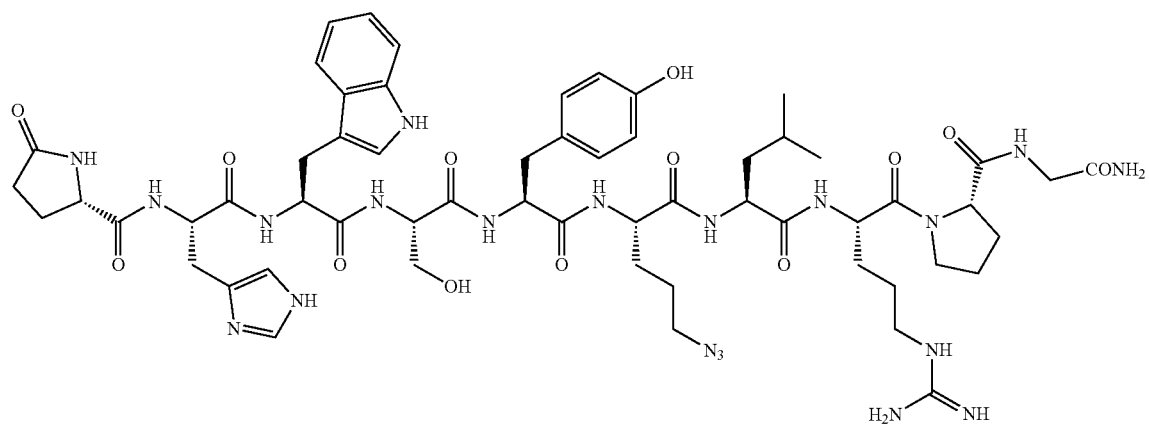

Chemical Formula: $C_{58}H_{80}N_{20}O_{13}$
Molecular Weight: 1265,41

D—N₃—Orn—LHRH

Following the general procedure B, 77 mg of D-N₃-Orn-LHRH as a white, amorphous TFA salt were obtained.

D-N₃-Orn-LHRH: LRMS (MALDI) [m/z]: 1265.7 [M+H]⁺, HRMS (ESI-IT) [m/z]: 633.3182, calculated 633.3180 for $C_{58}H_{82}N_{20}O_{13}$ [M+2H]²⁺, err [ppm] −0.300.

Synthesis of D-N₃-Orn-Goserellin—(S)—N-((6S,9S,12R,15S,18S,21S,24S)-21-((1H-indol-3-yl)methyl)-1-amino-12-(3-azidopropyl)-6-((S)-2-(2-carbamoylhydrazine-1-carbonyl)pyrrolidine-1-carbonyl)-15-(4-hydroxybenzyl)-18-(hydroxymethyl)-25-(1H-imidazol-4-yl)-1-imino-9-isobutyl-8,11,14,17,20,23-hexaoxo-2,7,10,13,16,19,22-heptaazapentacosan-24-yl)-5-oxopyrrolidine-2-carboxamide

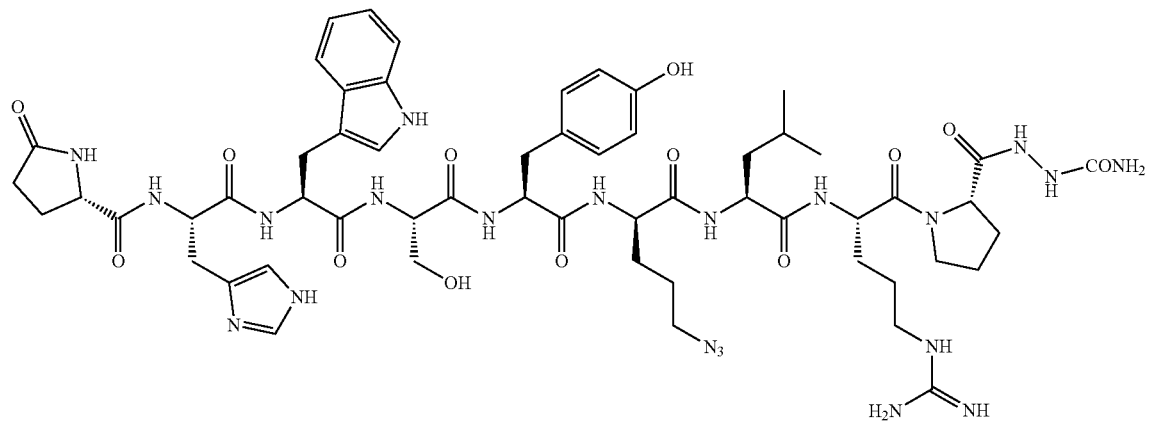

Chemical Formula: $C_{57}H_{79}N_{21}O_{13}$
Molecular Weight: 1266,39

D—N₃—Orn—Goserellin

Rapp S RAM resin (100 µmol, 0.8 mmol/g) was treated for 10 min with 20% piperidine in DMF at 23° C. to remove the Fmoc group, followed by washing with DMF (5×5 mL, 2 min) and DCM (5×5 mL, 2 min). 162 mg (1.0 mmol, 10.0 eq) carbonyldiimidazole in dry DCM (3 mL) were added and the mixture was incubated for 3 h at 23° C. with shaking, followed by washing with DCM (5×5 mL, 2 min) and DMF (5×5 mL, 2 min). The resin was then treated with hydrazine in DMF (5 mL, ca. 2 M)[9] for 1 h at 23° C.[10] Afterwards the resin was washed with DMF (5×5 mL, 2 min) and the peptide was assembled on a Syro Multiple Peptide Synthesizer, cleaved, purified and characterized as described in the general procedure B, yielding 20 mg of D-N$_3$-Orn-Goserellin.

[9] 5 mL Hydrazine-DMF solution were prepared from 10 mL 1 M hydrazine solution in THF by adding 5 mL DMF and evaporation of the THF at 20 mmHg and 37° C. over 30 min.

[10] Synthesis was designed analog to a procedure of Verhelst et al.[71]

D-N$_3$-Orn-Goserellin: LRMS (MALDI) [m/z]: 1266.8 [M+H]$^+$, HRMS (ESI-IT) [m/z]: 633.8156, calculated 633.8156 for $C_{57}H_{75}N_{21}O_{13}$ [M+2H]$^{2+}$, err [ppm] 0.0.

Synthesis of Imaging Probes 1.1.1.10 Synthesis of Clickable Fluorescence Dyes

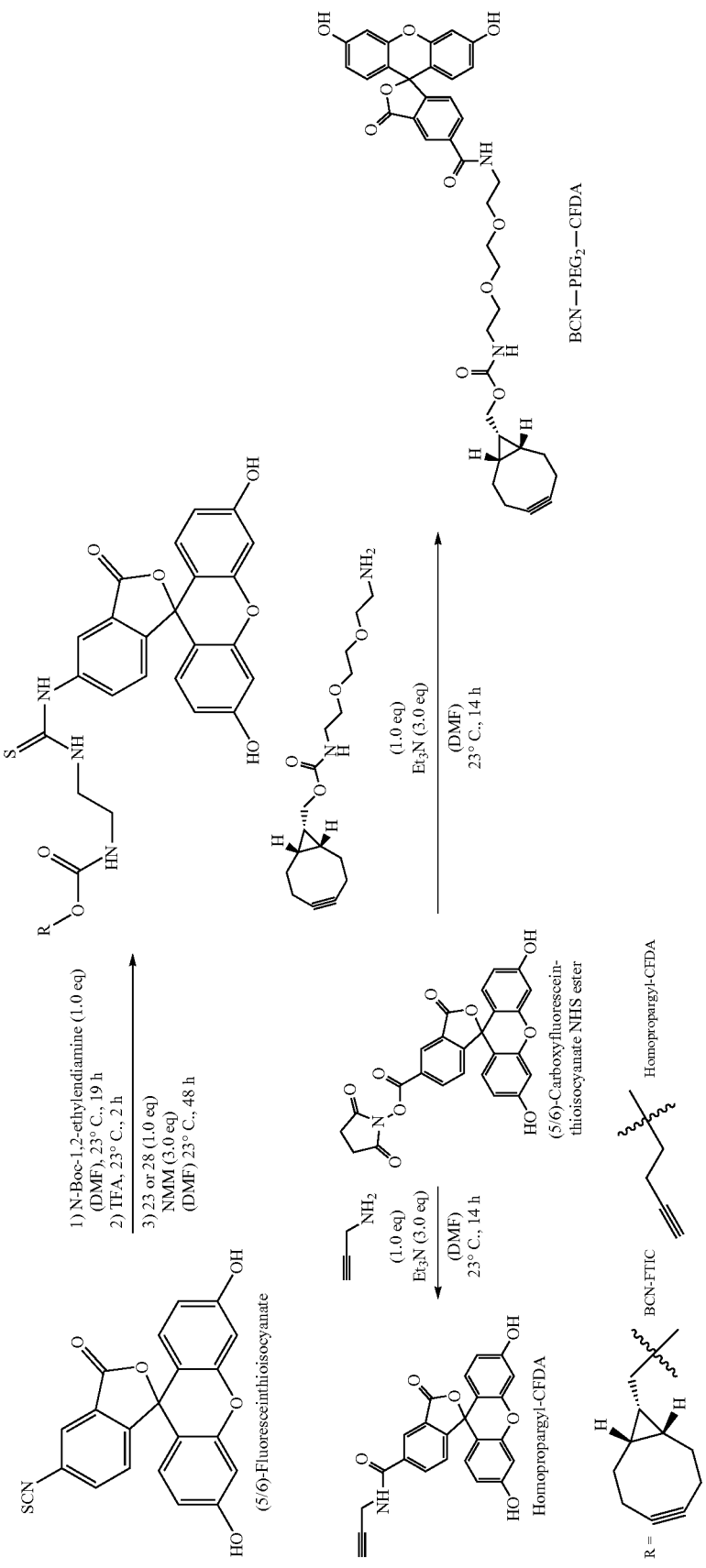

Synthesis of BCN-FTIC—((1R,8S,9s)-bicyclo[6.1.0]non-4-yn-9-yl)methyl (2-(3-(3',6'-dihydroxy-3-oxo-3H-spiro[isobenzofuran-1,9'-xanthen]-5/6-yl)thioureido)ethyl)carbamate

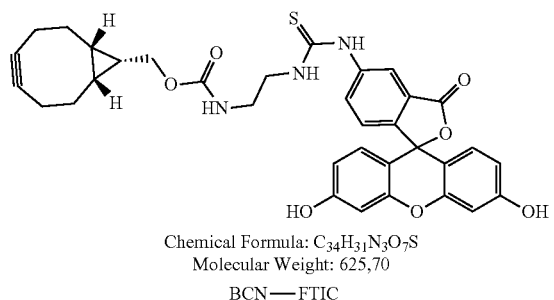

Chemical Formula: $C_{34}H_{31}N_3O_7S$
Molecular Weight: 625,70
BCN—FTIC

To a solution of 50 mg (128 μmol, 1.0 eq) 5/6-fluoresceinthioisocyanate (FTIC) in 1.3 mL dry DMF was added 20.5 mg (128 μmol, 1.0 eq) N-Boc-1,2-ethylendiamine and the mixture was stirred for 19 h at 23° C. The reaction mixture was diluted with toluene (5 mL), concentrated and coevaporated with toluene (4×5 mL) under reduced pressure. The residue was taken up in 130 μL TFA and stirred for 1.5 h at 23° C. The mixture was diluted with toluene (5 mL), concentrated and coevaporated with toluene (3×4 mL) under reduced pressure and the residue was dried in HV. The residue was then dissolved in 1.3 mL dry DMF, 43 μL (384 μmol, 3.0 eq) NMM and 40 mg (128 μmol, 1.0 eq) 28 were added and the mixture was stirred for 48 h at 23° C. The reaction mixture was diluted with toluene (5 mL), concentrated and coevaporated with toluene (5×5 mL) under reduced pressure. The residue was purified by preparative thin-layer chromatography ($CH_2Cl_2$:MeOH/9:1) yielding 36.6 mg (58.49 μmol, 46%) of BCN-FTIC as a deep orange, amorphous solid.

BCN-FTIC: TCL ($CH_2Cl_2$:MeOH/9:1) $R_f$: 0.35 [UV$^{254}$, Vis], $^1$H-NMR (500 MHz, MeOD-$d_4$) δ [ppm]: 8.07 (s, 1H), 7.75 (d, J=7.8 Hz, 1H), 7.17 (d, J=8.2 Hz, 1H), 6.74 (d, J=8.7 Hz, 2H), 6.68 (d, J=2.4 Hz, 2H), 6.55 (dd, J=8.7, 2.4 Hz, 2H), 4.10 (d, J=8.1 Hz, 2H), 3.80-3.66 (m, 2H), 3.37 (t, J=5.8 Hz, 1H), 3.35 (s, 1H), 2.17 (dq, J=32.4, 14.9, 14.3 Hz, 6H), 1.53 (q, J=8.5 Hz, 2H), 1.34 (dt, J=14.5, 7.3 Hz, 1H), 0.93-0.82 (m, 2H). 13C-NMR (126 MHz, MeOD-$d_4$) δ [ppm]: 183.13, 171.18, 162.56, 159.80, 154.60, 141.86, 131.82, 130.55, 126.33, 120.97, 114.26, 111.85, 103.55, 99.50, 92.45, 66.78, 63.97, 55.78, 40.93, 30.15, 21.92, 21.40, 18.91. LRMS (ESI-Quad) [m/z]: 626.2 [M+H]$^+$, HRMS (ESI-IT) [m/z]: 626.194754, calculated 626.195548 for $C_{34}H_{32}N_3O_7S$ [M+H]$^+$, err [ppm] 1.268.

Synthesis of Homopropargyl-FTIC—But-3-yn-1-yl (2-(3-(3',6'-dihydroxy-3-oxo-3H-spiro[isobenzofuran-1,9'-xanthen]-5/6-yl)thioureido)ethyl)carbamate

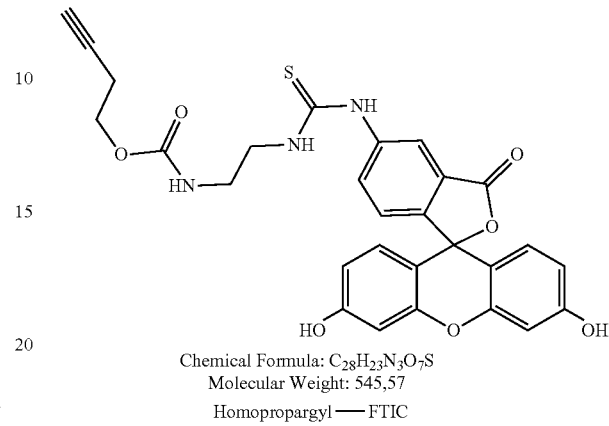

Chemical Formula: $C_{28}H_{23}N_3O_7S$
Molecular Weight: 545,57
Homopropargyl—FTIC To a solution of 50 mg (128 μmol, 1.0 eq) 5/6-fluoresceinthioisocyanate (FTIC) in 1.3 mL dry DMF was added 20.5 mg (128 μmol, 1.0 eq) N-Boc-1,2-ethylendiamine and the mixture was stirred for 19 h at 23° C. The reaction mixture was diluted with toluene (5 mL), concentrated and coevaporated with toluene (4×5 mL) under reduced pressure. The residue was taken up in 130 μL TFA and stirred for 1.5 h at 23° C. The mixture was diluted with toluene (5 mL), concentrated and coevaporated with toluene (3×4 mL) under reduced pressure and the residue was dried in HV. The residue was then dissolved in 1.3 mL dry DMF, 43 μL (384 μmol, 3.0 eq) NMM and 30 mg (128 μmol, 1.0 eq) 23 were added and the mixture was stirred for 48 h at 23° C. The reaction mixture was diluted with toluene (5 mL), concentrated and coevaporated with toluene (5×5 mL) under reduced pressure. The residue was purified by preparative thin-layer chromatography ($CH_2Cl_2$:MeOH/9:1) followed by purification by RP prep HPLC (Phenomenex Gemini C18 RP-column 00G-4435-PO-AX, 5 μm, 110 A, 250×21.20 mm, Flow: 9 mL/min, ACN:$H_2O$/20:90→95:5 in 45 min) yielding after lyophilization 43.6 mg (80.0 μmol, 63%) of Homopropargyl-FTIC as a deep orange, amorphous solid.

Homopropargyl-FTIC: TCL ($CH_2Cl_2$:MeOH/9:1) $R_f$: 0.20 [UV$^{254}$, Vis], $^1$H-NMR (500 MHz, DMSO-$d_6$) δ [ppm]: 8.13 (s, 1H), 7.80-7.66 (m, 1H), 7.17 (d, J=8.2 Hz, 1H), 6.73-6.63 (m, 4H), 6.55 (ddd, J=8.7, 3.9, 2.4 Hz, 2H), 4.15-4.05 (m, 2H), 3.76 (d, J=20.0 Hz, 2H), 3.38 (t, J=6.0 Hz, 2H), 2.81 (s, 10H), 2.48 (td, J=6.8, 2.6 Hz, 1H). LRMS (ESI-Quad) [m/z]: 546.1 [M+H]$^+$, HRMS (ESI-IT) [m/z]: 546.132346, calculated 546.132948 for $C_{28}H_{24}N_3O_7S$ [M+H]$^+$, err [ppm] 1.102.

Synthesis of BCN-PEG$_2$-CF—((1R,8S,9s)-bicyclo[6.1.0]non-4-yn-9-yl)methyl (2-(2-(2-(3',6'-dihydroxy-3-oxo-3H-spiro[isobenzofuran-1,9'-xanthene]-5/6-carboxamido)ethoxy)ethoxy)ethyl)carbamate

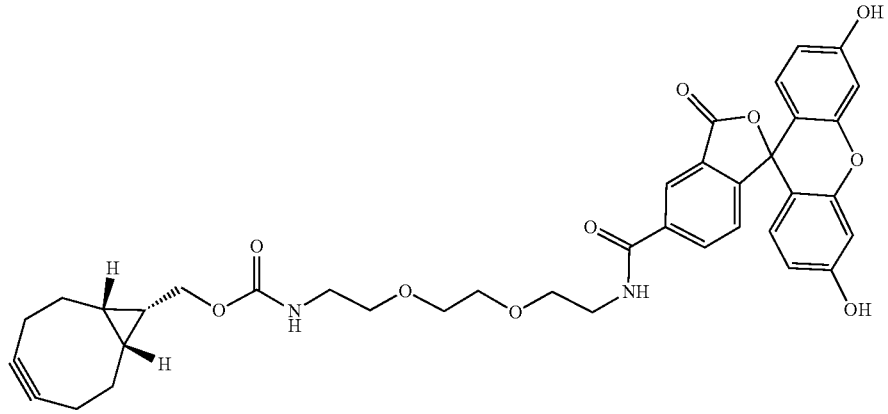

Chemical Formula: C$_{38}$H$_{38}$N$_2$O$_{10}$
Molecular Weight: 682,73
BCN—PEG$_2$—CF To a solution of 10 mg (30.8 µmol, 1.0 eq) of (5/6)-Carboxyfluoresceinthioisocyanate NHS ester and 12.8 µL (92.4 µmol, 3.0 eq) NMM in 1.23 mL DMF was added 14.6 mg (30.8 µmol, 1.0 eq) ((1R,8S,9s)-bicyclo[6.1.0]non-4-yn-9-yl)methyl (2-(2-(2-aminoethoxy)ethoxy)ethyl)carbamate and the mixture was stirred at 23° C. for 14 h. The solvent was removed under reduced pressure and the residue was coevaporated with toluene (2×10 mL). The residue was purified by preparative thin-layer chromatography (CH$_2$Cl$_2$:MeOH/9:1) yielding 14.1 mg (20.6 µmol, 67%) of BCN-PEG$_2$-CF as a mixture of the 5/6-isomers as white, amorphous solid.

BCN-PEG$_2$-CF: TCL (CH$_2$Cl$_2$:MeOH/9:1) R$_f$: 0.55 [UV$^{254}$, Vis], $^1$H-NMR (500 MHz, DMSO-d$_6$) δ [ppm]: $^1$H NMR (500 MHz, DMSO-d$_6$) δ 10.14 (s, 2H), 8.82 (dt, J=68.1, 5.6 Hz, 1H), 8.46-8.20 (m, 1H), 8.19-8.05 (m, 1H), 7.73-7.35 (m, 1H), 7.07 (dt, J=17.2, 5.6 Hz, 1H), 6.69 (dd, J=3.7, 2.3 Hz, 2H), 6.59 (dd, J=8.7, 1.7 Hz, 2H), 6.55 (ddd, J=8.6, 6.0, 2.3 Hz, 2H), 4.01 (dd, J=8.0, 3.3 Hz, 2H), 3.62-3.30 (m, 12H), 3.07 (dq, J=23.0, 6.0 Hz, 2H), 2.21 (t, J=13.1 Hz, 2H), 2.16-2.05 (m, 4H), 1.50 (d, J=9.5 Hz, 1H), 0.89-0.79 (m, 2H). $^{13}$C-NMR (126 MHz, MeOD-d$_4$) δ [ppm]: $^{13}$C NMR (126 MHz, DMSO) δ 172.73, 168.01, 164.66, 164.54, 159.57, 156.38, 154.64, 151.79, 140.51, 136.12, 134.64, 129.22, 129.14, 128.17, 126.46, 124.84, 124.22, 123.27, 112.64, 109.12, 109.06, 102.22, 98.96, 83.24, 69.54, 69.50, 69.44, 69.39, 69.13, 69.06, 68.72, 68.59, 61.33, 54.90, 48.57, 28.55, 25.21, 20.82, 19.52, 17.62. LRMS (ESI-Quad) [m/z]: 683.3 [M+H]$^+$, HRMS (ESI-IT) [m/z]: 683.259012, calculated 683.259922 for C$_{38}$H$_{39}$N$_2$O$_{10}$ [M+H]$^+$, err [ppm] 1.331.

Synthesis of Homopropargyl-CF—3',6'-dihydroxy-3-oxo-N-(prop-2-yn-1-yl)-3H-spiro[isobenzofuran-1,9'-xanthene]-5-carboxamide

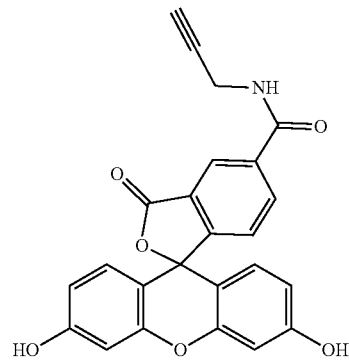

Chemical Formula: C$_{24}$H$_{15}$NO$_6$
Molecular Weight: 413,39
Homopropargyl-CF To a solution of 10.5 mg (22.18 µmol, 1.0 eq) of (5/6)-carboxyfluoresceinthioisocyanate NHS ester and 9.2 µL (66.54 µmol, 3.0 eq) triethylamine in 887 µL dry DMF was added 1.46 µL (22.18 µmol, 1.0 eq) propargylamine and the mixture was stirred at 23° C. for 4 h. The solvent was removed under reduced pressure and the residue was coevaporated with toluene (2×10 mL). The residue was purified by preparative thin-layer chromatography (CH$_2$Cl$_2$:MeOH/95:5) yielding 6.6 mg (15.6 µmol, 72%) of Homopropargyl-CF as a mixture of the 5/6-isomers as yellow, amorphous solid.

Homopropargyl-CF: TCL (CH$_2$Cl$_2$:MeOH/9:1) R$_f$: 0.56 [UV$^{254}$, Vis], $^1$H-NMR (700 MHz, DMSO-d$_6$) δ [ppm]: PK-10.15 (s, 2H), 9.22 (dt, J=109.3, 5.5 Hz, 1H), 8.49-8.22 (m, 1H), 8.20-8.06 (m, 1H), 7.71-7.34 (m, 1H), 6.69 (dd, J=6.9, 2.4 Hz, 2H), 6.59 (dd, J=8.7, 1.5 Hz, 2H), 6.56 (s, 2H), 4.11 (dd, J=5.5, 2.5 Hz, 1H), 3.99 (dd, J=5.5, 2.5 Hz, 1H), 3.17-3.16 (m, 1H). $^{13}$C-NMR (126 MHz, DMSO-d$_6$) δ [ppm]: 164.21, 159.62, 151.84, 139.85, 129.47, 129.23, 129.17, 124.99, 124.35, 123.44, 122.40, 112.73, 109.03, 102.24, 80.69, 73.10, 48.58, 28.73. LRMS (ESI-Quad) [m/z]: 414.2 [M+H]$^+$, HRMS (ESI-IT) [m/z]: 414.097870, calculated 414.097214 for C$_{24}$H$_{15}$NO$_6$ [M+H]$^+$, err [ppm] −1.585.

1.1.1.11 Synthesis of Folate-Fluorescein Conjugates

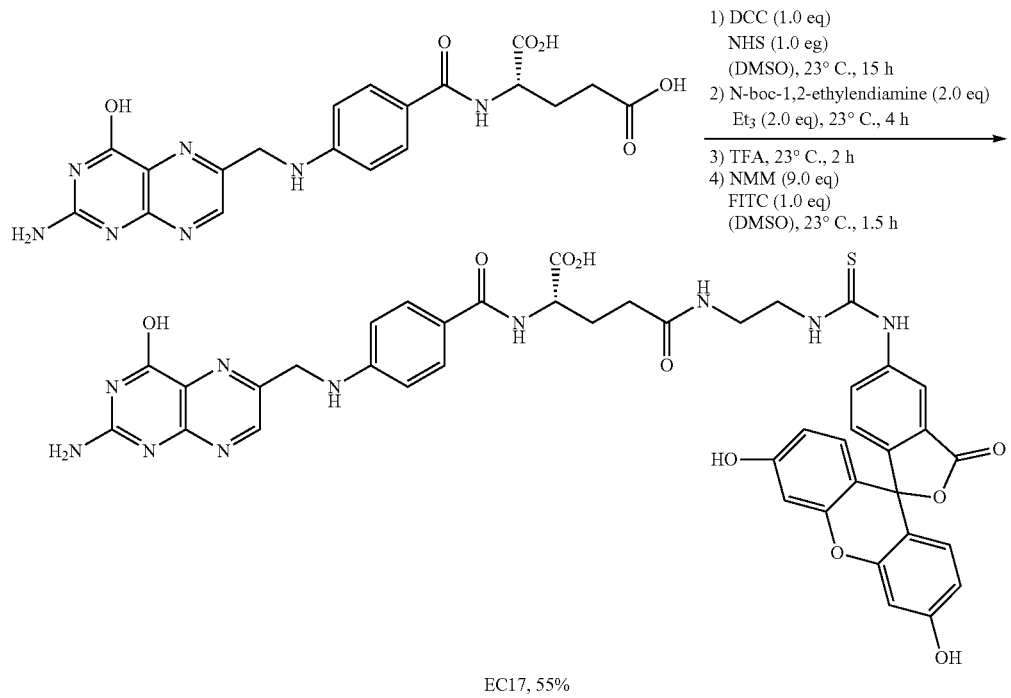

Scheme 11: Synthesis of EC17

EC17, 55%

Synthesis of EC17[62,63] —N$^2$-(4-(((2-amino-4-hydroxypteridin-6-yl)methyl)amino)benzoyl)-N$^5$-(2-(3-(3',6'-dihydroxy-3-oxo-3H-spiro[isobenzofuran-1,9'-xanthen]-5-yl)thioureido)ethyl)-L-glutamine

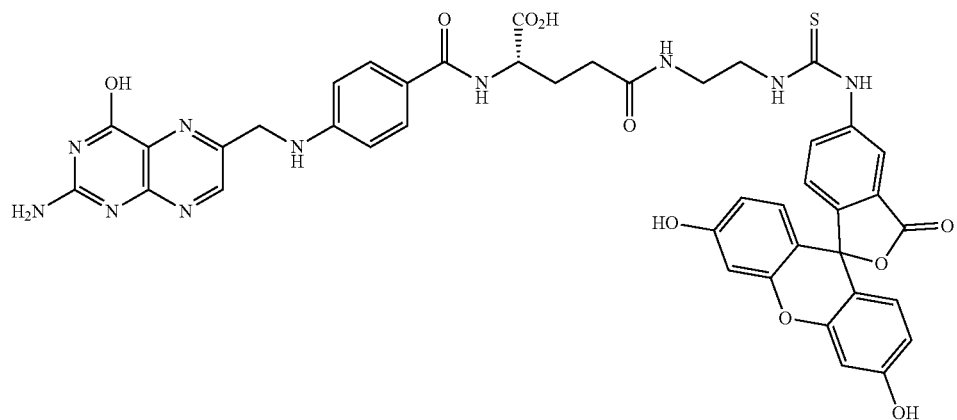

Chemical Formula: C$_{42}$H$_{36}$N$_{10}$O$_{10}$S
Molecular Weight: 872,87
EC17

To a solution of 100 mg (0.2265 mmol, 1.0 eq) folic acid and 26 mg (0.2265 mmol, 1.0 eq) N-hydroxysuccimimide in 1.13 mL dry DMSO was added 47 mg (0.2265 mmol, 1.0 eq) DCC and the mixture was stirred for 15 h at 23° C., before 62 µL (0.453 mmol, 2.0 eq) triethylamine and 71 µL (0.453 mmol, 2.0 eq) N-Boc-1,2-Ethylendiamine were added and the mixture was stirred for 24 h at 23° C. The mixture was then filtered through a Whatman® filter (45 µm), diluted with $H_2O$:ACN/70:30 (500 µL) and directly purified by RP prep HPLC (Phenomenex Gemini C18 RP-column 00G-4435-PO-AX, 5 µm, 110A, 250×21.20 mm, Flow: 9 mL/min, ACN:$H_2O$+0.1% TFA/10:90→95:5 in 35 min) yielding after lyophilization 84.6 mg (0.165 mmol, 73%) of $N^2$-(4-(((2-amino-4-hydroxypteridin-6-yl)methyl)amino)benzoyl)-$N^5$-(2-((tert-butoxycarbonyl)amino)ethyl)-L-glutamine as a deep orange, amorphous solid. 16 mg (27.4 µmol, 1.0 eq) of this compound were dissolved in 109 µL TFA and stirred at 23° C. for 2 h, before the mixture was concentrated, coevaporated with $CH_2Cl_2$ (3×2 mL) and dried in HV. The residue was redissolved in 137 µL dry DMSO, 27.1 µL (0.246 mmol, 9.0 eq) NMM and 10.7 mg (27.4 µmol, 1.0 eq) FITC were added and the mixture was stirred for 1.5 h at 23° C. The reaction mixture was diluted with 100 µL $H_2O$ and purified by RP prep HPLC (Phenomenex Gemini C18 RP-column 00G-4435-PO-AX, 5 µm, 110 A, 250×21.20 mm, Flow: 9 mL/min, ACN:$H_2O$+0.1% TFA/10:90→95:5 in 35 min) yielding after lyophilization 17.9 mg (20.55 µmol, 75%) of EC17 as a deep orange, amorphous solid.

EC17: HRMS (ESI-IT) [m/z]: 873.2409, calculated 873.2409 for $C_{42}H_{37}N_{10}O_{10}S$ [M+H]$^+$, err [ppm] 0.0.

1.1.1.11.1 General Procedure C for the Synthesis of Folate-Fluorescein Conjugates Via Copper-Free Click Reaction The corresponding FA-$N_3$ (1.1 eq) was dissolved in DMSO (0.2 M), a solution of BCN-FTIC (1.0 eq) in DMSO (0.2 M) was added and the mixture was stirred for 4-20 h at 23° C. under light exclusion until complete conversion was monitored by LCMS. The reaction mixture was diluted with 100 µL of MeOH, filtered through a Whatman® filter (45 µm) and directly purified by RP prep HPLC (Phenomenex Gemini C18 RP-column 00G-4435-PO-AX, 5 µm, 110 A, 250×21.20 mm, Flow: 9 mL/min, ACN:$H_2O$+0.1% TFA/10:90→95:5 in 45 min) yielding the Folate-Fluorescein Conjugates after lyophilization as a deep orange, amorphous solids.

FA-4a-(FITC)$_2$—$N^2$-$N^2$—((S)-4-(4-(((2-amino-4-hydroxypteridin-6-yl)methyl)amino)benzamido)-4-carboxy-butanoyl)-D-aspartyl-D-aspartyl-$N^6$-(4-(2-((5aR,6S,6aS)-6-((((2-(3-(3',6'-dihydroxy-3-oxo-3H-spiro[iso-benzofuran-1,9'-xanthen]-5-yl)thioureido)ethyl)carbamoyl)oxy)methyl)-5,5a,6,6a,7,8-hexahydrocyclopropa[5,6]cycloocta[1,2-d][1,2,3]triazol-1 (4H)-yl))-benzoyl)-L-lysyl-L-aspartyl-L-aspartyl-$N^6$-(4-(2-((5aR,6S,6aS)-6-((((2-(3-(3',6'-dihydroxy-3-oxo-3H-spiro[isobenzofuran-1,9'-xanthen]-5-yl)thio-ureido)ethyl)carbamoyl)oxy)methyl)-5,5a,6,6a,7,8-hexahydrocyclopropa[5,6]cycloocta[1,2-d][1,2,3]triazol-1 (4H)-yl))-benzoyl)-L-lysine

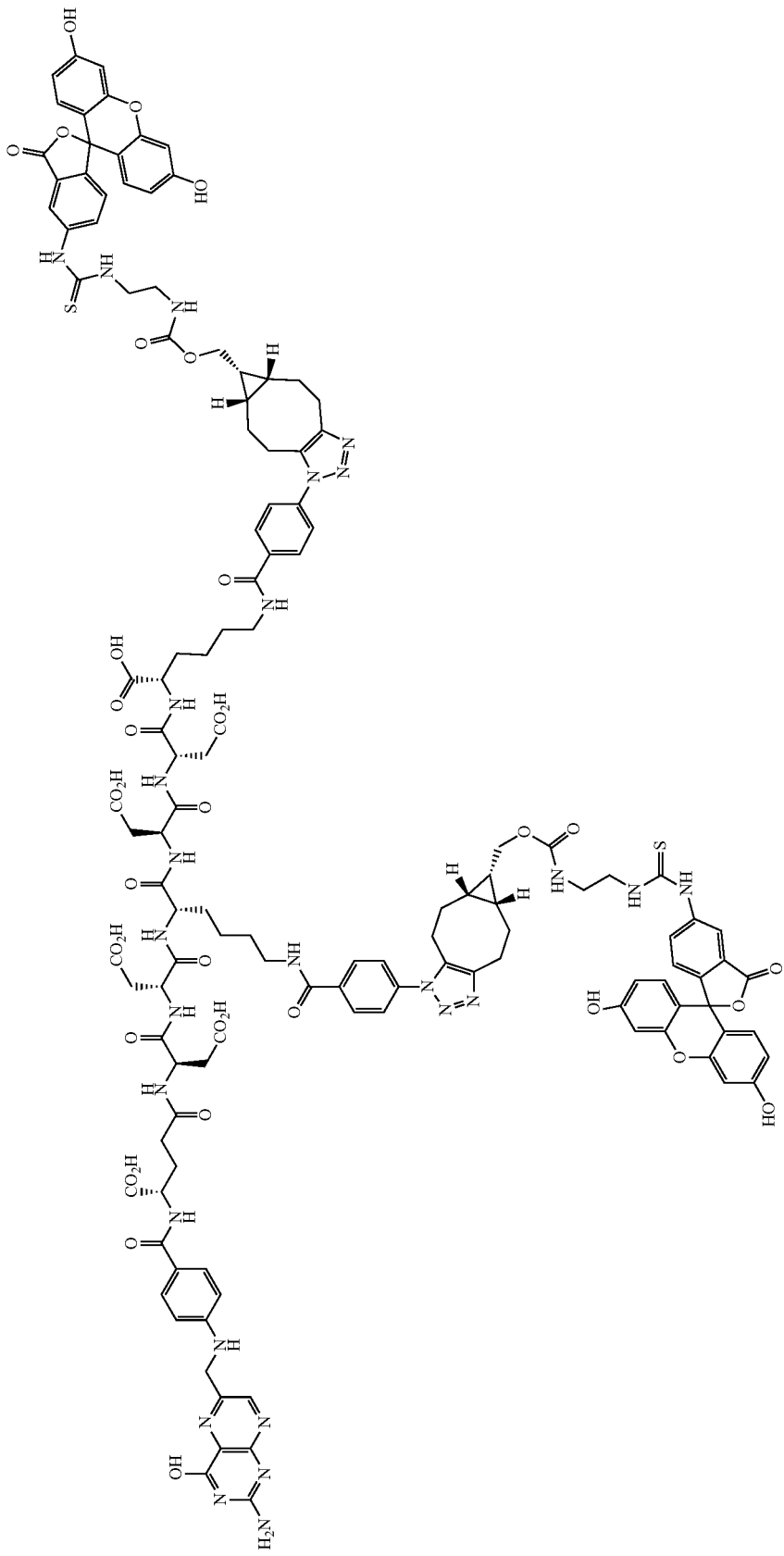

Applying FA-N₃-4 to the general procedure C, 1.4 mg (0.518 μmol, 17%) FA-4a-(FITC)₂ were obtained as a deep-orange solid.

FA-4a-(FITC)₂: LRMS (ESI-Quad) [m/z]: 1350.4 [M+2H]$^{2+}$, HRMS (ESI-IT) [m/z]: 898.61675, calculated 898.61689 for $C_{129}H_{128}N_{27}O_{36}S_2$ [M−3H]$^{3-}$, err [ppm] −0.155.

FA-3a-FITC—$N^2$—((S)-4-(4-(((2-amino-4-hydroxypteridin-6-yl)methyl)amino)benzamido)-4-carboxybutanoyl)-L-aspartyl-L-aspartyl-L-aspartyl-$N^6$ (4-((5aR,6S,6aS)-6-((((2-(3-(3',6'-dihydroxy-3-oxo-3H-spiro[isobenzofuran-1,9'-xanthen]-5-yl)thioureido)ethyl)carbamoyl)oxy)methyl)-5,5a,6,6a,7,8-hexahydrocyclopropa[5,6]cycloocta[1,2-d][1,2,3]triazol-1 (4H)-yl)benzoyl)-L-lysine

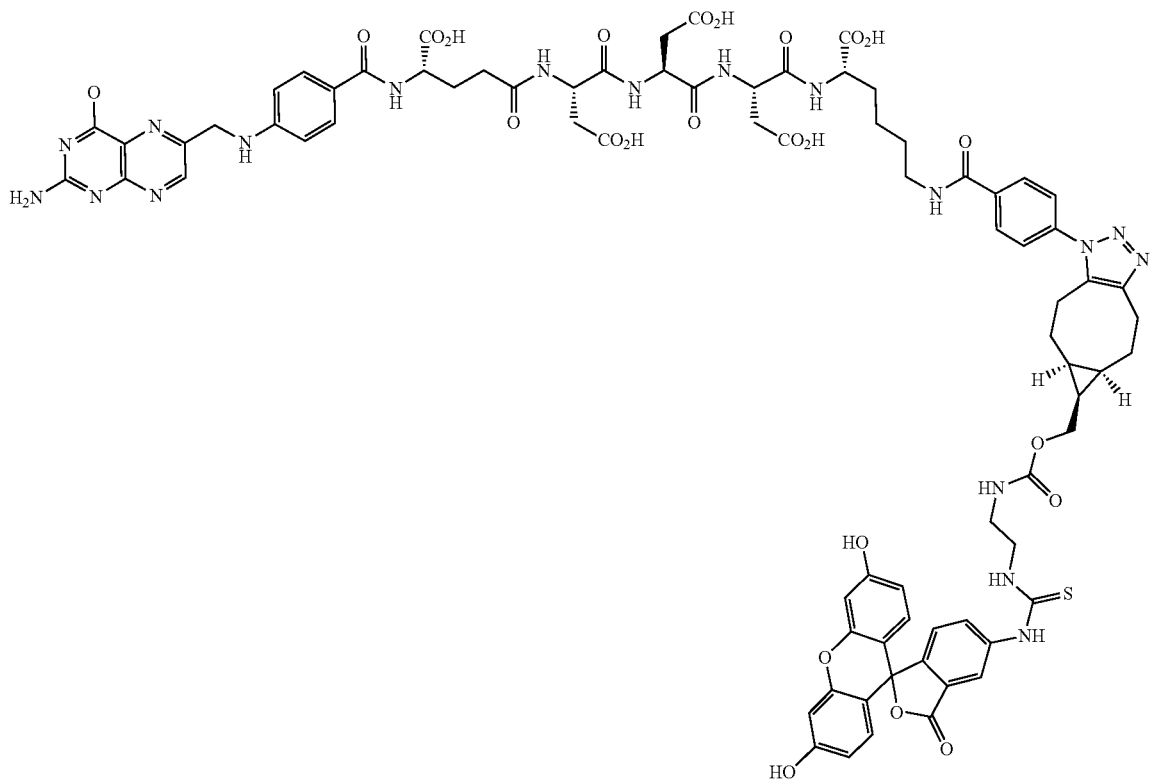

Chemical Formula: $C_{78}H_{80}N_{18}O_{24}S$
Molecular Weight: 1685,66
FA-3a-FITC Applying FA-N₃-3 to the general procedure C, 4.5 mg (2.669 μmol, 30%) FA-3a-FITC were obtained as a deep-orange solid.

FA-3a-FITC: LRMS (ESI-Quad) [m/z]: 1685.5 [M+H]$^+$, HRMS (ESI-IT) [m/z]: 841.25711, calculated 841.25840 for $C_{78}H_{78}N_{18}O_{24}S$ [M−2H]$^{2-}$, err [ppm] −1.53.

FA-1a-FITC—$N^2$-(4-(((2-amino-4-hydroxypteridin-6-yl)methyl)amino)benzoyl)-$N^5$—((S)-1-carboxy-4-(((S)-6-(4-((5aS,6R,6aR)-6-((((2-(3-(3',6'-dihydroxy-3-oxo-3H-spiro[isobenzofuran-1,9'-xanthen]-5-yl)thioureido)ethyl)carbamoyl)oxy)methyl)-5,5a,6,6a,7,8-hexahydrocyclopropa[5,6]cycloocta[1,2-d][1,2,3]triazol-1(4H)-yl)benzamido)-1-methoxy-1-oxohexan-2-yl)amino)-4-oxobutyl)-L-glutamine

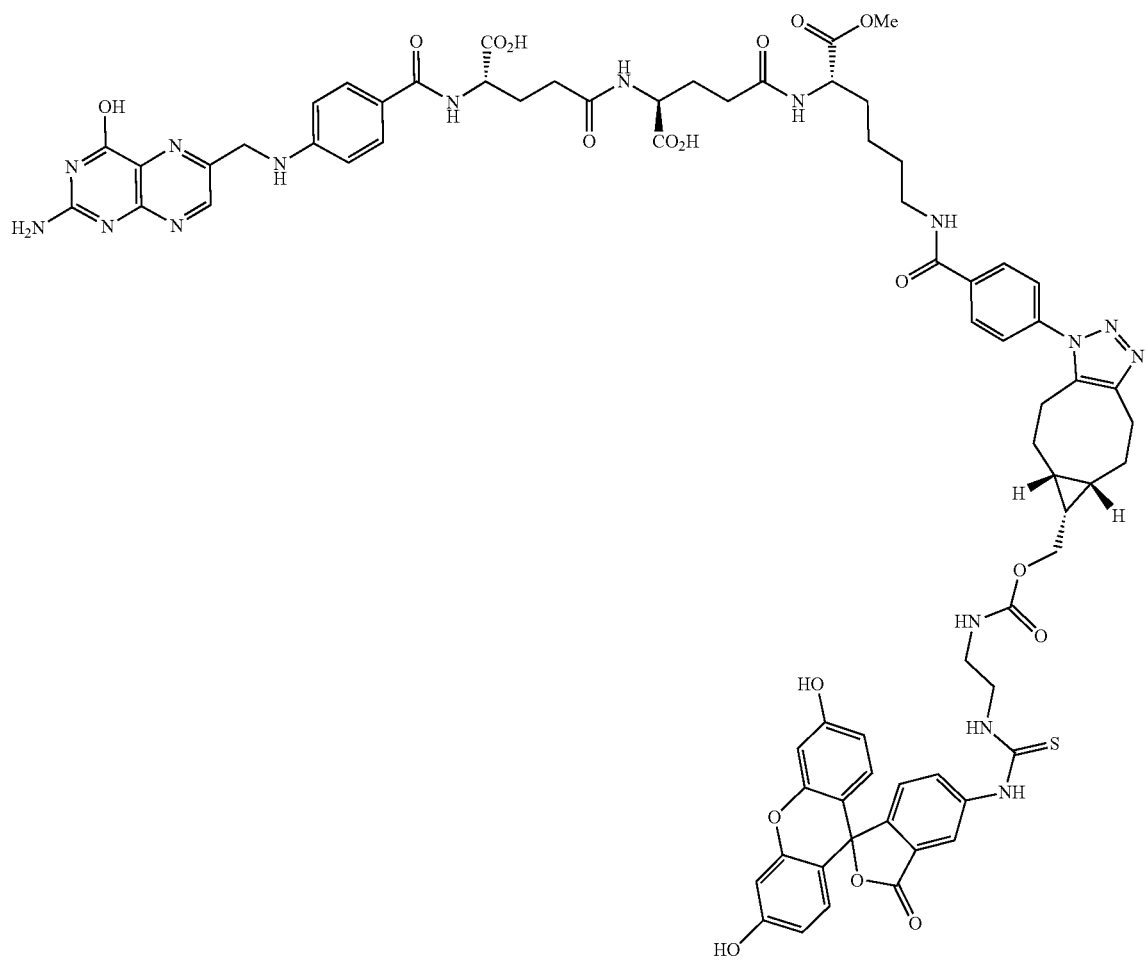

Chemical Formula: $C_{72}H_{74}N_{16}O_{18}S$
Molecular Weight: 1483,54
FA-1a-FITC Applying FA-$N_3$-1 to the general procedure C, 1.7 mg (1.145 μmol, 25%) FA-1a-FITC were obtained as a deep-orange solid.

FA-1a-FITC: LRMS (ESI-Quad) [m/z]: 1484.6 [M+H]$^+$, HRMS (ESI-IT) [m/z]: 742.2617, calculated 742.2617 for $C_{72}H_{76}N_{16}O_{18}S$ [M+2H]$^{2+}$, err [ppm] 0.0.

1.1.1.11.2 General Procedure D for the Synthesis of Folate-Fluorescein Conjugates Via Copper-Mediated Click Reaction The corresponding FA-$N_3$ (1.1 eq) and Homopropargyl-FTIC (1.0 eq) were dissolved in a mixture of DMSO:$H_2O$: tBuOH/2:1:1 (0.025 M) were added DiPEA (6.0 eq), TBTA (0.1 eq, 10 μL from a stock solution in DMSO), CuSO$_4$ (0.05 eq, 10 μL from a stock solution in $H_2O$) and sodium ascorbate (0.5 eq, 10 μL from a stock solution in $H_2O$) and the mixture was stirred under light exclusion for 4-24 h at 23° C. until complete conversion was monitored by LCMS. The reaction mixture was diluted with 100 μL of MeOH, filtered through a Whatman® filter (45 μm) and directly purified by RP prep HPLC (Phenomenex Gemini C18 RP-column 00G-4435-PO-AX, 5 μm, 110 A, 250×21.20 mm, Flow: 9 mL/min, ACN:$H_2O$+0.1% TFA/I 10:90→95:5 in 45 min) yielding the Folate-Fluorescein Conjugates after lyophilization as a deep orange, amorphous solids.

FA-9b-FITC—((S)-2-((S)-4-(4-(((2-amino-4-hydroxypteridin-6-yl)methyl)amino)benzamido)-4-carboxybutanamido)-5-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl)pentanoyl)-D-lysine

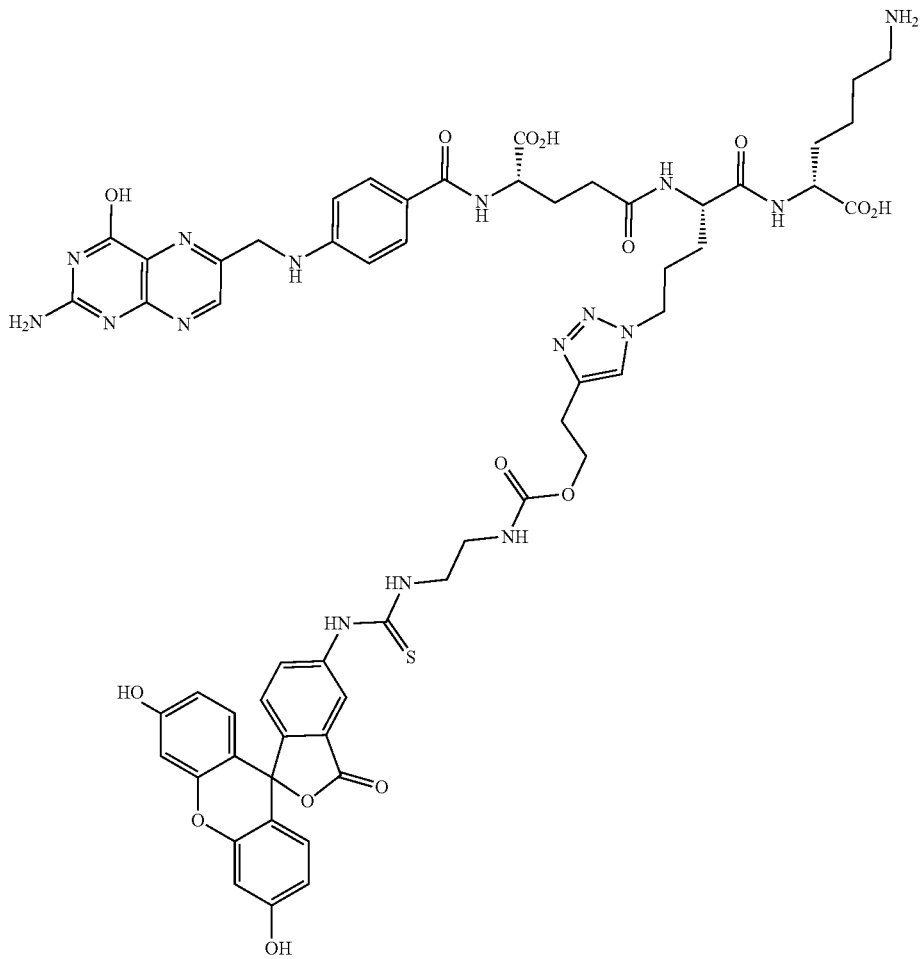

Chemical Formula: $C_{58}H_{62}N_{16}O_{15}S$
Molecular Weight: 1255,29
FA-9b-FITC Applying FA-N$_3$-9 to the general procedure D, 2.9 mg (2.36 µmol, 65%) FA-FITC-9b were obtained as a deep-orange solid.

FA-9b-FITC: LRMS (ESI-Quad) [m/z]: 1256.3 [M+H]$^+$, HRMS (ESI-IT) [m/z]: 628.22296, calculated 628.22234 for $C_{58}H_{64}N_{16}O_{15}S$ [M+2H]$^{2+}$, err [ppm]0.986.

FA-11b-(FITC)$_3$—N$^2$-(4-(((2-amino-4-hydroxypteridin-6-yl)methyl)amino)benzoyl)-N$^5$-((R)-3-carboxy-1-(((R)-3-carboxy-1-(((S)-1-(((R)-3-carboxy-1-(((R)-3-carboxy-1-(((S)-1-(((R)-3-carboxy-1-(((R)-3-carboxy-1-(((S)-1-carboxy-4-(2-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl))butyl)amino)-1-oxopropan-2-yl)amino)-1-oxopropan-2-yl)amino)-5-(2-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl))-1-oxopentan-2-yl)amino)-1-oxopropan-2-yl)amino)-1-oxopropan-2-yl)amino)-5-(2-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl))-1-oxopentan-2-yl)amino)-1-oxopropan-2-yl)amino)-1-oxopropan-2-yl)-L-glutamine

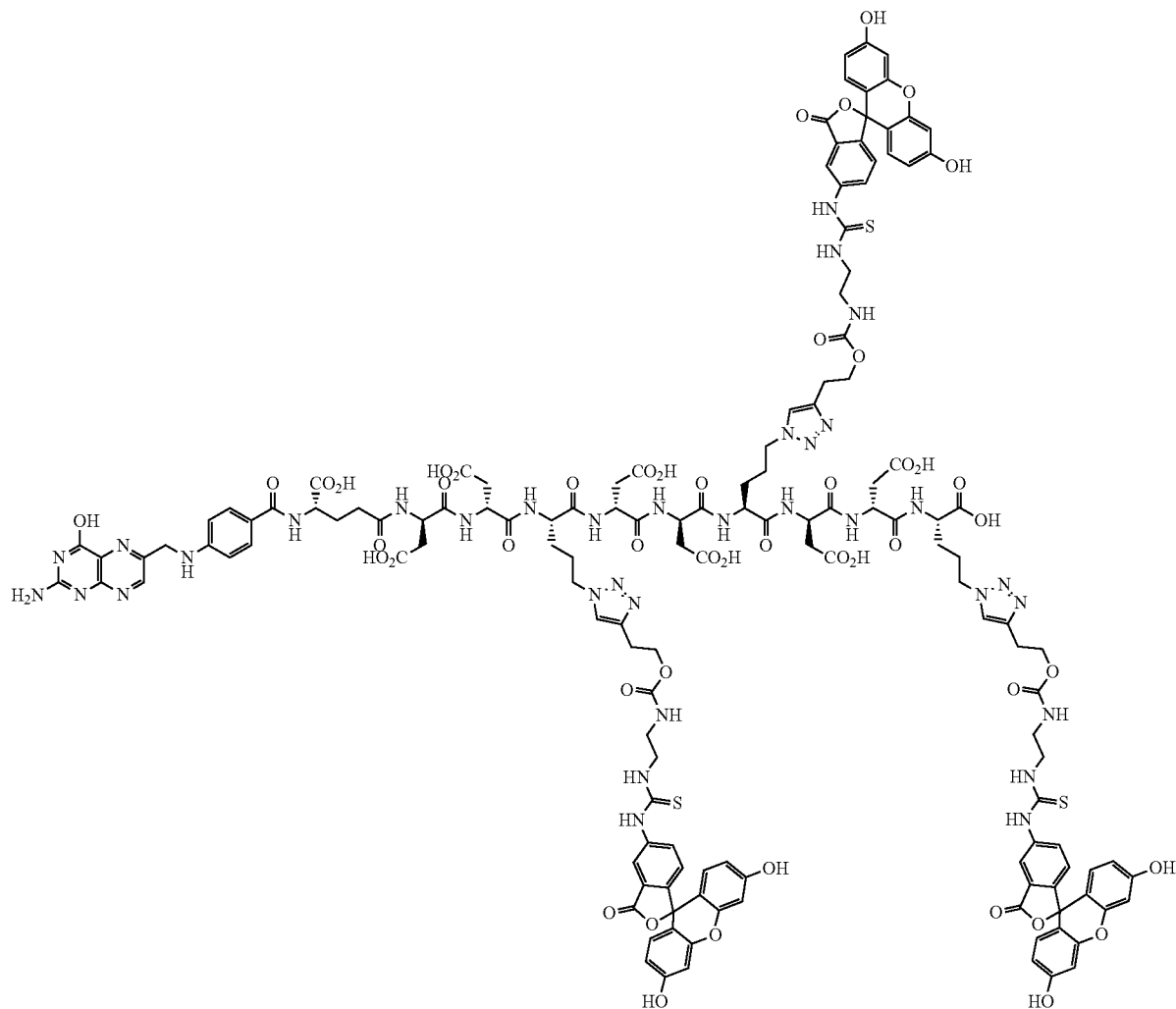

Chemical Formula: C$_{142}$H$_{142}$N$_{34}$O$_{48}$S$_3$
Molecular Weight: 3189,07
FA-11b-(FITC)$_3$ Applying FA-N3-11 to the general procedure D, 3.0 mg (0.94 μmol, 25%) FA-11b-(FITC)$_3$ were obtained as a deep-orange solid.

FA-11b-(FITC)$_3$: LRMS (ESI-Quad) [m/z]: 1064.32 [M+3H]$^{3+}$, HRMS (ESI-IT) [m/z]: 1063.9719, calculated 1063.9715 Formula: C$_{142}$H$_{142}$H$_{145}$N$_{34}$O$_{48}$S$_3$ [M+3H]$^{3+}$, err [ppm] 0.376.

FA-8b-FITC—N$^2$—((S)-4-(4-(((2-amino-4-hydroxypteridin-6-yl)methyl)amino)benzamido)-4-carboxybutanoyl)-N$^6$-(4-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl)benzoyl)-L-lysyl-D-lysine

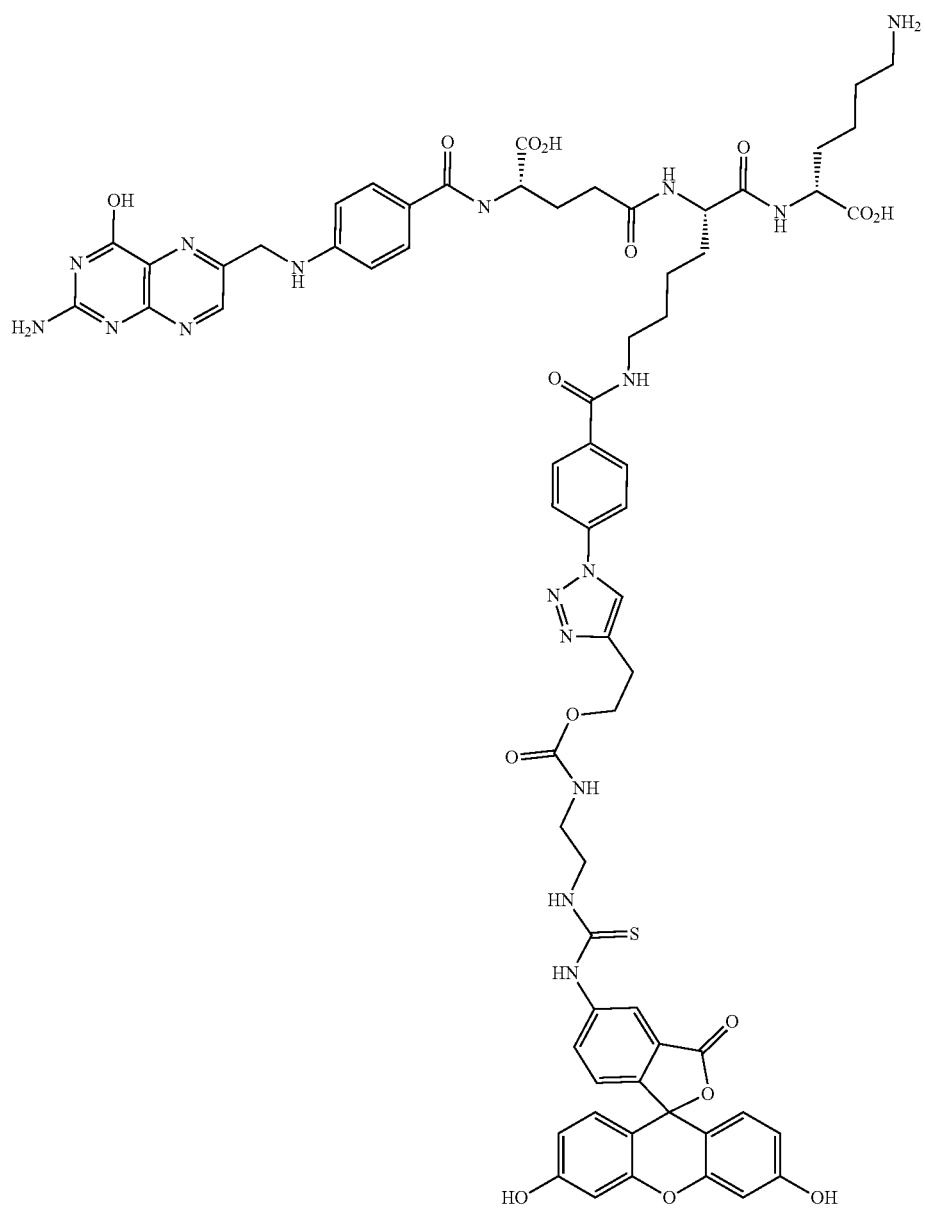

Chemical Formula: C$_{66}$H$_{69}$N$_{17}$O$_{16}$S
Molecular Weight: 1388,44
FA-FITC-8b Applying FA-N$_3$-8 to the general procedure D, 1.7 mg (1.25 µmol, 34%) FA-8b-FITC were obtained as a deep-orange solid.

FA-8b-FITC: LRMS (ESI-Quad) [m/z]: 694.6 [M+2H]$^{2+}$, HRMS (ESI-IT) [m/z]: 694.7487, calculated 694.7487 for $C_{66}H_{71}N_{17}O_{16}S$ [M+2H]$^{2+}$, err [ppm] 0.0.

FA-10b-FITC—((S)-2-((R)-2-((R)-2-((R)-2-((S)-4-(4-(((2-amino-4-hydroxypteridin-6-yl)methyl)amino)benzamido)-4-carboxybutanamido)-3-carboxypropanamido)-3-carboxypropanamido)-3-carboxypropanamido)-5-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl)pentanoyl)-D-aspartyl-D-aspartyl-D-lysine

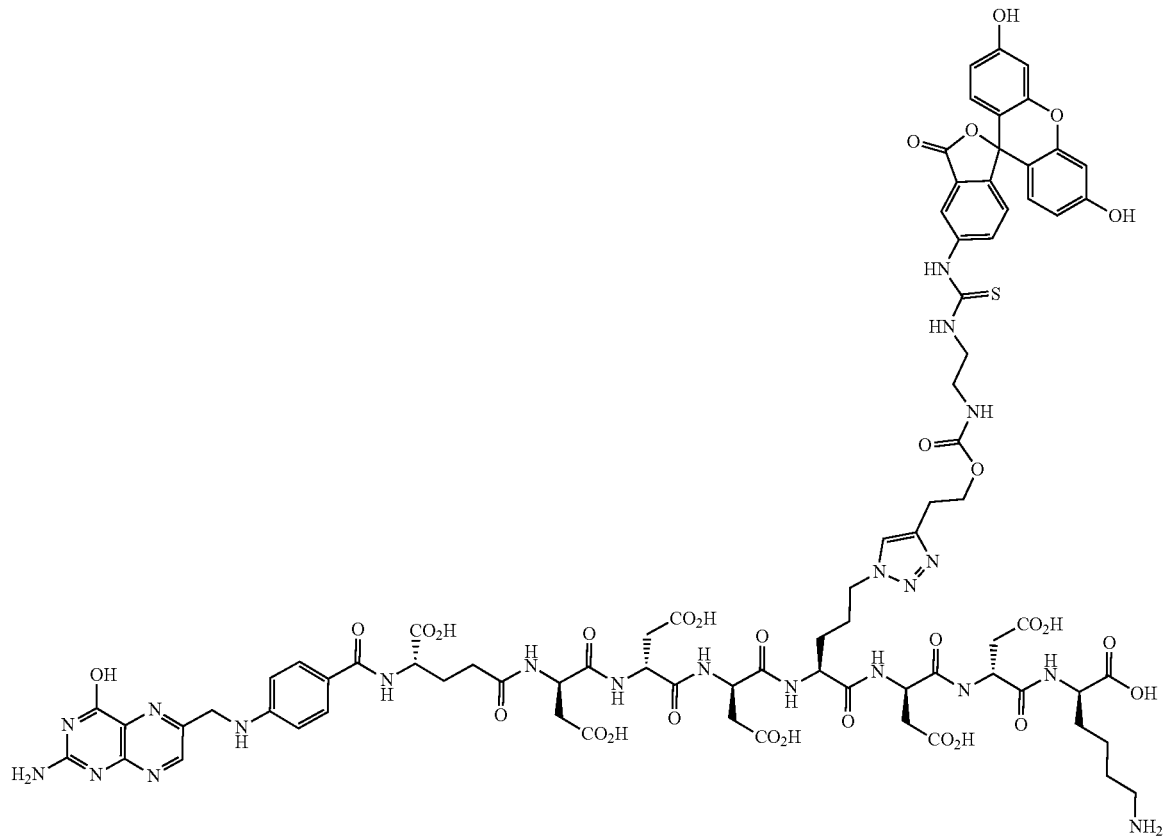

Chemical Formula: $C_{78}H_{87}N_{21}O_{30}S$
Molecular Weight: 1830,73
FA-10b-FITC Applying FA-N$_3$-10 to the general procedure D, 3.8 mg (2.08 µmol, 57%) FA-10b-FITC were obtained as a deep-orange solid.

FA-10b-FITC: LRMS (ESI-Quad) [m/z]: 915.9 [M+2H]$^{2+}$, HRMS (ESI-IT) [m/z]: 915.7897, calculated 915.7897 for $C_{78}H_{89}N_{21}O_{30}S$ [M+2H]$^{2+}$, err [ppm] 0.0.

FA-7b-FITC—N²-(4-(((2-amino-4-hydroxypteridin-6-yl)methyl)amino)benzoyl)-N⁵—((S)-1-carboxy-4-(((S)-1-carboxy-4-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl)butyl)amino)-4-oxobutyl)-L-glutamine

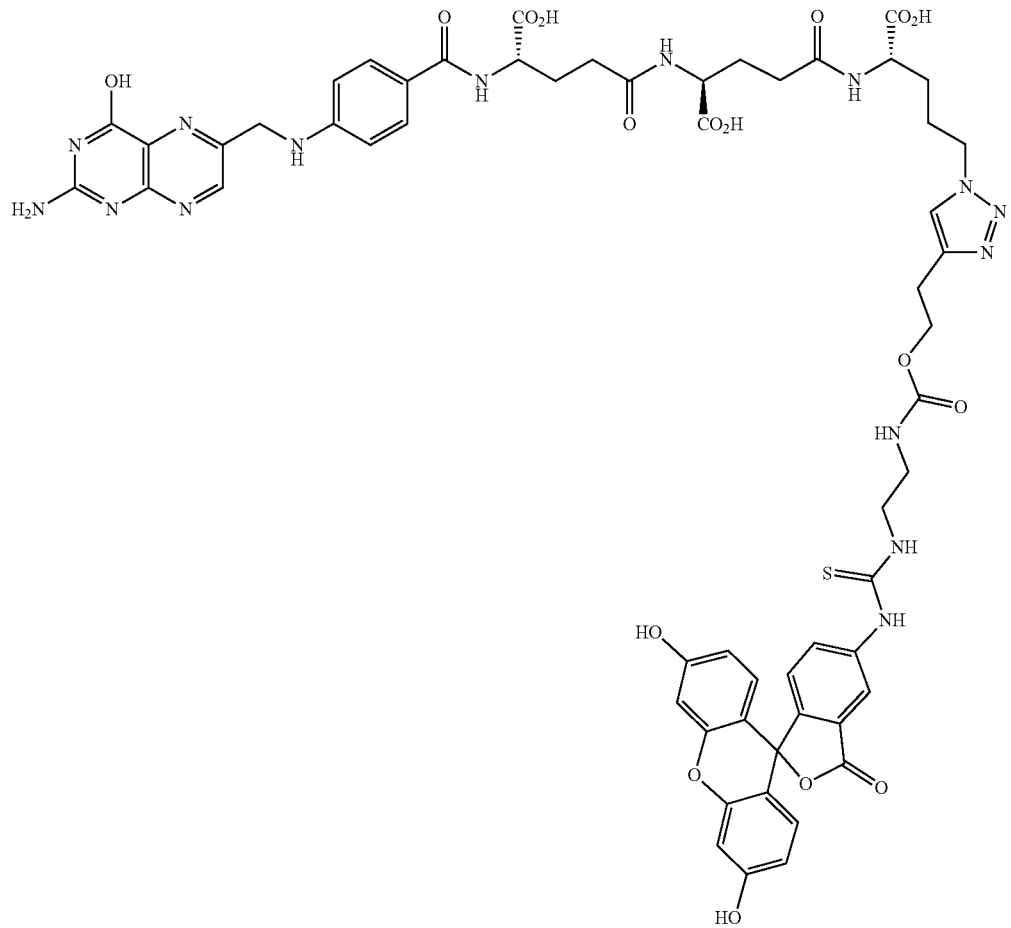

Chemical Formula: $C_{57}H_{57}N_{15}O_{17}S$
Molecular Weight: 1256.23
FA-7b-FITC Applying FA-N₃-7 to the general procedure D, 3.8 mg (2.08 μmol, 57%) FA-FITC-7b were obtained as a deep-orange solid.

FA-7b-FITC: LRMS (ESI-Quad) [m/z]: 915.8 $[M+2H]^{2+}$, HRMS (ESI-IT) [m/z]: 1256.3869, calculated 1256.3850 for $C_{57}H_{58}N_{15}O_{17}S$ $[M+H]^+$, err [ppm] −1.5.

FA-6b-FITC—(3S,8S,13S)-1-(4-(((2-amino-4-hydroxypteridin-6-yl)methyl)amino)phenyl)-19-(4-(((2-(3-(3',6'-dihydroxy-3-oxo-3H-spiro[isobenzofuran-1,9'-xanthen]-5-yl)thioureido)ethyl)carbamoyl)oxy)-1H-1,2,3-triazol-1-yl)phenyl)-1,6,11,19-tetraoxo-2,7,12,18-tetraazanonadecane-3,8,13-tricarboxylic acid

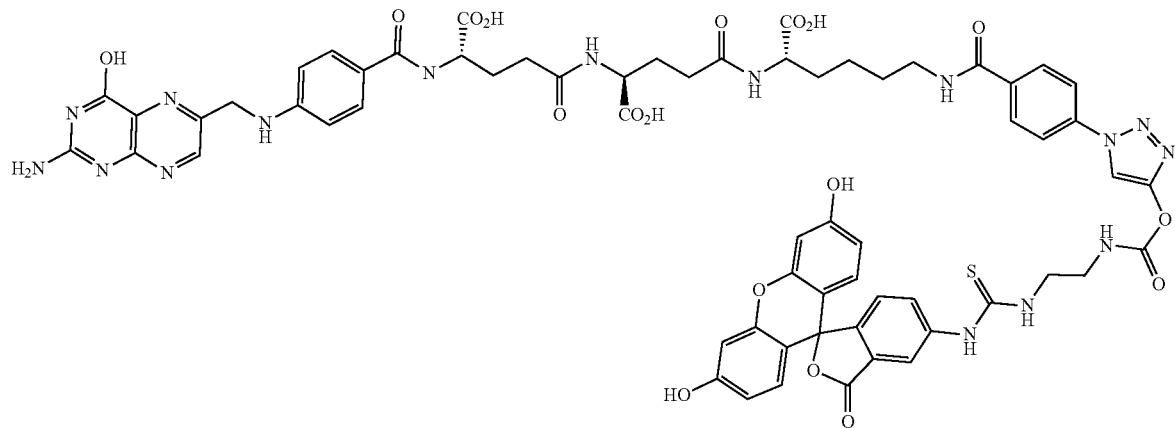

Chemical Formula: $C_{63}H_{60}N_{16}O_{18}S$
Molecular Weight: 1361,33
FA-6b-FITC Applying FA-N$_3$-6 to the general procedure D, 3.8 mg (2.08 μmol, 57%) FA-FITC-6b were obtained as a deep-orange solid.

FA-6b-FITC: LRMS (ESI-Quad) [m/z]: 681.3 $[M+2H]^{2+}$.

FA-3b-FITC—$N^2$—((S)-4-(4-(((2-amino-4-hydroxypteridin-6-yl)methyl)amino)benzamido)-4-carboxybutanoyl)-L-aspartyl-L-aspartyl-L-aspartyl-$N^6$-(4-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl)benzoyl)-L-lysine

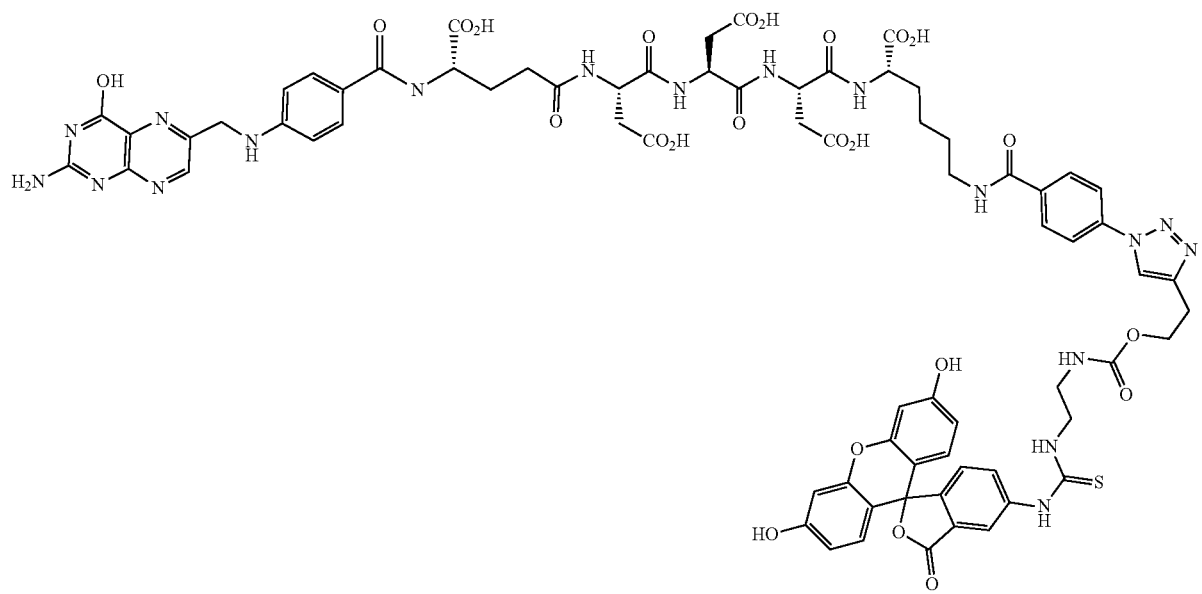

Chemical Formula: $C_{72}H_{72}N_{18}O_{24}S$
Molecular Weight: 1605,53
FA-3b-FITC Applying FA-N$_3$-3 to the general procedure D, 2.0 mg (1.24 μmol, 52%) FA-3b-FITC was obtained as a deep-orange solid.

FA-3b-FITC: LRMS (ESI-Quad) [m/z]: 803.2 [M+2H]$^{2+}$, HRMS (ESI-IT) [m/z]: 803.2417, calculated 803.2417 for C$_{72}$H$_{74}$N$_{18}$O$_{24}$S [M+2H]$^{2+}$, err [ppm] 0.0.

FA-4b-(FITC)$_2$—N$^2$-N$^2$—((S)-4-(4-(((2-amino-4-hydroxypteridin-6-yl)methyl)amino)benzamido)-4-carboxybutanoyl)-D-aspartyl-D-aspartyl-N$^6$-(4-(2-(4-(2-(((2-(3-(3',6'-dihydroxy-3-oxo-3H-spiro[isobenzofuran-1,9'-xanthen]-5-yl)thioureido)ethyl)carbamoyl)oxy)ethyl)-1H-1,2,3-triazol-1-yl))benzoyl)-L-lysyl-L-aspartyl-L-aspartyl-N$^6$-(4-fluorobenzoyl)-L-lysine

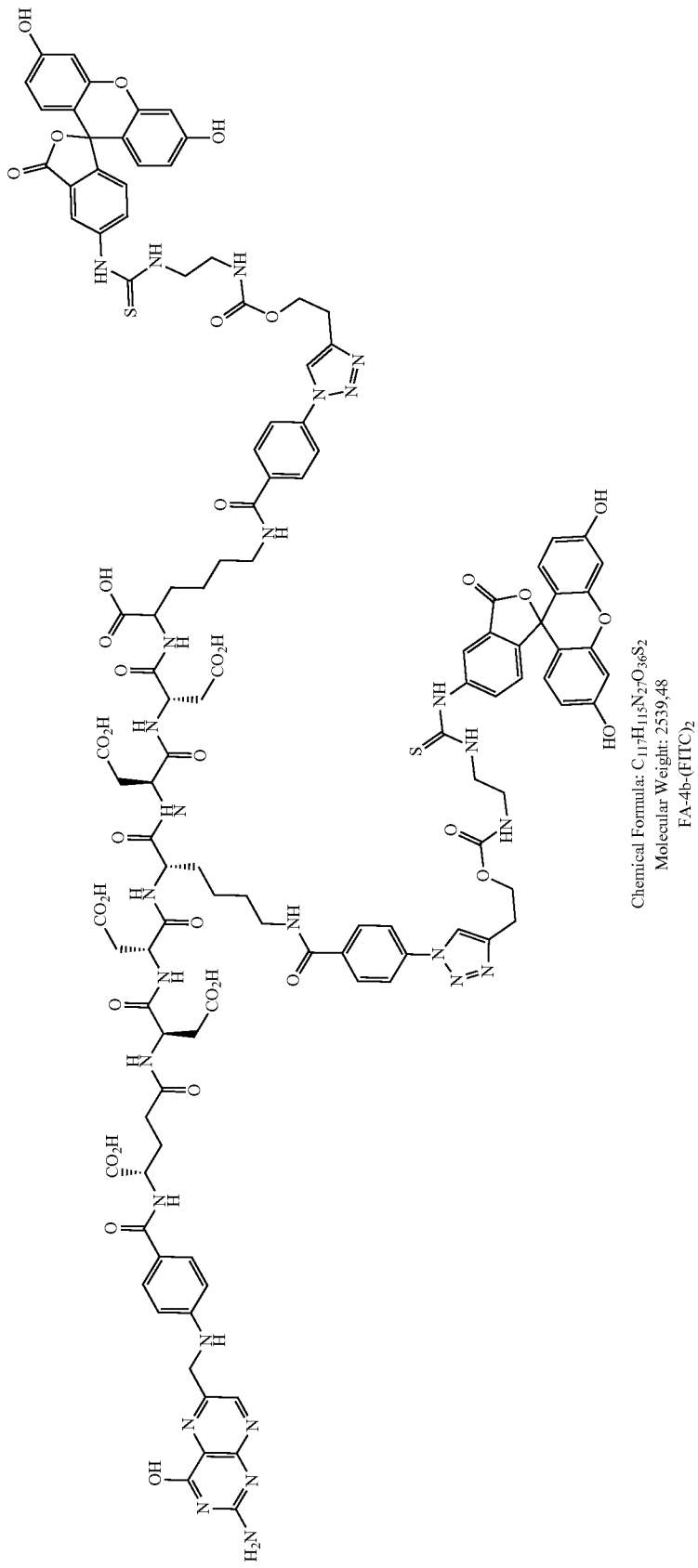

Applying FA-N₃-4 to the general procedure D, 1.4 mg (0.551 µmol, 27%) FA-4b-(FITC)₂ was obtained as a deep-orange solid.

FA-4b-(FITC)₂: LRMS (ESI-Quad) [m/z]: 1270.3 [M+2H]²⁺, HRMS (ESI-IT) [m/z]: 1269.8793, calculated 1269.8792 for $C_{117}H_{117}N_{27}O_{36}S_2[M+H]^+$, err [ppm] −0.078.

1.1.1.12 Synthesis of Gonadoliberin-Fluorescein Conjugates

Synthesis of D-Orn-LHRH-PEG₂-CF—((5aR,6S,6aS)-1-((3S,6S,9S,12S,15R)-3-((1H-imidazol-4-yl)methyl)-6-((1H-indol-3-yl)methyl)-15-(((S)-1-(((S)-1—((S)-2-((2-amino-2-oxoethyl)carbamoyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13-pentaoxo-1-((S)-5-oxopyrrolidin-2-yl)-2,5,8,11,14-pentaazaoctadecan-18-yl)-1,4,5,5a,6,6a,7,8-octahydrocyclopropa[5,6]cycloocta[1,2-d][1,2,3]triazol-6-yl)methyl (2-(2-(2-(3',6'-dihydroxy-3-oxo-3H-spiro[isobenzofuran-1,9'-xanthene]-5-carboxamido)ethoxy)ethoxy)ethyl)carbamate To a solution of 4 mg (2.678 µmol, 1.0 eq) D-N₃-Orn-LHRH in 27 µL dry DMSO was added a solution of 2.0 mg (2.946 µmol, 1.1 eq) BCN-PEG₂-CF in) 27 µL dry DMSO and the mixture was stirred for 16 h at 23° C. under light exclusion until complete conversion was monitored by LCMS. The reaction mixture was diluted with 100 µL of MeOH and directly purified by RP prep HPLC (Phenomenex Gemini C18 RP-column 00G-4435-PO-AX, 5 µm, 110 A, 250×21.20 mm, Flow: 9 mL/min, ACN:H₂O+0.1% TFA/10: 90→95:5 in 45 min) yielding after lyophilization 3.6 mg (1.847 µmol, 69%) of D-Orn-LHRH-PEG₂-CF as yellow, amorphous solid.

D-Orn-LHRH-PEG₂-CF: HRMS (ESI-IT) [m/z]: 974.4443, calculated 974.4443 for $C_{90}H_{120}N_{22}O_{23}$ [M+2H]²⁺, err [ppm] 0.0.

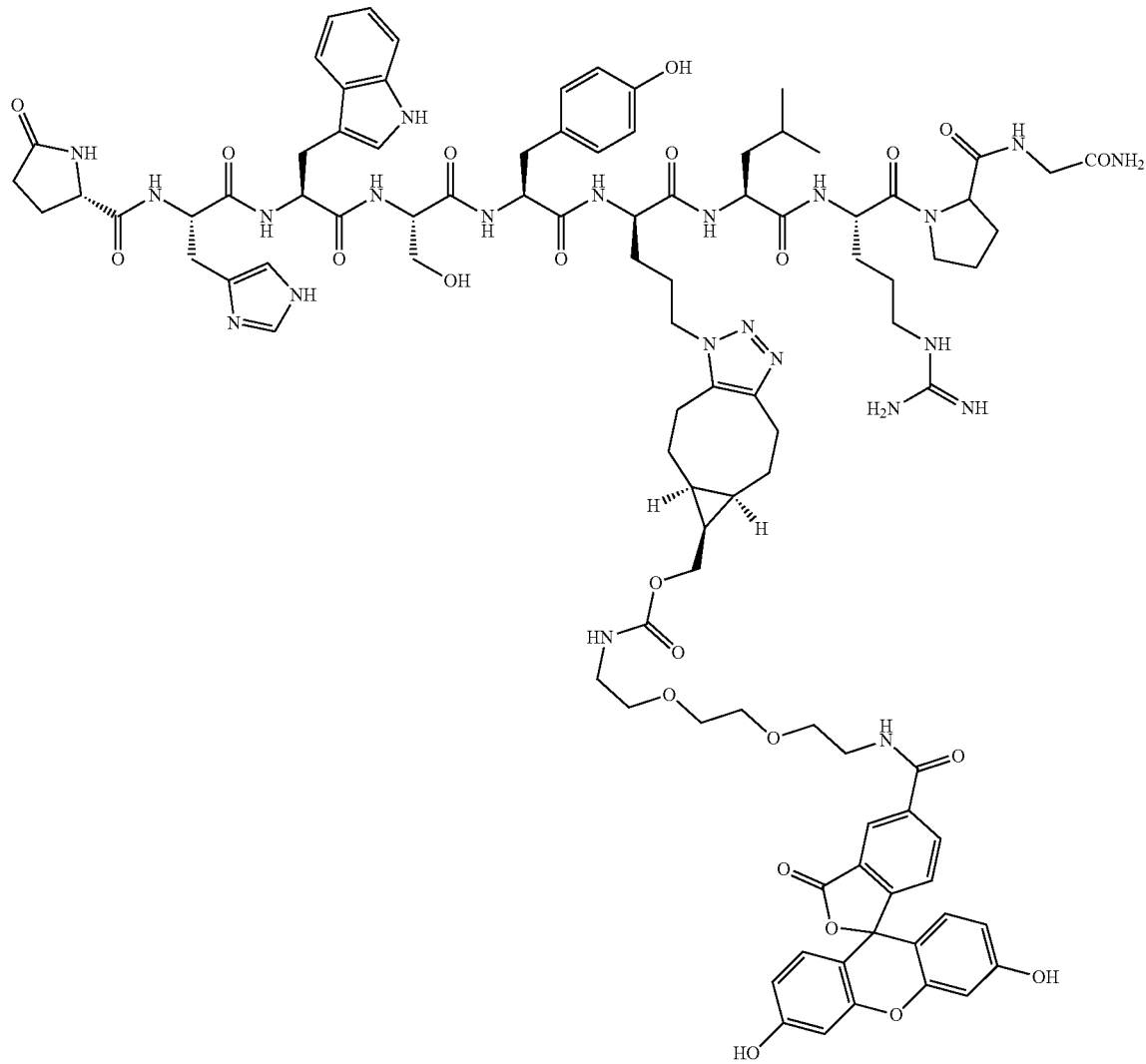

Chemical Formula: $C_{96}H_{118}N_{22}O_{23}$
Molecular Weight: 1948,13
D-Orn-LHRH-PEG₂-CF Synthesis of D-Orn-Goserellin-PEG$_2$-CF: CF-((5aR, 6S,6aS)-1-((3S,6S,9S,12S,15R)-3-((1H-imidazol-4-yl)methyl)-6-((1H-indol-3-yl)methyl)-15-(((S)-1-(((S)-1—((S)-2-(2-carbamoylhydrazine-1-carbonyl) pyrrolidin-1-yl)-5-guanidino-1-oxopentan-2-yl) amino)-4-methyl-1-oxopentan-2-yl)carbamoyl)-12-(4-hydroxybenzyl)-9-(hydroxymethyl)-1,4,7,10,13-pentaoxo-1-((S)-5-oxopyrrolidin-2-yl)-2,5,8,11,14-pentaazaoctadecan-18-yl)-1,4,5,5a,6,6a,7,8-octahydrocyclopropa[5,6]cycloocta[1,2-d][1,2,3] triazol-6-yl)methyl (2-(2-(2-(3',6'-dihydroxy-3-oxo-3H-spiro[isobenzofuran-1,9'-xanthene]-5-carboxamido)ethoxy)ethoxy)ethyl)carbamate

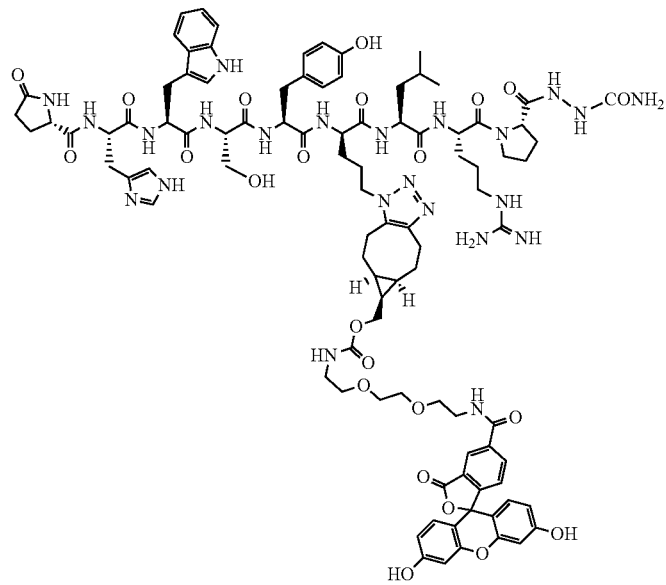

Chemical Formula: $C_{95}H_{117}N_{23}O_{23}$
Molecular Weight: 1949,12
D-Orn-Goserellin-PEG$_2$-CF To a solution of 4 mg (2.487 μmol, 1.0 eq) D-Orn-N$_3$-Goserellin in 25 μL dry DMSO was added a solution of 1.9 mg (2.735 μmol, 1.1 eq) BCN-PEG$_2$-CF in) 25 μL dry DMSO and the mixture was stirred for 16 h at 23° C. under light exclusion until complete conversion was monitored by LCMS. The reaction mixture was diluted with 100 μL of MeOH and directly purified by RP prep HPLC (Phenomenex Gemini C18 RP-column 00G-4435-PO-AX, 5 μm, 110 A, 250×21.20 mm, Flow: 9 mL/min, ACN:H$_2$O+0.1% TFA/10: 90→95:5 in 45 min) yielding after lyophilization 3.4 mg (1.744 μmol, 70%) of D-Orn-Goserellin-PEG$_2$-CF as yellow, amorphous solid.

D-Orn-Goserellin-PEG$_2$-CF:CF: HRMS (ESI-IT) [m/z]: 974.9419, calculated 974.9419 for $C_{95}H_{119}N_{23}O_{23}$ $[M+2H]^{2+}$, err [ppm] 0.0.

Synthesis of L-Orn-LHRH—CF—((S)-2-((S)-2-((S)-2-((S)-2-((S)-3-(1H-imidazol-4-yl)-2-((S)-5-oxopyrrolidine-2-carboxamido)propanamido)-3-(1H-indol-3-yl)propanamido)-3-hydroxypropanamido)-3-(4-hydroxyphenyl)propanamido)-5-(4-((3',6'-dihydroxy-3-oxo-3H-spiro[isobenzofuran-1,9'-xanthene]-5-carboxamido)methyl)-1H-1,2,3-triazol-1-yl)pentanoyl)-L-leucyl-L-arginyl-L-prolylglycine

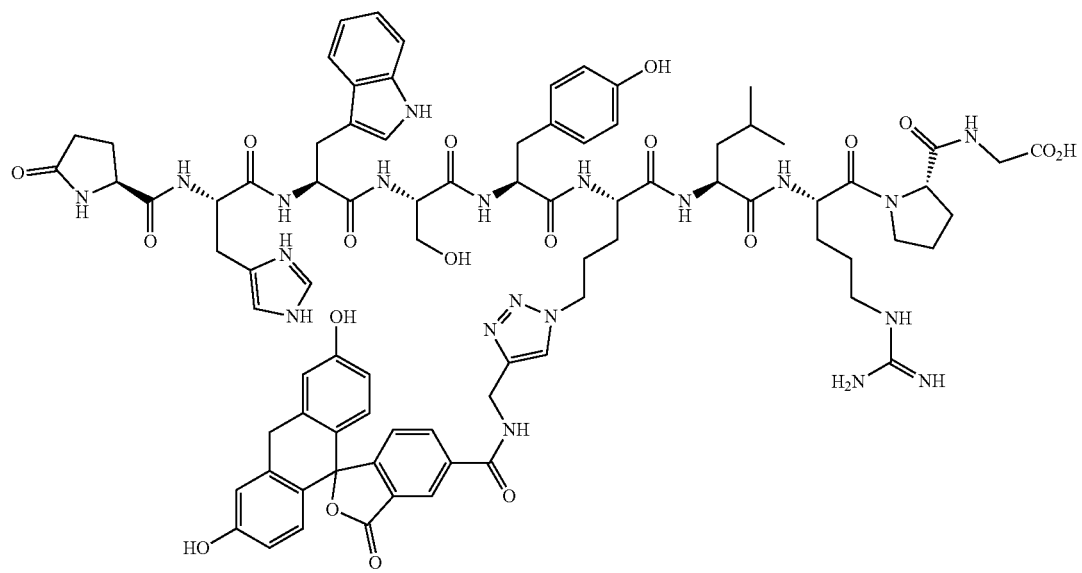

Chemical Formula: $C_{82}H_{94}N_{20}O_{20}$
Molecular Weight: 1679,77
D-Orn-LHRH-CF To a solution of 5.0 mg (3.34 μmol, 1.0 eq) L-N$_3$-Orn-LHRH and 1.52 mg (3.68 μmol, 1.1 eq) Homopropargyl-CF in a mixture of DMSO:pH=7 phosphate buffer:tBuOH/2:2:1 (133 μL) were added 0.443 μg (0.835 μmol, 0.25 eq, 10 μL from a stock solution in DMSO) TBTA, 53 μg (0.334 μmol, 0.1 eq, 10 μL from a stock solution in H$_2$O) CuSO$_4$, 1.47 mg (6.68 mol, 2.0 eq) zinc acetate and 661 μg (3.34 μmol, 0.5 eq, 10 μL from a stock solution in H$_2$O) sodium ascorbate and the mixture was stirred under light exclusion for 24 h at 23° C. until complete conversion was monitored by LCMS. The reaction mixture was diluted with 100 μL of MeOH and directly purified by RP prep HPLC (Phenomenex Gemini C18 RP-column 00G-4435-PO-AX, 5 μm, 110 A, 250× 21.20 mm, Flow: 9 mL/min, ACN:H$_2$O+0.1% TFA/ 10:90 →95:5 in 45 min) yielding after lyophilization 4.0 mg (2.09 μmol, 60%) L-Orn-LHRH—CF as a deep yellow, amorphous solid.

L-Orn-LHRH—CF: LRMS (ESI-Quad) [m/z]: 840.4 [M+2H]2+, HRMS (ESI-IT) [m/z]: 560.5794, calculated 560.5724 for $C_{82}H_{97}N_{10}O_{20}$ [M+3H]$^{3+}$, err [ppm] 12.487.

Conjugation of Ratjadone Derivatives to Carrier Molecules

1.1.1.13 Biotin-Ratjadone Conjugate

Synthesis of Biotin-PEG$_3$-16S-Aminoratjadone—2-(1-(13-oxo-17-((3aS,4S,6aR)-2-oxohexahydro-1H-thieno[3,4-d]imidazol-4-yl)-3,6,9-trioxa-12-azaheptadecyl)-1H-1,2,3-triazol-4-yl)ethyl ((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

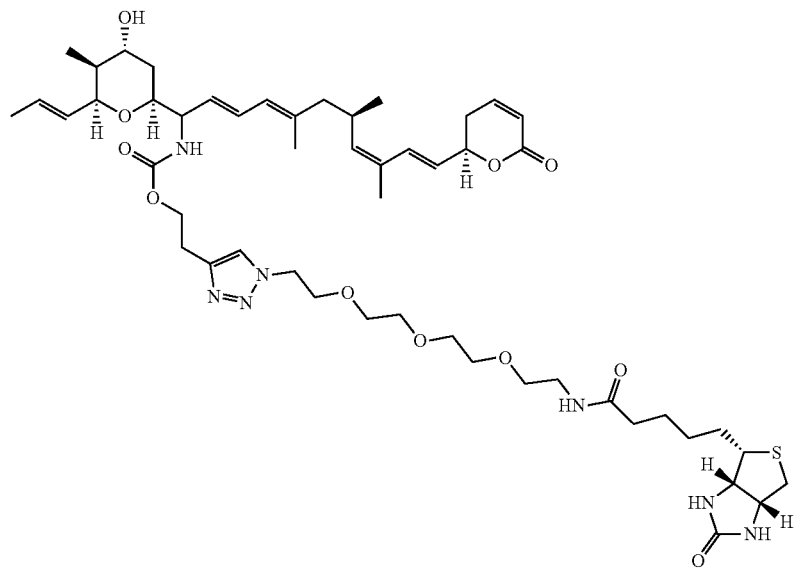

Chemical Formula: $C_{51}H_{77}N_7O_{11}S$
Molecular Weight: 996,28
Biotin-PEG$_3$-16S-Aminoratjadone To a solution of 3.6 mg (6.53 μmol, 1.0 eq) of 16S-Aminoratjadone derivative 25 and 3.2 mg (7.18 μmol, 1.1 eq) N-(2-(2-(2-(2-azidoethoxy)ethoxy)ethoxy)ethyl)-5-((3aS,4S,6aR)-2-oxohexahydro-1H-thieno[3,4-d]imidazol-4-yl)pentanamide in a mixture of DMSO:H$_2$O:tBuOH/2:1:1 were added 9.5 μL (19.6 mol, 3.0 eq) DiPEA, 10 μL (0.345 mg, 0.1 eq) of a stock solution (34.5 mg/1 mL) of TBTA in DMSO, 10 μL (0.052 mg, 0.05 eq) of a stock solution (5.2 mg/1 mL) of CuSO$_4$ in H$_2$O and 10 μL (0.646 mg, 0.1 eq) of a stock solution (64.6 mg/1 mL) of sodium ascorbate in H$_2$O. The mixture was stirred for 24 h at 23° C., before it was diluted with 100 μL of and 200 μL od DMSO and was purified by by RP prep HPLC (Phenomenex Gemini C18 RP-column 00G-4435-PO-AX, 5 μm, 110 A, 250×21.20 mm, Flow: 9 mL/min, ACN:H$_2$O+0.1% TFA/10:90→95:5 in 60 min) yielding after lyophilization 2.5 mg (2.51 μmol, 39%) of Biotin-PEG$_3$-16S-Aminoratjadone as a pale-yellow, amorphous solid.

Biotin-PEG$_3$-16S-Aminoratjadone: LRMS (ESI-Quad) [m/z]: 996.5 [M+H]$^+$, HRMS (ESI-IT) [m/z]: 996.546028, calculated 996.547454 for $C_{51}H_{78}N_7O_{11}S$ [M+H]$^+$, err [ppm] −1.431

1.1.1.14 Folate-Ratjadone Conjugates

1.1.1.14.1 General Procedure E for the Synthesis of Folate-Ratjadone Conjugates Via Copper-Free Click Reaction The corresponding FA-N$_3$ (1.1 eq) was dissolved in DMSO (0.2 M), a solution of BCN—O(CO)HN-Val-Cit-PABO(CO)NH-Ratja 31 (1.0 eq) in DMSO (0.2 M) was added and the mixture was stirred for 4-20 h at 23° C. under light exclusion until complete conversion was monitored by LCMS. The reaction mixture was diluted with 100 μL of MeOH, filtered through a Whatman® filter (45 μm) and directly purified by RP prep HPLC (Phenomenex Gemini C18 RP-column 00G-4435-PO-AX, 5 μm, 110 A, 250×21.20 mm, Flow: 9 mL/min, ACN:H$_2$O+0.1% TFA/10:90→95:5 in 45 min) yielding the Folate-Ratjadone Conjugates after lyophilization as a yellow, amorphous solids.

FA-1-Val-Cit-PABA-16R-Aminoratjadone—$N^2$-(4-(((2-amino-4-oxo-3,4-dihydropteridin-6-yl)methyl)amino)benzoyl)-$N^5$—((S)-1-carboxy-4-(((S)-6-(4-((5aR,6S,6aS)-6-(((((S)-1-(((S)-1-((4-(((((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1 (4H)-yl)benzamido)-1-methoxy-1-oxohexan-2-yl)amino)-4-oxobutyl)-L-glutamine

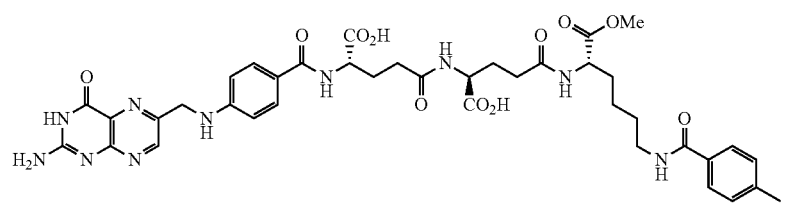

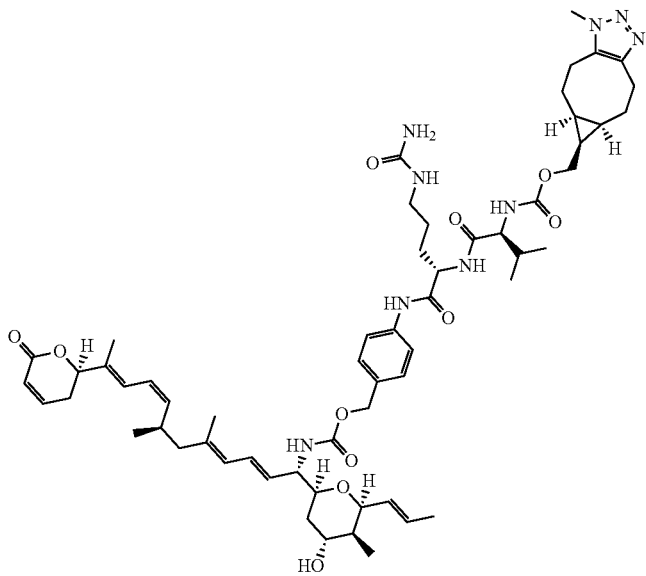

Chemical Formula: $C_{96}H_{123}N_{19}O_{22}$
Molecular Weight: 1895, 15
FA-1-Val-Cit-PABA-16R-Aminoratjadone Applying FA-$N_3$-1 to the general procedure E, 3.4 mg (17.49 μmol, 39%) FA-1-Val-Cit-PABA-16R-Aminoratjadone was obtained as a yellow, amorphous solid.

FA-1-Val-Cit-PABA-16R-Aminoratjadone: LRMS (ESI-Quad) [m/z]: 1896.0 [M+H]$^+$, HRMS (ESI-IT) [m/z]: 948.46350, calculated 948.46328 for $C_{96}H_{125}N_{19}O_{22}$ [M+2H]$^{2+}$, err [ppm] 0.231.

FA-2-Val-Cit-PABA-16R-Aminoratjadone—$N^2$-(4-(((2-amino-4-hydroxypteridin-6-yl)methyl)amino)benzoyl)-$N^5$—((S)-3-carboxy-1-(((S)-3-carboxy-1-(((S)-3-carboxy-1-(((S)-6-(4-((5aR,6S,6aS)-6-(((((S)-1-(((S)-1-((4-((((1S,2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1 (4H)-yl)benzamido)-1-methoxy-1-oxohexan-2-yl)amino)-1-oxopropan-2-yl)amino)-1-oxopropan-2-yl)amino)-1-oxopropan-2-yl)-L-glutamine

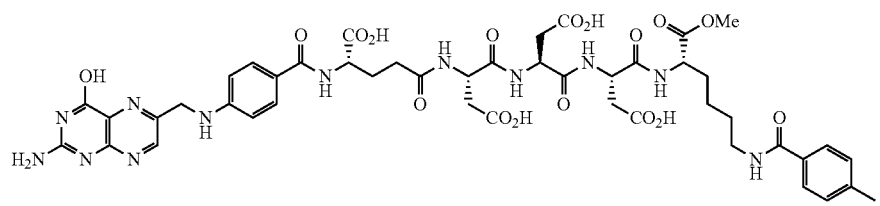

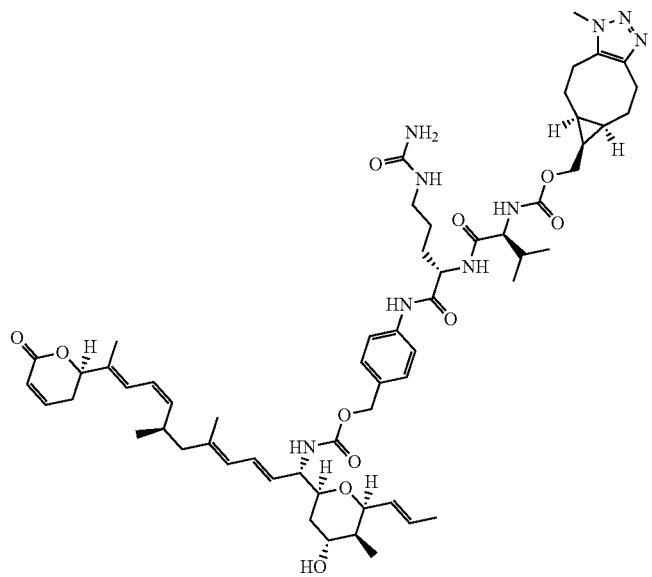

Chemical Formula: $C_{103}H_{131}N_{21}O_{28}$
Molecular Weight: 2111, 30
FA-2-Val-Cit-PABA-16R-Aminoratjadone Applying FA-$N_3$-2 to the general procedure E, 1.7 mg (0.805 μmol, 28%) FA-2-Val-Cit-PABA-16R-Aminoratjadone was obtained as a yellow, amorphous solid.

FA-2-Val-Cit-PABA-16R-Aminoratjadone: LRMS (ESI-Quad) [m/z]: 2112.9 [M+H]$^+$, HRMS (ESI-IT) [m/z]: 1056.4847, calculated 1056.4825 for $C_{103}H_{133}N_{21}O_{28}$ [M+2H]$^2$, err [ppm] 2.082.

FA-3-Val-Cit-PABA-16R-Aminoratjadone—$N^2$—((S)-4-(4-(((2-amino-4-hydroxypteridin-6-yl)methyl)amino)benzamido)-4-carboxybutanoyl)-D-aspartyl-L-aspartyl-L-aspartyl-$N^6$-(4-((5aR,6S,6aS)-6-(((((2S)-1-(((2S)-1-((4-(((((2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1(4H)-yl)benzoyl)-L-lysine

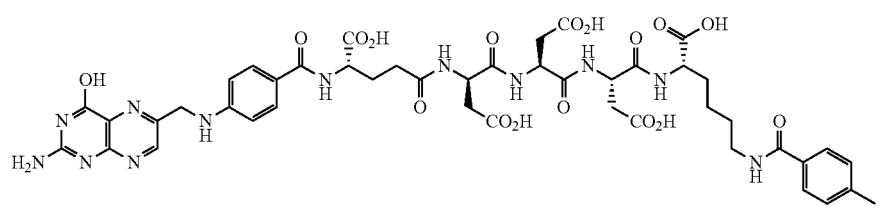

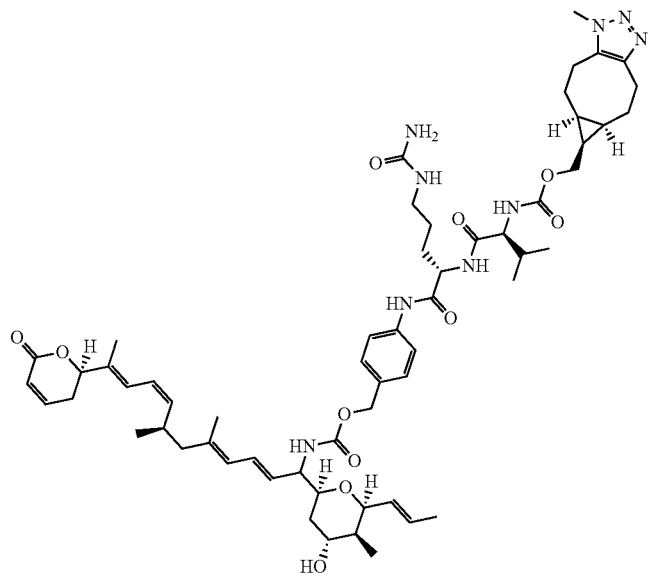

Chemical Formula: $C_{102}H_{129}N_{21}O_{28}$
Molecular Weight: 2097,27
FA-3-Val-Cit-PABA-16R-Aminoratjadone Applying FA-$N_3$-3 to the general procedure E, 3.3 mg (1.573 μmol, 54%) FA-3-Val-Cit-PABA-16R-Aminoratjadone was obtained as a yellow, amorphous solid.

FA-3-Val-Cit-PABA-16R-Aminoratjadone: LRMS (ESI-Quad) [m/z]: 1049.8 [M+2H]$^{2+}$, HRMS (ESI-IT) [m/z]: 1049.47480, calculated 1049.47475 for $C_{102}H_{131}N_{21}O_{28}$ [M+2H]$^{2+}$, err [ppm] 0.047.

FA-4-(Val-Cit-PABA-16R-Aminoratjadone)$_2$—N$^2$-N$^2$—((S)-4-(4-(((2-amino-4-hydroxypteridin-6-yl)methyl)amino)benzamido)-4-carboxybutanoyl)-D-aspartyl-D-aspartyl-N$^6$-(4-(2-((5aR,6S,6aS)-6-((5S,8S)-3-amino-8-((4-(((((2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1 (4H)-yl))benzoyl)-L-lysyl-L-asparty-L-asparty-N$^6$-(4-(2-((5aR,6S,6aS)-6-((5S,8S)-13-amino-8-((4-(((((2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1(4H)-yl))benzoyl)-L-lysine

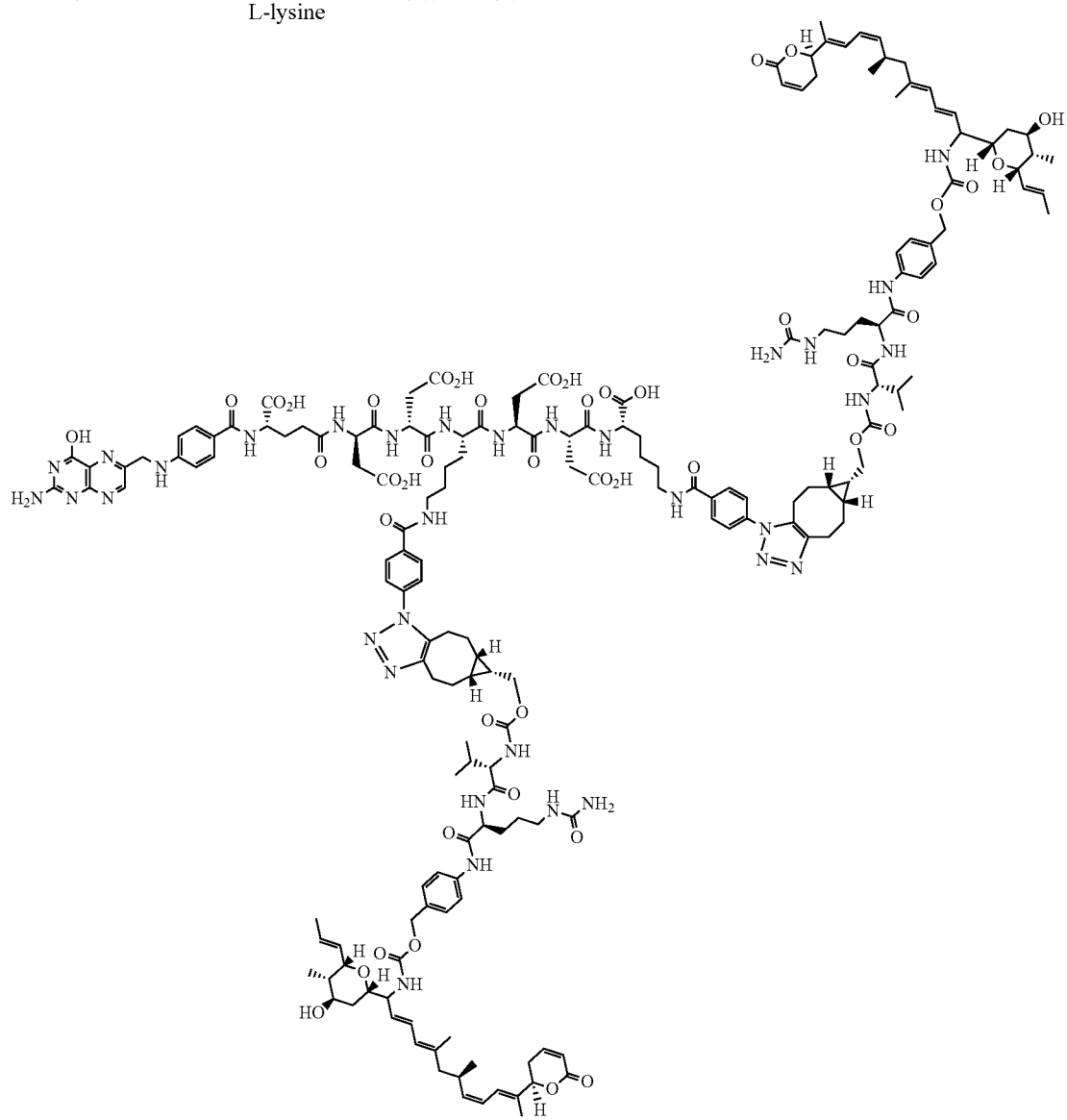

Chemical Formula: $C_{177}H_{229}N_{338}O_{44}$
Molecular Weight: 3522, 97
FA-4-(Val-Cit-PABA-16R-Aminoratjadone)$_2$ Applying FA-N₃-4 to the general procedure E (modification: 2.2 eq of BCN—O(CO)HN-Val-Cit-PABO(CO)NH-Ratja 31), 2.9 mg (0.80 mol, 36%) FA-4-(Val-Cit-PABA-16R-Aminoratjadone)₂ was obtained as a yellow, amorphous solid.

FA-4-(Val-Cit-PABA-16R-Aminoratjadone)₂: LRMS (ESI-Quad) [m/z]: 1175.4 $[M+3H]^{3+}$, HRMS (ESI-IT) [m/z]: 1174.89793, calculated 1174.89827 for $C_{177}H_{232}N_{33}O_{44}$ $[M+3H]^{3+}$, err [ppm] –0.289.

FA-5-Val-Cit-PABA-16R-Aminoratjadone—$N^2$-(4-(((2-amino-4-hydroxypteridin-6-yl)methyl)amino)-benzoyl)-$N^5$-((2R)-3-carboxy-1-(((2R)-3-carboxy-1-(((2R)-3-carboxy-1-(((2R)-3-carboxy-1-(((2R)-3-carboxy-1-(((1 S)-1-carboxy-4-((5aR,6S,6aS)-6-(((((2R)-1-(((2R)-1-((4-(((((2E,4E,7R,8Z,10E)-1-((2S,4R,5S,6S)-4-hydroxy-5-methyl-6-((E)-prop-1-en-1-yl)tetrahydro-2H-pyran-2-yl)-5,7-dimethyl-11-((R)-6-oxo-3,6-dihydro-2H-pyran-2-yl)dodeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1 (4H)-yl)butyl)amino)-1-oxopropan-2-yl)amino)-1-oxopropan-2-yl)amino)-1-oxopropan-2-yl)amino)-1-oxopropan-2-yl)amino)-1-oxopropan-2-yl)-L-glutamine

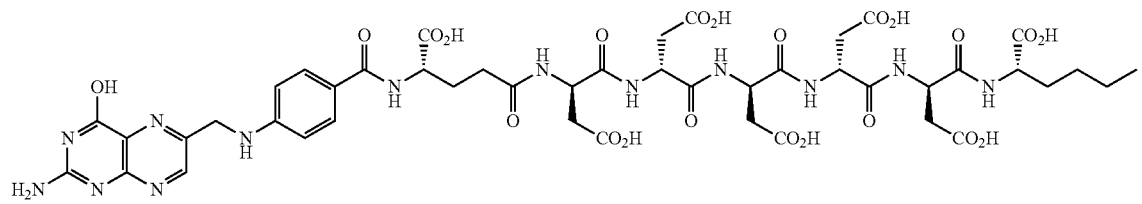

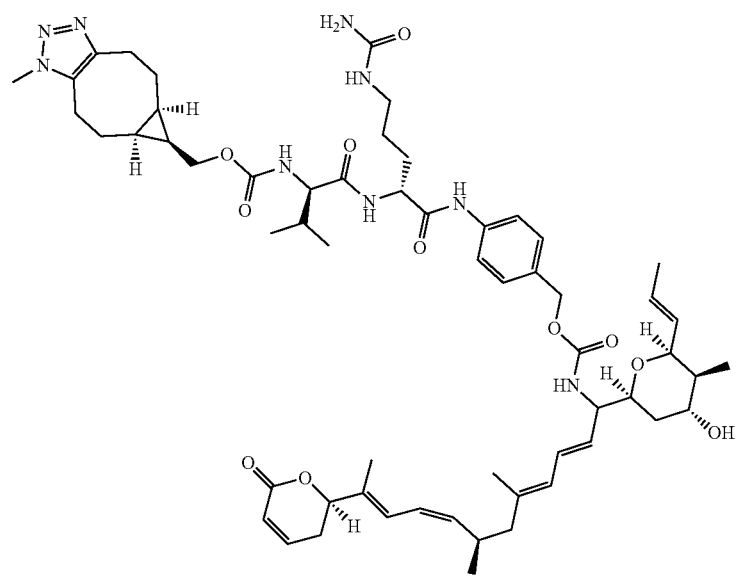

Chemical Formula: $C_{102}H_{132}N_{22}O_{33}$
Molecular Weight: 2194, 30
FA-5-Val-Cit-PABA-16R-Aminoratjadone Applying FA-N$_3$-5 to the general procedure E, 3.9 mg (1.78 μmol, 61%) FA-5-Val-Cit-PABA-16R-Aminoratjadone was obtained as a yellow, amorphous solid.

FA-5-Val-Cit-PABA-16R-Aminoratjadone: LRMS (ESI-Quad) [m/z]: 1097.7 [M+2H]$^{2+}$, HRMS (ESI-IT) [m/z]: 1097.97430, calculated 1097.9753 for C$_{102}$H$_{134}$N$_{22}$O$_{33}$ [M+2H]$^{2+}$, err [ppm] −0.919

FA-6-Val-Cit-PABA-16R-Aminoratjadone—(3S,8S,13S)-1-(4-(((2-amino-4-hydroxypteridin-6-yl)methyl)amino)phenyl)-19-(4-((5aR,6S,6aS)-6-((5S,8S)-13-amino-8-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1(4H)-yl)phenyl)-1,6,11,19-tetraoxo-2,7,12,18-tetraazanonadecane-3,8,13-tricarboxylic acid

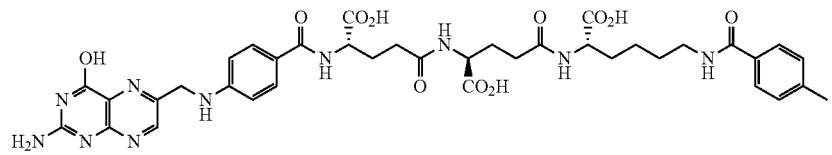

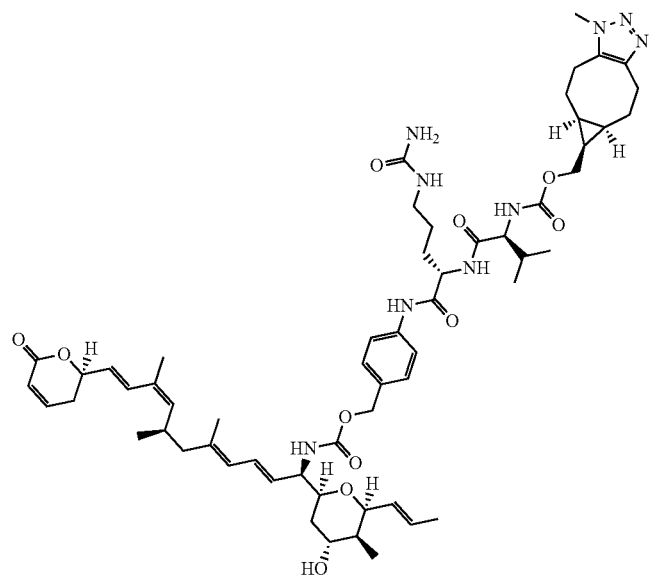

Chemical Formula: C$_{95}$H$_{121}$N$_{19}$O$_{22}$
Molecular Weight: 1881.12
FA-6-Val-Cit-PABA-16R-Aminoratjadone Applying FA-N$_3$-6 to the general procedure E, 2.2 mg (1.17 μmol, 49%) FA-6-Val-Cit-PABA-16R-Aminoratjadone was obtained as a yellow, amorphous solid.

FA-6-Val-Cit-PABA-16R-Aminoratjadone: LRMS (ESI-Quad) [m/z]: 1882.6 [M+H]$^+$, HRMS (ESI-IT) [m/z]: 940.9543, calculated 940.9540 for C$_{95}$H$_{123}$N$_{19}$O$_{22}$ [M+2H]$^{2+}$, err [ppm] 0.318.

FA-7-Val-Cit-PABA-16R-Aminoratjadone—N²-(4-(((2-amino-4-hydroxypteridin-6-yl)methyl)amino)benzoyl)-N⁵—((S)-1-carboxy-4-(((S)-1-carboxy-4-((5aR,6S,6aS)-6-(((((S)-1-(((S)-1-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1 (4H)-yl)butyl)amino)-4-oxobutyl)-L-glutamine

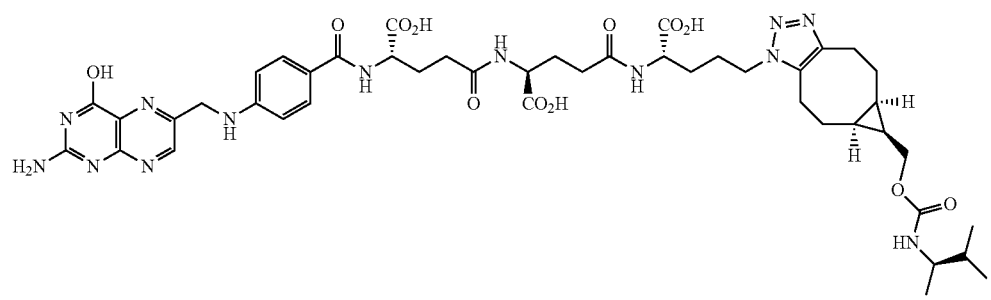

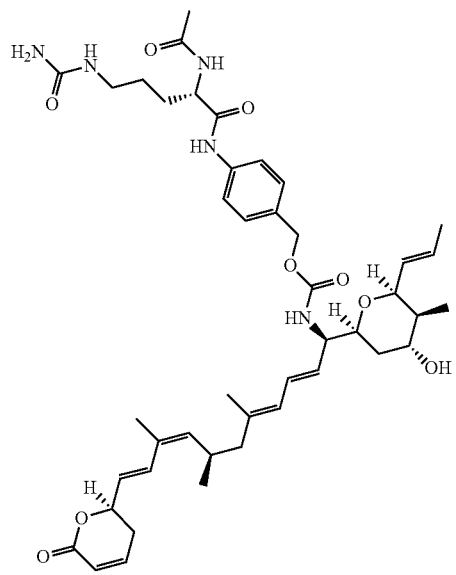

Chemical Formula: $C_{87}H_{114}N_{18}O_{21}$
Molecular Weight: 1747, 97
FA-7-Val-Cit-PABA-16R-Aminoratjadone Applying FA-N₃-7 to the general procedure E, 1.1 mg (0.629 μmol, 26%) FA-7-Val-Cit-PABA-16R-Aminoratjadone was obtained as a yellow, amorphous solid.

FA-7-Val-Cit-PABA-16R-Aminoratjadone: LRMS (ESI-Quad) [m/z]: 1748.6 [M+H]⁺, HRMS (ESI-IT) [m/z]: 874.4274, calculated 874.4276 for $C_{87}H_{116}N_{18}O_{21}$ [M+2H]²⁺, err [ppm] −0.228.

FA-8-Val-Cit-PABA-16R-Aminoratjadone—$N^2$—((S)-4-(4-(((2-amino-4-hydroxypteridin-6-yl)methyl)amino)benzamido)-4-carboxybutanoyl)-$N^6$-(4-((5aR,6S,6aS)-6-(((((S)-1-(((S)-1-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)amino)-1-oxo-5-ureidopentan-2-yl)amino)-3-methyl-1-oxobutan-2-yl)carbamoyl)oxy)methyl)-5,5a,6,6a,7,8-hexahydrocyclopropa[5,6]cycloocta[1,2-d][1,2,3]triazol-1 (4H)-yl)benzoyl)-L-lysyl-D-lysine

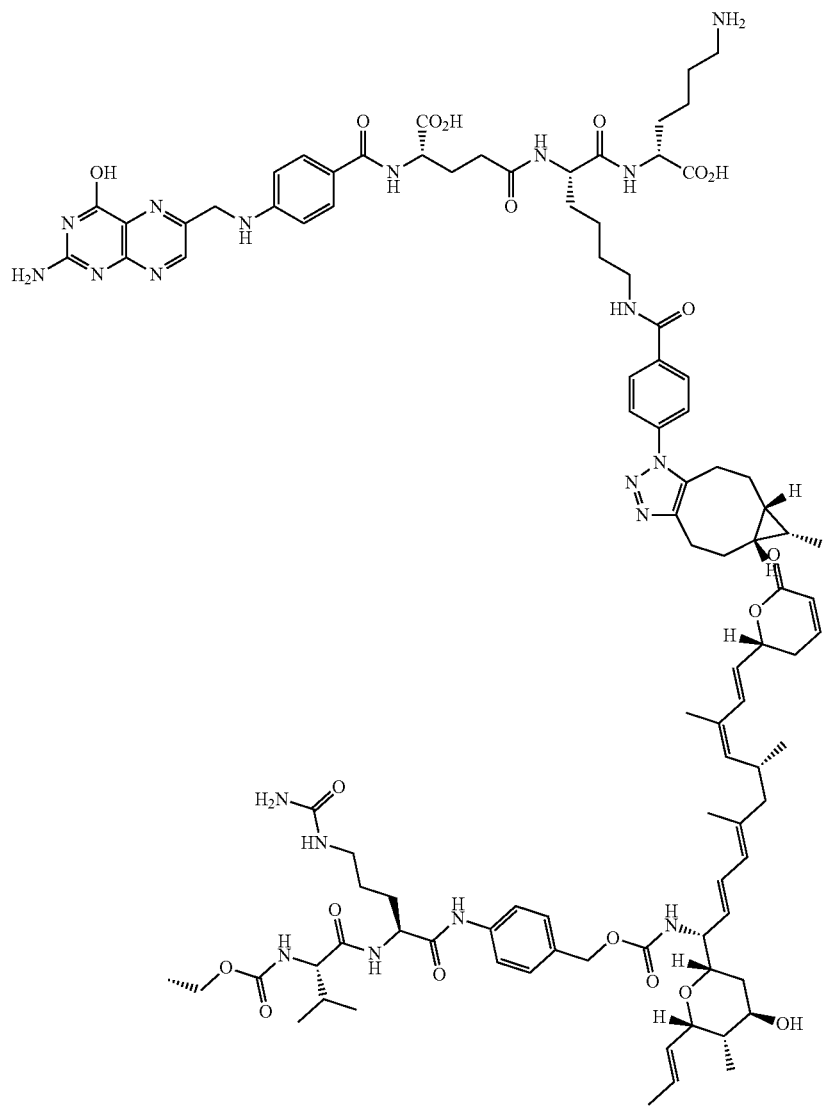

Chemical Formula: $C_{96}H_{126}N_{20}O_{20}$
Molecular Weight: 1880, 18
FA-8-Val-Cit-PABA-16R-Aminoratjadone Applying FA-$N_3$-8 to the general procedure E, 1.3 mg (0.691 μmol, 32%) FA-8-Val-Cit-PABA-16R-Aminoratjadone was obtained as a yellow, amorphous solid.

FA-8-Val-Cit-PABA-16R-Aminoratjadone: LRMS (ESI-Quad) [m/z]: 940.6 [M+2H]$^{2+}$, HRMS (ESI-IT) [m/z]: 940.98325, calculated 940.98163 for $C_{96}H_{128}N_{20}O_{20}$ [M+2H]$^{2+}$, err [ppm] 1.76.

FA-9-Val-Cit-PABA-16R-Aminoratjadone—((S)-2-
((S)-4-(4-(((2-amino-4-hydroxypteridin-6-yl)methyl)
amino)benzamido)-4-carboxybutanamido)-5-((5aR,
6S,6aS)-6-(((((S)-1-(((S)-1-((4-(((((1R,2E,4E,7R,8Z,
10E)-1-((2S,4R,5S,6S)-4-hydroxy-5-methyl-6-((E)-
prop-1-en-1-yl)tetrahydro-2H-pyran-2-yl)-5,7,9-
trimethyl-11-((R)-6-oxo-3,6-dihydro-2H-pyran-2-yl)
undeca-2,4,8,10-tetraen-1-yl)carbamoyl)oxy)methyl)
phenyl)amino)-1-oxo-5-ureidopentan-2-yl)amino)-3-
methyl-1-oxobutan-2-yl)carbamoyl)oxy)methyl)-5,
5a,6,6a,7,8-hexahydrocyclopropa[5,6]cycloocta[1,2-
d][1,2,3]triazol-1 (4H)-yl)pentanoyl)-D-lysine

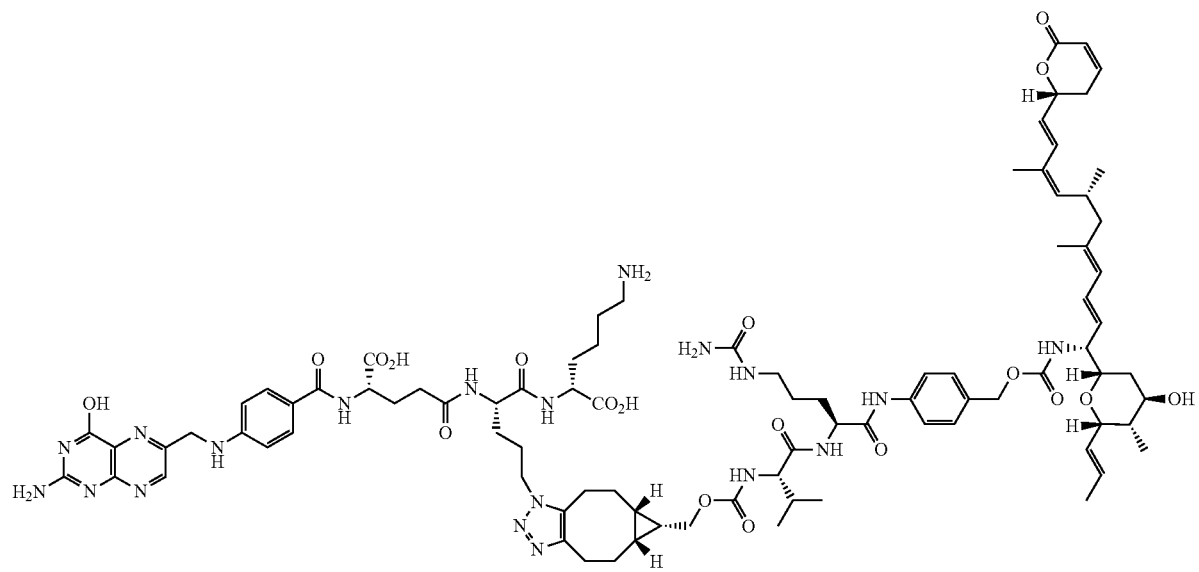

Chemical Formula: $C_{88}H_{119}N_{19}O_{19}$
Molecular Weight: 1747, 03
FA-9-Val-Cit-PABA-16R-Aminoratjadone Applying FA-$N_3$-9 to the general procedure E, 1.0 mg (0.572 μmol, 26%) FA-9-Val-Cit-PABA-16R-Aminoratjadone was obtained as a yellow, amorphous solid.

FA-9-Val-Cit-PABA-16R-Aminoratjadone: LRMS (ESI-Quad) [m/z]: 1748.0 [M+H]$^+$, HRMS (ESI-IT) [m/z]: 873.9538, calculated 873.9538 for $C_{88}H_{121}N_{19}O_{19}$ [M+2H]$^{2+}$, err [ppm] 0.0.

FA-10-Val-Cit-PABA-16R-Aminoratjadone—((S)-2-
((R)-2-((R)-2-((R)-2-((S)-4-(4-(((2-amino-4-hy-
droxypteridin-6-yl)methyl)amino)benzamido)-4-
carboxybutanamido)-3-carboxypropanamido)-3-
carboxypropanamido)-3-carboxypropanamido)-5-
((5aR,6S,6aS)-6-(((((S)-1-(((S)-1-((4-(((((1R,2E,4E,
7R,8Z,10E)-1-((2S,4R,5S,6S)-4-hydroxy-5-methyl-
6-((E)-prop-1-en-1-yl)tetrahydro-2H-pyran-2-yl)-5,
7,9-trimethyl-11-((R)-6-oxo-3,6-dihydro-2H-pyran-
2-yl)undeca-2,4,8,10-tetraen-1-yl)carbamoyl)oxy)
methyl)phenyl)amino)-1-oxo-5-ureidopentan-2-yl)
amino)-3-methyl-1-oxobutan-2-yl)carbamoyl)oxy)
methyl)-5,5a,6,6a,7,8-hexahydrocyclopropa[5,6]
cycloocta[1,2-d][1,2,3]triazol-1 (4H)-yl)pentanoyl)-
D-aspartyl-D-aspartyl-D-lysine

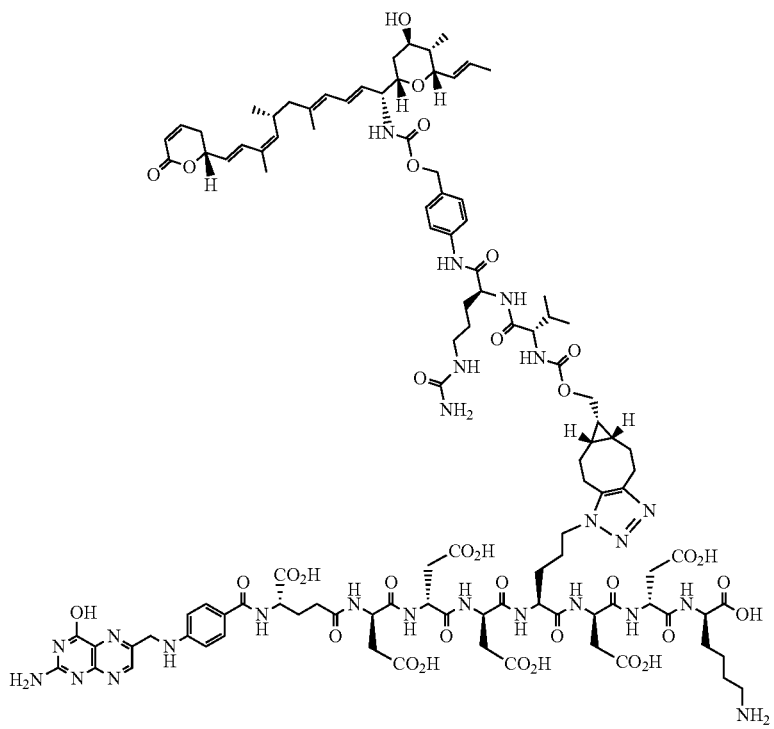

Chemical Formula: $C_{108}H_{144}N_{24}O_{34}$
Molecular Weight: 2322, 47
FA-10-Val-Cit-PABA-16R-Aminoratjadone Applying FA-N$_3$-10 to the general procedure E, 1.8 mg (0.78 μmol, 24%) FA-10-Val-Cit-PABA-16R-Aminoratjadone was obtained as a yellow, amorphous solid.

FA-10-Val-Cit-PABA-16R-Aminoratjadone: LRMS (ESI-Quad) [m/z]: 1162.1 [M+H]$^+$, HRMS (ESI-IT) [m/z]: 775.01786, calculated 775.01762 for $C_{108}H_{147}N_{24}O_{34}$ [M+3H]$^3$F, err [ppm] 0.309.

157

FA-11-(Val-Cit-PABA-16R-Aminoratjadone)—$N^2$-(4-(((2-amino-4-hydroxypterdridin-6-yl)methyl)amino)-benzoyl)-$N^5$-((R)-3-carboxy-1-(((R)-3-carboxy-1-(((S)-1-(((R)-3-carboxy-1-(((R)-3-carboxy-1-(((S)-1-(((R)-3-carboxy-1-(((R)-3-carboxy-1-(((S)-1-carboxy-4-(2-((5aR,6S,6aS)-6-((5S,8S)-13-amino-8-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1(4H)-yl))butyl)amino)-1-oxopropan-2-yl)amino)-1-oxopropan-2-yl)amino)-5-(2-((5aR,6S,6aS)-6-((5S,8S)-13-amino-8-((4-(((((1R,2E,4E,7R,8Z,10E)-1-((2S,4R,5S,6S)-4-hydroxy-5-

158 methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1 (4H)-yl))-1-oxopentan-2-yl)amino)-1-oxopropan-2-yl)amino)-1-oxopropan-2-yl)amino)-5-(2-((5aR,6S,6aS)-6-((5S,8S)-13-amino-8-((4-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)methyl)phenyl)carbamoyl)-5-isopropyl-3,6,13-trioxo-2-oxa-4,7,12-triazatridecyl)-5,5a,6,6a,7,8-hexahydrocyclopropa[5,6]cycloocta[1,2-d][1,2,3]triazol-1 (4H)-yl))-1-oxopentan-2-yl)amino)-1-oxopropan-2-yl)amino)-1-oxopropan-2-yl)-L-glutamine

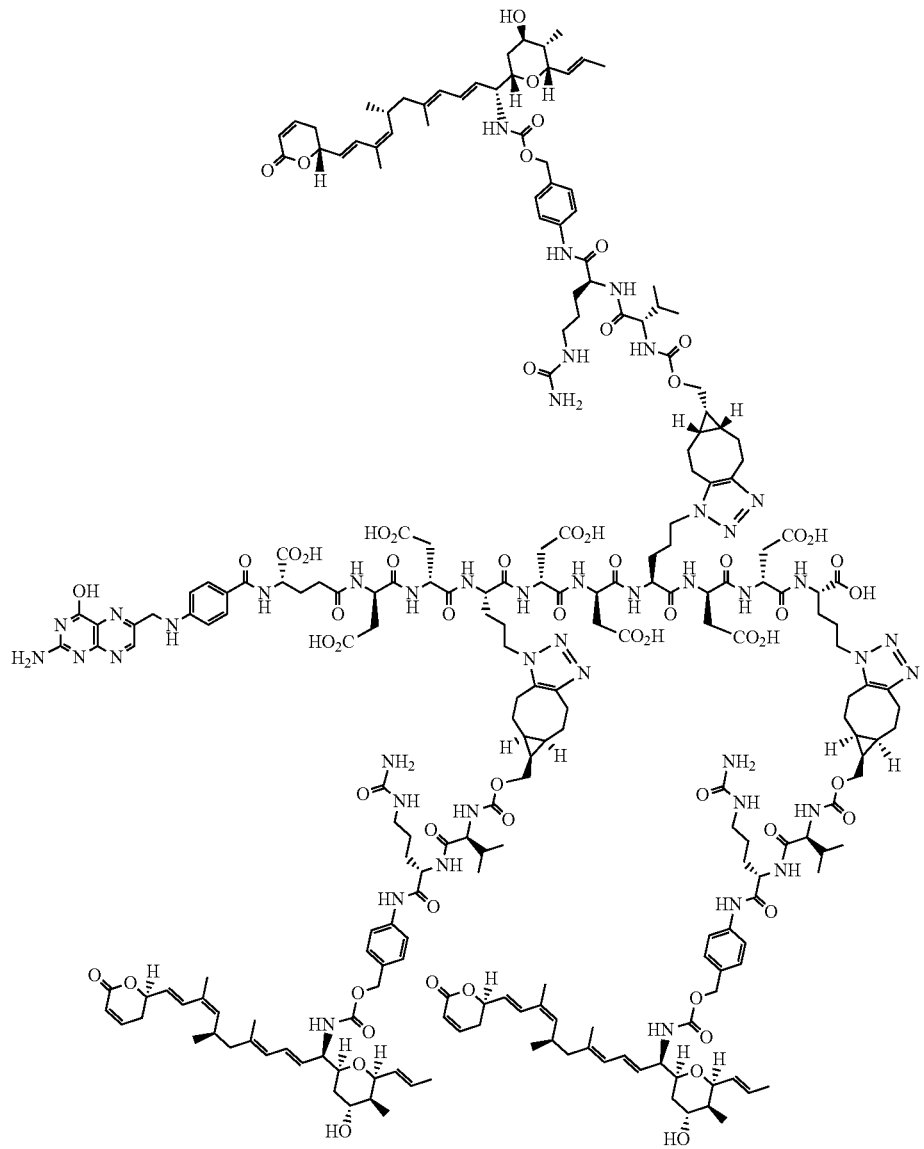

Chemical Formula: $C_{232}H_{313}N_{43}O_{60}$
Molecular Weight: 4664, 30
FA-11-(Val-Cit-PABA-16R-Aminoratjadone)$_3$ Applying FA-N$_3$-11 to the general procedure E (modification 3.3 eq of BCN—O(CO)HN-Val-Cit-PABO(CO)NH-Ratja 31), 4.7 mg (1.007 µmol, 54%) FA-11-(Val-Cit-PABA-16R-Aminoratjadone)$_3$ was obtained as a yellow, amorphous solid.

FA-11-(Val-Cit-PABA-16R-Aminoratjadone)$_3$: LRMS (ESI-Quad) [m/z]: 1555.5 [M+3H]$^{3+}$ 1.1.1.14.2 General Procedure F for the Synthesis of Folate-Ratjadone Conjugates Via Copper-Mediated Click Reaction The corresponding FA-N$_3$ (1.1 eq) and the corresponding Ratjadone payload (22, 24 or 41) (1.0 eq) were dissolved in a mixture of DMSO:H$_2$O:tBuOH/2:1:1 were added DiPEA (6.0 eq), TBTA (0.1 eq, 10 µL from a stock solution in DMSO), CuSO$_4$ (0.05 eq, 10 µL from a stock solution in H$_2$O) and sodium ascorbate (0.5 eq, 10 µL from a stock solution in H$_2$O) and the mixture was stirred under light exclusion for 4-24 h at 23° C. until complete conversion was monitored by LCMS. The reaction mixture was diluted with 100 µL of MeOH, filtered through a Whatman® filter (45 µm) and directly purified by RP prep HPLC (Phenomenex Gemini C18 RP-column 00G-4435-PO-AX, 5 µm, 110 A, 250×21.20 mm, Flow: 9 mL/min, ACN:H$_2$O+0.1% TFA/10: 90→95:5 in 45 min) yielding the Folate-Ratjadone Conjugates after lyophilization as yellow, amorphous solids.

FA-3-16R-Aminoratjadone—N$^2$—((S)-4-(4-(((2-amino-4-hydroxypteridin-6-yl)methyl)amino)benzamido)-4-carboxybutanoyl)-D-aspartyl-L-aspartyl-L-aspartyl-N$^6$-(4-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)benzoyl)-L-lysine

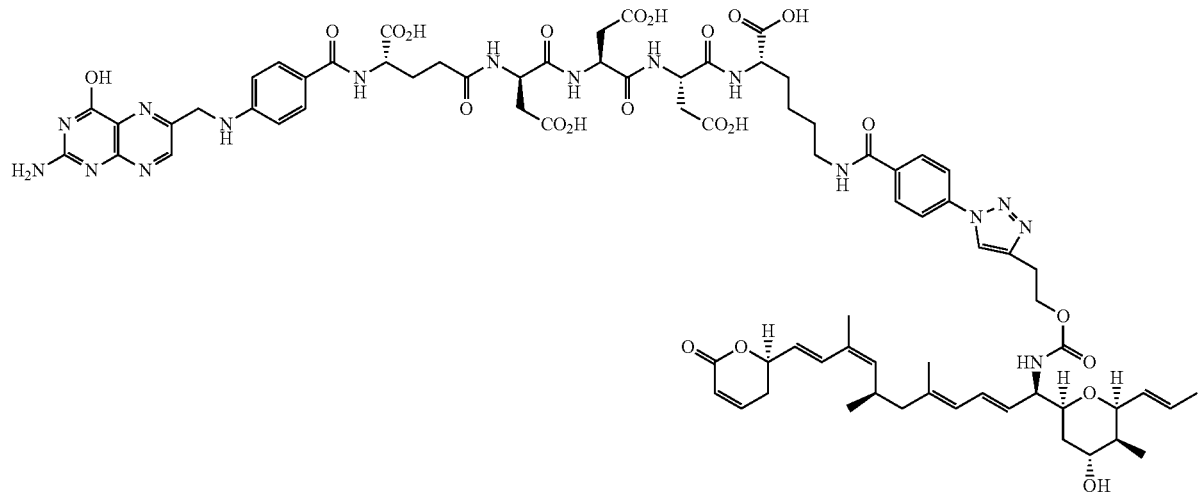

Chemical Formula: C$_{77}$H$_{94}$N$_{16}$O$_{23}$
Molecular Weight: 1611, 69
FA-3-16R-Aminoratjadone Applying FA-N$_3$-3 and 16R-Aminoratjadone derivative 24 to the general procedure F, 2.7 mg (1.58 µmol, 42%) FA-3-16R-Aminoratjadone was obtained as a yellow, amorphous solid.

FA-3-16R-Aminoratjadone: LRMS (ESI-Quad) [m/z]: 1612.4 [M+H]$^+$, HRMS (ESI-IT) [m/z]: 806.3405, calculated 806.3412 for C$_{77}$H$_{96}$N$_{16}$O$_{23}$ [M+2H]$^{2+}$, err [ppm] −0.639.

FA-3-19-Aminoratjadone—$N^2$—((S)-4-(4-(((2-amino-4-hydroxypteridin-6-yl)methyl)amino)benzamido)-4-carboxybutanoyl)-D-aspartyl-L-aspartyl-L-aspartyl-$N^6$-(4-(4-((((2S,3S,6S)-6-((1R,2E,4E,7R,8Z,10E)-1-hydroxy-5,7,9-trimethyl-11-((R)-6-oxo-3,6-dihydro-2H-pyran-2-yl)undeca-2,4,8,10-tetraen-1-yl)-3-methyl-2-((E)-prop-1-en-1-yl)tetrahydro-2H-pyran-4-yl)amino)methyl)-1H-1,2,3-triazol-1-yl)benzoyl)-L-lysine

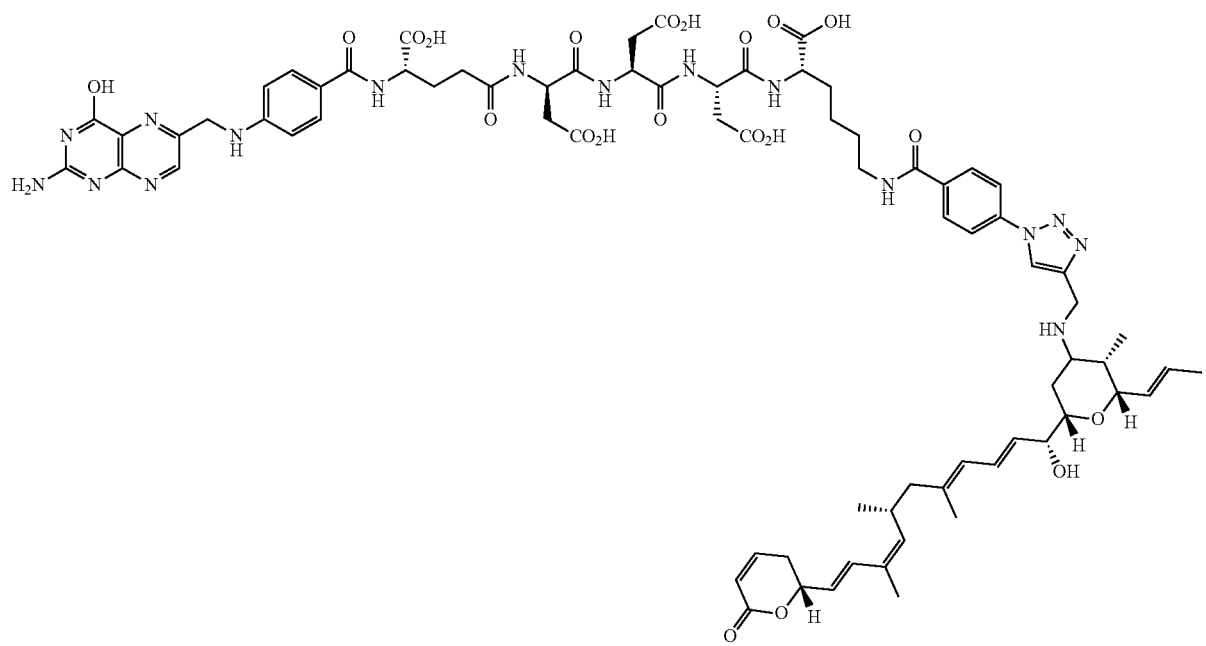

Chemical Formula: $C_{75}H_{92}N_{16}O_{21}$
Molecular Weight: 1553.65
FA-3-19-Aminoratjadone Applying FA-$N_3$-3 and 19-Aminoratjadone derivative 41 to the general procedure F, 1.2 mg (0.77 μmol, 10%) FA-3-19-Aminoratjadone was obtained as a yellow, amorphous solid.

FA-3-19-Aminoratjadone: LRMS (ESI-Quad) [m/z]: 777.8 $[M+2H]^2$, HRMS (ESI-IT) [m/z]: 777.3384, calculated 777.3384 for $C_{75}H_{94}N_{16}O_{21}$ [M+2H]2+, err [ppm] 0.0.

FA-3b-16R-Aminoratjadone—N²—((S)-4-(4-(((2-amino-4-hydroxypteridin-6-yl)methyl)amino)benzamido)-4-carboxybutanoyl)-D-aspartyl-L-aspartyl-L-aspartyl-Ned as a (4-(4-(3-(((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)amino)-3-oxopropyl)-1H-1,2,3-triazol-1-yl)benzoyl)-L-lysine

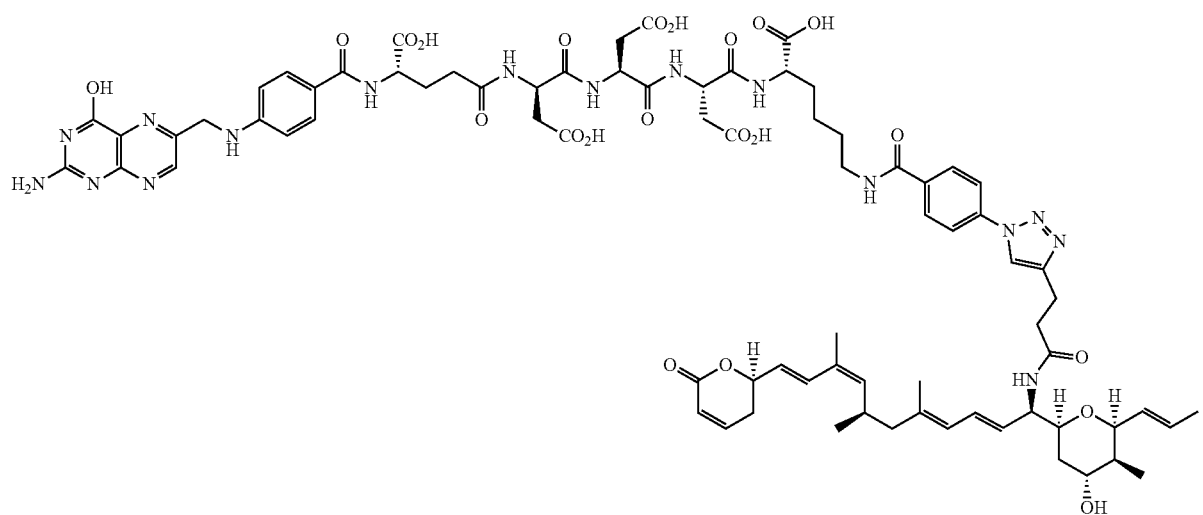

Chemical Formula: $C_{77}H_{94}N_{16}O_{22}$
Molecular Weight: 1595.69
FA-3b-16R-Aminoratjadone Applying FA-N₃-3 and 16R-Aminoratjadone derivative 22 to the general procedure F, 1.9 mg (1.19 μmol, 17%) FA-3b-16R-Aminoratjadone was obtained as a yellow, amorphous solid.

FA-3b-16R-Aminoratjadone: LRMS (ESI-Quad) [m/z]: 1596.7 [M+H]⁺, HRMS (ESI-IT) [m/z]: 798.34173, calculated 798.34370 for $C_{77}H_{96}N_{16}O_{22}$ [M+H]⁺, err [ppm] −2.41

FA-5-16R-Aminoratjadone—N²-(4-(((2-amino-4-hydroxypteridin-6-yl)methyl)amino)benzoyl)-N⁵-((R)-3-carboxy-1-(((R)-3-carboxy-1-(((R)-3-carboxy-1-(((R)-3-carboxy-1-(((R)-3-carboxy-1-(((S)-1-carboxy-4-(4-(2-((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)butyl)amino)-1-oxopropan-2-yl)amino)-1-oxopropan-2-yl)amino)-1-oxopropan-2-yl)amino)-1-oxopropan-2-yl)amino)-1-oxopropan-2-yl)-L-glutamine

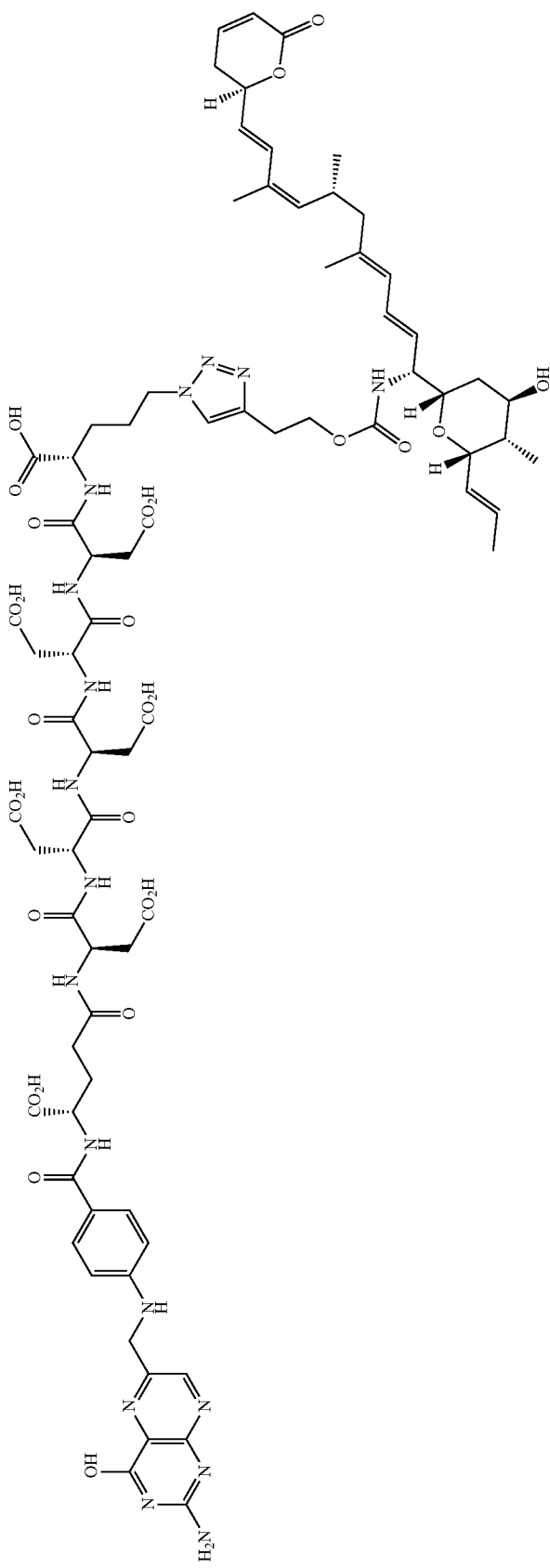
Chemical Formula: $C_{77}H_{97}N_{17}O_{28}$
Molecular Weight: 1708.71
FA-5-16R-Aminoratjadone Applying FA-N$_3$-5 and 16R-Aminoratjadone derivative 24 to the general procedure F, 1.1 mg (0.68 μmol, 18%) FA-5-16R-Aminoratjadone was obtained as a yellow, amorphous solid.

FA-5-16R-Aminoratjadone: LRMS (ESI-Quad) [m/z]: 1709.9 [M+H]$^+$, HRMS (ESI-IT) [m/z]: 854.8417, calculated 854.8417 for C$_{77}$H$_{99}$N$_{17}$O$_{28}$ [M+2H]$^{2+}$, err [ppm] 0.0.

FA-6-16R-Aminoratjadone—(3S,8S,13S)-1-(4-(((2-amino-4-hydroxypteridin-6-yl)methyl)amino)phenyl)-19-(4-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-1-((R)-6-oxo-3,6-dihydro-2H-pyran-2-yl)undeca-2,4,8,10-tetraen-1-yl)carbamoyl)oxy)ethyl)-1H-1,2,3-triazol-1-yl)phenyl)-1,6,11,19-tetraoxo-2,7,12,18-tetraazanonadecane-3,8,13-tricarboxylic acid

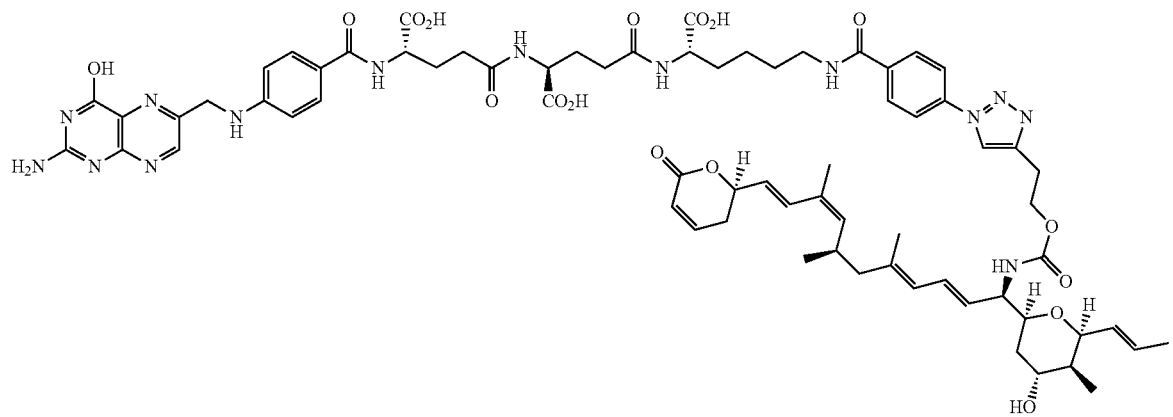

Chemical Formula: C$_{70}$H$_{86}$N$_{14}$O$_{17}$
Molecular Weight: 1395.54
FA-6-16R-Aminoratjadone Applying FA-N$_3$-6 and 16R-Aminoratjadone derivative 24 to the general procedure F, 3.6 mg (2.58 μmol, 64%) FA-6-16R-Aminoratjadone was obtained as a yellow, amorphous solid.

FA-6-16R-Aminoratjadone: LRMS (ESI-Quad) [m/z]: 1396.3 [M+H]$^+$, HRMS (ESI-IT) [m/z]: 698.32208, calculated 698.32204 for C$_{70}$H$_{87}$N$_{14}$O$_{17}$ [M+2H]$^{2+}$, err [ppm] 0.057

FA-7-16R-Aminoratjadone—$N^2$-(4-(((2-amino-4-hydroxypteridin-6-yl)methyl)amino)benzoyl)-$N^5$—((S)-1-carboxy-4-(((S)-1-carboxy-4-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)butyl)amino)-4-oxobutyl)-L-glutamine

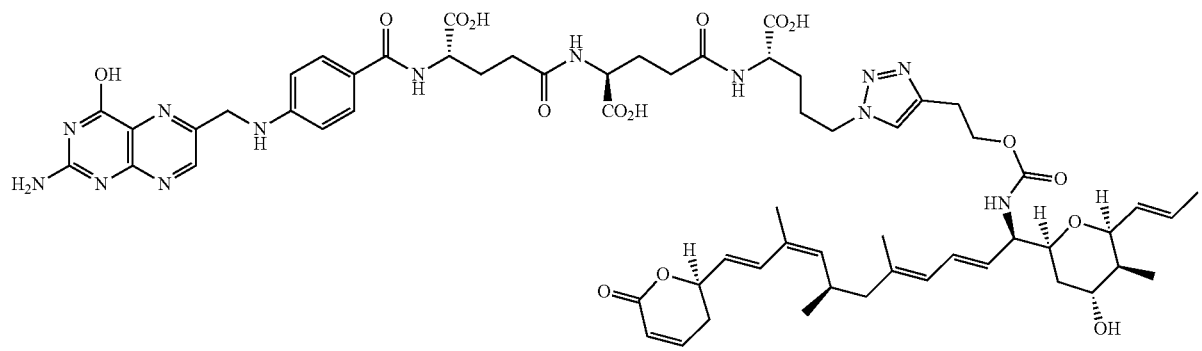

Chemical Formula: $C_{62}H_{79}N_{13}O_{16}$
Molecular Weight: 1262.39
FA-7-16R-Aminoratjadone Applying FA-$N_3$-7 and 16R-Aminoratjadone derivative 24 to the general procedure F, 2.4 mg (1.90 µmol, 48%) FA-7-16R-Aminoratjadone was obtained as a yellow, amorphous solid.

FA-7-16R-Aminoratjadone: LRMS (ESI-Quad) [m/z]: 1263.8 [M+H]$^+$, HRMS (ESI-IT) [m/z]: 631.79626, calculated 631.79566 for $C_{62}H_{81}N_{13}O_{16}$ [M+2H]$^{2+}$ err [ppm] −0.949

FA-8-16R-Aminoratjadone—$N^2$—((S)-4-(4-(((2-amino-4-hydroxypteridin-6-yl)methyl)amino)benzamido)-4-carboxybutanoyl)-$N^6$-(4-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)benzoyl)-L-lysyl-D-lysine

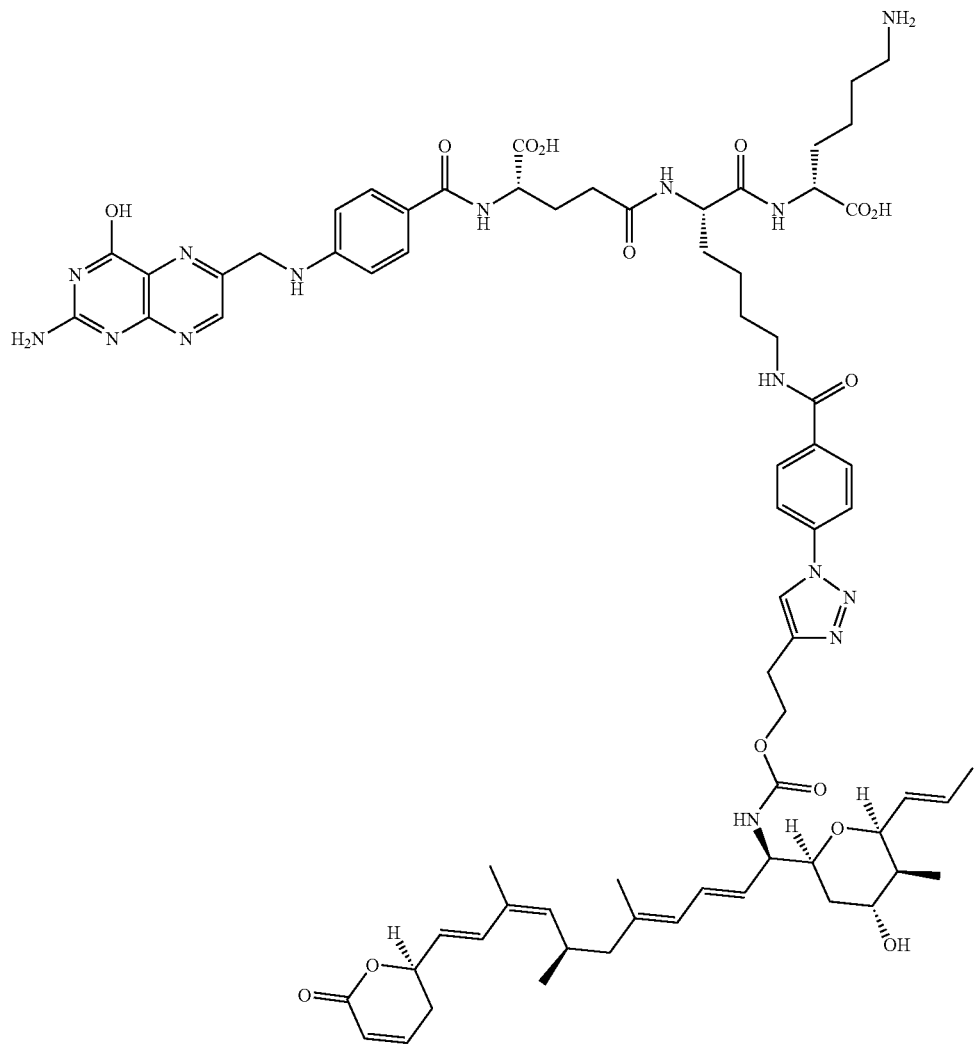

Chemical Formula: $C_{71}H_{91}N_{15}O_{15}$
Molecular Weight: 1394.60
FA-8-16R-Aminoratjadone Applying FA-$N_3$-8 and 16R-Aminoratjadone derivative 24 to the general procedure F, 1.4 mg (1.00 μmol, 28%) FA-8-16R-Aminoratjadone was obtained as a yellow, amorphous solid.

FA-8-16R-Aminoratjadone: LRMS (ESI-Quad) [m/z]: 698.2 $[M+2H]^{2+}$, HRMS (ESI-IT) [m/z]: 697.84802, calculated 697.84823 for $C_{23}H_{34}N_5O_6$ $[M+H]^+$, err [ppm] −0.288.

FA-9-16R-Aminoratjadone—((S)-2-((S)-4-(4-(((2-amino-4-hydroxypteridin-6-yl)methyl)amino)benzamido)-4-carboxybutanamido)-5-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)pentanoyl)-D-lysine

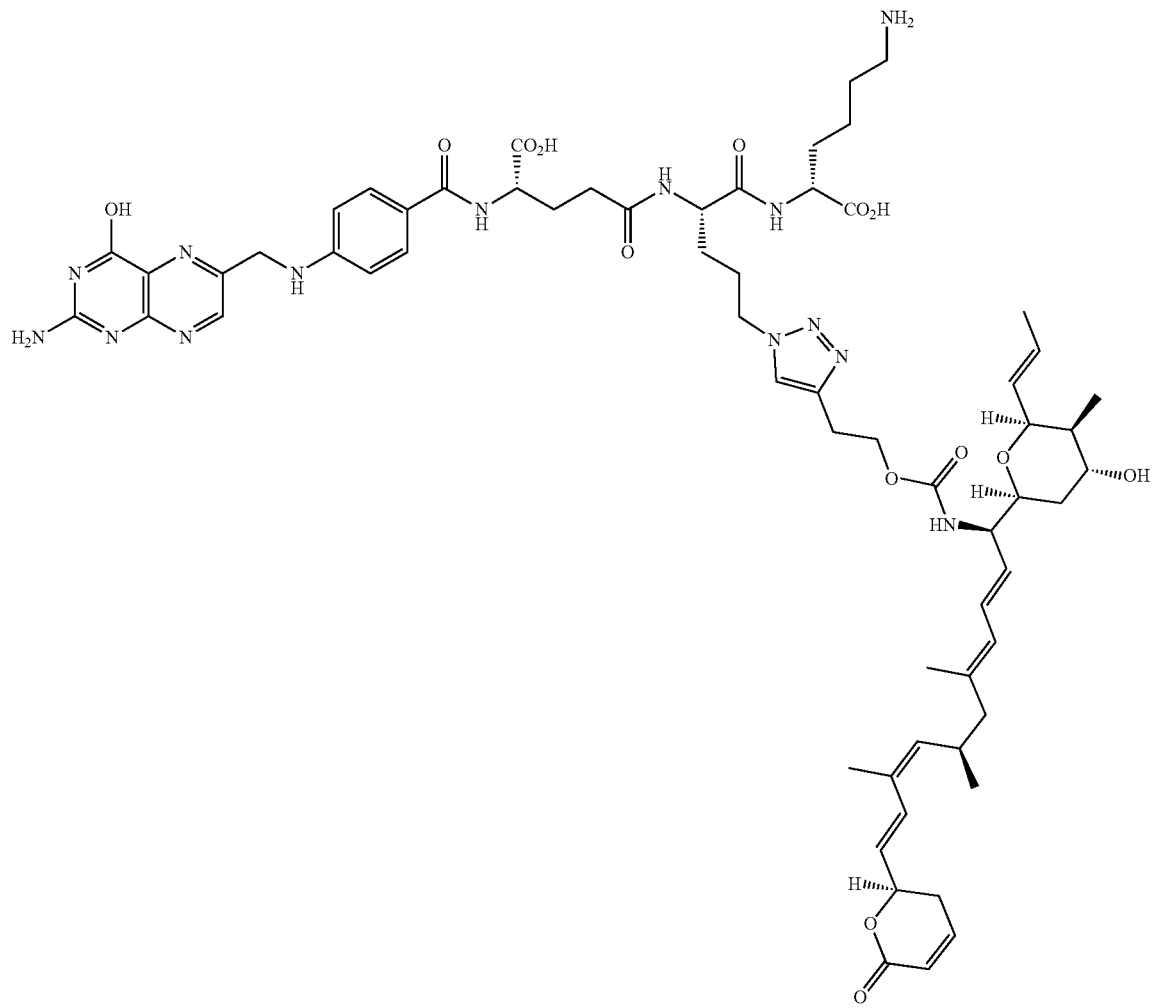

Chemical Formula: $C_{63}H_{84}N_{14}O_{14}$
Molecular Weight: 1261.45
FA-9-16R-Aminoratjadone Applying FA-N$_3$-9 and 16R-Aminoratjadone derivative 24 to the general procedure F, 1.6 mg (1.26 mol, 35%) FA-9-16R-Aminoratjadone was obtained as a yellow, amorphous solid.

FA-9-16R-Aminoratjadone: LRMS (ESI-Quad) [m/z]: 1261.9 [M+H]$^+$, HRMS (ESI-IT) [m/z]: 613.3218, calculated 613.3218 for $C_{63}H_{86}N_{14}O_{14}$ [M+H]$^+$, err [ppm] 0.0.

FA-10-16R-Aminoratjadone—((S)-2-((R)-2-((R)-2-((R)-2-((S)-4-(4-(((2-amino-4-hydroxypteridin-6-yl)methyl)amino)benzamido)-4-carboxybutanamido)-3-carboxypropanamido)-3-carboxypropanamido)-3-carboxypropanamido)-5-(4-(2-(((((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamoyl)oxy)ethyl)-1H-1,2,3-triazol-1-yl)pentanoyl)-D-aspartyl-D-aspartyl-D-lysine

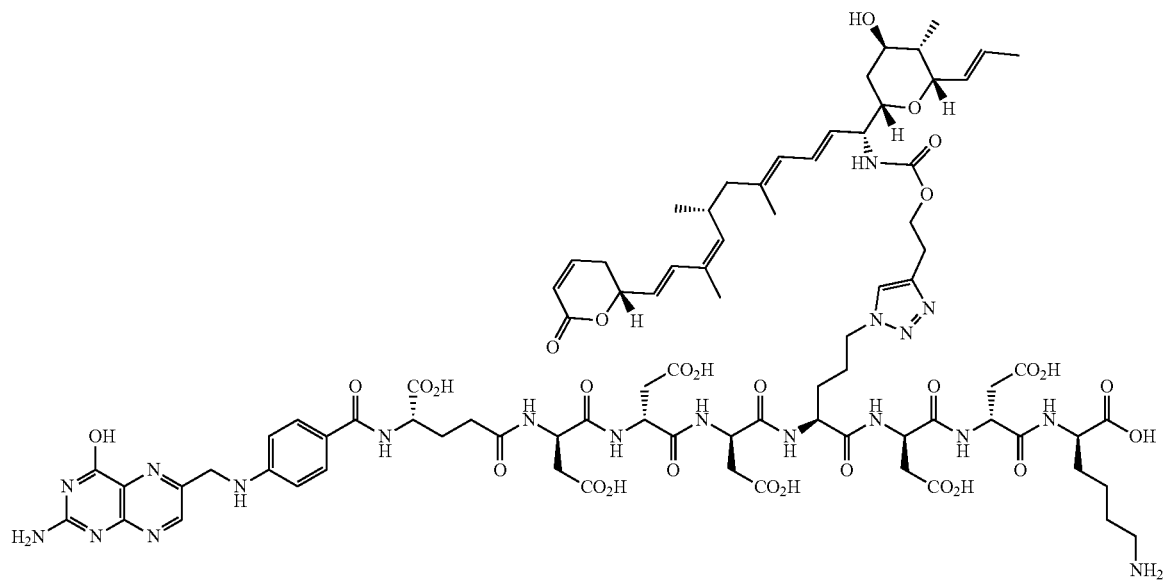

Chemical Formula: $C_{83}H_{109}N_{19}O_{29}$
Molecular Weight: 1836.89
FA-10-16R-Aminoratjadone Applying FA-N$_3$-10 and 16R-Aminoratjadone derivative 24 to the general procedure F, 2.5 mg (1.36 μmol, 34%) FA-10-16R-Aminoratjadone was obtained as a yellow, amorphous solid.

FA-10-16R-Aminoratjadone: LRMS (ESI-Quad) [m/z]: 919.8 [M+2H]$^{2+}$, HRMS (ESI-IT) [m/z]: 918.89078, calculated 918.88920 for $C_{83}H_{111}N_{19}O_{29}$ [M+2H]$^{2+}$, err [ppm] 1.719.

Synthesis of FA-SS-16R-Aminoratjadone—N²-(4-(((2-amino-4-hydroxypteridin-6-yl)methyl)amino)benzoyl)-N⁵-((R)-1-carboxy-2-((3-(((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)amino)-3-oxopropyl)disulfaneyl)ethyl)-L-glutamine

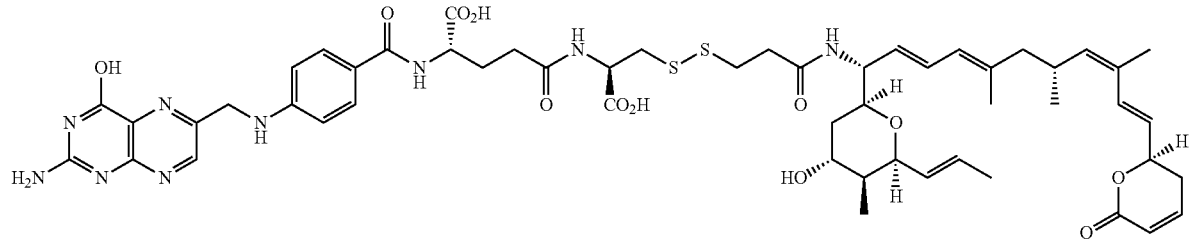

Chemical Formula: $C_{53}H_{67}N_9O_{12}S_2$
Molecular Weight: 1086.29
FA-SS-16R-Aminoratjadone To a solution of 2.6 mg (4.72 µmol, 1.1 eq) FA-SH-1 in 1.22 mL ACN under Argon atm. was added a solution of 2.8 mg (4.28 µmol, 1.0 eq) 2-PySS(CH₂)₂(CO)NH-Ratja 35 in 1.22 mL PBS buffer (pH=7.4) and the mixture was stirred for 4 h at 23° C. The ACN was removed by a nitrogen flow and 50 µL DMSO were added. The mixture was filtered through a Whatman® filter (45 µm) and directly purified by RP prep HPLC (Phenomenex Gemini C18 RP-column 00G-4435-PO-AX, 5 µm, 110 A, 250×21.20 mm, Flow: 9 mL/min, ACN:H₂O+0.1% TFA/I 10:90→95:5 in 45 min) yielding after lyophilization 1.5 mg (1.38 µmol, 32%) FA-SS-16R-Aminoratjadone as yellow, amorphous solid.

FA-SS-16R-Aminoratjadone: LRMS (ESI-Quad) [m/z]: 1086.5 [M+H]⁺, HRMS (ESI-IT) [m/z]: 1086.44132, calculated 1086.44233 for $C_{53}H_{68}N_9O_{12}S_2$[M+H]⁺, err [ppm] –0.929

1.1.1.15 Gonadoliberin-Ratjadone Conjugates

Synthesis of L-Orn-LHRH-16R-Aminoratjadone—2-(1-((3S,6S,9S,12S,15S)-3-((1H-imidazol-4-yl)methyl)-6-((1H-indol-3-yl)methyl)-15-(((S)-1-(((S)-1—((S)-2-((2-amino-2-oxoethyl)carbamoyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13-pentaoxo-1-((S)-5-oxopyrrolidin-2-yl)-2,5,8,11,14-pentaazaoctadecan-18-yl)-1H-1,2,3-triazol-4-yl)ethyl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

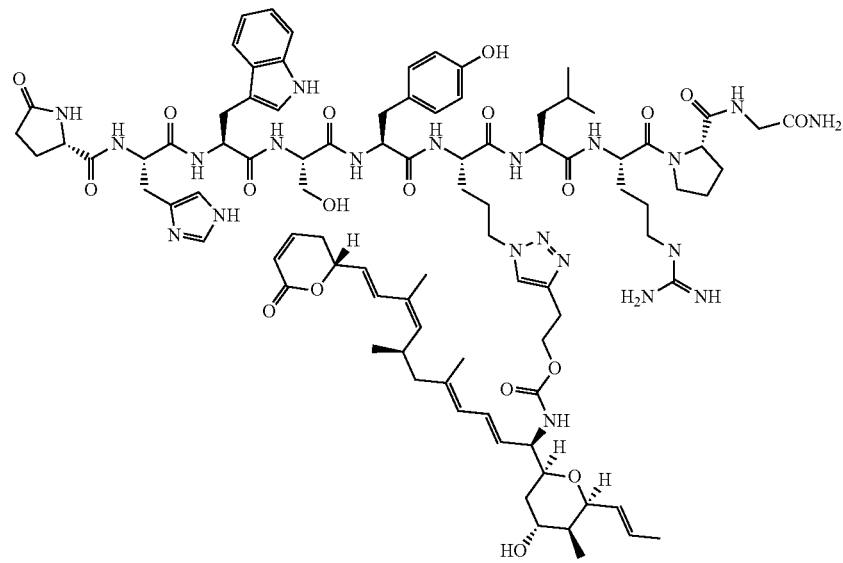

Chemical Formula: $C_{91}H_{125}N_{21}O_{19}$
Molecular Weight: 1817.13
L-Orn-LHRH-16R-Aminoratjadone To a solution of 5.4 mg (3.63 µmol, 1.0 eq) L-N$_3$-Orn-LHRH and 2.0 mg (3.63 µmol, 1.0 eq) the 16R-Aminoratjadone derivative 24 in a mixture of DMSO:pH=7 phosphate buffer (100 nM):tBuOH/2:2:1 (72 µL) were added 0.48 mg (0.9065 µmol, 0.25 eq, 10 µL from a stock solution in DMSO) TBTA, 66 µg (0.363 µmol, 0.1 eq, 10 µL from a stock solution in H$_2$O) CuOAc, 2.39 mg (10.875 µmol, 3.0 eq) zinc acetate and 718 µg (3.63 µmol, 1.0 eq, 10 µL from a stock solution in H$_2$O) sodium ascorbate and the mixture was stirred under light exclusion for 1 h at 23° C. until complete conversion was monitored by LCMS. The reaction mixture was diluted with 100 µL of MeOH, filtered through a Whatman® filter (45 µm) and directly purified by RP prep HPLC (Phenomenex Gemini C18 RP-column 00G-4435-PO-AX, 5 µm, 110 A, 250×21.20 mm, Flow: 9 mL/min, ACN:H$_2$O+0.1% TFA/10:90→95:5 in 45 min) yielding after lyophilization 4.6 mg (2.53 µmol, 70%) L-Orn-LHRH-16R-Aminoratjadone as a white, amorphous solid.

L-Orn-LHRH-16R-Aminoratjadone: LRMS (ESI-Quad) [m/z]: 909.6 [M+H]$^+$, HRMS (ESI-IT) [m/z]: 908.97884, calculated 908.98031 for C$_{23}$H$_{34}$N$_5$O$_6$ [M+H]$^+$, err [ppm] −1.617.

L-Orn-LHRH-Val-Cit-PABA-16R-Aminoratjadone—4-((S)-2-((S)-2-(((2-(1-((3S,6S,9S,12S,15S)-3-((1H-imidazol-4-yl)methyl)-6-((1H-indol-3-yl)methyl)-15-(((S)-1-(((S)-1-((S)-2-((2-amino-2-oxoethyl)carbamoyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13-pentaoxo-1-((S)-5-oxopyrrolidin-2-yl)-2,5,8,11,14-pentaazaoctadecan-18-yl)-1H-1,2,3-triazol-4-yl)ethoxy)carbonyl)amino)-3-methylbutanamido)-5-ureidopentanamido) benzyl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl) carbamate

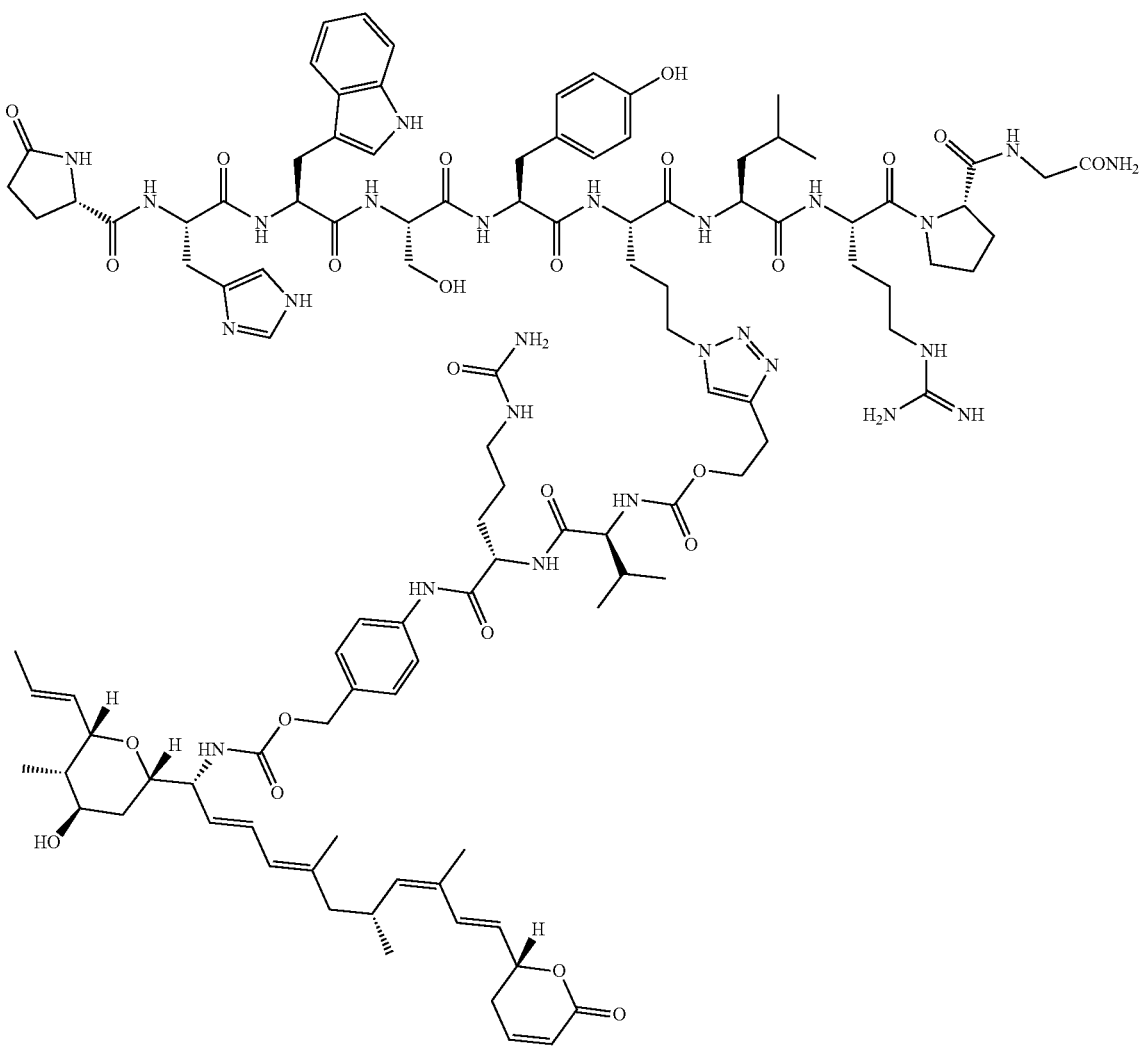

Chemical Formula: C$_{110}$H$_{152}$N$_{26}$O$_{24}$
Molecular Weight: 2222.58
L-Orn-LHRH-Val-Cit-PABA-16R-Aminoratjadone To a solution of 2.97 mg (1.99 μmol, 1.0 eq) L-N$_3$-Orn-LHRH and 2.0 mg (2.09 μmol, 1.05 eq) Homopropargyl-O(CO)HN-Val-Cit-PABO(CO)NH-Ratja 34 in a mixture of DMSO:pH=7 phosphate buffer:tBuOH/2:2:1 (80 μL) were added 0.443 μg (0.835 μmol, 0.25 eq, 10 μL from a stock solution in DMSO) TBTA, 36 μg (0.199 μmol, 0.1 eq, 10 μL from a stock solution in H$_2$O) CuOAc, 1.31 mg (5.97 μmol, 3.0 eq) zinc acetate and 394 μg (1.99 μmol, 1.0 eq, 10 μL from a stock solution in H$_2$O) sodium ascorbate and the mixture was stirred under light exclusion for 2 h at 23° C. until complete conversion was monitored by LCMS. The reaction mixture was diluted with 100 μL of MeOH, filtered through a Whatman® filter (45 μm) and directly purified by RP prep HPLC (Phenomenex Gemini C18 RP-column OOG-4435-PO-AX, 5 μm, 110 A, 250×21.20 mm, Flow: 9 mL/min, ACN:H$_2$O+0.1% TFA/10:90→95:5 in 45 min) yielding after lyophilization 2.2 mg (0.898 μmol, 45%) L-Orn-LHRH-Val-Cit-PABA-16R-Aminoratjadone as a white, amorphous solid.

L-Orn-LHRH-Val-Cit-PABA-16R-Aminoratjadone: LRMS (ESI-Quad) [m/z]: 1112.3 [M+2H]2+, HRMS (ESI-IT) [m/z]: 112.0826, calculated 1112.0827 for C$_{110}$H$_{154}$N$_{26}$O$_{24}$ [M+2H]2+, err [ppm] −0.089.

D-Orn-LHRH-Val-Cit-PABA-16R-Aminoratjadone—4-((S)-2-((S)-2-(((((5aR,6S,6aS)-1-((3S,6S,9S,12S,15R)-3-((1H-imidazol-4-yl)methyl)-6-((1H-indol-3-yl)methyl)-15-(((S)-1-(((S)-1—((S)-2-((2-amino-2-oxoethyl)carbamoyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13-pentaoxo-1—((S)-5-oxopyrrolidin-2-yl)-2,5,8,11,14-pentaazaoctadecan-18-yl)-1,4,5,5a,6,6a,7,8-octahydrocyclopropa[5,6]cycloocta[1,2-d][1,2,3]triazol-6-yl)methoxy)carbonyl)amino)-3-methylbutanamido)-5-ureidopentanamido)benzyl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

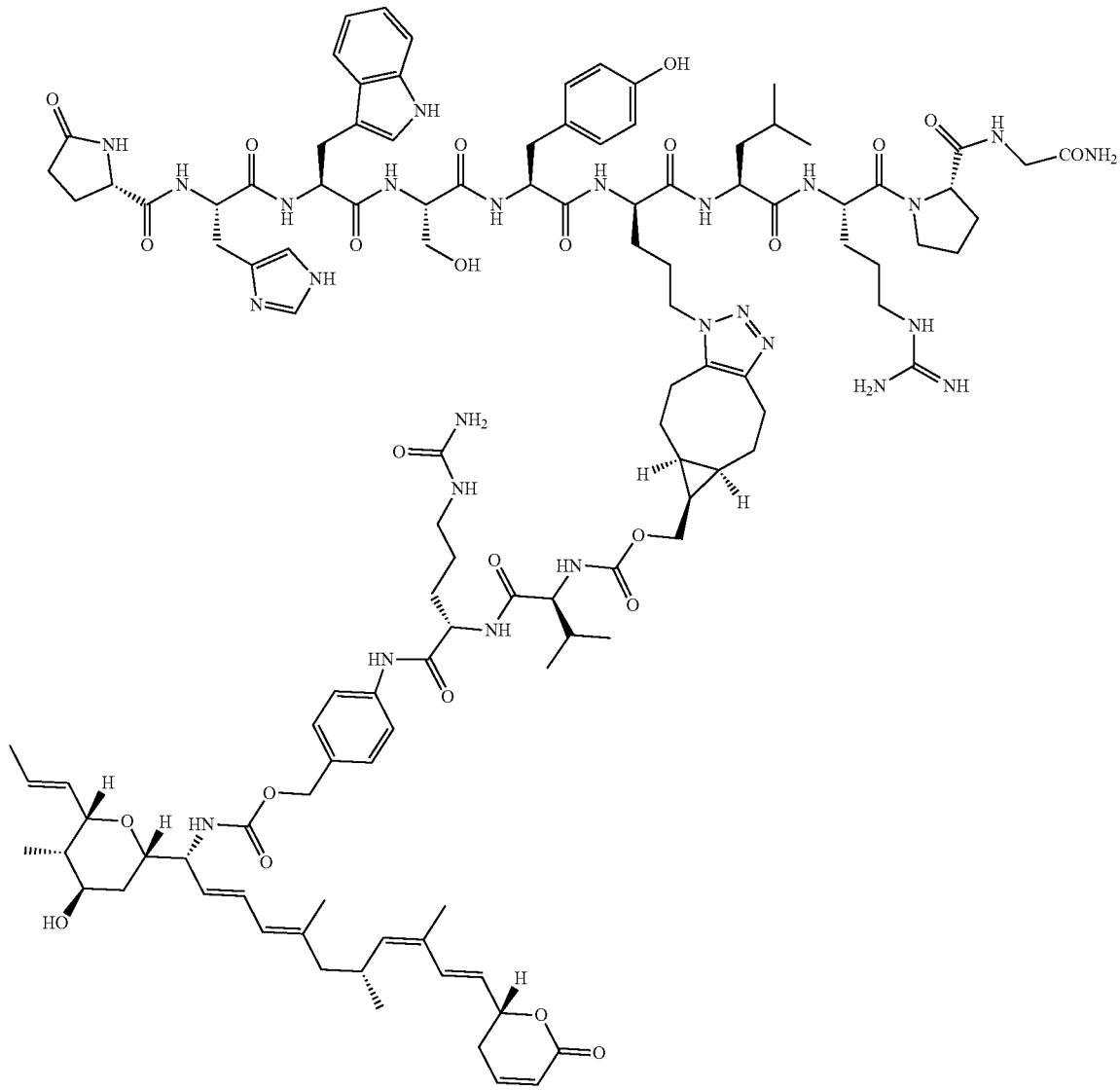

Chemical Formula: C$_{116}$H$_{160}$N$_{26}$O$_{24}$
Molecular Weight: 2302.71
D-Orn-LHRH-Val-Cit-PABA-16R-Aminoratjadone To a solution of 4 mg (2.678 µmol, 1.0 eq) D-N₃-Orn-LHRH in 54 µL dry DMSO was added a solution of 3.0 mg (2.946 µmol, 1.1 eq) BCN—O(CO)HN-Val-Cit-PABO(CO)NH-Ratja 31 in 54 µL dry DMSO and the mixture was stirred for 2 h at 23° C. under light exclusion until complete conversion was monitored by LCMS. The reaction mixture was diluted with 100 µL of MeOH, filtered through a Whatman® filter (45 µm) and directly purified by RP prep HPLC (Phenomenex Gemini C18 RP-column 00G-4435-PO-AX, 5 µm, 110 A, 250×21.20 mm, Flow: 9 mL/min, ACN:H₂O+0.1% TFA/10:90→95:5 in 45 min) yielding after lyophilization 3.7 mg (1.6 µmol, 60%) of D-Orn-LHRH-Val-Cit-PABA-16R-Aminoratjadone as white, amorphous solid.

D-Orn-LHRH-Val-Cit-PABA-16R-Aminoratjadone: HRMS (ESI-IT) [m/z]: 2302.2203, calculated 2302.2171 for $C_{116}H_{161}N_{26}O_{24}$ [M+H]⁺, err [ppm] 1.389.

D-Orn-Goserellin-Val-Cit-PABA-16R-Aminoratjadone—4-((S)-2-((S)-2-(((((5aR,6S,6aS)-1-((3S,6S,9S,12S,15R)-3-((1H-imidazol-4-yl)methyl)-6-((1H-indol-3-yl)methyl)-15-(((S)-1-(((S)-1-((S)-2-(2-carbamoylhydrazine-1-carbonyl)pyrrolidin-1-yl)-5-guanidino-1-oxopentan-2-yl)amino)-4-methyl-1-oxopentan-2-yl)carbamoyl)-12-(4-hydroxybenzyl)-9-(hydroxymethyl)-1,4,7,10,13-pentaoxo-1-((S)-5-oxopyrrolidin-2-yl)-2,5,8,11,14-pentaazaoctadecan-18-yl)-1,4,5,5a,6,6a,7,8-octahydrocyclopropa[5,6]cycloocta[1,2-d][1,2,3]triazol-6-yl)methoxy)carbonyl)amino)-3-methylbutanamido)-5-ureidopentanamido)benzyl ((1R,2E,4E,7R,8Z,10E)-1-((2S,4R,5S,6S)-4-hydroxy-5-methyl-6-((E)-prop-1-en-1-yl)tetrahydro-2H-pyran-2-yl)-5,7,9-trimethyl-11-((R)-6-oxo-3,6-dihydro-2H-pyran-2-yl)undeca-2,4,8,10-tetraen-1-yl)carbamate

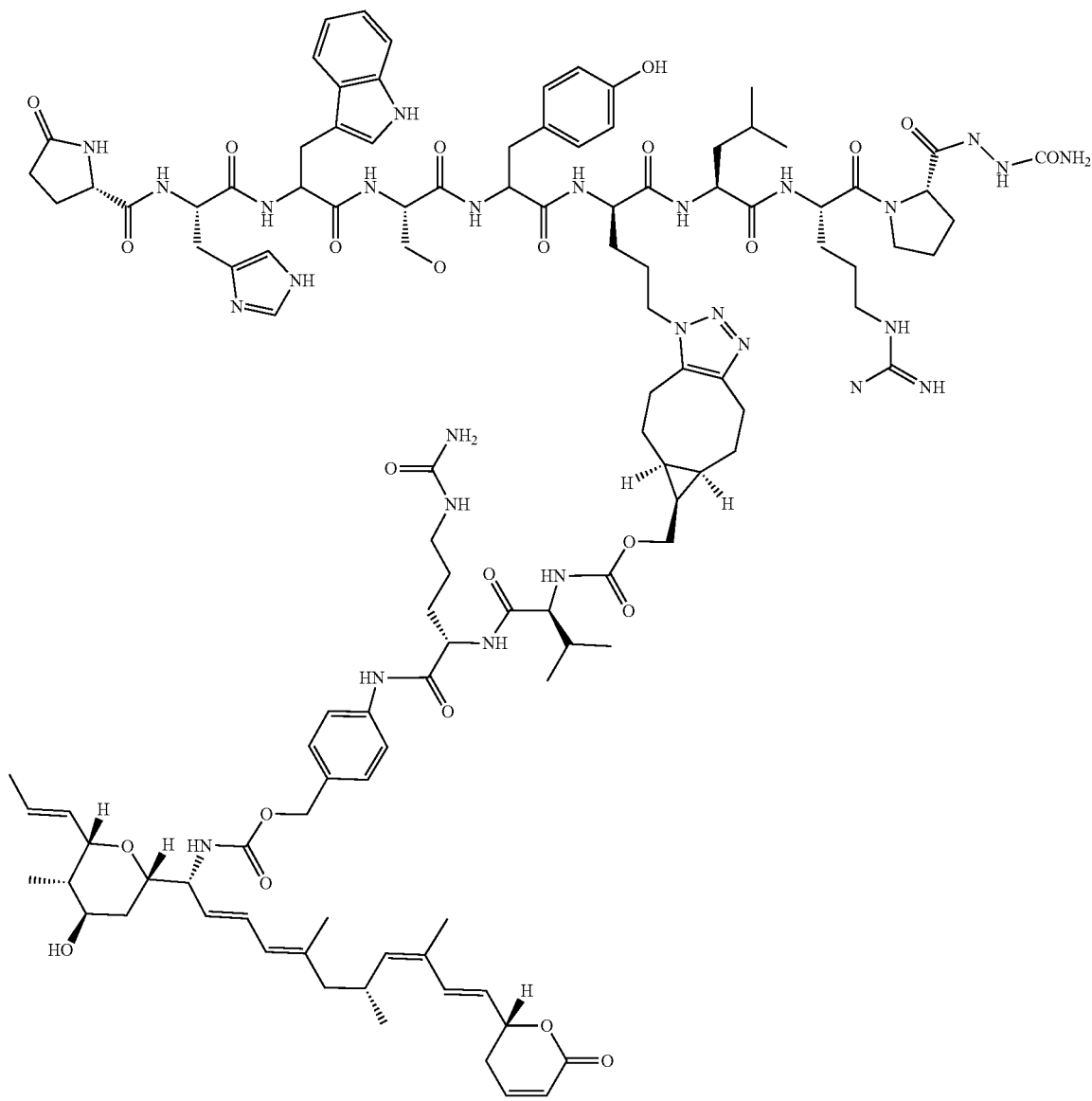

Chemical Formula: $C_{115}H_{159}N_{27}O_{24}$
Molecular Weight: 2303.70
D-Orn-Goserellin-Val-Cit-PABA-16R-Aminoratjadone To a solution of 4 mg (2.487 µmol, 1.0 eq) D-N$_3$-Orn-Goserellin in 25 µL dry DMSO was added a solution of 2.84 mg (2.735 µmol, 1.1 eq) BCN—O(CO)HN-Val-Cit-PABO(CO)NH-Ratja 31 in 25 µL dry DMSO and the mixture was stirred for 16 h at 23° C. under light exclusion until complete conversion was monitored by LCMS. The reaction mixture was diluted with 100 µL of MeOH, filtered through a Whatman® filter (45 µm) and directly purified by RP prep HPLC (Phenomenex Gemini C18 RP-column 00G-4435-PO-AX, 5 µm, 110A, 250×21.20 mm, Flow: 9 mL/min, ACN:H$_2$O+0.1% TFA/10:90-95:5 in 45 min) yielding after lyophilization 3.9 mg (1.69 µmol, 68%) of D-Orn-Goserellin-Val-Cit-PABA-16R-Aminoratjadone as white, amorphous solid.

D-Orn-Goserellin-Val-Cit-PABA-16R-Aminoratjadone: HRMS (ESI-IT) [m/z]: 768.4090, calculated 768.4090 for $C_{115}H_{162}N_{27}O_{24}$ $[M+3H]^{3+}$, err [ppm] 0.0.

Biological Evaluation of the Compounds

Cell Proliferation Assay

The corresponding cells were cultivated at 37° C. and 10% CO$_2$ in the medium given in table 1. 60 µL of serial dilutions of the test compound were given to 120 µL of suspended cells (50.000/mL) in wells of 96-well plates. After 5 days of incubation growth inhibition (IC$_{50}$) was determined using an MTT assay.[64]

TABLE 1

Medium conditions for different cell types.

| Cell type | Medium | Additives |
| --- | --- | --- |
| L-929 (DSMZ ACC 2) | DME medium (high glucose) (Gibco) | 10% fetal calf serum (Gibco) |
| SKOV-3 DSMZ ATCC HTB 77) | Mc Coys-Medium (Gibco) | 10% fetal calf serum (Gibco) |
| MCF-7 (DSMZ ACC 115) | RPMI-Medium (Gibco) | 10% fetal calf serum (Gibco), 1% MEM NEAA, 0,25% Human Insulin (Gibco) |
| A549 (DSMZ ACC 107) | DME medium (high glucose) (Gibco) | 10% fetal calf serum (Gibco) |
| KB 3.1 (DSMZ ACC 158) | DME medium (high glucose) (Gibco) | 10% fetal calf serum (Gibco) |

TABLE 2

Antiproliferative activities of novel Ratjadone derivatives.

| | IC$_{50}$ [nM] | | | | |
| --- | --- | --- | --- | --- | --- |
| Compound | KB-3.1 | A-549 | SK-OV-3 | MCF-7 | L-929 |
| Ratjadone A 1 | 0.46 | 0.15 | 0.24 | 0.11 | 0.68 |
| 16-Oxo-Ratjadone 8 | 2.57 | 1.76 | 0.24 | 0.22 | 12.56 |
| 19-Oxo-Ratjadone 9 | 0.36 | 0.10 | 0.16 | 0.48 | 24.30 |
| 16,19-Dioxo-Ratjadone 10 | 3.98 | 9.72 | 1.59 | 2.87 | |
| 16R-Amino-Ratjadone | 0.39 | 0.31 | 0.61 | 0.26 | |
| 16R-Amino-Ratjadone | 1.59 | 1.31 | 0.81 | 0.36 | |
| Compound 13 | 115.6 | | | | |
| Compound 14 | 165.4 | | | | |
| 16R-Amino-Ratjadone methyl carbamate 19 | 2.53 | | | | |
| 16S-Amino-Ratjadone methyl carbamate 20 | 8.18 | | | | |
| Compound 22 | 1.05 | 0.58 | 0.44 | 0.40 | |
| Compound 24 | 0.47 | 1.25 | 0.45 | 0.27 | |
| Compound 25 | 1.23 | 2.45 | 1.20 | 0.62 | |
| BCN—O(CO)HN-Val-Cit-PABO(CO)NH-Ratja 31 | 25.06 | 39.52 | 34.70 | 20.24 | |
| Homopropargyl-O(CO)HN-Val-Cit-PABO(CO)NH-Ratia | 9.20 | 25.07 | 13.58 | 12.53 | |
| 2-PySS(CH$_2$)$_2$(CO)NH-Ratja 35 | 8.80 | 30.6 | 24.6 | 26.0 | |
| HCC(CH$_2$)$_2$(CO)—NH—(CH$_2$)$_2$SS(CH$_2$)$_2$(CO)—NH-Ratia 39 | 1.86 | 0.86 | 1.09 | 0.17 | |
| 19-Amino-Ratjadone 40 | 6.67 | 4.39 | 1.40 | 2.10 | |
| N-Propargyl-19-amino-Ratjadone 42 | 1.23 | 1.12 | 2.63 | 1.31 | |

TABLE 3

Antiproliferative activities of Carrier molecules.

| | IC$_{50}$ [nM] | | | |
| --- | --- | --- | --- | --- |
| Compound | KB-3.1 | A-549 | SK-OV-3 | MCF-7 |
| FA-N$_3$-5 | >8.64 × 10$^4$ | >8.64 × 10$^4$ | | |
| FA-N$_3$-6 | >1.18 × 10$^5$ | >1.18 × 10$^5$ | | |
| FA-N$_3$-9 | >1.40 × 10$^5$ | >1.40 × 10$^5$ | | |
| LHRH | >4.05 × 10$^5$ | >4.05 × 10$^5$ | >4.05 × 10$^5$ | >4.05 × 10$^5$ |
| L-N$_3$-Orn-LHRH | >7.27 × 10$^5$ | >7.27 × 10$^5$ | >7.27 × 10$^5$ | >7.27 × 10$^5$ |
| D-N$_3$-Orn-LHRH | 1106.3 | 318.4 | 189.7 | 47.4 |
| D-N$_3$-Orn-Goserellin | >6.63 × 10$^5$ | >6.63 × 10$^5$ | >6.63 × 10$^5$ | >6.63 × 10$^5$ |

TABLE 4

Antiproliferative activity of novel Gonadoliberin-Ratjadone Conjugates

| Compound | IC$_{50}$ [nM] A-549 |
| --- | --- |
| L-Orn-LHRH-16R-Aminoratjadone | 1600 |
| L-Orn-LHRH-Val-Cit-PABA-16R-Aminoratjadone | 1200 |
| D-Orn-LHRH-Val-Cit-PABA-16R-Aminoratjadone | 23.0 |
| D-Orn-Goserellin-Val-Cit-PABA-16R-Aminoratjadone | 12.8 |

Cell Proliferation Assay Under Folate Free Conditions

KB 3.1 (DSMZ ACC 158) cells were cultivated at 37° C. and 10% C00$_2$ in RMPI-medium without folic acid (Gibco) with 10% fetal calf serum (Gibco). 120 µL of suspended cells (100.000/mL) were seeded in in wells of 96-well plates and after 24 h at 37° C. and 10% CO$_2$ the medium was removed, the cells were washed with PBS and RPMI-medium without folic acid (Gibco)+10% dialyzed fetal calf serum (Sigma) were added to the cells, before after additional 24 h at 37° C. and 10% C00$_2$ 60 µL of serial dilutions of the test compound were given to cells. After 1, 2 and 5 days of incubation growth inhibition (IC$_{50}$) was determined using an MTT assay.[64]

TABLE 5

Antiproliferative activity of novel Folate-Ratjadone Conjugates.

| Compound | IC$_{50}$ [nM] KB 3.1 |
|---|---|
| FA-1-Val-Cit-PABA-16R-Aminoratjadone | 168.9 |
| FA-2-Val-Cit-PABA-16R-Aminoratjadone | 336.3 |
| FA-3-Val-Cit-PABA-16R-Aminoratjadone | 209.8 |
| FA-4-(Val-Cit-PABA-16R-Aminoratjadone)$_2$ | 147.6 |
| FA-5-Val-Cit-PABA-16R-Aminoratjadone | 237.0 |
| FA-6-Val-Cit-PABA-16R-Aminoratjadone | 223.3 |
| FA-7-Val-Cit-PABA-16R-Aminoratjadone | 34.3 |
| FA-8-Val-Cit-PABA-16R-Aminoratjadone | 39.9 |
| FA-9-Val-Cit-PABA-16R-Aminoratjadone | 50.9 |
| FA-10-Val-Cit-PABA-16R-Aminoratjadone | 35.3 |
| FA-11-(Val-Cit-PABA-16R-Aminoratjadone)$_3$ | 45.0 |
| FA-3-16R-Aminoratjadone | 29.8 |
| FA-3-19-Aminoratjadone | 48.3 |
| FA-3b-16R-Aminoratjadone | 94.0 |
| FA-5-16R-Aminoratjadone | 50.3 |
| FA-6-16R-Aminoratjadone | 150.5 |
| FA-7-16R-Aminoratjadone | 190.1 |
| FA-8-16R-Aminoratjadone | 129.1 |
| FA-9-16R-Aminoratjadone | 47.6 |
| FA-10-16R-Aminoratjadone | 707.7 |
| FA-SS-16R-Aminoratjadone | 294.6 |

Monitoring Export Inhibitory Activity

Figure 4:
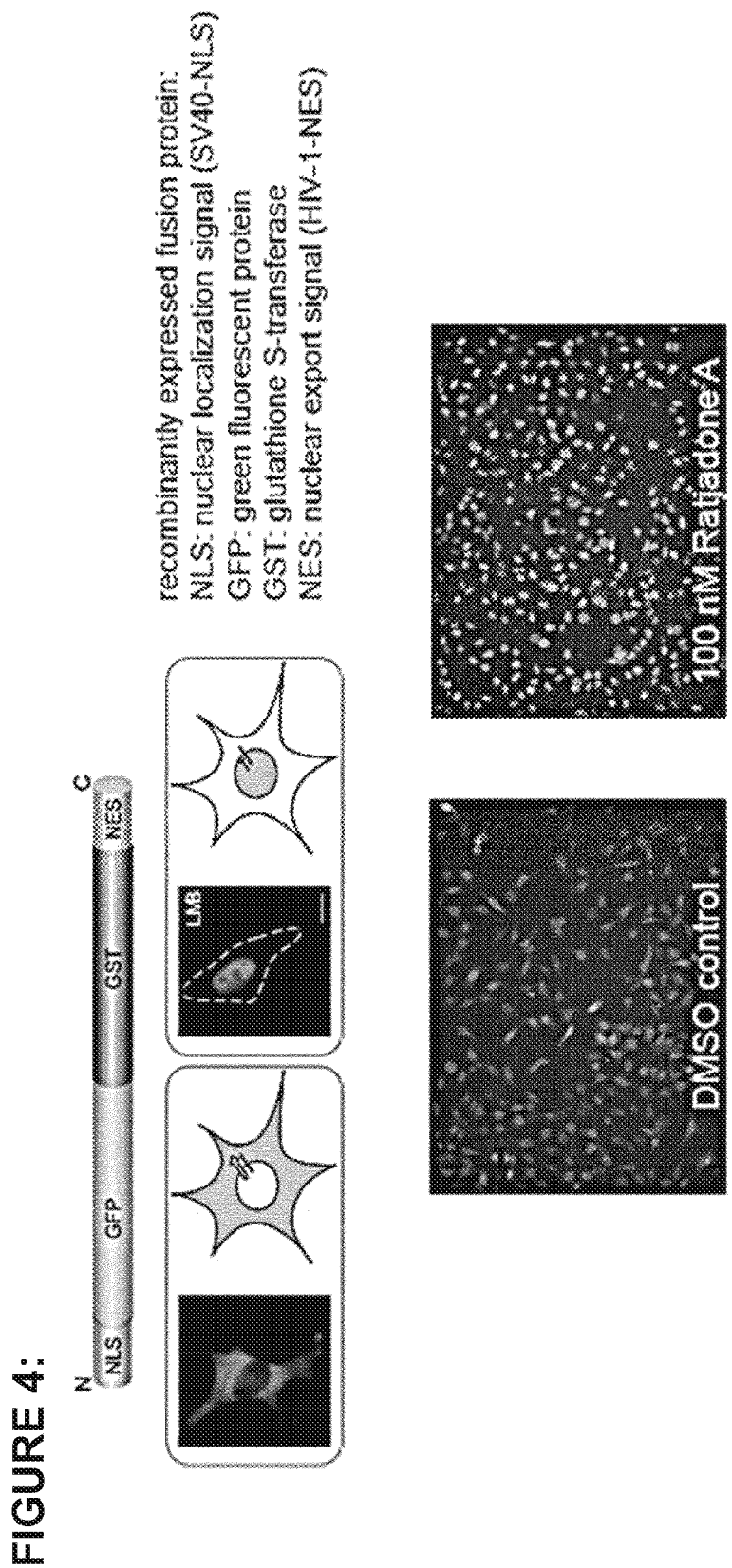
FIG. 4 and FIG. 5 show the results of the assay determining the export inhibitory ability.
Figure 5:
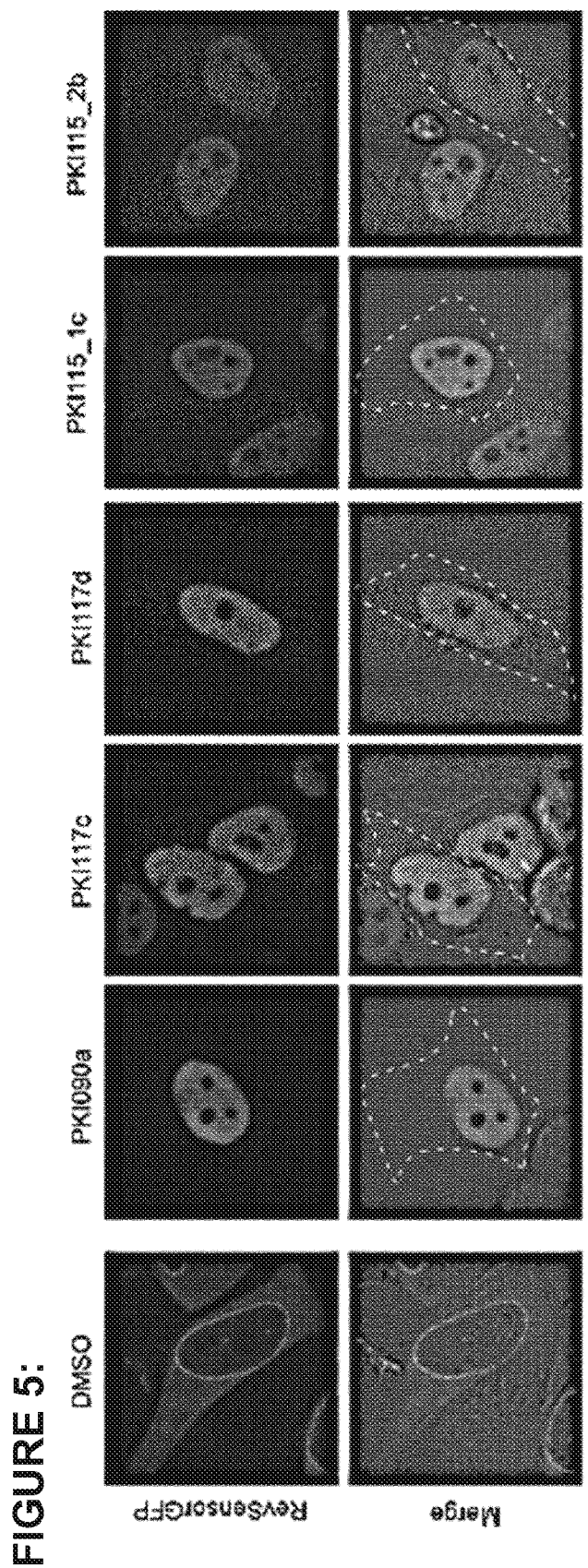

Export inhibitory ability of compounds was evaluated with the translocation biosensor system. This cellular assay depends on a recombinantly expressed fusion protein consisting of a nuclear localization signal (SV40-NLS), glutathione S-transferase (GST), green fluorescent protein (GFP) and a nuclear export signal (HIV1-RevNES). Due to the two transport signals (NLS/NES), the biosensor is permanently shuttling between nucleus and cytoplasm but resides prominently in the cytoplasm due to a comparatively stronger NES. Export inhibiting compound induce a nuclear accumulation of the GFP-signal[65,66] Cell lines were maintained as recommended by the American Type Culture Collection in DMEM containing 5% glutamine (Thermo Fisher Scientific, Waltham, USA) supplemented with 10% FBS (Thermo Fisher Scientific, Waltham, USA). For quantifying the nuclear export inhibitory effect, HeLa cells stably expressing a fluorescent translocation biosensor (HeLa$_{RevBio}$)[67] were seeded into black 96 well µclear plates (Greiner, Germany). They next day compounds were added covering an appropriate concentration range. After 1h of incubation, cells were fixed in 4% PFA for 10 min and permeabilized with 0.1% Triton X 100 in PBS for 5 min. After washing with PBS nuclei were labeled with Hoechst H33342 (30 min 10 µg/ml). The intracellular distribution of the biosensor-dependent GFP signal was quantitatively evaluated with the high content imaging system ImageXpress MicroXLS (Molecular Devices, Sunnyvale, USA). By using the translocation enhanced application module (Molecular Devices, Sunnyvale, USA) the GFP-intensity was quantified in the cytoplasm and nuclear region. As final readout the difference of Mean Inner and Mean Outer Intensity was calculated. IC$_{50}$s of nuclear export inhibition were calculated using Sigma Plot with four parameter logistics curve regression (Systat Software GmbH, Erkrath, Germany). For confocal microscopy cells were seeded at a density of 0.2*10$^5$ cells/well into 8 well microscopy chambers (Ibidi GmbH, Martinsried, Germany). The following day compounds were added at 125 nM final concentration. After 1h the cells were imaged on an ECLIPSE Ti (Nikon) equipped with UltraVIEW VoX spinning disc (Perkin Elmer, Waltham, US), ORCA-R$^2$ camera (Ham Hamamatsu Photonics, Japan) and Volocity software 6.1.1 (Perkin Elmer, Waltham, US) (see FIGS. 4 and 5).

TABLE 6

CRM1 Inhibitory activities of novel Ratjadone derivatives

| Compound | IC$_{50}$ [nM] CRM1 |
|---|---|
| Ratiadone A 1 | 1.2 |
| 16-Oxo-Ratiadone 8 | 52.5 |
| 19-Oxo-Ratiadone 9 | 13.3 |
| 16,19-Dioxo-Ratiadone 10 | 17.5 |
| 16R-Amino-Ratiadone 11 | 2.7 |
| 16R-Amino-Ratiadone 12 | 2.8 |
| 16R-Amino-Ratiadone methyl carbamate 19 | 12.5 |
| 16S-Amino-Ratiadone methyl carbamate 20 | 23.5 |
| 19-Amino-Ratiadone 40 | 70.0 |
| N-Propargyl-19-amino-Ratiadone 42 | 18.3 |
| Compound 22 | 23.2 |
| 2-PySS(CH$_2$)$_2$(CO)NH-Ratia 35 | 44.1 |
| Compound 24 | 46.1 |
| Compound 25 | 12.0 |
| BCN-O(CO)HN-Val-Cit-PABO(CO)NH-Ratia 31 | 346 |
| L-Orn-LHRH-16R-Aminoratjadone | 1060 |
| Biotin-PEG$_3$-16S-Aminoratjadone | 152 |

Analysis of Cell Labeling with Fluorescein-Labeled Conjugates

Figure 6:
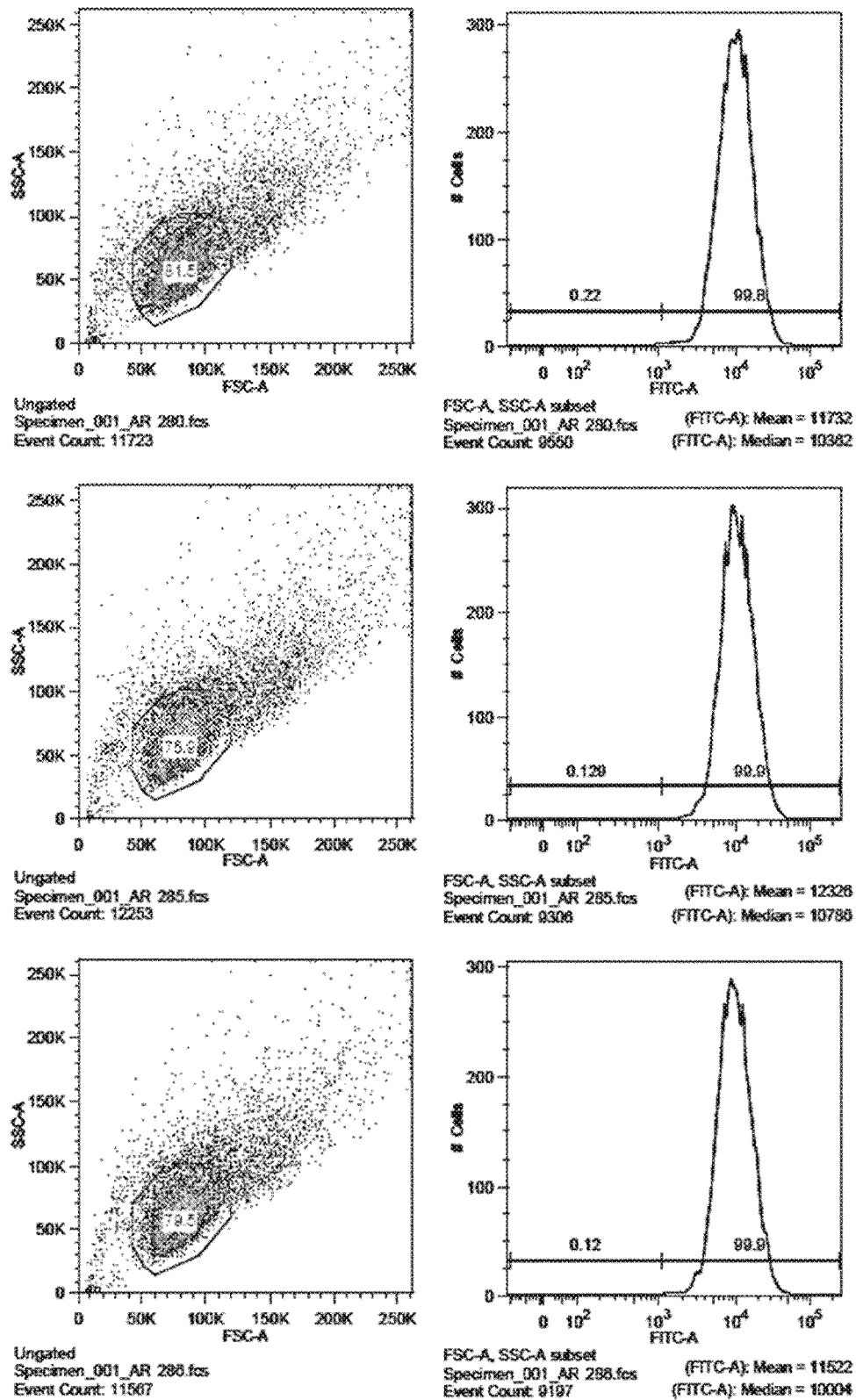
FIG. 6 shows the results of flow cytometry experiments: left columns: Flow cytometry of KB 3.1 cells labeled with different Folate-Fluorescein Conjugates (AR280=FA-1a-FITC, AR285=FA-10b-FITC, AR286=FA-3a-FITC, AR287=FA-6b-FITC, AR288=FA-3b-FITC, AR289=FA-4a-(FITC)2) shown in a dotplot, (SSC=side scatter, FSC=forward scatter), right columns: fluorescence intensity per cell number.
Figure 7:
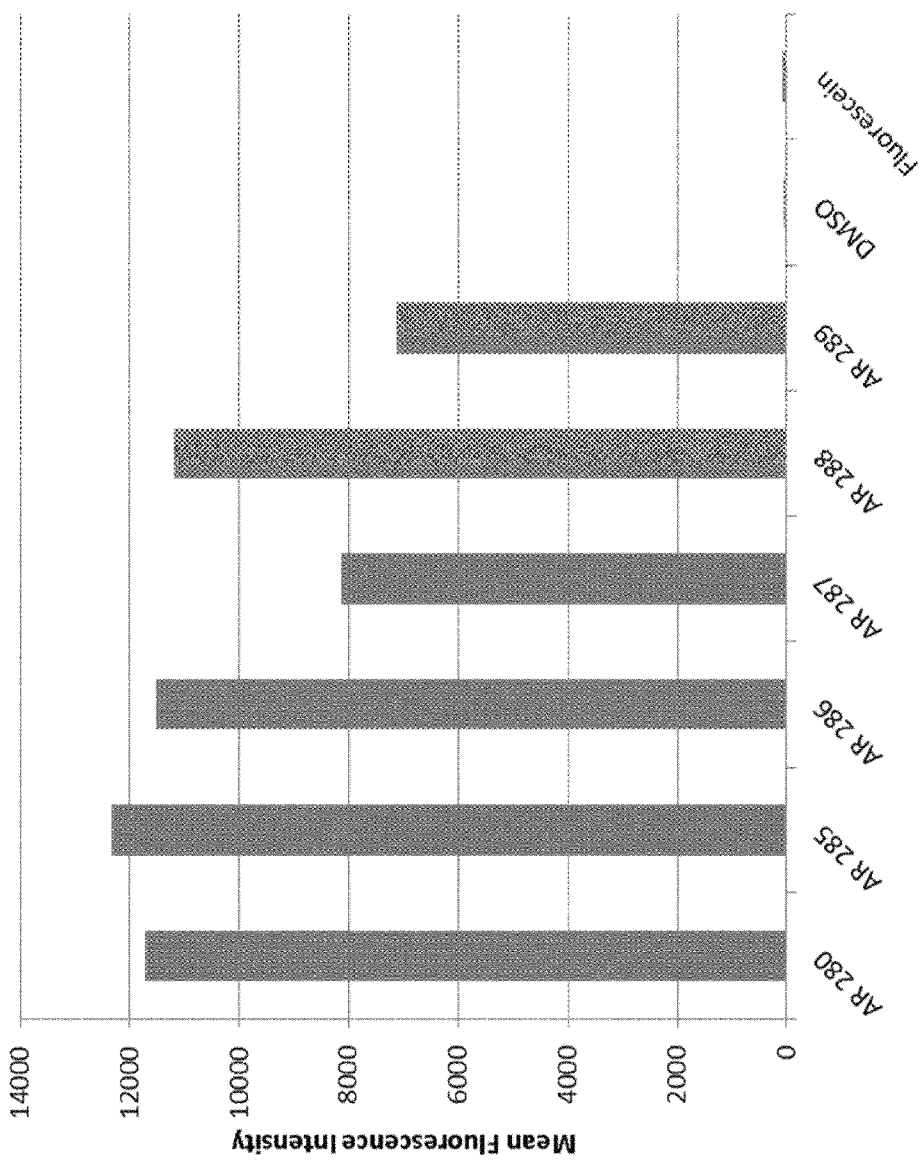
FIG. 7 shows a bar plot of fluorescence intensity per cell number (AR280=FA-1a-FITC, AR285=FA-10b-FITC, AR286=FA-3a-FITC, AR287=FA-6b-FITC, AR288=FA-3b-FITC, AR289=FA-4a-(FITC)₂).

All cell lines were maintained as recommended by the American Type Culture Collection in DMEM or RPMI containing 5% glutamine (Thermo Fisher Scientific, Waltham, USA) supplemented with 10% FBS (Thermo Fisher Scientific, Waltham, USA). For flow cytometric analysis cells were detached by trypsin and the density was adjusted to 2×10$^6$ cells/ml. The cell suspension was incubated with compounds at 1 µM final concentration for 30 min at 37° C., followed by two washing steps in PBS. For analysis of fluorescein intensity a LSRFortessa™ with FACSDiva™ software (BD Biosciences, Heidelberg, Germany) with the 488 nm laser in combination with 525/50 nm band pass filter was used. Data was evaluated using FlowJo software (FLOWJO LLC, Oregon, US) (see FIGS. 6 and 7).

Figure 8:
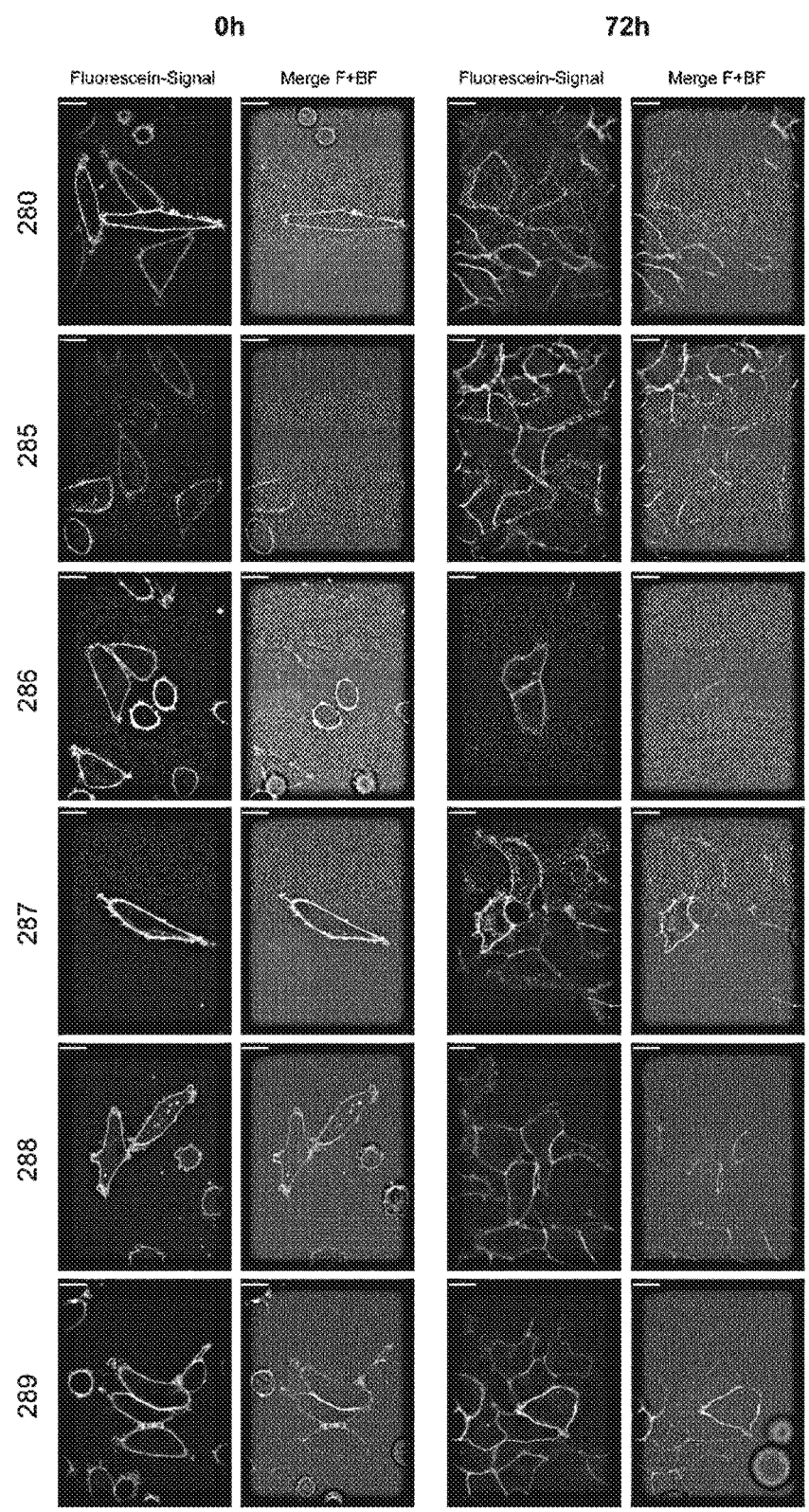
FIG. 8 shows the results of cell imaging of KB 3.1 cells treated with 1 µM of different Folate-Fluorescein Conjugates in folate-free RPMI medium with 10% folate-containing FCS at two different time points (AR280=FA-1a-FITC, AR285=FA-10b-FITC, AR286=FA-3a-FITC, AR287=FA-6b-FITC, AR288=FA-3b-FITC, AR289=FA-4a-(FITC)₂).
Figure 9:
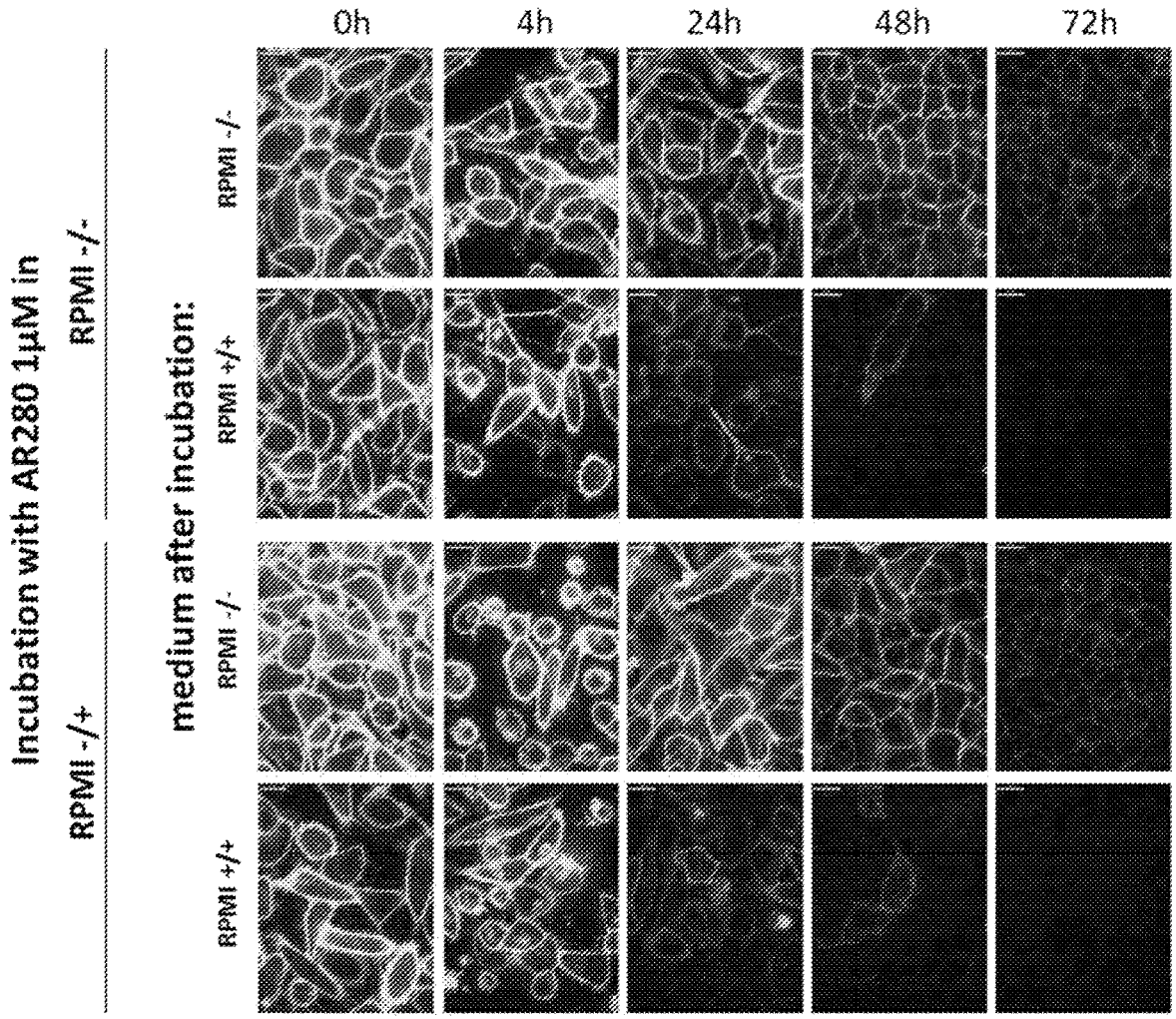
FIG. 9 shows the results of cell imaging of KB3.1 cells treated with 1 µM FA-1a-FITC (AR280) in different media at different time points. RPMI+/+=folate containing RPMI medium with 10% folate containing FCS, RPMI+/−=folate containing RPMI medium with 10% dialyzed folate-free FCS, RPMI −/+=folate-free RPMI medium with 10% folate containing FCS, RPMI −/−=folate-free RPMI medium with 10% dialyzed folate-free FCS.
Figure 10:
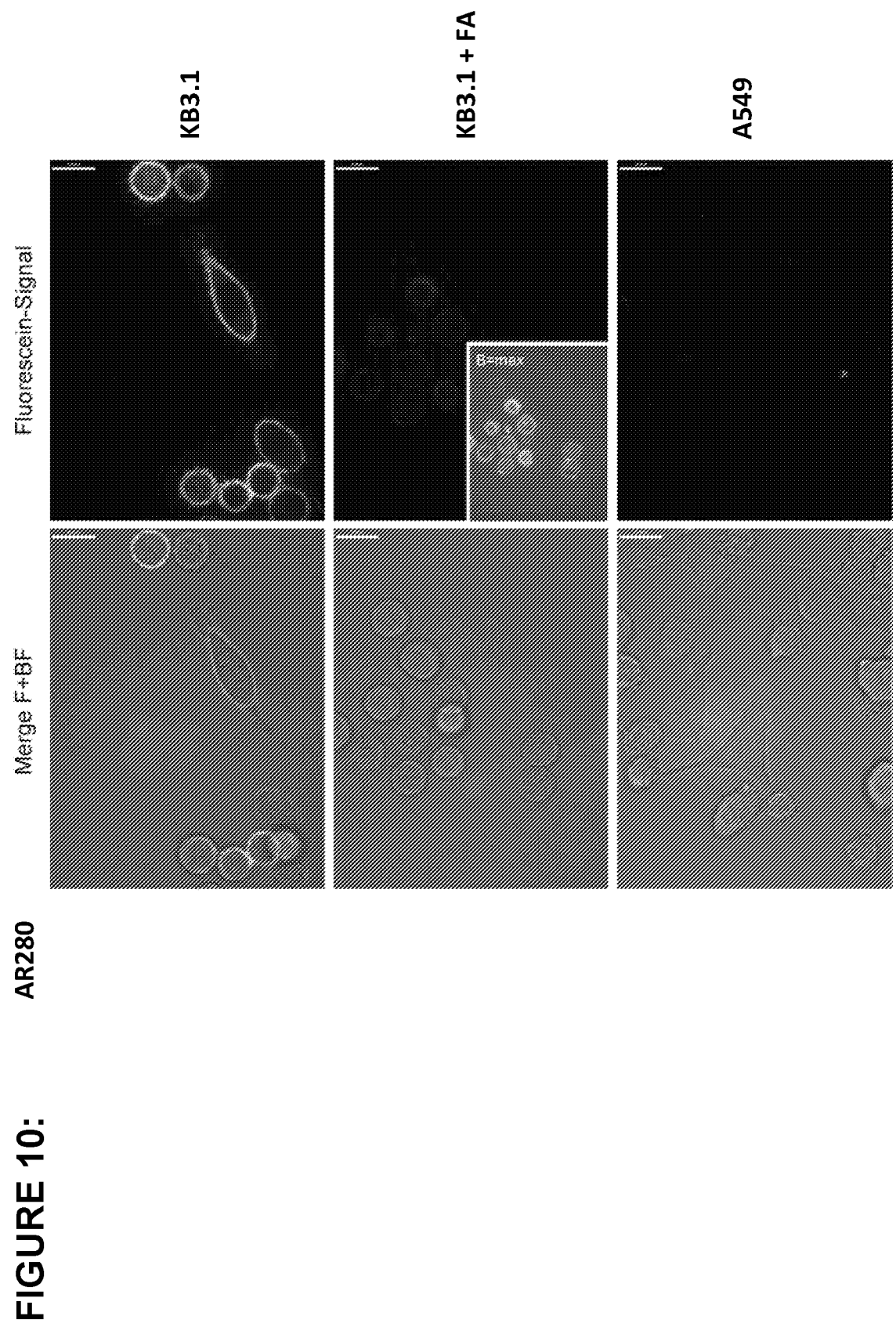
FIG. 10 shows the results of cell imaging of KB 3.1 cells in presence and absence of folates and A549 cells treated with 8.6 µM FA-1a-FITC (AR280) in in folate-free RPMI medium with 10% folate-containing FCS.

For confocal microscopy cells were seeded at a density of 0.2*10$^5$ cells/well into 8 well microscopy chambers (Ibidi GmbH, Martinsried, Germany). The following day compounds were added at 1 µM final concentration. Cells were imaged after indicated time points on an ECLIPSE Ti (Nikon) equipped with UltraVIEW VoX spinning disc (Perkin Elmer, Waltham, US), ORCA-R$^2$ camera (Ham Hamamatsu Photonics, Japan) and Volocity software 6.1.1 (Perkin Elmer, Waltham, US) (see FIGS. 8 to 10).

Pull-Down with Ratjadone-Biotin

Figure 11:
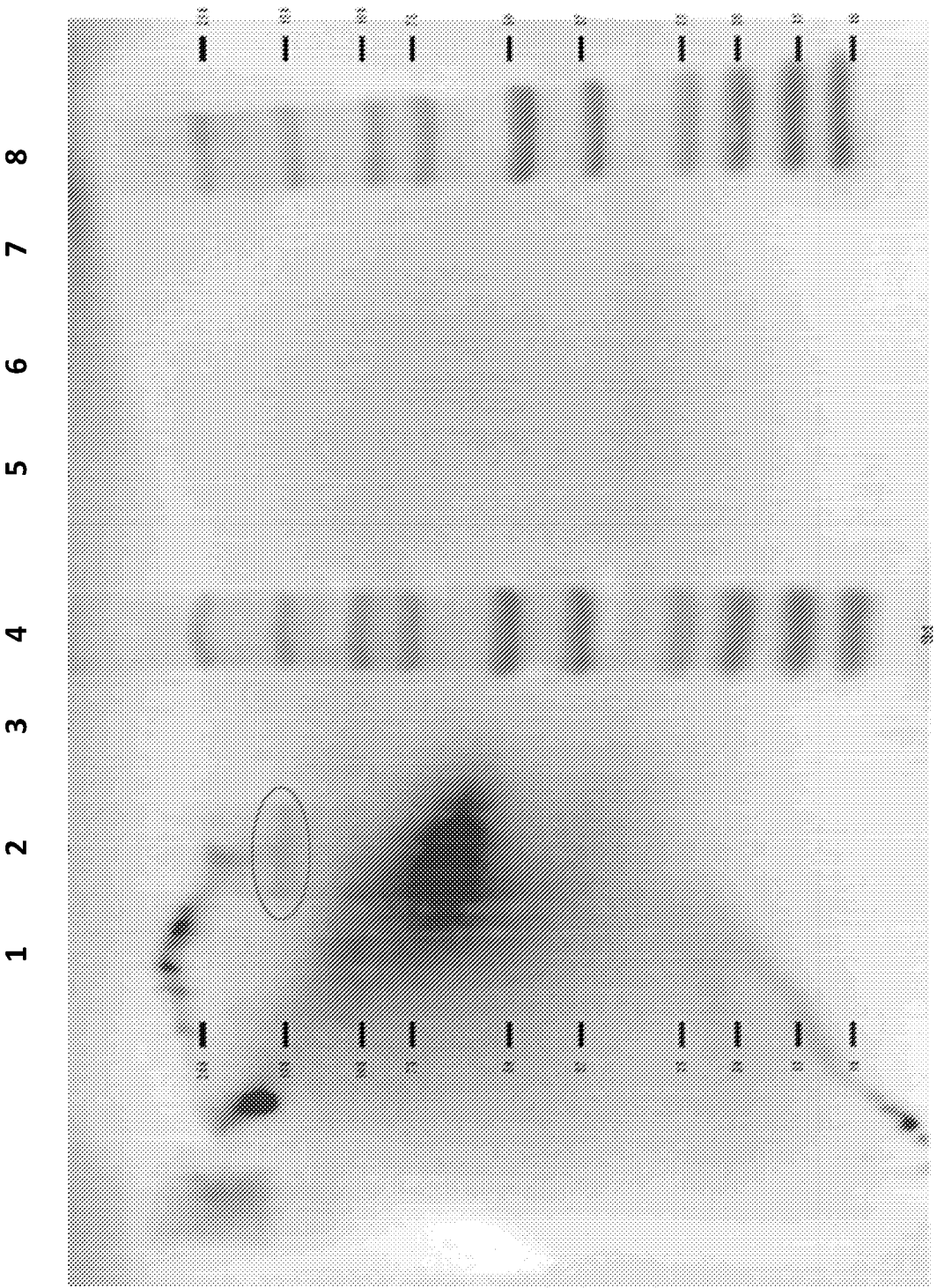
FIG. 11 shows the gel of a-streptavidin pulldown experiment: identification of protein band in the eluate of biotin-PEG₃-16S-aminoratjadone. Lane 1: Eluat+bio-Rat+Rat; lane 2: Eluat+bio-Rat; lane 3: Eluat+Rat; lane 4: Marker; lane 5: Lysat+bio-Rat +Rat; lane 6: Lysat+bio-Rat; lane 7: Lysat+Rat; lane 8: Marker.
Figure 12:
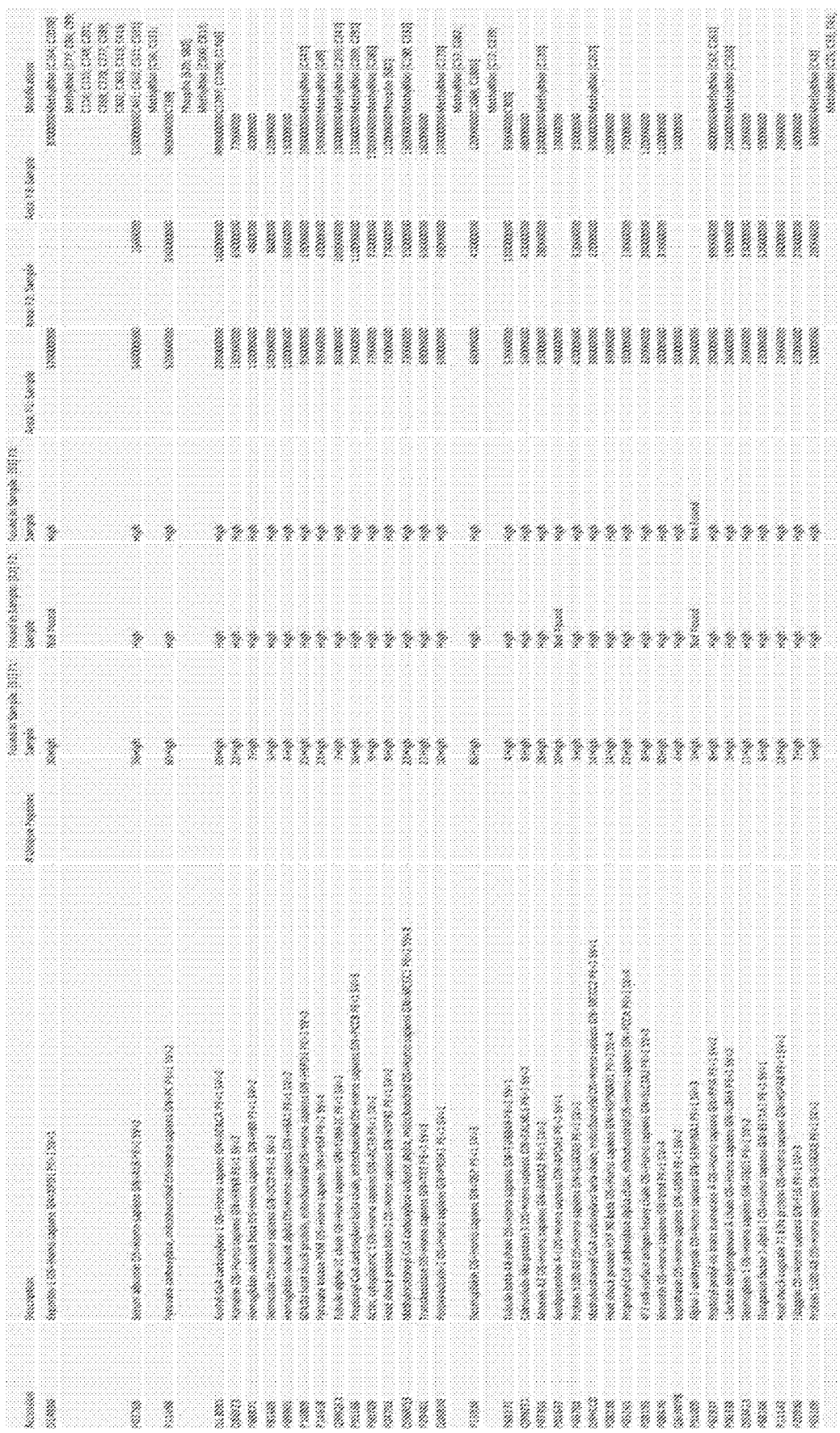
FIG. 12 shows the results of a LC-MS proteomic approach for target identification.
Figure 12:
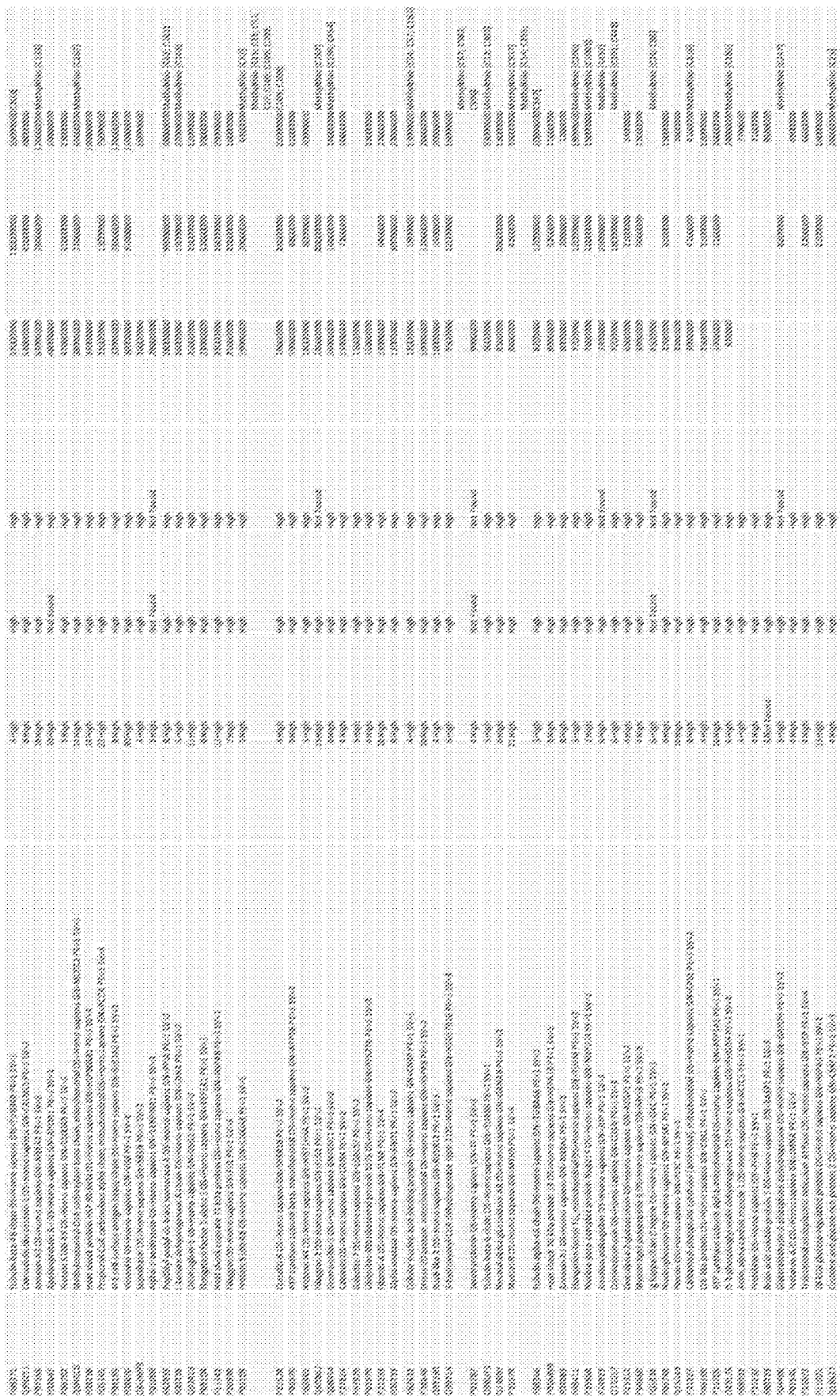

Binding of Ratjadone to the nuclear export receptor Crm1 was shown in a chemical pull down. HeLa cells were treated with ratjadone-biotin, ratjadone or both at 0.1 µg/ml final concentration for 5h. Cells were detached by scraping, washed twice in PBS and lysed in MPER-buffer (Thermo Fisher, Waltham, USA) supplemented with complete protease inhibitor (Roche, Mannheim, Germany). After 5 min incubation on ice the lysate was centrifuged (20 min, 13000 rpm, 4° C.) and the supernatant was incubated with streptavidin sepharose high performance (GE healthcare, Freiburg, Germany) overnight at 4° C. The next day beads were washed twice with PBS and resuspended in elution buffer (Roth) and heated to 95° C. for 10 min. 5% were tested on WesternBlot with a biotin-specific antibody (see FIG. 11). The eluate was given to the proteomics platform (J. Wissing) for identification of proteins. FIG. 12 shows the results of an LC-MS proteomic approach for target identification. In total, 79 proteins were identified, with CRM1 having the highest area.

Plasma Stability Assay

Figure 13:
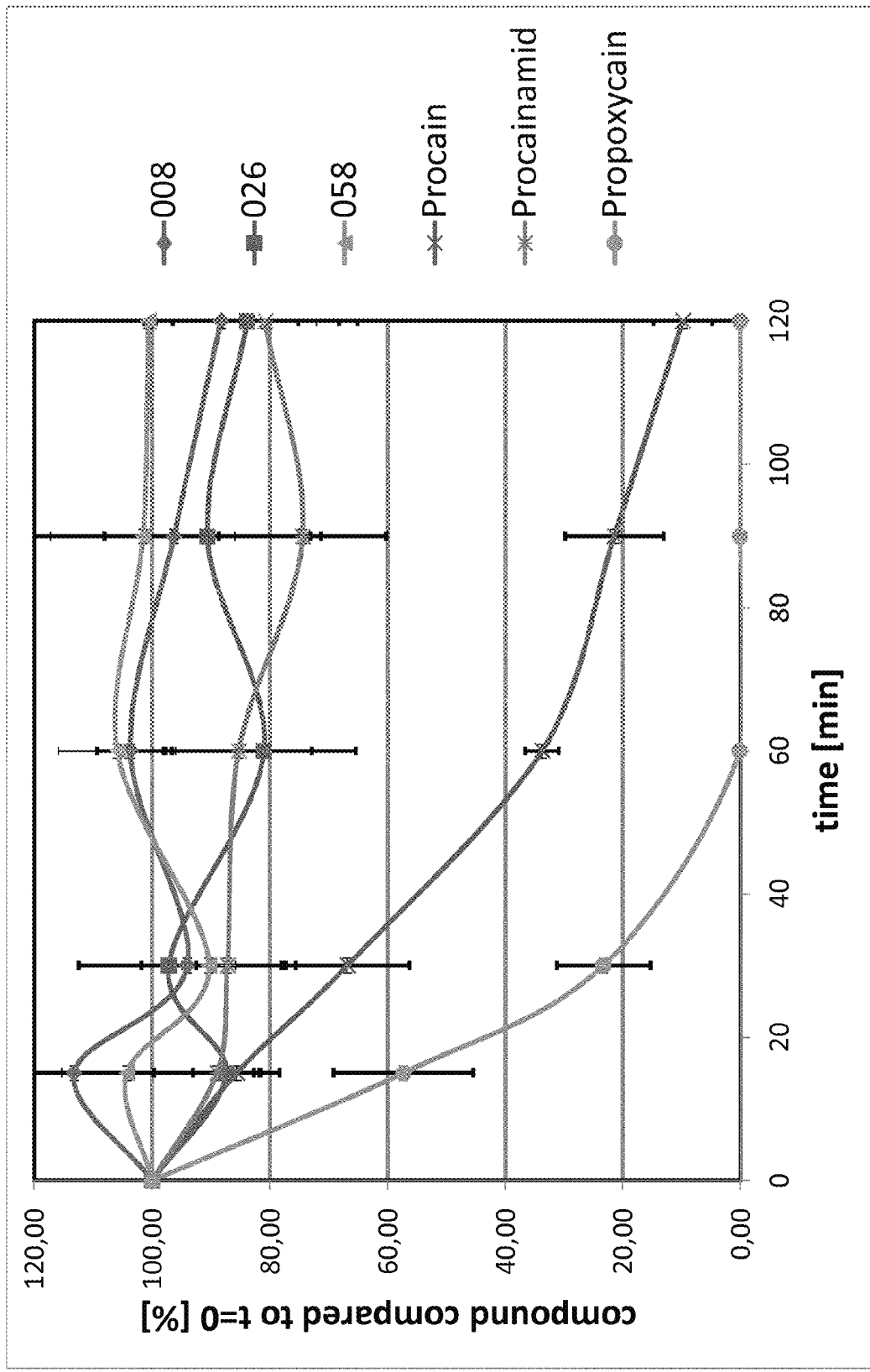
FIG. 13 and FIG. 14 show the results of the plasma stability assay.
Figure 14:
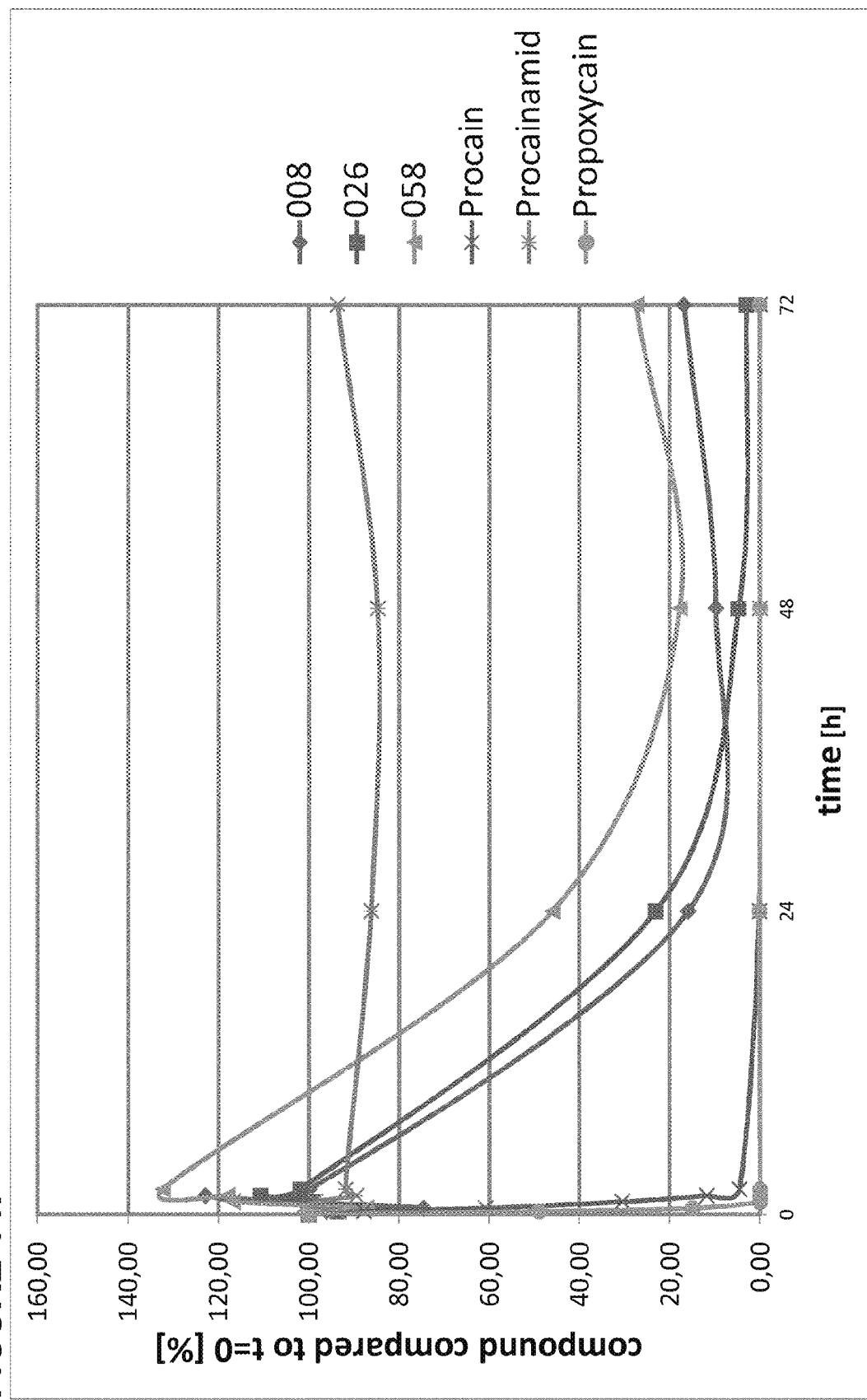

FA-7-Val-Cit-PABA-16R-Aminoratjadone (PK008a), FA-SS-16R-Aminoratjadone (PK026a) and FA-3b-16R-Aminoratjadone (PK058a) were dissolved in DMSO were added to mouse plasma (pH 7.4, 37° C.) to yield a final concentration of 25 µM. In addition, procaine, propoxycaine and procainamide (dissolved in DMSO) were added to mouse plasma (pH 7.4, 37° C.) to yield a final concentration of 250 µM. Procaine and propoxycaine served as positive controls as they are known to be unstable in mouse plasma. Procainamide served as negative control as it is known to be stable in mouse plasma. The samples were incubated for 0 min, 15 min, 30 min, 60 min, 90 min, 120 min, 24 h, 48 h and 72 h at 37° C. At each time point 7.5 µl of the respective sample was extracted with 22.5 µl methanol containing an internal standard for 5 min at 2000 rpm on a shaking incubator (Eppendorf). Then samples were centrifuged for 2 min at 13.000 rpm and the supernatants were transferred to HPLC-glass vials. All samples were analyzed via HPLC-MS using an Agilent 1290 HPLC system equipped with a diode array UV detector and coupled to an AB Sciex QTrap 6500 mass spectrometer. HPLC conditions were as follows: column: Agilent Zorbax Eclipse Plus C18, 50×2.1 mm, 1.8 µm; temperature: 30° C.; injection volume: 1 µl; flow rate 700 µl/min; solvent A: water+0.1% HCOOH; solvent B: acetonitrile+0.1% HCOOH; gradient: 99% A at 0 min, 99%-0% A from 0.1 min to 5.50 min, 0% A until 6.00 min, then 99% A post-run for 2 min; UV detection 190-400 nm. Mass spectrometric conditions were as follows: Scan type: Q1 MS; scan rate: 1000 Da/sec; scan start: 100 Da; scan stop: 1000 Da. All compounds were detected in positive scan mode. Peak areas of each compound and of the internal standard were analyzed using MultiQuant 3.0 software (AB Sciex). Peaks were quantified using the following m/z search windows (Table 7). Peak areas of the respective compound were normalized to the respective peak areas at time point 0 min: B/A*100 with A: peak area of the respective compound at time point 0 min, B: peak area of the respective internal standard at the respective time point. Every experiment was at least repeated three times independently (see FIGS. 13 and 14).

TABLE 7 m/z search windows for the compounds

| Compound | start-stop [m/z] |
| --- | --- |
| procaine | 236-237.5 |
| procainamide | 235.5-236.6 |
| propoxycaine | 294.4-295.8 |
| FA-7-Val-Cit-PABA-16R-Aminoratjadone | 874.0-875.0 |
| FA-SS-16R-Aminoratjadone | 543.0-545.0 |
| FA-3b-16R-Aminoratjadone | 797.5-799.5 |

REFERENCES

[1] G. Casi, D. Neri, *J. Control. Release* 2012, 161, 422-428.
[2] F. Dosio, B. Stella, S. Cerioni, D. Gastaldi, S. Arpicco, *Recent Pat. Anticancer. Drug Discov.* 2014, 9, 35-65.
[3] S. Panowski, S. Bhakta, H. Raab, P. Polakis, J. R. Junutula, *MAbs* 2014, 6, 34-45.
[4] R. V. J. Chari, M. L. Miller, W. C. Widdison, *Angew. Chem. Int. Ed.* 2014, 53, 3796-3827.
[5] A. Thomas, B. A. Teicher, R. Hassan, *Lancet Oncol.* 2016, 17, e254-e262.
[6] Y. Wang, A. G. Cheetham, G. Angacian, H. Su, L. Xie, H. Cui, *Adv. Drug Deliv. Rev.* 2016, DOI 10.1016/j.addr.2016.06.015.
[7] B. Narasimhan, J. T. Goodman, J. E. Vela Ramirez, *Annu. Rev. Biomed. Eng* 2016, 18, 25-49.
[8] I. Vergote, C. P. Leamon, *Ther. Adv. Med. Oncol.* 2015, 7, 206-218.
[9] P. Polakis, *Pharmacol. Rev.* 2016, 68, 3-19.
[10] H. Bouchard, C. Viskov, C. Garcia-echeverria, *Bioorg. Med. Chem. Lett.* 2014, 24, 5357-5363.
[11] N. L. Henry, D. F. Hayes, *Mol. Oncol.* 2012, 6, 140-146.
[12] J. A. Ludwig, J. N. Weinstein, *Nat. Rev. Cancer* 2005, 5, 845-856.
[13] M. Kleppe, R. L. Levine, *Nat. Med.* 2014, 20, 342-4.
[14] H. Shen, D. Hu, J. Du, X. Wang, Y. Liu, Y. Wang, J. min Wei, D. Ma, P. Wang, L. Li, *Eur. J. Pharmacol.* 2008, 601, 23-29.
[15] R. Jaskula-Sztul, Y. Xiao, A. Javadi, J. Eide, W. Xu, M. Kunnimalaiyaan, H. Chen, S. Gong, *Cancer Res.* 2012, 4, 7185-7193.
[16] X. Qi, Y. Chen, N. Ma, Z. Zhang, J. Xing, X. Zhu, Z. Li, Z. Wu, *J. Drug Target.* 2014, 22, 428-438.
[17] M. Lelle, S. Kaloyanova, C. Freidel, M. Theodoropoulou, M. Musheev, C. Niehrs, G. Stalla, K. Peneva, *Mol. Pharm.* 2015, 12, 4290-4300.
[18] O. Argyros, T. Karampelas, X. Asvos, A. Varela, N. Sayyad, A. Papakyriakou, C. H. Davos, A. G. Tzakos, D. Fokas, C. Tamvakopoulos, *Cancer Res.* 2016, 76, 1181-1192.
[19] J. Engel, G. Emons, J. Pinski, A. V Schally, *Expert Opin. Investig. Drugs* 2012, 21, 891-9.
[20] D. Wen, D. Chitkara, H. Wu, M. Danquah, R. Patil, D. D. Miller, R. I. Mahato, *Pharm. Res.* 2014, 31, 2784-2795.
[21] C. Yates, S. Sharp, J. Jones, D. Topps, M. Coleman, R. Aneja, J. Jaynes, T. Turner, *Biochem. Pharmacol.* 2011, 81, 104-110.
[22] H. M. Vishwasrao, A. M. Master, Y. G. Seo, X. M. Liu, N. Pothayee, Z. Zhou, D. Yuan, M. D. Boska, T. K. Bronich, R. M. Davis, et al., *Chem. Mater.* 2016, 28, 3024-3040.
[23] A. M. Hohlbaum, A. Skerra, *Expert Rev. Clin. Immunol.* 2007, 3, 491-501.
[24] M. Gebauer, A. Skerra, *Anticalins: Small Engineered Binding Proteins Based on the Lipocalin Scaffold, Elsevier Inc.*, 2012.
[25] A. Skerra, *Rev. Mol. Biotechnol.* 2001, 74, 257-275.
[26] I. R. Vlahov, C. P. Leamon, *Bioconjug. Chem.* 2012, 23, 1357-1369.
[27] J. A. Reddy, R. Dorton, E. Westrick, A. Dawson, T. Smith, L. C. Xu, M. Vetzel, P. Kleindl, I. R. Vlahov, C. P. Leamon, *Cancer Res.* 2007, 67, 4434-4442.
[28] C. P. Leamon, P. S. Low, *Drug Discov. Today* 2001, 6, 44-51.
[29] P. S. Low, S. A. Kularatne, *Curr. Opin. Chem. Biol.* 2009, 13, 256-262.
[30] F. Michor, K. Polyak, *Cancer Prev. Res.* 2010, 3, 1361-1364.
[31] M. R. Junttila, F. J. de Sauvage, *Nature* 2013, 501, 346-354.
[32] J. P. B. O'Connor, *Semin. Cell Dev. Biol.* 2016, 1-10.

[33] A. Persidis, *Nat. Biotechnol.* 1999, 17, 94-95.
[34] G. Housman, S. Byler, S. Heerboth, K. Lapinska, M. Longacre, N. Snyder, S. Sarkar, *Cancers (Basel).* 2014, 6, 1769-1792.
[35] D. Schummer, K. Gerth, H. Reichenbach, G. Hofle, *Liebigs Ann.* 1995, 685-688.
[36] K. Gerth, D. Schummer, G. Hofle, H. Irschik, H. Reichenbach, *J. Antibiot. (Tokyo).* 1995, 48, 973-976.
[37] M. Köster, S. Lykke-Andersen, Y. A. Elnakady, K. Gerth, P. Washausen, G. Höfle, F. Sasse, J. Kjems, H. Hauser, *Exp. Cell Res.* 2003, 286, 321-331.
[38] E. Fleta-Soriano, J. P. Martinez, B. Hinkelmann, K. Gerth, P. Washausen, J. Diez, R. Frank, F. Sasse, A. Meyerhans, *Microb. Cell Fact.* 2014, 13, 17.
[39] T. Meissner, E. Krause, U. Vinkemeier, *FEBS Lett.* 2004, 576, 27-30.
[40] G. Gravina, W. Senapedis, D. McCauley, E. Baloglu, S. Shacham, C. Festuccia, *J. Hematol. Oncol.* 2014, 7, 85.
[41] J. G. Turner, J. Dawson, D. M. Sullivan, *Biochem. Pharmacol.* 2012, 83, 1021-1032.
[42] J. G. Turner, J. Dawson, C. L. Cubitt, R. Baz, D. M. Sullivan, *Semin. Cancer Biol.* 2014, 27, 62-73.
[43] M. El-Tanani, E. H. Dakir, B. Raynor, R. Morgan, *Cancers (Basel).* 2016, 8, 1-11.
[44] M. Kalesse, M. Christmann, U. Bhatt, M. Quitschalle, E. Claus, A. Saeed, A. Burzlaff, C. Kasper, L. O. Haustedt, E. Hofer, et al., *ChemBioChem* 2001, 2, 709-714.
[45] U. Bhatt, M. Christmann, M. Quitschalle, E. Claus, M. Kalesse, *J. Org. Chem.* 2001, 66, 1885-1893.
[46] A. Burzlaff, C. Kasper, T. Scheper, M. Kalesse, U. Bhatt, K. Chary, C. Eckhard, M. Christmann, M. Quitschalle, W. Beil, *Ratjadone Derivatives for Inhibiting Cell Growth,* 2004, US2004/0092581 A1.
[47] A. Burzlaff, C. Kasper, T. Scheper, M. Kalesse, U. Bhatt, K. Chary, C. Eckhard, M. Christmann, M. Quitschalle, W. Beil, *Ratjadone Derivatives for Inhibiting Cell Growth,* 2002, EP2002/1383764 A0.
[48] A. Burzlaff, C. Kasper, T. Scheper, M. Kalesse, U. Bhatt, K. Chary, C. Eckhard, M. Christmann, M. Quitschalle, W. Beil, *Ratjadone Derivatives for Inhibiting Cell Growth,* 2002, WO2002/064587 A1.
[49] H. Bouchard, A. Commercon, R. V. J. Chari, *Leptomycin Derivatives,* 2003, US2010/7816543 B2.
[50] H. Bouchard, A. Commercon, R. V. J. Chari, *Leptomycin Derivatives,* 2007, WO2007/144709 A3.
[51] H. Bouchard, A. Commercon, R. V. J. Chari, *Leptomycin Derivatives,* 2011, US2011/002947 A1.
[52] H. Bouchard, A. Commercon, R. V. J. Chari, *Leptomycin Derivatives,* 2010, US2010/7816543 B2.
[53] H. Bouchard, A. Commercon, R. V. J. Chari, *Leptomycin Derivatives,* 2007, EP2007/2032172 B1.
[54] S. D. Dong, D. V. Santi, D. C. Myles, B. Hearn, *Leptomycin-Type Compounds,* 2005, WO2005/117894 A1.
[55] D. V. Santi, B. Hearn, *Conjugates with Reduced Adverse Systemic Affects,* 2005, US2005/0287155 A1.
[56] H. Reichenbach, G. Höfle, K. Gerth, P. Washausen, *Antibiotic and Antitumoral Compound, Process for the Manufacture Thereof,* 1998, WO1998011084.
[57] T. R. Hoye, M. K. Renner, *J. Org. Chem.* 1996, 7, 8489-8495.
[58] J. A. Dale, D. L. Dull, H. Mosher, *J. Org. Chem.* 1969, 34, 2543-2549.
[59] D. A. Allen, A. E. Tomaso, O. P. Priest, W. S. Colleges, *J. Chem. Educ.* 2008, 85, 698-700.
[60] M. Galibert, P. Dumy, D. Boturyn, *Angew. Chem. Int. Ed.* 2009, 48, 2576-2579.
[61] F. L. Van Delft, R. Van Geel, M. antonia Wijdeven, *Modified Antibody, Antibody-Conjugate and Process for the Preparation Thereof,* 2014, WO2014/065661 A1.
[62] O. T. Okusanya, E. M. Dejesus, J. X. Jiang, R. P. Judy, O. G. Venegas, C. G. Deshpande, D. F. Heitjan, S. Nie, P. S. Low, S. Singhal, *J. Thorac. Cardiovasc. Surg.* 2015, 150, 28-35.
[63] G. M. van Dam, G. Themelis, L. M. Crane, N. J. Harlaar, R. G. Pleijhuis, W. Kelder, A. Sarantopoulos, J. S. de Jong, H. J. Arts, A. G. van der Zee, et al., *Nat. Med.* 2011, 17, 1315-1319.
[64] T. Mosmann, *J. Immunol. Methods* 1983, 65, 55-63.
[65] S. K. Knauer, S. Moodt, T. Berg, U. Liebel, R. Pepperkok, R. H. Stauber, *Traffic* 2005, 6, 594-606.
[66] S. K. Knauer, R. H. Stauber, *Anal. Chem.* 2005, 77, 4815-4820.
[67] V. Fetz, S. K. Knauer, C. Bier, J. P. von Kries, R. H. Stauber, *Sensors* 2009, 9, 5423-5445.
[68] M. Frigerio, M. Santagostino, S. Sputore, *J. Org. Chem.* 1999, 64, 4537-4538.
[69] J. Dommerholt, S. Schmidt, R. Temming, L. J. A. Hendriks, F. P. J. T. Rutjes, J. C. M. Van Hest, D. J. Lefeber, P. Friedl, F. L. Van Delft, *Angew. Chem. Int. Ed.* 2010, 49, 9422-9425.
[70] C. B. Vu, R. J. Bridges, C. Pena-Rasgado, A. E. Lacerda, C. Bordwell, A. Sewell, A. J. Nichols, S. Chandran, P. Lonkar, D. Picarella, et al., *J. Med. Chem.* 2017, 60, 458-473.
[71] S. H. L. Verhelst, M. D. Witte, S. Arastu-Kapur, M. Fonovic, M. Bogyo, *ChemBioChem* 2006, 7, 943-950.
[72] E. Ruijter, *Design And Synthesis Of Ratjadone Analogues,* PhD Thesis; Vrije Universiteit Amsterdam, 2005.

The invention claimed is:

1. A compound according to Formula I

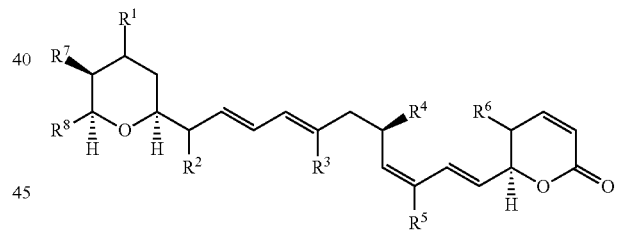

wherein:
one of $R^1$ and $R^2$ is $NHR^9$ and one is selected from H and OH;
$R^3$, $R^4$ and $R^5$ are independently of one another selected from the group that consists of H, $CH_3$ and $C_2H_5$;
$R^6$ is $CH_3$ or $C_2H_5$;
$R^7$ and $O^R$ are independently of one another selected from the group that consists of H, $CH_3$, $C_2H_5$, n-$C_3H_7$,

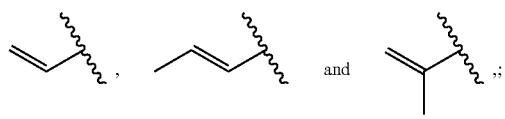

and
$R^9$ is H.

2. A compound according to Formula I, wherein:
$R^1$ to $R^8$ are as defined in claim 1; and $R^9$ is L-RM*, wherein L is a linker, particularly a self-immolative linker, RM* is selected from RM and RM', wherein RM is a reactive moiety being able to form a covalent bond with a targeting moiety, particularly a target-binding antibody or functional fragment thereof, and wherein RM' is a moiety RM carrying a protecting group.

3. A compound according to Formula I, wherein:
$R^1$ to $R^8$ are as defined in claim 1; and
$R^9$ is L-TM, wherein L is a linker, particularly a self-immolative linker, and TM is a targeting moiety.

4. The compound according to claim 1, wherein $R^1$ is OH and $R^2$ is $NHR^9$.

5. The compound of claim 4, wherein $R^2$ is 16R-$NHR^9$.

6. The compound of claim 4, wherein $R^2$ is 16S-$NHR^9$.

7. The compound according to claim 1, wherein $R^1$ is $NHR^9$ and $R^2$ is OH.

8. A method of synthesizing a compound according to claim 2, comprising the step of reacting a compound according to claim 1 via the amino group $R^1$ or $R^2$ with a compound X-L-RM*, wherein
X is a group that is (i) able to react with an amine, or (ii) can be replaced by an amine; and
L' is a linker;
wherein the reaction of said amino group with the moiety X-L' results in the formation of the moiety NH-L-RM*.

9. The method according to claim 8, wherein RM* is RM', further comprising the deprotection of the moiety RM' to result in RM.

10. A method of synthesizing a compound according to claim 3, comprising the step of reacting a compound according to claim 2 with a targeting moiety.

11. A pharmaceutical composition comprising the compound according to claim 3.

12. The pharmaceutical composition according to claim 11 for use in the treatment of cancer.

13. A method for the treatment of cancer comprising the step of administering the compound according to claim 3.

14. A pharmaceutical composition comprising a compound synthesized according to the method according to claim 10.

15. A method for the treatment of cancer comprising the step of administering the pharmaceutical composition according to claim 11 to a patient in need of such treatment.

16. A method for the treatment of cancer comprising the step of administering the pharmaceutical composition according to claim 12 to a patient in need of such treatment.

\* \* \* \* \*